United States Patent
Mansoorabadi

(10) Patent No.: US 11,920,171 B1
(45) Date of Patent: *Mar. 5, 2024

(54) SYNTHESIS AND OXIDATION OF METHANE

(71) Applicant: AUBURN UNIVERSITY, Auburn, AL (US)

(72) Inventor: Steven Mansoorabadi, Auburn, AL (US)

(73) Assignee: Auburn University, Auburn, AL (US)

(*) Notice: Subject to any disclaimer, the term of this patent is extended or adjusted under 35 U.S.C. 154(b) by 620 days.

This patent is subject to a terminal disclaimer.

(21) Appl. No.: 16/898,009

(22) Filed: Jun. 10, 2020

Related U.S. Application Data

(63) Continuation of application No. 15/588,396, filed on May 5, 2017, now Pat. No. 10,793,863.

(60) Provisional application No. 62/332,658, filed on May 6, 2016.

(51) Int. Cl.
| | |
|---|---|
| C12N 9/88 | (2006.01) |
| C12N 9/00 | (2006.01) |
| C12N 9/02 | (2006.01) |
| C12N 15/52 | (2006.01) |
| C12N 15/62 | (2006.01) |
| C12N 15/74 | (2006.01) |
| C12P 5/02 | (2006.01) |

(52) U.S. Cl.
CPC ............ *C12N 9/88* (2013.01); *C12N 9/0095* (2013.01); *C12N 9/93* (2013.01); *C12N 15/52* (2013.01); *C12N 15/62* (2013.01); *C12N 15/74* (2013.01); *C12P 5/023* (2013.01); *C12Y 499/01003* (2013.01); *C12Y 603/02013* (2013.01); *C12Y 603/05011* (2013.01)

(58) Field of Classification Search
CPC ........... C12N 9/0095; C12N 9/88; C12N 9/93
See application file for complete search history.

(56) References Cited

U.S. PATENT DOCUMENTS 10,314,895 B2  6/2019 Altemann et al.

OTHER PUBLICATIONS

Studer. Residue mutations and their impact on protein structure and function: detecting beneficial and pathogenic changes. Biochem. J. (2013) 449, 581-594.*

Lessner. An unconventional pathway for reduction of CO2 to methane in CO-grown Methanosarcina acetivorans revealed by proteomics. Proc Natl Acad Sci U S A. Nov. 21, 2006; 103(47): 17921-17926.*

(Continued)

*Primary Examiner* — Yong D Pak
(74) *Attorney, Agent, or Firm* — Nicholas J. Landau; Maynard Nexsen PC

(57) ABSTRACT

The present disclosure describes genes and proteins of the coenzyme F430 synthetic pathway. The genes and proteins in the pathway find uses as isolated nucleic acids, transformation vectors, a transformation media, genetically modified cells, methods of modulating methanogenesis, methods of modulating methane oxidation, methods of making a tetrapyrrole compound, methods of oxidizing methane, methods of biogenic methane synthesis is provided, methods of assaying an organism for potential methanogenic or methanotrophic activity, and isolated proteins.

20 Claims, 9 Drawing Sheets

Specification includes a Sequence Listing.

(56) References Cited

OTHER PUBLICATIONS

Zhang et al.; "Directed Mutagenesis and Plasmid-Based Complementation in the Methanogenic Archaeon Methanosarcina acetivorans C2A Demonstrated by Genetic Analysis of Proline Biosynthesis;" Journal of Bacteriology, Mar. 2002, pp. 1449-1454, vol. 184, No. 5.
Zheng et al.; The biosynthetic pathway of coenzyme F430 in methanogenic and methanotrophic archaea; Research Reports; Oct. 21, 2016; vol. 354 Issue 6310.
Maeder et al.; The Methanosarcina barkeri Genome: Comparative Analysis with Methanosarcina acetivorans and Methanosarcina mazei Reveals Extensive Rearrangement within Methanosarcinal Genomes; Journal of Bacteriology; Nov. 2006, doi:10.1128/JB. 00810-06.
Leahy et al.; The Genome Sequence of the Rumen Methanogen Methanobrevibacter ruminantium Reveals New Possibilities for Controlling Ruminant Methane Emissions; Plos ONE 5(1): e8926, doi:10.1371/journal.pone.0008926.
Kaster et al.; More Than 200 Genes Required for Methane Formation from H2 and CO2 and Energy Conservation Are Present in Methanothermobacter marburgensis and Methanothermobacter thermautotrophicus; Hindawi Publishing Corporation; Archaea; vol. 2011, Article ID 973848; doi:10.1155/2011/973848.
Brindley et al.; A Story of Chelatase Evolution; The Journal of Biological Chemistry; The American Society for Biochemistry and Molecular Biology, Inc.; vol. 278, No. 25, Issue of Jun. 20, 2003.
Galagan et al., Genome Res., 12:532-542 (Year: 2002).
Thauer RK, et al. "Methanogenic archaea: ecologically relevant differences in energy conservation" Nature Reviews/Microbiology; vol. 6, Aug. 2008, pp. 579-592.
Pachauri, Rajendra K., et al. "Climate Change 2014 Synthesis Report" IPCC, 2014: Contribution of Working Groups I, II, and III to the Fifth Assessment Report of the Intergovernmental Panel on Climate Change; Geneva, ☐ Switzerland, pp. 1-168.
Ferry, James G. "Methane: small molecule, big impact" Science, vol. 278, No. 5342, 1997, p. 1413+.
Ermler, Ulrich, et al. "Crystal Structure of Methyl-Coenzyme M Reductase: The Key Enzyme of Biological Methane Formation" Science, vol. 278; Nov. 21, 1997; pp. 1457-1463.
Diekert, Gabriele, et al. "Biosynthetic Evidence for a Nickel Tetrapyrrole Structure of Factor F 430 From Methanobacterium Thermoautotrophicum" FEBS Letters, vol. 119, No. 1, Sep. 1980; pp. 118-120.
Knittel, Kartin, et al. "Anaerobic Oxidation of Methane: Progress with an Unknown Process" Annu. Rev. Microbial. 2009:63,pp. 311-334.
Scheller, Silvan "The key nickel enzyme of methanogenesis catalyses the anaerobic oxidation of methane" Nature, vol. 465,3 Jun. 201 O; pp. 606-609.
British Petroleum Co. "BP Statistical Review of World Energy Jun. 2015" 64th Edition, pp. 1-48.
U.S. Department of Energy—Office of Fossil Energy "Modern Shale Gas Development in the United States A Primer" Apr. 2009, pp. 1-116.
Lunsford, Jack H. "Catalytic conversion of methane to more useful chemicals and fuels: a challenge for the 21st century" Catalysis Today 63 (2000) pp. 165-174.
Mueller, Thomas J., et al. "Methane oxidation by anaerobic archaea for conversion to liquid fuels" J Ind Microbial Biotechnol (2015) 42:391-401.
Schubert, Heidi L., et al. "Common Chelatase Design in the Branched Tetrapyrrole Pathways of Heme and Anaerobic Cobalamin Synthesis" Biochemistry 1999, 38, 10660-10669.
Mucha, Helmut, et al. "Sirohydrochlorin, a precursor of factor F 430 biosynthesis in Methanobacterium thermoautotrophicum" FESS 2962 (1985), vol. 190:1; pp. 169-171.
Roth, John R. "Characterization of the Cobalamin (Vitamin 812) Biosynthetic Genes of *Salmonella typhimurium*" Journal of Bacteriology, Jun. 1993, vol. 175:11, p. 3303-3316.
Schindelin, Hermann, et al. . "Structure of ADP—AIF 4-stabilized nitrogenase complex and its implications for signal transduction" Nature, vol. 387, May 22, 1997; pp. 370-376.
Muraki, Norifumi, et al. "X-ray crystal structure of the light-independent protochlorophyllide reductase" nature, vol. 465, May 6, 2010, pp. 110-115.
Staples, Christopher R., et al. "Expression and Association of Group IV Nitrogenase NifD and NifH Homologs in the Non-Nitrogen-Fixing Archaeon Methanocaldococcus jannaschii" Journal of Bacteriology, Oct. 2007, p. 7392-7398.
Pratviel-Sosa, Flore, et al. "Over-production, purification and properties of the uridine diphosphate N-acetylmuramoyl-L-alanine: D-glutamate ligase from *Escherichia coli*" Eur. J. Biochem. 202, 1169-1176 (1991).
Sarmiento, Felipe, et al. "Genome-scale analysis of gene function in the hydrogenotrophic methanogenic archaeon Methanococcus maripaludis" PNAS, Mar. 19, 2013, vol. 110:12, pp. 4726-4731.
Warren, Martin J., et al. "Enzymatic synthesis of dihydrosirohydrochlorin (precorrin-2) and of a novel pyrrocorphin by uroporphyrinogen III methylase" FESS 08106, vol. 261:1, Feb. 1990, pp. 76-80.
Leech, H.K., et al. "Production of cobalamin and sirohaem in Bacillus megaterium: an investigation into the role of the branch-point chelatases sirohydrochlorin ferrochelatase (SirB) and sirohydrochlorin cobalt chelatase (CbiX)" Biochemical Society Transactions (2002) vol. 30:4, pp. 610-613.
Deery, Evelyne, et al. "An enzyme-trap approach allows isolation of intermediates in cobalamin biosynthesis" Nat Chem Biol. Nov. 2012; 8(11 ): 933-940.
Fresquet, Vicente, et al. "Mechanism of Cobyrinic Acid, a,c-Diamide Synthetase from *Salmonella typhimurium* LT2" Biochemistry 2004, 43, 10619-10627.
Pfaltz, Andreas, et al. "Biosynthesis of coenzyme F430 in methanogenic bacteria Identification of 15, 11?seco-F430-17.1!'.acid as an intermediate" Eur. J. Biochem. 170, 459-467 (1987) pp. 459-468.
Fani, Renato, et al. "Molecular Evolution of Nitrogen Fixation: The Evolutionary History of the nifD, nifK, nifE, and nifN Genes" J Mol Evol (2000) 51: 1-11.
Kouldml, Imene, et al. "The biology of Mur ligases as an antibacterial target" Molecular Microbiology (2014) 94(2), 242-253.
Bo Kranz, Martin, et al. "Nucleotide sequence of the methyl coenzyme M reductase gene cluster from Methanosarcina barkeri" Nucleic Acids Research, vol. 15: 10 (1987), pp. 1-2.
Prakash, Divya, et al. "Elucidating the Process of Activation of Methyl-Coenzyme M Reductase" Journal of Bacteriology, Jul. 2014, vol. 196, No. 13, pp. 2491-2498.
Sherf, Bruce A., et al. "Identification of the mcrD Gene Product and Its Association with Component C of Methyl Coenzyme M Reductase in Methanococcus vannielii" Journal of Bacteriology, Apr. 1990, vol. 172, No. 4, p. 1828-1833.

\* cited by examiner

| Gene | Primer | SEQ |
|---|---|---|
| hemC | Forward: 5'-GCGGCCATATGTTAGACAATGTTTTAAGAATTGCC-3' | 174 |
| | Reverse: 5'-TATAACTCGAGTCATGCCGGAGCGTC-3' | 175 |
| hemD | Forward: 5'-TGGGCCATATGAGTATCCTGGTC-3' | 176 |
| | Reverse: 5'-TAGGACTCGAGTTATTGTAATGCCCG-3' | 177 |
| sirA | Forward: 5'-CGGCGCATATGTCAGAAAATTACGG-3' | 178 |
| | Reverse: 5'-ATGAGCTCGAGTCAGAAATCCTTTCCTGC-3' | 179 |
| sirC | Forward: 5'-GAGGACATATGATGGCTGAAACAAATAATTTTC-3' | 180 |
| | Reverse: 5'-TAGGACTCGAGTTATTCGAGCTTATCCGAG-3' | 181 |
| cfbA | Forward: 5'-GGCACCATATGACTGAGAAACTCGG-3' | 182 |
| | Reverse: 5'-ATTACGGATCCTTACAGGGCTTCCTG-3' | 183 |
| cfbB | Forward: 5'-CCACACATATGTCCCACAGCAAACAATC-3' | 184 |
| | Reverse: 5'-ATTAAGGTACCCTACCGGGGAGCCC-3' | 185 |
| cfbC | Forward: 5'-CGCTGCATATGAAAAAACAAAGATCGTTGC-3' | 186 |
| | Reverse 1: 5'-CCGCGAAGCTTTTATTTTGTCATTTCCC-3' | 187 |
| | Reverse 2: 5'-ATTATGGCCGGCCTTATTTTGTCATTTCCC-3' | 188 |
| cfbD | Forward: 5'-CGCCGTCATGACTCAAAAAGAGATCTC-3' | 189 |
| | Reverse: 5'-ATCACAAGCTTTCAGGCTTCTTTTGCAAC-3' | 190 |
| cfbE | Forward: 5'-GACACCATATGGACCTGTTCCGG-3' | 191 |
| | Reverse: 5'-CGCACCTCGAGTTAACGGAAACATTTC-3' | 192 |
| mcrD | Forward: 5'-AATCTCATATGTCAGACTCTGCTTCAAACACG-3' | 193 |
| | Reverse: 5'-GCTCTCTCGAGTCACTCATCTTTATCAGTGTC-3' | 194 |

FIG. 3

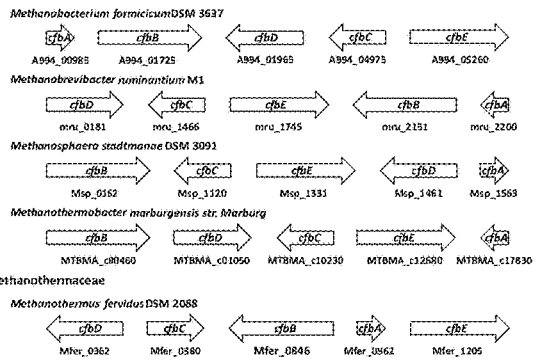
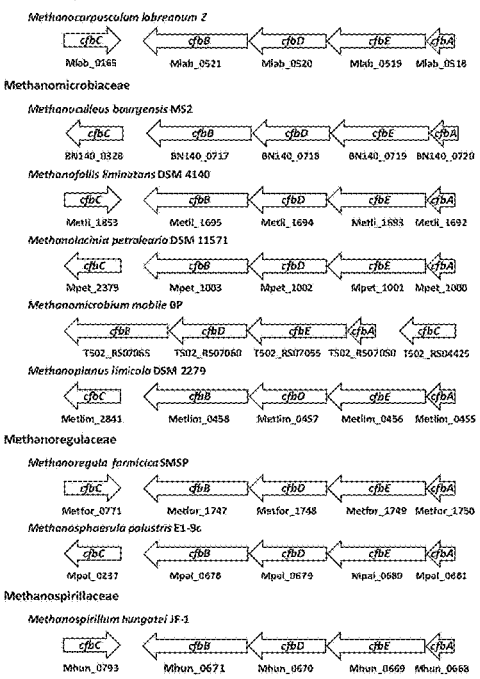
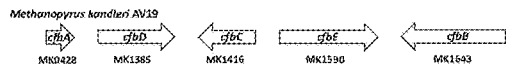
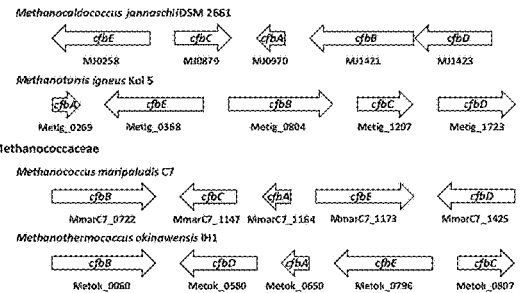
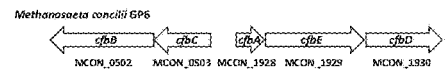
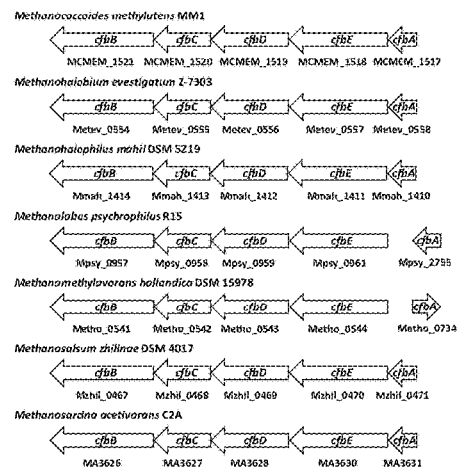
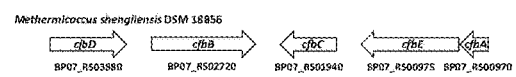
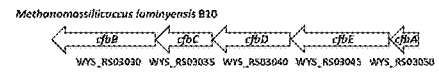
FIG. 4

SEQUENCE LISTING

<160> NUMBER OF SEQ ID NOS: 195

<210> SEQ ID NO 1
<211> LENGTH: 149
<212> TYPE: PRT
<213> ORGANISM: Methanobacterium formicicum

<400> SEQUENCE: 1

Met Val Thr Asn Ser Asn Ser Asn Ser Asn Val Gly Ile Val Leu Val
1               5                   10                  15

Gly His Gly Ser Arg Leu Pro Tyr Gly Lys Asp Val Leu Ser Gln Leu
            20                  25                  30

Ala Glu Ile Tyr Arg Gln Glu Ser Asp His Pro Val Glu Val Gly Phe
        35                  40                  45

Met Asn Met Asn Lys Pro Ser Ile Pro Ser Ser Ile Asn Lys Leu Ala
50                  55                  60

Gln Met Gly Val Glu Lys Ile Val Thr Pro Val Phe Leu Ala Pro
65                  70                  75                  80

Gly Val His Thr Thr Glu Asp Ile Pro Arg Ile Leu Gly Leu Gly Asn
            85                  90                  95

Gly Asp Glu Thr His Glu His Ser His Glu His Gly His Ser His Asp
            100                 105                 110

His Gly Glu Thr Glu Glu Ile His Phe His Gly Glu Ile Ile Tyr Thr
            115                 120                 125

Asp Pro Leu Gly Pro Asp Pro Lys Ile Val Ser Ile Ile Gln Asp Arg
        130                 135                 140

Val Asn Glu Ala Leu
145

<210> SEQ ID NO 2
<211> LENGTH: 322
<212> TYPE: PRT
<213> ORGANISM: Methanobrevibacter ruminantium M1

<400> SEQUENCE: 2

Met Ile Ile Met Ser Glu Asp Thr Ala Val Leu Leu Leu Ser His Gly
1               5                   10                  15

Ser Ser Leu Pro Tyr Ala Glu Glu Val Phe Lys Asp Ile Cys Ala Lys
            20                  25                  30

Phe Lys Glu Gln Thr Glu Phe Asp Ala Glu Val Gly Tyr Met Lys Val
        35                  40                  45

Ala Lys Pro Ser Leu Pro Glu Ala Ile Asn Ile Leu Lys Glu Arg Asn
50                  55                  60

Pro Gly Leu Lys Arg Ile Ile Ala Thr Pro Val Phe Leu Ala Pro Gly
65                  70                  75                  80

Ile His Thr Asn Ile Asp Ile Pro Ile Ile Leu Gly Leu Glu Pro Lys
            85                  90                  95

Glu Thr Asp Pro Arg Gln Pro Asp Gly Asn Tyr Pro Glu Gly His Tyr
            100                 105                 110

Leu Tyr Gly Leu Glu Glu Val Asp Phe Asp Gly Glu Leu Lys Leu Ile
        115                 120                 125

Asp Ala Ile Gly Pro Asn Pro Arg Leu Ile Glu Ile Ile Asn Asn Arg
        130                 135                 140

Ile Asp Thr Ala Leu Glu Asp Ser Lys Leu Asp Asp Ala Lys Thr
145                 150                 155                 160

Ala Val Leu Leu Val Ser His Gly Ser Arg Leu Asn Tyr Asn Lys Glu

```
                165                 170                 175
Phe Ile Ser Cys Val Phe Gln Gln Phe Glu Glu Gln Thr Asp Tyr Val
            180                 185                 190

Cys Asp Phe Ala Phe Met Glu Leu Val Asp Pro Asn Ile Pro Thr Thr
        195                 200                 205

Ile Asn Lys Leu Val Ser Glu Asn Glu Val Asp Arg Leu Ile Val Val
    210                 215                 220

Pro Val Phe Ile Ala Pro Gly Val His Thr Thr Arg Asp Ile Pro Thr
225                 230                 235                 240

Ile Leu Gly Leu Ile Glu Asp Gly Ser Gly His His His His
                245                 250                 255

His His Asp His Asp His Asp His Ser His Asp His Gly His Asp His
                260                 265                 270

Asp His Gly His Ser His Gly His His His His His Ala His Gly
                275                 280                 285

Asp Glu Lys Met Glu Phe Asp Gly Gly Ile Leu Tyr Pro Glu Pro Ile
        290                 295                 300

Cys Asp Asp Asp Ile Leu Ile Glu Ile Leu Glu Thr Met Val Lys Glu
305                 310                 315                 320

Ala Leu

<210> SEQ ID NO 3
<211> LENGTH: 143
<212> TYPE: PRT
<213> ORGANISM: Methanocaldococcus jannaschii DSM 2661

<400> SEQUENCE: 3

Met Glu Ala Leu Val Leu Val Gly His Gly Ser Arg Leu Pro Tyr Ser
1               5                   10                  15

Lys Glu Leu Leu Val Lys Leu Ala Glu Lys Val Lys Glu Arg Asn Leu
            20                  25                  30

Phe Pro Ile Val Glu Ile Gly Leu Met Glu Phe Ser Glu Pro Thr Ile
        35                  40                  45

Pro Gln Ala Val Lys Lys Ala Ile Glu Gln Gly Ala Lys Arg Ile Ile
    50                  55                  60

Val Val Pro Val Phe Leu Ala His Gly Ile His Thr Thr Arg Asp Ile
65                  70                  75                  80

Pro Arg Leu Leu Gly Leu Ile Glu Asp Asn His Glu His His His Glu
                85                  90                  95

His Ser His His His His His His His Glu His Glu Lys Leu
            100                 105                 110

Glu Ile Pro Glu Asp Val Glu Ile Ile Tyr Arg Glu Pro Ile Gly Ala
        115                 120                 125

Asp Asp Arg Ile Val Asp Ile Ile Asp Arg Ala Phe Gly Arg
    130                 135                 140

<210> SEQ ID NO 4
<211> LENGTH: 133
<212> TYPE: PRT
<213> ORGANISM: Methanocella arvoryzae MRE50

<400> SEQUENCE: 4

Met Glu Asn Gln Lys Phe Gly Leu Leu Val Val Gly His Gly Ser Ser
1               5                   10                  15

Met Pro Tyr Asn Lys Glu Leu Ile Glu Asp Ile Ala Ala Arg Ile Ala
            20                  25                  30
```

```
Lys Lys Met Pro Asp Ala Val Arg Val Gly Phe Met Asn Met Asn
            35                  40                  45

Lys Pro Thr Ile Lys Glu Gly Leu Asp Ser Phe Asn Gly Thr Gly Val
 50                  55                  60

Arg Lys Ile Val Val Phe Pro Leu Phe Leu Ala Lys Gly Val His Ile
 65                  70                  75                  80

Lys Glu Asp Ile Pro Asn Leu Ile Gly Leu Lys Glu Gly Gln Lys Arg
                 85                  90                  95

Ile Thr Tyr Asn Gly Tyr Asp Ile Val Tyr Ala Asp Pro Leu Gly Ser
            100                 105                 110

Asp Asp Leu Ile Ala Glu Leu Ser Cys Arg Arg Val Thr Gln Ala Phe
            115                 120                 125

Ala Val Tyr Glu Ser
        130

<210> SEQ ID NO 5
<211> LENGTH: 131
<212> TYPE: PRT
<213> ORGANISM: Methanococcoides methylutens MM1

<400> SEQUENCE: 5

Met Ser Glu Lys Ile Gly Ile Leu Ala Ile Gly His Gly Ser Arg Leu
 1               5                  10                  15

Pro Tyr Asn Lys Glu Val Val Ser Glu Ile Ala Asp Thr Ile Ala Lys
                 20                  25                  30

Lys His Pro Glu Tyr Val Val Lys Val Gly Phe Met Glu Asn Cys Gly
            35                  40                  45

Pro Ser Val Asp Glu Gly Leu Ala Ser Phe Glu Gly Thr Gly Val Thr
 50                  55                  60

Lys Ile Ala Ala Val Pro Val Phe Leu Ala Ser Gly Val His Ile Thr
 65                  70                  75                  80

Glu Asp Ile Pro Glu Ile Leu Lys Leu Asp Ala Glu Thr Asn Glu Gly
                 85                  90                  95

Lys Tyr Thr Val Asp Gly Gln Glu Val Pro Val Val Tyr Gly Lys Pro
            100                 105                 110

Leu Gly His His Glu Leu Leu Ala Asp Leu Val Phe Glu Arg Ala Ser
            115                 120                 125

Glu Val Leu
    130

<210> SEQ ID NO 6
<211> LENGTH: 146
<212> TYPE: PRT
<213> ORGANISM: Methanococcus maripaludis C7

<400> SEQUENCE: 6

Met Glu Ala Leu Val Leu Val Gly His Gly Ser Arg Leu Pro His Ser
 1               5                  10                  15

Lys Asn Val Val Thr Glu Val Ala Glu Lys Ile Lys Ala Arg Asn Ile
                 20                  25                  30

Tyr Asp Ile Val Glu Val Gly Met Met Glu Phe Asn Glu Pro Thr Ile
            35                  40                  45

Pro Glu Ala Ile Lys Lys Val Ile Asp Ala Gly Ala Lys Lys Val Ile
 50                  55                  60

Val Thr Pro Val Phe Leu Ala Pro Gly Asn His Thr Glu Arg Asp Ile
 65                  70                  75                  80
```

-continued

Pro Lys Ile Leu Gly Ile Tyr Glu Gly Asp Asp Cys Gly His His
                85                  90                  95

His His His Asp His Asp Cys Glu His His His His His Asp Thr
            100                 105                 110

Glu Lys Val Asp Ile Pro Glu Gly Val Glu Leu Val Tyr Arg Lys Pro
        115                 120                 125

Met Gly Ala Asp Asp Arg Ile Ile Asp Ile Val Leu Asp Arg Ala Asn
    130                 135                 140

Gly Leu
145

<210> SEQ ID NO 7
<211> LENGTH: 143
<212> TYPE: PRT
<213> ORGANISM: Methanocorpusculum labreanum Z

<400> SEQUENCE: 7

Met Thr Asn Gln Lys His Met Ser Ala Lys Gly Leu Leu Val Gly
1               5                   10                  15

His Gly Ser Arg Leu Gln Tyr Asn Lys Glu Leu Ile Thr Thr Thr Ala
            20                  25                  30

Glu Met Met Lys Glu Ser Gly Gly Asp Tyr Leu Ile Lys Ser Cys Phe
        35                  40                  45

Leu Glu Tyr Ser Asn Pro Thr Val Ala Glu Gly Leu Asp Leu Met Arg
    50                  55                  60

Ser Glu Asp Leu Glu Ile Leu Ile Val Val Pro Leu Phe Leu Ala Lys
65                  70                  75                  80

Gly Ile His Ile Leu Arg Asp Ile Pro Lys Ile Leu Gly Leu Glu Ala
                85                  90                  95

Gly Lys Lys Arg Gly Thr Phe Thr Leu Ala Asp Gly Arg Val Val Pro
            100                 105                 110

Leu Val Tyr Ala Glu Pro Ile Gly Ile Asp Pro Leu Leu Ala Glu Leu
        115                 120                 125

Met Leu Lys Asn Ala Ala Asn Ala Leu Thr Leu Pro Glu Asp Ala
    130                 135                 140

<210> SEQ ID NO 8
<211> LENGTH: 130
<212> TYPE: PRT
<213> ORGANISM: Methanoculleus bourgensis MS2

<400> SEQUENCE: 8

Met Leu Leu Val Gly His Gly Ser Lys Leu Pro Tyr Asn Lys Glu Leu
1               5                   10                  15

Ile Glu Thr Thr Ala Glu Phe Ile Ala Glu Lys Thr Asp Glu Tyr Ile
            20                  25                  30

Val Lys Pro Gly Phe Met Ser Ile Asn Ala Pro Thr Val Glu Glu Gln
        35                  40                  45

Leu Asp Ala Phe Arg Thr Glu Asp Ile Asn Met Leu Val Val Val Pro
    50                  55                  60

Leu Phe Leu Ala Arg Gly Val His Ile Asp Gln Asp Ile Pro Gly Ile
65                  70                  75                  80

Leu Gly Leu Pro Glu Gly Gly Arg Lys Gly Thr Phe Arg Met Asn Gly
                85                  90                  95

Lys Thr Val Pro Leu Val Tyr Ala Asn Pro Ile Gly Ser Asp Pro Leu
            100                 105                 110

```
Leu Ala Glu Leu Met Leu Lys Asn Ala Ser Asp Ala Ile Ala Glu Leu
            115                 120                 125

Asp Pro
    130

<210> SEQ ID NO 9
<211> LENGTH: 134
<212> TYPE: PRT
<213> ORGANISM: Methanofollis liminatans DSM 4140

<400> SEQUENCE: 9

Met Ala Arg Thr Gly Leu Leu Val Gly His Gly Ser Lys Leu Pro
1               5                   10                  15

Tyr Asn Lys Glu Leu Ile Glu Ser Thr Ala Ala Leu Ile Ala Ser Gln
            20                  25                  30

His Pro Glu Tyr Leu Val Arg Pro Gly Phe Met Ser Met Asn Glu Pro
        35                  40                  45

Ser Val Asp Glu Ala Leu Asp Ala Phe Lys Lys Asp Glu Ile Asp Leu
    50                  55                  60

Leu Ile Val Val Pro Leu Phe Leu Ala Lys Gly Val His Ile Leu Gln
65                  70                  75                  80

Asp Ile Pro Glu Leu Leu Gly Leu Pro Glu Gly Ala Lys Lys Gly Thr
                85                  90                  95

Phe Ala His Ala Thr Gly Ala Ile Pro Leu Val Tyr Ala Asp Pro Ile
            100                 105                 110

Gly Gly Asp Pro Leu Leu Ala Asp Leu Met Val Lys Asn Ala Glu Ala
        115                 120                 125

Ala Ile Arg Ser Asn Ser
    130

<210> SEQ ID NO 10
<211> LENGTH: 134
<212> TYPE: PRT
<213> ORGANISM: Methanohalobium evestigatum Z-7303

<400> SEQUENCE: 10

Met Ser Glu Asn Ser Lys Leu Gly Ile Leu Ala Ile Gly His Gly Ser
1               5                   10                  15

Lys Leu Pro Tyr Asn Lys Gln Val Val Thr Asp Ile Ala Asn Arg Ile
            20                  25                  30

Ala Asp Lys His Glu Asp Val Val Arg Ala Gly Phe Met Glu Lys
        35                  40                  45

Asn Glu Pro Thr Val Glu Glu Ala Leu Gln Ser Phe Glu Gly Thr Gly
    50                  55                  60

Ile Ser Lys Ile Ala Ala Val Pro Val Phe Leu Ala Ser Gly Val His
65                  70                  75                  80

Ile Thr Gln Asp Ile Pro Glu Ile Leu Gly Ile Asp Pro Asp Ser Lys
                85                  90                  95

Glu Gly Ser Ile Lys Leu Asn Gly Thr Glu Ile Pro Ile Val Tyr Gly
            100                 105                 110

Asn Pro Leu Gly Ser Asp Asp Leu Leu Ala Glu Leu Val Tyr Asn Arg
        115                 120                 125

Ala Gln Glu Ala Leu Asp
    130

<210> SEQ ID NO 11
```

-continued

```
<211> LENGTH: 131
<212> TYPE: PRT
<213> ORGANISM: Methanohalophilus mahii DSM 5219

<400> SEQUENCE: 11

Met Ser Glu Lys Ile Gly Ile Leu Ala Ile Gly His Gly Ser Arg Leu
1               5                   10                  15

Pro Tyr Asn Lys Glu Val Val Thr Asn Ile Ala Asn Thr Ile Ala Glu
            20                  25                  30

Lys His Pro Glu Tyr Val Ile Arg Thr Gly Phe Met Glu Asn Cys Gly
        35                  40                  45

Pro Ser Val Gln Glu Ala Met Lys Glu Phe Glu Gly Thr Gly Val Thr
    50                  55                  60

Arg Ile Ala Ala Val Pro Val Phe Leu Ala Ser Gly Ile His Ile Thr
65                  70                  75                  80

Glu Asp Ile Pro Glu Ile Leu Lys Leu Asp Pro Gln Thr Asn Glu Gly
                85                  90                  95

Lys Ile Glu Val Asp Gly Asn Glu Val Pro Val Val Tyr Gly Lys Pro
            100                 105                 110

Leu Gly Asn His Glu Met Leu Ala Asp Leu Val Phe Glu Arg Ala Lys
        115                 120                 125

Glu Val Ile
    130

<210> SEQ ID NO 12
<211> LENGTH: 134
<212> TYPE: PRT
<213> ORGANISM: Methanolacinia petrolearia DSM 11571

<400> SEQUENCE: 12

Met Pro Lys Ile Gly Phe Leu Leu Val Gly His Gly Ser Lys Lys Pro
1               5                   10                  15

Tyr Asn Lys Gln Leu Ile Asp Asn Thr Ala Lys Ile Ile Ala Gly Lys
            20                  25                  30

Glu Ala Gly Tyr Ile Val Lys Thr Gly Phe Met Glu Phe Ser Glu Pro
        35                  40                  45

Thr Ile Pro Glu Ala Leu Glu Ser Phe Arg Gly Glu Asp Ile Glu Met
    50                  55                  60

Leu Gln Val Val Pro Leu Phe Leu Ala Arg Gly Met His Ile Asp Lys
65                  70                  75                  80

Asp Ile Pro Glu Ile Leu Gly Ile Glu Glu Gly His Asn Gly Thr
                85                  90                  95

Phe Lys Leu Asn Asp Lys Glu Ile Pro Leu Val Phe Ala Asp Pro Ile
            100                 105                 110

Gly Glu Asn Glu Leu Leu Ala Asp Leu Met Ile Val Asn Gly Lys Lys
        115                 120                 125

Ala Val Glu Asp Tyr Leu
    130

<210> SEQ ID NO 13
<211> LENGTH: 131
<212> TYPE: PRT
<213> ORGANISM: Methanolobus psychrophilus R15

<400> SEQUENCE: 13

Met Thr Glu Lys Met Gly Ile Leu Thr Ile Gly His Gly Ser Arg Leu
1               5                   10                  15
```

```
Pro Tyr Asn Asn Gln Val Val Ser Glu Ile Ala Asp Met Ile Ala Lys
                20                  25                  30

Lys His Pro Glu Tyr Ile Val Lys Ser Gly Phe Met Glu Met Ser Thr
            35                  40                  45

Pro Ser Val Glu Glu Ala Leu Leu Ser Phe Ala Gly Thr Gly Val Thr
        50                  55                  60

Lys Ile Ala Ala Val Pro Val Phe Leu Ala Ser Gly Val His Ile Thr
 65                  70                  75                  80

Lys Asp Ile Pro Glu Ile Leu Lys Leu Asp Pro Glu Thr Lys Gln Gly
                85                  90                  95

Lys Val Lys Leu Asp Gly Lys Asp Val Thr Ile Val Tyr Gly Lys Pro
            100                 105                 110

Leu Gly Ser Asp Glu Leu Ile Ala Glu Leu Ile Phe Lys Arg Ala Gln
        115                 120                 125

Glu Val Leu
        130
```

```
<210> SEQ ID NO 14
<211> LENGTH: 131
<212> TYPE: PRT
<213> ORGANISM: Methanomassiliicoccus luminyensis B10

<400> SEQUENCE: 14

Met Thr Asn Gly Val Leu Leu Ile Gly His Gly Ser Lys Leu Gln Tyr
 1               5                  10                  15

Asn Lys Asp Leu Val Val Ser Thr Ala Glu Lys Met Gly Lys Met Asn
                20                  25                  30

Leu Gly Pro Val Ala Ala Ala Phe Met Gln Leu Asn Thr Pro Thr Ile
            35                  40                  45

Lys Glu Gly Ile Lys Thr Leu Val Gly Gln Gly Val Asp Asp Ile Tyr
        50                  55                  60

Ile Gln Pro Cys Phe Leu Ala Ser Gly Ala His Leu Thr Glu Asp Ile
 65                  70                  75                  80

Pro Gly Glu Ile Gly Leu Lys Ala Gly Asp Thr Glu Thr Lys Met Thr
                85                  90                  95

Val Asp Gly Lys Thr Val Thr Leu Arg Tyr Cys Asp Pro Ile Gly Asp
            100                 105                 110

Asp Asp Arg Ile Ala Ala Ile Leu Ala Asp Arg Val Arg Thr Arg Met
        115                 120                 125

Gln Lys Ala
        130
```

```
<210> SEQ ID NO 15
<211> LENGTH: 131
<212> TYPE: PRT
<213> ORGANISM: Methanomethylovorans hollandica DSM 15978

<400> SEQUENCE: 15

Met Ser Glu Lys Ile Gly Ile Leu Ala Ile Gly His Gly Ser Arg Leu
 1               5                  10                  15

Pro Tyr Asn Asn Gln Val Val Thr Glu Ile Ala Gly Met Ile Ala Lys
                20                  25                  30

Lys His Pro Glu Tyr Val Val Lys Ala Gly Phe Met Glu Met Ser Thr
            35                  40                  45

Pro Ser Val Glu Glu Ala Leu Leu Ser Phe Glu Gly Thr His Val Ser
        50                  55                  60
```

```
Thr Ile Val Ala Val Pro Val Phe Leu Ala Ser Gly Val His Ile Thr
 65                  70                  75                  80

Lys Asp Ile Pro Ala Ile Leu Lys Leu Asp Pro Glu Lys Asn Gln Gly
                 85                  90                  95

Ser Ile Glu Met Asn Gly Gln Gln Val Lys Ile Leu Tyr Gly Lys Pro
            100                 105                 110

Leu Gly Ser Asp Glu Leu Ile Ala Asp Leu Ile Phe Lys Arg Ala Leu
        115                 120                 125

Glu Val Leu
        130
```

<210> SEQ ID NO 16
<211> LENGTH: 134
<212> TYPE: PRT
<213> ORGANISM: Methanomicrobium mobile BP

<400> SEQUENCE: 16

```
Met Ser Lys Thr Gly Phe Leu Leu Val Gly His Gly Ser Thr Lys Pro
 1               5                  10                  15

Tyr Asn Lys Gln Leu Ile Glu Asn Thr Ala Lys Leu Ile Ala Gln Lys
            20                  25                  30

Glu Lys Asp Tyr Ile Val Lys Cys Ala Phe Met Glu Asn Ser Thr Pro
        35                  40                  45

Ser Ile Pro Glu Ile Ile Glu Thr Phe Arg Asn Glu Asp Ile Asp Lys
    50                  55                  60

Met Leu Val Val Pro Leu Phe Leu Ala Arg Gly Val His Ile Asp Val
 65                  70                  75                  80

Asp Ile Pro Glu Ile Leu Gly Ile Pro Glu Cys Gly His Arg Gly Thr
                 85                  90                  95

Phe Lys Thr Ala Lys Gly Glu Ile Pro Leu Val Phe Ala Ser Pro Ile
            100                 105                 110

Gly Asp Asn Pro Met Leu Ala Asp Leu Met Ile Ser Ser Ala Lys Asn
        115                 120                 125

Ala Leu Lys Glu Tyr Leu
        130
```

<210> SEQ ID NO 17
<211> LENGTH: 134
<212> TYPE: PRT
<213> ORGANISM: Methanoplanus limicola DSM 2279

<400> SEQUENCE: 17

```
Met Val Lys Lys Gly Phe Leu Leu Val Gly His Gly Ser Lys Lys Pro
 1               5                  10                  15

Tyr Asn Lys Gln Leu Ile Glu Ser Thr Ala Ala Ile Ile Ser Gly Lys
            20                  25                  30

Glu Asp Gly Tyr Ile Val Lys Ser Ala Phe Met Glu Asn Ser Ser Pro
        35                  40                  45

Thr Ile Gln Glu Met Leu Glu Glu Phe Lys Lys Glu Glu Ile Asp Thr
    50                  55                  60

Leu Val Val Val Pro Leu Phe Leu Ala Arg Gly Ile His Ile Asp Lys
 65                  70                  75                  80

Asp Ile Pro Glu Ile Leu Gly Ile Glu Glu Gly Gly His Lys Gly Thr
                 85                  90                  95

Phe Glu Thr Asp Ala Gly Glu Val Pro Leu Val Phe Ala Gln Pro Ile
            100                 105                 110
```

Gly Asp Asn Pro Met Leu Ala Asp Leu Met Ile Glu Ser Ala Asn Leu
            115                 120                 125

Ala Leu Glu Asn Tyr Leu
    130

<210> SEQ ID NO 18
<211> LENGTH: 143
<212> TYPE: PRT
<213> ORGANISM: Methanopyrus kandleri AV19

<400> SEQUENCE: 18

Met Val Ala Val Val Leu Val Gly His Gly Ser Arg Leu Pro Tyr Ser
1               5                   10                  15

Arg Gln Val Val Glu Lys Ile Ala Glu Tyr Val Glu Glu Met Gly Asp
                20                  25                  30

Phe Glu Thr Val Glu Val Gly Phe Met Glu Leu Cys Glu Pro Thr Val
            35                  40                  45

Gln Glu Ala Val Lys Lys Ala Ala Glu Ser Gly Val Asp Lys Ile Val
    50                  55                  60

Val Val Pro Val Phe Leu Ala His Gly Val His Thr Lys Arg Asp Ile
65                  70                  75                  80

Pro Lys Met Leu Gly Leu Glu Pro Glu Trp Asp Asp Glu Asp Glu Asp
                85                  90                  95

His Asp His His His His His Arg Asp Tyr Thr Pro Val Asp Val
            100                 105                 110

Asp Ala Glu Ile Val Tyr Ala Glu Pro Leu Gly Ala Asp Pro Arg Ile
        115                 120                 125

Ala Glu Ile Val Ile Asp Arg Ile Lys Glu Ala Leu Gly Glu Glu
    130                 135                 140

<210> SEQ ID NO 19
<211> LENGTH: 132
<212> TYPE: PRT
<213> ORGANISM: Methanoregula formicica SMSP

<400> SEQUENCE: 19

Met Ser Lys Lys Gly Met Leu Leu Val Gly His Gly Ser Thr Met Pro
1               5                   10                  15

Tyr Asn Gln Glu Leu Val Glu Lys Thr Ala Ala Met Ile Gln Ala Lys
                20                  25                  30

Asn Asn Asp Phe Ile Val Lys Cys Gly Phe Met Asn Ile Asn Lys Pro
            35                  40                  45

Thr Ile Arg Glu Ser Met Asp Ala Phe Arg Lys Glu Gln Ile Asp Ala
    50                  55                  60

Leu Val Val Val Pro Leu Phe Leu Ala Lys Gly Val His Ile Glu Lys
65                  70                  75                  80

Asp Ile Pro Gly Glu Ile Gly Leu Pro Glu Gly Val Lys Lys Gly Ala
                85                  90                  95

Phe Gln Leu Asn Gly Lys Ser Ile Pro Leu Val Tyr Ala Asn Pro Ile
            100                 105                 110

Gly Ser Asp Pro Leu Leu Ala Asp Leu Met Val Lys Asn Ala Asn Lys
        115                 120                 125

Ala Leu Thr Leu
    130

<210> SEQ ID NO 20
<211> LENGTH: 131

```
<212> TYPE: PRT
<213> ORGANISM: Methanosaeta concilii GP6

<400> SEQUENCE: 20

Met Lys Asp Val Gly Ile Leu Val Gly His Gly Ser Ser Leu Pro
1               5                   10                  15

Phe Asn Lys Glu Leu Val Glu Ser Leu Ala Gln Met Ile Gly Lys Asn
                20                  25                  30

Asn Ser Ser Gly Pro Val Arg Thr Ala Tyr Leu Asn Met Asn Gln Pro
            35                  40                  45

Asp Ile Pro Ala Gly Leu Lys Ser Phe Gln Gly Thr Gly Val Lys Lys
        50                  55                  60

Ile Val Ala Leu Pro Leu Phe Leu Ala His Gly Val His Thr Arg Gln
65                  70                  75                  80

Asp Ile Pro His Glu Leu Gly Val Asp Pro Lys Arg Arg Gly Val
                85                  90                  95

Leu Asn Ile Trp Gly Asp Glu Val Glu Val Ile Cys Ala Glu Pro Leu
                100                 105                 110

Gly Val Asp Glu Cys Ile Ala Ala Leu Ala Ile Lys Arg Ala Glu Glu
            115                 120                 125

Ser Leu Glu
    130

<210> SEQ ID NO 21
<211> LENGTH: 131
<212> TYPE: PRT
<213> ORGANISM: Methanosalsum zhilinae DSM 4017

<400> SEQUENCE: 21

Met Thr Glu Lys Ile Gly Ile Leu Ala Ile Gly His Gly Ser Arg Leu
1               5                   10                  15

Pro Tyr Asn Lys Glu Val Val Thr Ser Ile Ala Asn Asn Ile Ala Glu
                20                  25                  30

Lys Tyr Glu Asn Val Val Val Arg Ala Gly Phe Met Glu His Cys Gly
            35                  40                  45

Pro Ser Val Glu Glu Ala Leu Lys Ala Phe Asp Gly Thr Gly Val Thr
        50                  55                  60

Lys Ile Val Ala Val Pro Val Phe Leu Ala Ser Gly Val His Ile Thr
65                  70                  75                  80

Lys Asp Ile Pro Ala Ile Leu Gln Leu Asp Pro Glu Thr Gln Lys Gly
                85                  90                  95

Ser Val Glu Val Asp Gly Lys Glu Val Pro Leu Leu Tyr Gly Lys Pro
            100                 105                 110

Leu Gly Asn His Glu Leu Ile Ala Asp Leu Val Tyr Thr Arg Ala Gln
        115                 120                 125

Glu Val Leu
    130

<210> SEQ ID NO 22
<211> LENGTH: 130
<212> TYPE: PRT
<213> ORGANISM: Methanosarcina acetivorans C2A

<400> SEQUENCE: 22

Met Thr Glu Lys Leu Gly Ile Leu Ala Ile Gly His Gly Ser Lys Leu
1               5                   10                  15

Pro Tyr Asn Lys Glu Val Val Ser Gln Ile Ala Asp Tyr Ile Ala Gln
```

```
                    20                  25                  30
Lys His Ser Asp Val Val Arg Ala Gly Phe Met Glu Asn Ser Glu
                35                  40                  45

Pro Thr Leu Glu Glu Ala Ile Ala Gly Phe Ala Gly Thr Gly Val Thr
    50                  55                  60

Lys Ile Ala Ala Val Pro Val Phe Leu Ala Ser Gly Val His Ile Thr
65                  70                  75                  80

Lys Asp Ile Pro Gly Ile Leu Ser Leu Asp Glu Lys Gly Cys Gly Ile
                85                  90                  95

Leu Asn Ile Asp Gly Lys Asp Val Pro Leu Cys Tyr Ala Lys Pro Leu
            100                 105                 110

Gly Ala Asp Glu Leu Ile Ala Asp Leu Val Phe Lys Arg Val Gln Glu
        115                 120                 125

Ala Leu
    130

<210> SEQ ID NO 23
<211> LENGTH: 161
<212> TYPE: PRT
<213> ORGANISM: Methanosphaera stadtmanae DSM 3091

<400> SEQUENCE: 23

Met Asp Thr Asn Ser Asn Ser Lys Asn Asp Thr Gly Ile Leu Leu Ile
1               5                   10                  15

Gly His Gly Ser Arg Leu Pro Tyr Asn Lys Glu Val Ile Ser Ala Ile
                20                  25                  30

Ala Glu Lys Tyr Ala Gln Thr Lys Pro Asp Tyr Asn Ile Glu Val Gly
            35                  40                  45

Phe Met Glu Leu Ala Gly Pro Asn Ile Pro Thr Ala Phe Asn Lys Leu
        50                  55                  60

Lys Glu Thr Gly Val Asn Arg Ile Ile Val Thr Pro Ile Phe Leu Ala
65                  70                  75                  80

His Gly Met His Thr Lys Arg Asp Ile Pro Thr Ile Leu Gly Leu Glu
                85                  90                  95

Pro Glu Val Lys Glu Glu Pro Asn Gly His His His Glu His Glu
            100                 105                 110

His His His Glu His Gly His His His His His Gly Glu Val
        115                 120                 125

Glu Lys Val Glu Phe Asp Gly Glu Ile Ile Tyr Thr Glu Pro Ile Gly
    130                 135                 140

Ala Asp Asp Lys Ile Val Asp Ile Val Ser Glu Lys Val Asn Lys Tyr
145                 150                 155                 160

Leu

<210> SEQ ID NO 24
<211> LENGTH: 133
<212> TYPE: PRT
<213> ORGANISM: Methanosphaerula palustris E1-9c

<400> SEQUENCE: 24

Met Ser Ser Lys Gly Leu Leu Leu Val Gly His Gly Ser Lys Leu Gln
1               5                   10                  15

Tyr Asn Lys Glu Leu Ile Leu Glu Thr Gly Lys Met Ile Thr Gly Lys
                20                  25                  30

Ser Ser Glu Phe Met Val Lys Cys Gly Phe Met Ser Met Asn Glu Pro
            35                  40                  45
```

```
Ser Val Glu Lys Met Leu Glu Phe Ser His Thr Ala Ile Asp Val
             50                  55                  60

Leu Val Val Val Pro Leu Phe Leu Ala Lys Gly Val His Ile Glu Lys
 65                  70                  75                  80

Asp Ile Pro Ser Leu Leu Gly Leu Pro Glu Gly Gly Arg Lys Gly Thr
                 85                  90                  95

Phe Lys Thr Asp Asn Gly Thr Ile Pro Leu Val Tyr Ala Glu Pro Ile
                100                 105                 110

Gly Val Asp Pro Leu Leu Ala Asp Leu Met Leu Lys Asn Ala Glu Asn
            115                 120                 125

Ala Leu Lys Leu Val
        130
```

<210> SEQ ID NO 25
<211> LENGTH: 133
<212> TYPE: PRT
<213> ORGANISM: Methanospirillum hungatei JF-1

<400> SEQUENCE: 25

```
Met Thr Lys Thr Gly Ile Leu Leu Val Gly His Gly Ser Lys Lys Glu
  1               5                  10                  15

Tyr Asn Lys Asn Leu Ile Thr Lys Thr Ala Glu Ile Ile Ala Gln Lys
                 20                  25                  30

Asn Pro Asp Tyr Ile Val Arg Cys Gly Phe Met Glu Phe Asn Glu Pro
             35                  40                  45

Thr Ile Arg Glu Ser Leu Asp Ser Phe Lys Gln Asp Glu Val Asp Ser
 50                  55                  60

Ile Ala Val Val Pro Leu Phe Leu Ala Arg Gly Val His Ile Asp Glu
 65                  70                  75                  80

Asp Ile Pro Gly Ile Leu Gly Leu Ala Pro Gly Gln Lys Lys Gly Leu
                 85                  90                  95

Phe Ser Leu Thr Gly Lys Glu Val Pro Leu Val Tyr Ala Asp Pro Ile
                100                 105                 110

Gly Pro Asn Pro Leu Leu Ala Asp Leu Met Met Glu Asn Ala Lys Ala
            115                 120                 125

Ala Leu Asp Leu Ile
        130
```

<210> SEQ ID NO 26
<211> LENGTH: 141
<212> TYPE: PRT
<213> ORGANISM: Methanothermobacter marburgensis str. Marburg

<400> SEQUENCE: 26

```
Met Asp Ser Asn Ser Gly Gln Lys Thr Lys Ile Gly Val Leu Leu Val
  1               5                  10                  15

Gly His Gly Ser Arg Leu Pro Tyr Gly Glu Glu Val Ile Asn Gly Ile
                 20                  25                  30

Ala Asp Ile Tyr Arg Lys Glu Val Asp His Pro Val Ala Val Gly Phe
             35                  40                  45

Met Asn Ile Ser Arg Pro Ser Ile Pro Glu Ala Ile Asn Glu Leu Ala
 50                  55                  60

Ala Met Gly Val Glu Lys Ile Ile Val Thr Pro Val Phe Leu Ala His
 65                  70                  75                  80

Gly Val His Thr Lys His Asp Ile Pro His Ile Leu Gly Leu Asp Asn
                 85                  90                  95
```

-continued

Gly Thr Glu His His His His Glu His Glu Glu Phe Glu
            100                 105             110

Phe Asp Gly Glu Ile Val Tyr Thr Glu Pro Leu Gly Ala Asp Pro Arg
        115                 120                 125

Ile Ala Glu Ile Ile Arg Asp Arg Val Lys Ser Ala Ile
    130                 135                 140

<210> SEQ ID NO 27
<211> LENGTH: 109
<212> TYPE: PRT
<213> ORGANISM: Methanothermococcus okinawensis IH1

<400> SEQUENCE: 27

Met Met Glu Phe Asn Glu Pro Thr Ile Pro Gln Ala Ile Asn Lys Val
1               5                   10                  15

Ile Glu Lys Gly Ala Lys Lys Ile Ile Val Pro Val Phe Leu Ala
            20                  25                  30

His Gly Asn His Thr Lys Arg Asp Ile Pro Lys Ile Leu Gly Ile Tyr
        35                  40                  45

Glu Gly Gly Asp Glu Glu His His His His Glu His Gly Glu
    50                  55                  60

Glu His His His His His His Asp Thr Glu Lys Val Glu Leu
65                  70                  75                  80

Pro Glu Gly Val Glu Ile Ile Tyr Arg Glu Pro Met Gly Ala Asp Asp
                85                  90                  95

Arg Ile Val Asp Ile Val Leu Asp Arg Ala Gln Gly Asn
        100                 105

<210> SEQ ID NO 28
<211> LENGTH: 146
<212> TYPE: PRT
<213> ORGANISM: Methanothermus fervidus DSM 2088

<400> SEQUENCE: 28

Met Ala Ser Asn Leu Asp Gln Lys Asn Asp Ile Ala Val Leu Leu Val
1               5                   10                  15

Gly His Gly Ser Arg Leu Pro Tyr Ser Lys Glu Val Ile Met Lys Leu
            20                  25                  30

Ala Glu Met Tyr Lys Glu Arg Thr Asp His Leu Val Asp Val Ala Phe
        35                  40                  45

Met Glu Leu Ala Lys Pro Ser Ile Pro Glu Thr Val Asn Lys Leu Ala
    50                  55                  60

Lys Lys Gly Val Arg Lys Ile Ile Val Ile Pro Val Phe Leu Ala His
65                  70                  75                  80

Gly Val His Thr Lys His Asp Ile Pro His Ile Leu Gly Leu Lys Asp
                85                  90                  95

Asp His Glu His Ser His Gly His Gln His Glu His Glu Thr Val Asp
            100                 105                 110

Phe Asp Gly Glu Ile Ile Tyr Thr Glu Pro Leu Gly Ala Asp Pro Arg
        115                 120                 125

Ile Val Glu Ile Ile Glu Glu Arg Val Glu Asp Ala Ile Lys Gln Gln
    130                 135                 140

Asn Ser
145

<210> SEQ ID NO 29

```
<211> LENGTH: 145
<212> TYPE: PRT
<213> ORGANISM: Methanotorris igneus Kol 5

<400> SEQUENCE: 29

Met Glu Ala Leu Val Leu Val Gly His Gly Ser Arg Leu Pro Tyr Ser
1               5                   10                  15

Lys Glu Val Val Glu Lys Ile Ala Glu Lys Ile Arg Ala Lys Asn Ile
            20                  25                  30

Tyr Pro Ile Val Glu Val Gly Met Met Glu Phe Asn Glu Pro Thr Ile
        35                  40                  45

Pro Gln Ala Val Lys Lys Ala Ile Glu Gln Gly Ala Lys Lys Ile Ile
    50                  55                  60

Val Val Pro Val Phe Leu Ala His Gly Asn His Thr Lys Arg Asp Ile
65                  70                  75                  80

Pro Arg Ile Leu Gly Leu Ile Glu Asp Asp Gly Glu His His His Asn
                85                  90                  95

His Lys His Glu His His His His His His His Glu His Glu
            100                 105                 110

Lys Leu Glu Ile Pro Asp Asp Val Glu Ile Ile Tyr Arg Glu Pro Leu
        115                 120                 125

Gly Ala Asp Asp Arg Ile Val Asp Ile Val Leu Asp Arg Ala Ala Gly
    130                 135                 140

Arg
145

<210> SEQ ID NO 30
<211> LENGTH: 137
<212> TYPE: PRT
<213> ORGANISM: Methermicoccus shengliensis DSM 18856

<400> SEQUENCE: 30

Met His Gly Glu Phe Ile Met Lys Arg Gly Val Leu Val Leu Gly His
1               5                   10                  15

Gly Ser Lys Leu Pro Tyr Asn Arg Glu Val Val Glu Ser Val Cys Ser
            20                  25                  30

Met Leu Arg Gln Met Arg Asp Asp Ile Met Val Val Pro Ala Phe Met
        35                  40                  45

Glu Leu Cys Glu Pro Thr Ile Glu Asp Gly Leu Glu Glu Leu Ala Lys
    50                  55                  60

Ser Gly Val Ser Glu Val Ala Val Val Pro Leu Phe Leu Ala His Gly
65                  70                  75                  80

Val His Thr Leu Lys Asp Ile Pro Ala Arg Leu Gly Leu Glu Asp Gly
                85                  90                  95

Lys Arg Glu Cys Thr Tyr Glu Cys Gly Gly Val Gln Leu Arg Ile Tyr
            100                 105                 110

Tyr Ala Asp Pro Leu Gly Pro Ala Glu Ala Ile Ala Arg Leu Val Tyr
        115                 120                 125

Glu Arg Ala Leu Glu Ala Leu Gly Glu
    130                 135

<210> SEQ ID NO 31
<211> LENGTH: 136
<212> TYPE: PRT
<213> ORGANISM: Methanoperedens nitroreducens

<400> SEQUENCE: 31
```

```
Met Ile Met Ser Glu Lys Ile Gly Ile Leu Ala Leu Gly His Gly Ser
1               5                   10                  15

Lys His Pro His Asn Lys Asp Val Val Thr Gly Val Ala Glu Leu Ile
            20                  25                  30

Ala Lys Lys Tyr Ser Asn Val Val Arg Thr Gly Phe Met Asn Met
        35                  40                  45

Asn Ser Pro Thr Met Lys Glu Gly Leu Asp Ala Phe Gln Gly Thr Gly
    50                  55                  60

Val Ser Thr Ile Val Ala Val Pro Ile Phe Leu Ala His Gly Val His
65                  70                  75                  80

Thr Met Glu Asp Ile Pro Gln Ile Leu Gly Ile Ser Arg Glu Thr Arg
                85                  90                  95

Arg Thr Thr Ile Lys Ile Asp Gly Arg Asp Val Thr Leu Ile Tyr Ser
                100                 105                 110

Glu Pro Leu Gly Thr Asp Glu Leu Ile Ala Asp Leu Ala Phe Arg Arg
            115                 120                 125

Ala Lys Glu Ala Leu Leu Ala Asp
        130                 135
```

<210> SEQ ID NO 32
<211> LENGTH: 450
<212> TYPE: PRT
<213> ORGANISM: Methanobacterium formicicum DSM 3637

<400> SEQUENCE: 32

```
Met Arg Leu Val Leu Ala Gly Thr Gly Ser Ala Val Gly Lys Thr Thr
1               5                   10                  15

Ile Ser Thr Gly Ile Met Lys Ala Leu Ser His Glu Gln Glu Val Gln
            20                  25                  30

Pro Tyr Lys Ala Gly Pro Asp Tyr Ile Asp Thr Thr Tyr His Thr Met
        35                  40                  45

Ala Thr Gly Asn Ile Ser Arg Asn Leu Asp Ser Phe Phe Met Ser Asp
    50                  55                  60

Gly Gln Ile Arg Glu Ala Phe Glu Arg Gly Leu Lys Ile Ser Asn Ser
65                  70                  75                  80

Lys Val Gly Val Ile Glu Gly Val Arg Gly Leu Tyr Glu Gly Ile Ser
                85                  90                  95

Pro Thr Gly Asp Val Gly Asn Thr Ala Ser Ile Ala Lys Ala Leu Asn
            100                 105                 110

Ala Pro Val Val Leu Ile Leu Asn Ser Arg Ser Leu Val Lys Ser Ala
        115                 120                 125

Ala Ala Ile Val Ile Gly Phe Lys Thr Leu Asp Pro Thr Ile Arg Ile
    130                 135                 140

Glu Gly Val Ile Leu Asn Leu Val Lys Asn Arg Lys His Tyr Leu Lys
145                 150                 155                 160

Thr Lys Glu Ala Val Glu Lys Leu Ala Glu Thr Pro Val Ile Gly Gly
                165                 170                 175

Ile Pro Arg Asp Asp Val Ile Thr Val Glu Gln Arg His Leu Gly Leu
            180                 185                 190

Val Pro Ala Val Glu Arg Glu Asn Ile Lys Arg Asn Ile Glu Asp Trp
        195                 200                 205

Gly Arg Val Met Glu Glu Asn Ile Asp Leu Asp Ala Leu Thr Ser Ile
    210                 215                 220

Met Lys Gly Ala Gly Lys Leu Pro Glu Gly Arg Glu Pro Leu Phe Gln
225                 230                 235                 240
```

```
Gln Glu Asn Asn Arg Lys Val Lys Met Gly Ile Ala Arg Asp Glu Val
                245                 250                 255

Phe Thr Phe Tyr Tyr Gln Asp Asn Leu Glu Ala Leu Glu Asp Asn Asn
            260                 265                 270

Ala Glu Leu Val Tyr Phe Ser Pro Leu His Asp Glu Val Pro Asp
        275                 280                 285

Val Asp Gly Ile Tyr Ile Gly Gly Tyr Pro Glu Ile Phe Ala Arg
    290                 295                 300

Glu Leu Glu Ala Asn Arg Ala Met Arg Ser Ser Ile Asn Lys Phe His
305                 310                 315                 320

Gln Glu Ala Arg Pro Ile Tyr Ala Glu Cys Gly Gly Leu Met Tyr Leu
                325                 330                 335

Thr Arg Ser Ile Asn Gln His Gln Met Cys Asp Val Phe Gly Tyr Asp
            340                 345                 350

Ser His Met Thr Lys Lys Pro Gln Ala Leu Ser Tyr Val Ile Ala Arg
        355                 360                 365

Ala Ala Gln Asp Asn Ile Ile Ile Pro Glu Gly Glu Thr Phe His Gly
    370                 375                 380

His Glu Phe His Tyr Ser Lys Leu Glu Leu Glu Gly Ser Lys Pro Lys
385                 390                 395                 400

Phe Ala Phe Asp Ile Leu Arg Gly Arg Gly Val Thr Asp Ser Met Asp
                405                 410                 415

Gly Leu Met Ser Lys Asn Thr Leu Ala Ser Tyr Val His Thr His Val
            420                 425                 430

Ala Ala Cys Pro Thr Phe Ala Ser Arg Leu Val Lys Thr Ala Ala Glu
        435                 440                 445

Asp Tyr
    450

<210> SEQ ID NO 33
<211> LENGTH: 480
<212> TYPE: PRT
<213> ORGANISM: Methanobrevibacter ruminantium M1

<400> SEQUENCE: 33

Met Lys Val Val Leu Ala Gly Thr Gly Ser Ala Val Gly Lys Thr Thr
1               5                   10                  15

Ile Ser Thr Gly Ile Met Lys Ala Leu Ser Asp Glu Asn Val Gln Pro
            20                  25                  30

Phe Lys Val Gly Pro Asp Phe Ile Asp Pro Ser Tyr His Thr Ile Ala
        35                  40                  45

Thr Gly Asn Val Ser Arg Asn Leu Asp Ser Phe Phe Met Thr Asp Phe
    50                  55                  60

Gln Ile Ile Asn Ser Phe Glu Arg Ala Leu Lys Lys Ser Asn Ser Asn
65                  70                  75                  80

Met Gly Ile Ile Glu Gly Val Arg Gly Leu Tyr Glu Gly Ile Ser Pro
                85                  90                  95

Ile Gly Asp Val Gly Asn Thr Ala Ser Ile Ala Lys Ala Ile Asp Ala
            100                 105                 110

Pro Val Val Leu Leu Met Asp Ala Arg Ser Leu Val Lys Ser Ala Ala
        115                 120                 125

Ala Val Val Leu Gly Phe Lys Ala Leu Asp Pro Asp Val Arg Ile Glu
    130                 135                 140

Gly Val Ile Leu Asn Lys Val Lys Gly Gln Arg His Tyr Lys Lys Ala
```

```
145                 150                 155                 160
Lys Glu Ser Val Glu Lys Leu Ala Asp Val Pro Val Ile Gly Gly Ile
                165                 170                 175

Pro Arg Asp Asp Lys Ile Thr Val Glu Glu Arg His Leu Gly Leu Val
                180                 185                 190

Pro Ala Leu Glu Lys Glu Arg Ile Thr Arg Asn Ile Asn Leu Trp Gly
                195                 200                 205

Glu Ile Ala Glu Glu Tyr Ile Asp Leu Asp Ala Leu Lys Asp Ile Met
                210                 215                 220

Lys Thr Ser Ser Lys Ser Thr Ala Arg Asp Asn Lys Asn Ile Ala Met
225                 230                 235                 240

Glu Lys His Glu Asp Phe Asn Arg Glu His Thr Glu Ala Ile Asp
                245                 250                 255

Leu Glu Val Thr Asn Asp Ser Lys Pro Gly Gln Leu Trp Lys Thr Gly
                260                 265                 270

Asn Arg Asn Lys Val Lys Ile Gly Val Ala Gln Asp Glu Ile Phe Thr
                275                 280                 285

Phe Tyr Tyr Lys Glu Thr Leu Glu Ser Leu Glu Glu Asn Ser Ala Glu
                290                 295                 300

Ile Val Pro Phe Ser Pro Leu Lys Asp Glu His Leu Pro Asp Val Asp
305                 310                 315                 320

Ala Leu Tyr Ile Gly Gly Gly Tyr Pro Glu Val Phe Lys Lys Glu Leu
                325                 330                 335

Ser Asp Asn Lys Thr Met Leu Asn Asp Ile Asn Lys Phe His Lys Glu
                340                 345                 350

Asn Arg Pro Ile Tyr Gly Glu Cys Gly Gly Leu Ile Tyr Leu Ser Lys
                355                 360                 365

Ser Ile Asp Gly Leu Asp Met Val Gly Ala Val Pro Tyr Ser Ser Glu
                370                 375                 380

Met Thr Asn Lys Val Gln Gly Leu Asn Tyr Val Val Ala Arg Ala Asn
385                 390                 395                 400

Gln Asp Asn Leu Ile Ser Asn Glu Gly Asp Val Phe Arg Ala His Glu
                405                 410                 415

Phe His Tyr Thr Lys Leu Asn Ile Asp Lys Thr Asp Ser Leu Val Phe
                420                 425                 430

Asp Val Leu Arg Gly Arg Gly Val Leu Asn Asn Met Asp Gly Val Cys
                435                 440                 445

Val Asn Asn Thr Leu Ala Asn Tyr Ile His Ile His Ala Cys Ser His
450                 455                 460

Pro Asn Phe Gly Tyr Asn Phe Thr Ile Asn Ile Ser Glu Leu Asp Ile
465                 470                 475                 480

<210> SEQ ID NO 34
<211> LENGTH: 443
<212> TYPE: PRT
<213> ORGANISM: Methanocaldococcus jannaschii DSM 2661

<400> SEQUENCE: 34

Met Ile Met Lys Arg Val Val Ile Ala Gly Thr Ser Ser Glu Val Gly
1               5                   10                  15

Lys Thr Val Ile Ser Thr Gly Ile Met Lys Ala Leu Ser Lys Lys Tyr
                20                  25                  30

Asn Val Gln Gly Tyr Lys Val Gly Pro Asp Tyr Ile Asp Pro Thr Tyr
                35                  40                  45
```

His Thr Ile Ala Thr Gly Asn Lys Ser Arg Asn Leu Asp Ser Phe Phe
 50                  55                  60

Met Asn Lys Glu Gln Ile Lys Tyr Leu Phe Gln Lys His Ser Lys Asp
 65                  70                  75                  80

Lys Asp Ile Ser Val Ile Glu Gly Val Arg Gly Leu Tyr Glu Gly Ile
                 85                  90                  95

Ser Ala Ile Asp Asp Ile Gly Ser Thr Ala Ser Val Ala Lys Ala Leu
                100                 105                 110

Asp Ser Pro Ile Ile Leu Leu Val Asn Ala Lys Ser Leu Thr Arg Ser
            115                 120                 125

Ala Ile Ala Ile Ile Lys Gly Phe Met Ser Phe Asp Asn Val Lys Ile
130                 135                 140

Lys Gly Val Ile Phe Asn Phe Val Arg Ser Glu Asn His Ile Lys Lys
145                 150                 155                 160

Leu Lys Asp Ala Met Ser Tyr Tyr Leu Pro Asp Ile Glu Ile Ile Gly
                165                 170                 175

Phe Ile Pro Arg Asn Glu Asp Phe Lys Val Glu Gly Arg His Leu Gly
            180                 185                 190

Leu Val Pro Thr Pro Glu Asn Leu Lys Glu Ile Glu Ser Lys Ile Val
        195                 200                 205

Leu Trp Gly Glu Leu Val Glu Lys Tyr Leu Asp Leu Asp Lys Ile Val
210                 215                 220

Glu Ile Ala Asp Glu Asp Phe Glu Glu Val Asp Asp Val Phe Leu Trp
225                 230                 235                 240

Glu Val Asn Glu Asn Tyr Lys Lys Ile Ala Val Ala Tyr Asp Lys Ala
                245                 250                 255

Phe Asn Phe Tyr Tyr Trp Asp Asn Phe Glu Ala Leu Lys Glu Asn Lys
            260                 265                 270

Ala Lys Ile Glu Phe Phe Ser Pro Leu Lys Asp Ser Glu Val Pro Asp
        275                 280                 285

Ala Asp Ile Leu Tyr Ile Gly Gly Tyr Pro Glu Leu Phe Lys Glu
290                 295                 300

Glu Leu Ser Arg Asn Lys Glu Met Ile Glu Ser Ile Lys Glu Phe Asp
305                 310                 315                 320

Gly Tyr Ile Tyr Gly Glu Cys Gly Gly Leu Met Tyr Ile Thr Lys Ser
                325                 330                 335

Ile Asp Asn Val Pro Met Val Gly Leu Leu Asn Cys Ser Ala Val Met
            340                 345                 350

Thr Lys His Val Gln Gly Leu Ser Tyr Val Lys Ala Glu Phe Leu Glu
        355                 360                 365

Asp Cys Leu Ile Gly Arg Lys Gly Leu Lys Phe Lys Gly His Glu Phe
370                 375                 380

His Tyr Ser Lys Leu Val Asn Ile Lys Glu Glu Arg Phe Ala Tyr Lys
385                 390                 395                 400

Ile Glu Arg Gly Arg Gly Ile Ile Asn Asn Leu Asp Gly Ile Phe Asn
                405                 410                 415

Gly Lys Val Leu Ala Gly Tyr Leu His Asn His Ala Val Ala Asn Pro
            420                 425                 430

Tyr Phe Ala Ser Ser Met Val Asn Phe Gly Glu
        435                 440

<210> SEQ ID NO 35
<211> LENGTH: 464
<212> TYPE: PRT

<213> ORGANISM: Methanocella arvoryzae MRE50

<400> SEQUENCE: 35

```
Met Ile Lys Ile Pro Arg Val Ile Leu Ala Gly Asp Arg Ser Ser Ala
1               5                   10                  15

Gly Lys Thr Thr Ile Ser Val Gly Ile Met Ala Leu Leu Lys Glu Gln
            20                  25                  30

Gly Lys Thr Val Gln Pro Phe Lys Val Gly Leu Asp Tyr Ile Asp Pro
        35                  40                  45

Ser Tyr His Ser Met Ile Thr Gly Lys Gln Gly Gly Asn Leu Asp Gly
    50                  55                  60

Tyr Leu Met Ser Asp Lys Ala Ile Ala Glu Ala Phe Val His Ser Ser
65                  70                  75                  80

Glu Gly Ser Asp Ile Ser Ile Ile Glu Gly Val Arg Gly Leu Tyr Glu
                85                  90                  95

Gly Leu Glu Ser Leu Ser Asp Val Gly Ser Thr Ala Gln Ile Ala Lys
            100                 105                 110

Val Leu Lys Thr Pro Val Ile Leu Ile Val Asp Ala Gln Ser Ile Thr
        115                 120                 125

Arg Ser Thr Ala Ala Ile Val Lys Gly Tyr Arg Asp Phe Asp Arg Gly
    130                 135                 140

Val Asn Ile Arg Gly Val Ile Leu Asn Lys Ile Gly Ser Glu Arg His
145                 150                 155                 160

Ala Glu Lys Ala Arg Met Ala Ile Glu Lys Tyr Thr Gly Val Glu Val
                165                 170                 175

Leu Gly Ala Ile Pro Arg Ser Asn Ser Met Lys Leu Thr Met Arg His
            180                 185                 190

Leu Gly Leu Ile Pro Ala Arg Glu Gly Ala Ser Arg Val Glu Gly Phe
        195                 200                 205

Asp Ser Lys Leu Glu Lys Ile Lys Glu Thr Ile Arg Asp Asn Leu Asn
    210                 215                 220

Leu Lys Arg Ile Val Glu Ile Ala Ala Gly Ala Pro Pro Leu Arg Glu
225                 230                 235                 240

Pro Lys Pro Asp Ile Phe Val Arg Lys Asn Pro Gly Gly Val Arg Ile
                245                 250                 255

Gly Leu Ala Leu Asp Glu Ala Phe Asn Phe Tyr Tyr Lys Asp Asn Ile
            260                 265                 270

Asp Leu Leu Gln Cys Arg Gly Ala Glu Ile Val His Phe Ser Pro Val
        275                 280                 285

Asn Asp Ala Gly Ile Pro Glu Val Asp Gly Leu Ile Ile Gly Gly Gly
    290                 295                 300

Tyr Pro Glu Val Phe Ala Ala Glu Leu Ala Gln Asn Glu Ala Met Arg
305                 310                 315                 320

Lys Ser Ile Phe Glu Ala Ser Arg Arg Gly Met Pro Ile Tyr Ala Glu
                325                 330                 335

Cys Gly Gly Leu Met Tyr Leu Met Lys Ser Leu Glu Thr Glu Asp Gly
            340                 345                 350

Ser Arg His Asp Met Ala Gly Val Phe Glu Gly Val Ala Ser Met Lys
        355                 360                 365

His Val Arg Thr Ile Gly Tyr Val Ser Gly Arg Phe Ala Met Asp Thr
    370                 375                 380

Pro Ile Gly Gln Glu Gly Ala Leu Phe Lys Gly His Glu Phe His His
385                 390                 395                 400
```

```
Ser Val Ile Thr Asp Leu Ala Ser Asn Ala Arg Phe Ala Cys Arg Leu
                405                 410                 415

Asp Arg Gly Thr Gly Ile His Asn Gly Leu Asp Gly Ile Met Ser Asp
            420                 425                 430

Asn Thr Leu Ala Thr Tyr Thr His Leu His Ala Ala Ser Tyr Val Pro
            435                 440                 445

Phe Ser Gly Lys Phe Val Glu Ser Cys Ala Val Tyr His Glu Lys Gly
        450                 455                 460

<210> SEQ ID NO 36
<211> LENGTH: 490
<212> TYPE: PRT
<213> ORGANISM: Methanococcoides methylutens MM1

<400> SEQUENCE: 36

Met Pro Ala Glu Thr Ala Asp Arg Lys Met Asp Met Pro Arg Ile Leu
1               5                   10                  15

Leu Ala Ala Asp Arg Ser Ser Gly Lys Thr Thr Ile Thr Ala Gly
            20                  25                  30

Leu Leu Ala Ala Leu Thr Ser Arg Gly Tyr Ser Val Gln Pro Phe Lys
        35                  40                  45

Val Ala Leu Asp Tyr Ile Asp Pro Ser Tyr His Ser Glu Ile Thr Gly
    50                  55                  60

Arg Arg Ala Arg Asn Leu Asp Gly Tyr Leu Met Glu Glu Gly Val
65                  70                  75                  80

Leu Asp Val Phe Thr His Ala Cys Asp Val Asp Gly Lys Ala Asp Ile
                85                  90                  95

Ala Val Ile Glu Gly Val Arg Gly Leu Phe Glu Gly Leu Glu Ser Leu
            100                 105                 110

Gly Glu Thr Gly Ser Thr Ala Gln Val Ala Lys Met Leu Asn Cys Pro
        115                 120                 125

Val Ile Leu Ile Ile Asn Ala Arg Ser Ile Thr Arg Ser Ala Ala Ala
    130                 135                 140

Leu Val Asn Gly Tyr Lys Asn Phe Asp Pro Asp Val Asn Ile Val Gly
145                 150                 155                 160

Val Ile Leu Asn Asn Ile Gly Gly Met Arg His Ala Lys Lys Ala Lys
                165                 170                 175

Glu Ala Val Glu His Phe Thr Gly Val Pro Val Leu Gly Ile Ile Pro
            180                 185                 190

Arg Asp Asn Ala Met Gln Ile Ser Met Arg His Leu Gly Leu Val Pro
        195                 200                 205

Ala Ile Glu Glu Arg Arg Ile Asn Asp Leu Asp Glu Arg Ile Thr
    210                 215                 220

Ala Ile Glu Lys Arg Val Ser Glu Gly Ile Asp Ile Asp Lys Val Leu
225                 230                 235                 240

Glu Leu Ala Arg Gln Ala Glu Pro Val Glu Lys Pro Glu Ser Ser Val
                245                 250                 255

Phe Thr Ala Arg Lys Thr Glu Gly Glu Ala Pro Val Ile Gly Val Ala
            260                 265                 270

Leu Asp Glu Ala Phe Asn Phe Tyr Tyr His Asn Asn Leu Glu Leu Leu
        275                 280                 285

Glu Leu Ala Gly Ala Lys Ile Glu Tyr Phe Ser Pro Ile His Asp Lys
    290                 295                 300

Ser Leu Pro Asp Val Asp Ala Leu Tyr Leu Gly Gly Gly Tyr Pro Glu
305                 310                 315                 320
```

-continued

```
Leu Phe Ala Ser Glu Leu Glu Ala Asn Glu Ser Met Lys Gln Asp Ile
                325                 330                 335

Lys Lys Ala Ser Glu Ala Gly Leu Pro Ile Tyr Gly Glu Cys Gly Gly
            340                 345                 350

Leu Met Tyr Leu Thr Glu Arg Ile Thr Thr Gly Val Lys Gly Lys Gly
        355                 360                 365

Thr Tyr His Met Ala Glu Met Pro Glu Ser Thr His Glu Met Val Gly
    370                 375                 380

Ala Leu Pro Gly His Ser Leu Met Gly His Lys Arg Val Val Ser Tyr
385                 390                 395                 400

Asn Ile Gly Ala Leu Asp Val Asp Thr Ile Ile Gly Lys Cys Gly Asn
                405                 410                 415

Ser Phe Ile Gly His Glu Phe His Ser Glu Val Thr Glu Leu Pro
            420                 425                 430

Ser Asp Ala Lys Phe Ala Ile Lys Leu Ser Arg Gly Thr Gly Ile Val
        435                 440                 445

Asp Gly Trp Asp Gly Leu Val Lys Asn Asn Thr Leu Gly Ala Tyr Ala
    450                 455                 460

His Leu Glu Ala Ser Ser Tyr Lys Asp Phe Ala Thr Thr Phe Val Asp
465                 470                 475                 480

Ala Ala Ala Lys Tyr Arg Ser Glu Lys Ala
                485                 490

<210> SEQ ID NO 37
<211> LENGTH: 447
<212> TYPE: PRT
<213> ORGANISM: Methanococcus maripaludis C7

<400> SEQUENCE: 37

Met Lys Arg Ile Val Ile Ala Gly Thr Ser Ser Met Val Gly Lys Thr
1               5                   10                  15

Thr Ile Ser Thr Gly Ile Met Lys Ala Leu Ser Lys Lys Asn Asn Val
            20                  25                  30

Gln Pro Tyr Lys Ile Gly Pro Asp Tyr Ile Asp Pro Thr Tyr His Thr
        35                  40                  45

Glu Ala Thr Glu Asn Lys Ser Arg Asn Leu Asp Ser Phe Phe Met Asp
    50                  55                  60

Lys Leu Gln Ile Arg Ser Leu Phe Lys Lys His Ser Lys Asn Lys Asp
65                  70                  75                  80

Ile Ser Val Ile Glu Gly Val Arg Gly Leu Tyr Glu Gly Ile Ser Pro
                85                  90                  95

Tyr Asn Asp Ile Gly Ser Thr Ala Ser Val Ala Lys Thr Leu Asn Ala
            100                 105                 110

Pro Val Ile Leu Leu Met Asp Ala Arg Ser Leu Thr Arg Ser Ala Ala
        115                 120                 125

Ala Ile Ile Lys Gly Phe Lys Ser Phe Asp Thr Glu Leu Asn Ile Lys
    130                 135                 140

Gly Val Ile Phe Asn Lys Ile Arg Gly Glu Gly His Leu Asn Lys Leu
145                 150                 155                 160

Lys Glu Ala Val Lys Tyr Tyr Asp Asn Glu Ile Glu Ile Ile Gly Ala
                165                 170                 175

Ile Pro Arg Asp Glu Gly Leu Ser Val Ser Gln Arg His Leu Gly Leu
            180                 185                 190

Val Pro Thr Pro Glu Asn Lys Gln Gly Leu Leu Glu Arg Ile Asp Leu
```

```
                195                 200                 205
Trp Gly Asn Thr Val Glu Glu Cys Leu Asp Ile Glu Lys Ile Val Glu
    210                 215                 220

Leu Ser Asp Lys Ser Phe Asp Phe Cys Val Asp Glu Lys Asn Lys Asp
225                 230                 235                 240

Glu Thr Leu Trp Lys Val Glu Lys Asn Asn Ser Lys Ile Ala Val Ala
                245                 250                 255

Phe Asp Glu Ser Phe Asn Phe Tyr Tyr Trp Asp Asn Phe Asp Ala Met
            260                 265                 270

Glu Glu Asn Gly Ala Lys Leu Lys Phe Phe Ser Pro Leu Asn Asp Ser
        275                 280                 285

Glu Val Pro Asp Cys Asp Thr Ile Tyr Leu Gly Gly Tyr Pro Glu
290                 295                 300

Ile Phe Ser Glu Lys Leu Ser Glu Asn Lys Ser Met Ile Asp Ser Ile
305                 310                 315                 320

Arg Asn Phe Asp Gly Lys Ile Tyr Gly Glu Cys Gly Leu Met Tyr
                325                 330                 335

Leu Thr Asn Ser Ile Asp Gly Lys Glu Met Leu Lys Leu Ile Asp Ala
            340                 345                 350

Asn Ala Val Met Thr Pro Asn Val Gln Gly Leu Ser Tyr Val Lys Gly
        355                 360                 365

Thr Phe Glu Lys Asp Cys Ile Ile Gly Glu Lys Ser Lys Glu Phe Lys
370                 375                 380

Ala His Glu Phe His Tyr Ser Lys Leu Ile Asn Ile Asn Glu Asn Asp
385                 390                 395                 400

Phe Ser Tyr Arg Ile Asn Arg Gly Lys Gly Ile Ile Asn Ser Met Asp
                405                 410                 415

Gly Ile Thr Ser Lys Gly Gly Asp Ile Val Gly Gly Tyr Ala His Gln
            420                 425                 430

His Cys Ile Gly Asn Pro Tyr Phe Ala Ala Ser Leu Ser Lys Ile
        435                 440                 445

<210> SEQ ID NO 38
<211> LENGTH: 467
<212> TYPE: PRT
<213> ORGANISM: Methanocorpusculum labreanum Z

<400> SEQUENCE: 38

Met Lys Ser Phe Leu Ile Ser Gly Asp Arg Ser Gly Ala Gly Lys Thr
1               5                   10                  15

Ser Ile Thr Leu Gly Leu Ala Gly Leu Leu Ala Lys Asp Ala Val Val
                20                  25                  30

Gln Thr Tyr Lys Val Ala Met Asp Tyr Ile Asp Thr Ser Tyr Leu Ser
            35                  40                  45

Gly Val Thr Gly Arg Pro Ser Tyr Asn Leu Asp Thr Phe Val Gln Thr
        50                  55                  60

Asp Glu Glu Leu Ala Gly Leu Phe Ser Tyr Gly Ala Glu Gly Ala Asp
65                  70                  75                  80

Ile Gly Ile Val Glu Gly Val Arg Gly Leu Tyr Glu Gly Arg Asp Ser
                85                  90                  95

Phe Thr Asp Val Gly Ser Thr Ala Ile Ala Lys Arg Phe Ser Leu
            100                 105                 110

Pro Thr Ile Leu Val Ile Asp Ala Arg Ser Ile Thr Arg Ser Ala Ala
        115                 120                 125
```

```
Ala Leu Val Lys Gly Phe Gln Ala Phe Asp Pro Asp Val Arg Ile Lys
        130                 135                 140

Gly Val Ile Leu Asn Asn Thr Gly Gly His His Val Thr Lys Ala
145                 150                 155                 160

Thr Glu Ala Ile Glu His Tyr Cys Gly Ile Pro Val Leu Gly Ala Val
                165                 170                 175

Pro Arg Ser Pro Glu Met Asp Leu Ser Met Arg His Leu Gly Leu Val
            180                 185                 190

Pro Phe Val Glu Gly Met Arg Asp Pro Gly Phe Ala Lys Thr Ile Asp
        195                 200                 205

Gly Ile Ile Arg His Val Gly Ala His Val Asp Leu Asp Ala Ile Lys
210                 215                 220

Ala Leu Ala Glu Asp Val Thr Pro Gln Pro Asn Asn Ile Thr Ala Ser
225                 230                 235                 240

Leu Ala Ser Arg Pro Ala Ala Ser Arg Thr Val Ala Ile Ala Phe Asp
                245                 250                 255

Glu Ala Phe Thr Phe Tyr Tyr Gly Glu Leu Glu Ala Val Leu Lys Ser
            260                 265                 270

Gln Gly Cys Asp Val Val Arg Phe Ser Pro Leu His Asp Thr Leu Pro
        275                 280                 285

Glu Ala Asp Gly Tyr Ile Phe Gly Gly Gly Tyr Pro Glu Met Phe Ala
290                 295                 300

Glu Glu Leu Ser Lys Asn Val Leu Met Arg Glu Ala Val His Ala Lys
305                 310                 315                 320

Ala Lys Asp Gly Val Pro Ile Tyr Ala Glu Cys Gly Gly Leu Met Tyr
                325                 330                 335

Leu Thr Arg Ser Ile Thr Leu Lys Asn Gly Trp Leu Gly Arg Glu Gly
            340                 345                 350

Asp Ala Val Tyr Pro Met Cys Gly Ile Phe Ala Gly Asp Thr Val Met
        355                 360                 365

Pro Ala Gly Lys Thr Leu Arg Tyr Val Glu Gly Thr Ala Val Leu Ala
370                 375                 380

Gly Lys Ser Tyr Pro Phe Lys Gly His Glu Phe His Tyr Ser Gly Val
385                 390                 395                 400

Ser Met Asp Ala Asp Ser Arg Phe Leu Tyr Thr Leu Ser Arg Gly Thr
                405                 410                 415

Gly Ile Ile Asp Gly Lys Asp Gly Val Val Phe Asn Asn Ala Leu Gly
            420                 425                 430

Ser Tyr Thr His Leu Met Pro Val Ser Ala Glu Gly Ile Leu Ala Glu
        435                 440                 445

Ile Phe Gly Glu Glu Arg Gly Lys Gln Tyr Ile Lys Ala Asp Ser Pro
450                 455                 460

Gln Thr Leu
465

<210> SEQ ID NO 39
<211> LENGTH: 456
<212> TYPE: PRT
<213> ORGANISM: Methanoculleus bourgensis MS2

<400> SEQUENCE: 39

Met Lys Gly Leu Leu Ile Ala Gly Asp Arg Ser Gly Ser Gly Lys Thr
1               5                   10                  15

Ser Ile Thr Leu Ala Leu Ser Ala Leu Leu Ala Thr Thr Arg Ala Val
                20                  25                  30
```

-continued

```
Gln Thr Phe Lys Val Gly Met Asp Tyr Ile Asp Pro Ser Tyr Leu Thr
         35                  40                  45
Gly Val Thr Gly Arg Pro Cys Arg Asn Leu Asp Asp Tyr Val Met Ser
         50                  55                  60
Pro Asp Glu Val Arg Ala Ile Phe Ser His Gly Cys Arg Gly Ala Asp
 65              70                  75                  80
Ile Ala Ile Val Glu Gly Val Arg Gly Leu Phe Glu Gly Ala Glu Ala
                 85                  90                  95
Leu Thr Asp Leu Gly Ser Thr Ala Ala Ile Ala Lys Arg Leu Asp Leu
                100                 105                 110
Pro Val Val Leu Val Ile Asp Ala Arg Ser Ile Thr Arg Ser Ala Ala
                115                 120                 125
Ala Ile Val Lys Gly Phe Gln Ala Phe Asp Pro Asp Val Ala Ile Arg
            130                 135                 140
Gly Val Ile Leu Asn Lys Ile Ser Gly Ser Arg His Arg Glu Lys Thr
145                 150                 155                 160
Ile Arg Ala Val Glu His Tyr Cys Gly Val Pro Val Ile Gly Ala Ile
                    165                 170                 175
Pro Arg Met Glu Glu Met Glu Leu Ala Ala Arg His Leu Gly Leu Val
                180                 185                 190
Pro Tyr Arg Glu Gly Ala Glu Gly Gly Phe Leu Glu Arg Ile Asp
            195                 200                 205
Ile Ile Lys Arg Met Ile Gly Glu His Val Asp Leu Asp Ala Leu Leu
        210                 215                 220
Gly Ile Ala Gly Glu Phe Val Leu Pro Ala Glu Ser Pro Leu Tyr
225                 230                 235                 240
Ala Val Pro Glu Ala Pro Asp Val Arg Val Gly Val Ala Met Asp Gln
                245                 250                 255
Ala Phe Asn Phe Tyr Tyr Ala Asp Leu Phe Asp Val Leu Ala Ser Leu
                260                 265                 270
Gly Ala Glu Val Val Pro Phe Ser Pro Leu Arg Asp Arg Leu Pro Glu
            275                 280                 285
Ala Asp Gly Tyr Ile Leu Gly Gly Gly Tyr Pro Glu Leu Tyr Gly Ala
        290                 295                 300
Glu Leu Glu Ala Asn Val Ala Met Arg Glu Gly Leu Arg Glu Val Ser
305                 310                 315                 320
Arg Asn Gly Thr Pro Val Tyr Ala Glu Cys Gly Gly Leu Ile Tyr Leu
                325                 330                 335
Thr Asp Arg Met Val Leu Ala Pro Gly Phe Ala Gly Val Asp Glu Gly
            340                 345                 350
Arg Ala Tyr Asp Leu Ala Gly Val Phe Ala Gly Glu Ala Arg Met Pro
        355                 360                 365
Ala Arg Arg Met Leu Gly Tyr Val Val Gly Thr Ser Ala Ala Met Ser
370                 375                 380
Pro Met Gly Glu Ala Ala Phe Arg Gly His Glu Phe His Tyr Ser Asp
385                 390                 395                 400
Val Arg Leu Leu Pro Gly Thr Arg Tyr Ala Tyr Arg Leu Thr Arg Gly
                405                 410                 415
Ser Gly Ile Arg Asp Gly Leu Asp Gly Ala Leu Arg Asp Arg Thr Ile
            420                 425                 430
Gly Ser Tyr Thr His Leu His Pro Val Thr Ser Arg Gly Met Leu Ala
        435                 440                 445
```

```
His Phe Val Asp Cys Cys Arg Ala
    450                 455
```

<210> SEQ ID NO 40
<211> LENGTH: 459
<212> TYPE: PRT
<213> ORGANISM: Methanofollis liminatans DSM 4140

<400> SEQUENCE: 40

```
Met Lys Ala Leu Leu Val Thr Gly Asp Arg Ser Gly Ser Gly Lys Thr
1               5                   10                  15

Ser Ile Thr Leu Ala Val Ala Ala Leu Leu Ala Gln Glu Ala Pro Val
            20                  25                  30

Gln Thr Tyr Lys Val Ala Met Asp Tyr Ile Asp Pro Ser Tyr Leu Thr
        35                  40                  45

Ala Val Thr Gly Arg Pro Cys Arg Asn Leu Asp Ser Tyr Val Met Asp
    50                  55                  60

Pro Thr Leu Ile Arg Ala Val Phe Glu His Gly Ala Lys Gly Ala Glu
65                  70                  75                  80

Ile Ala Leu Val Glu Gly Val Arg Gly Leu Tyr Glu Gly Ala Glu Ala
                85                  90                  95

Ile Gly Asp Ala Gly Ser Thr Ala Ser Val Ala Lys Ala Leu Asp Leu
            100                 105                 110

Pro Val Val Leu Val Val Asp Ala Arg Ser Ile Thr Arg Ser Ala Ala
        115                 120                 125

Ala Leu Val Lys Gly Phe Ala Ala Phe Asp Pro Lys Val Arg Ile Val
    130                 135                 140

Gly Val Ile Leu Asn Asn Ile Ser Ser Glu Gly His Arg Arg Lys Thr
145                 150                 155                 160

Val Gln Ala Val Glu His Phe Cys Asn Ile Pro Val Ile Gly Ala Ile
                165                 170                 175

Pro Lys Ser Glu Glu Met Arg Leu Ala Met Arg His Leu Gly Leu Val
            180                 185                 190

Pro Tyr Arg Glu Gly Gln Glu Ser Gly Asp Phe Leu Asp Arg Ile Asn
        195                 200                 205

Ala Val Lys Glu Val Ile Gly Ser Tyr Ile Asp Leu Asp Ala Leu Lys
    210                 215                 220

Ala Leu Met Glu Asp Tyr Arg Phe Val Gly Ala Ser Gly Pro Phe Ala
225                 230                 235                 240

Arg Thr His Glu Ala Asp Val Thr Val Ala Val Ala Tyr Asp Glu Ala
                245                 250                 255

Phe Asn Phe Tyr Tyr Asn Asp Leu Phe Asp Val Leu His Ala Gly Gly
            260                 265                 270

Ala Glu Ile Arg Thr Phe Ser Pro Val His Asp Pro Leu Pro Ala Ala
        275                 280                 285

Asp Gly Tyr Ile Val Gly Gly Gly Tyr Pro Glu Met His Ala Pro Ala
    290                 295                 300

Leu Glu Ala Asn Asp Arg Cys Arg Glu Ala Leu Lys Glu Ala Ala Ala
305                 310                 315                 320

Asn Gly Val Pro Ile Tyr Ala Glu Cys Gly Gly Leu Ile Tyr Leu Thr
                325                 330                 335

Glu Arg Leu Val Leu Arg Ala Gly Trp Gln Gly Arg Glu Arg Glu Glu
            340                 345                 350

Thr Cys Thr Met Cys Gly Val Phe Ser Gly Glu Thr Val Met Pro Ala
        355                 360                 365
```

His Arg Thr Leu Gly Tyr Val Glu Gly Arg Ala Gly Ala Ala Cys Pro
    370                 375                 380

Phe Gly Glu Gly Ala Phe Arg Gly His Glu Phe His Tyr Ser Glu Val
385                 390                 395                 400

Arg Leu Ala Pro Glu Thr Thr Phe Ala Tyr Thr Leu Ser Arg Gly Thr
                405                 410                 415

Gly Ile Lys Gly Ala Leu Asp Gly Ala Val Thr Glu Gln Thr Leu Ala
                420                 425                 430

Ser Tyr Thr His Leu His Pro Ala Ala Ser Ala Asp Phe Phe Arg Gly
                435                 440                 445

Phe Leu Gln Ala Cys Arg Gln Gly Pro Arg Ser
    450                 455

<210> SEQ ID NO 41
<211> LENGTH: 491
<212> TYPE: PRT
<213> ORGANISM: Methanohalobium evestigatum Z-7303

<400> SEQUENCE: 41

Met Ser Gln Gln Lys Asn Asp Lys Asn Arg Ile Lys Ile Pro Met Pro
1               5                   10                  15

Arg Val Leu Leu Ala Ala Asp Arg Ser Ser Gly Lys Thr Thr Ile
                20                  25                  30

Thr Ser Gly Leu Leu Ala Ala Leu Thr Phe Gln Gly Tyr Arg Pro Gln
            35                  40                  45

Pro Phe Lys Val Gly Leu Asp Tyr Ile Asp Pro Ser Tyr His Ser Glu
    50                  55                  60

Ile Thr Gly Ile Lys Ala Arg Asn Leu Asp Gly Tyr Leu Met Asp Asp
65                  70                  75                  80

Asp Lys Ile Leu Asp Val Phe Thr His Ala Phe Glu Ser Glu Lys Ala
                85                  90                  95

Asp Leu Ala Val Ile Glu Gly Val Arg Gly Leu Phe Glu Gly Leu Glu
                100                 105                 110

Ser Phe Ser Asp Thr Gly Ser Thr Ala Gln Ile Ala Lys Thr Leu Asp
            115                 120                 125

Cys Pro Val Val Leu Ile Ile Asn Ala Arg Ser Ile Thr Arg Ser Ala
    130                 135                 140

Ala Ala Ile Val Asn Gly Tyr Val Asn Phe Asp Pro Asp Val Asn Ile
145                 150                 155                 160

Ala Gly Val Ile Leu Asn Asn Ile Gly Gly Gly Arg His Ala Lys Lys
                165                 170                 175

Ala Lys Asp Ala Ile Glu Tyr Tyr Thr Gly Val Pro Val Leu Gly Ile
                180                 185                 190

Ile Pro Arg Asp Asp Ser Met Gln Ile Ser Met Arg His Leu Gly Leu
            195                 200                 205

Val Pro Ala Ile Glu Gly Arg Gln Lys Asp Ser Glu Phe Arg Lys Arg
    210                 215                 220

Ile Tyr Ser Ile Glu Ser Ile Ile Lys Glu Asn Val Asp Ile Glu Lys
225                 230                 235                 240

Ile Ile Glu Ile Ser His Asn Ala Ser Pro Val Glu Lys Pro Glu Tyr
                245                 250                 255

Thr Leu Phe Lys Pro Asn Gln Ile Asn Tyr Lys Pro Thr Ile Gly Ile
                260                 265                 270

Ala Leu Asp Glu Ala Phe Asn Phe Tyr Tyr His Asn Asn Ile Glu Leu

```
                275                 280                 285
Leu Glu Leu Glu Gly Ala Arg Ile Lys Tyr Phe Ser Pro Ile His Asp
290                 295                 300

Ala His Leu Pro Lys Val Asp Gly Leu Tyr Ile Gly Gly Tyr Pro
305                 310                 315                 320

Glu Leu Phe Gly Asp Glu Leu Glu Ser Asn Glu Ser Ile Arg Asn Asp
                325                 330                 335

Ile Lys Glu Ala Ser Gly Gln Gly Leu Pro Ile Tyr Ala Glu Cys Gly
                340                 345                 350

Gly Leu Met Tyr Leu Thr Glu Lys Met Thr Thr Gly Val Gln Asn Lys
                355                 360                 365

His Lys Gly Lys Tyr His Met Ala Glu Met Gln Glu Ser Thr Tyr Asn
                370                 375                 380

Met Val Gly Ala Leu Pro Gly His Thr Leu Met Gly His Thr Arg Val
385                 390                 395                 400

Val Ser Tyr Asn Ile Gly Met Phe Lys Cys Asp Ser Val Ile Gly Lys
                405                 410                 415

Ala Gly Asn Ser Phe Arg Gly His Glu Phe His His Ser Glu Ile Thr
                420                 425                 430

Asn Leu Pro Ser Asn Ser Asn Phe Ala Ile Lys Leu Ser Arg Gly Thr
                435                 440                 445

Gly Ile Val Ser Gly Trp Asp Gly Leu Thr Val Asn Asn Thr Met Gly
450                 455                 460

Ser Tyr Ala His Leu Glu Ala Val Ser Tyr Glu Ala Phe Ala Ser Ser
465                 470                 475                 480

Phe Val Asp Cys Ile Phe Arg Ser Asp Asn Phe
                485                 490

<210> SEQ ID NO 42
<211> LENGTH: 481
<212> TYPE: PRT
<213> ORGANISM: Methanohalophilus mahii DSM 5219

<400> SEQUENCE: 42

Met Pro Asp Gln Asn Leu Met Glu Met Pro Arg Leu Leu Ile Ser Ala
1               5                   10                  15

Asp Arg Ser Ser Gly Lys Thr Thr Ile Val Ala Gly Met Leu Ala
                20                  25                  30

Ala Leu Thr Ala Arg Gly Tyr Arg Val Gln Pro Phe Lys Val Gly Leu
                35                  40                  45

Asp Tyr Ile Asp Pro Ser Tyr His Ser Glu Ile Thr Gly Arg Asn Ala
            50                  55                  60

Arg Asn Ile Asp Gly Tyr Leu Met Asp Glu Glu Gly Ile Arg Asp Val
65                  70                  75                  80

Phe Thr His Gly Cys Glu Thr Asp Glu Met Ala Asp Val Ala Ile Ile
                85                  90                  95

Glu Gly Val Arg Gly Leu Tyr Glu Gly Phe Asp Ser Phe Thr Asp Thr
                100                 105                 110

Gly Ser Thr Ala Gln Ile Ala Lys Ile Leu Asn Cys Pro Val Val Leu
                115                 120                 125

Val Ile Asn Ala Arg Ser Ile Thr Arg Ser Ala Ala Ala Leu Val Lys
                130                 135                 140

Gly Tyr Thr Ser Phe Asp Glu Ser Ile Asn Ile Ala Gly Val Ile Leu
145                 150                 155                 160
```

```
Asn Asn Ile Gly Asn Pro Arg His Ala Lys Ala Ser Glu Ala Ile
            165                 170                 175

Glu His Tyr Thr Gly Ile Pro Val Leu Gly Thr Ile Arg Arg Asp Asn
        180                 185                 190

Ala Met Gln Ile Ser Met Arg His Leu Gly Leu Ile Pro Ala Leu Glu
        195                 200                 205

Gly Arg Arg Cys Ile Ser Asp Leu Asp Gln Arg Ile Gly Thr Ile Arg
    210                 215                 220

Asp Arg Val Asp Glu Gly Val Asp Ile Ala Glu Ile Leu Asn Ile Ala
225                 230                 235                 240

Arg Ser Ala Glu Pro Val Glu Lys Pro Pro Lys Thr Met Phe Thr Ser
                245                 250                 255

Arg Asp Ile Lys Gly Lys Ser Pro Lys Ile Gly Val Ala Leu Asp Glu
            260                 265                 270

Ala Phe Asn Phe Tyr Tyr Asp Asn Ile Glu Leu Leu Gln Leu Ala
        275                 280                 285

Gly Ala Asp Leu Glu Tyr Phe Ser Pro Val His Asp Ser Lys Leu Pro
    290                 295                 300

Asp Val Asp Gly Leu Tyr Ile Gly Gly Gly Tyr Pro Glu Leu Phe Ala
305                 310                 315                 320

Pro Gln Leu Gln Asp Asn Glu Pro Leu Arg Arg Glu Ile Arg Glu Ala
                325                 330                 335

Ser Arg Ala Gly Met Pro Ile Tyr Ala Glu Cys Gly Gly Leu Met Tyr
            340                 345                 350

Leu Thr Glu Lys Leu Thr Thr Gly Val Lys Gly Lys Gly Thr Tyr His
        355                 360                 365

Met Ala Glu Met Pro Glu Ala Thr Thr Glu Met Val Gly Ala Leu Pro
    370                 375                 380

Gly His Thr Leu Met Gly His Thr Arg Val Val Ser Tyr Asn Asn Gly
385                 390                 395                 400

Gln Ile Val Lys Asp Ala Ile Gly Lys Lys Gly Asn Thr Phe Arg
                405                 410                 415

Gly His Glu Phe His His Ser Glu Ile Arg Asp Ile Pro Asp Asn Thr
            420                 425                 430

Asp Phe Ala Ile Lys Leu Ser Arg Gly Ile Gly Ile Lys Gly Glu Trp
        435                 440                 445

Asp Gly Met Thr Val Gly Asn Thr Leu Gly Ser Tyr Ala His Leu Glu
    450                 455                 460

Gly Ile Ser Tyr Arg Glu Phe Ala Ser Ser Phe Val Asp Ser Ile Leu
465                 470                 475                 480

Glu

<210> SEQ ID NO 43
<211> LENGTH: 502
<212> TYPE: PRT
<213> ORGANISM: Methanolobus psychrophilus R15

<400> SEQUENCE: 43

Met Gln Gln Thr Ser Pro Thr Asp Lys Asn Pro Glu Ala Ser Glu Leu
1               5                   10                  15

Pro Ala Pro Thr Phe Lys Glu Ile Pro Arg Ile Leu Leu Ser Ala Gly
            20                  25                  30

Ser Ser Ser Ser Gly Lys Thr Thr Ile Thr Ile Gly Leu Leu Ala Ala
        35                  40                  45
```

```
Leu Thr Glu Ala Gly Tyr Asn Val Gln Pro Phe Lys Val Gly Leu Asp
 50                  55                  60

Tyr Ile Asp Pro Ser Tyr Ser Glu Ile Thr Gly Arg Arg Ala Arg
 65                  70                  75                  80

Asn Met Asp Gly Phe Leu Met Lys Gly Glu Ser Val Arg Asp Val Phe
                     85                  90                  95

Ile His Gly Cys Glu Val Asp Gly Glu Ala Asp Leu Ala Val Ile Glu
                 100                 105                 110

Gly Val Arg Gly Leu Phe Glu Gly Phe Asp Ser Phe Thr Asp Val Gly
             115                 120                 125

Ser Thr Ala Gln Ile Ala Lys Ile Leu Lys Cys Ser Val Val Leu Ile
 130                 135                 140

Ile Asn Ala Arg Ser Ile Thr Arg Ser Ala Ala Leu Val Asn Gly
 145                 150                 155                 160

Phe Lys Asp Phe Asp Lys Asp Val His Ile Ala Ala Val Ile Leu Asn
                 165                 170                 175

Asn Ile Gly Gly Pro Arg His Ala Lys Lys Ala Lys Glu Ala Ile Glu
                 180                 185                 190

Phe Tyr Thr Gly Ile Pro Val Ile Gly Val Ile His Arg Asn Gly Ser
                 195                 200                 205

Met Lys Ile Ser Met Arg His Leu Gly Leu Val Pro Ala Ile Glu Glu
 210                 215                 220

Arg Arg Arg Ala Asp Asn Phe Asp Glu Arg Ile Thr Phe Ile Arg Asp
 225                 230                 235                 240

Thr Ile Lys Glu Gly Leu Asp Ile Asp Arg Leu Leu Glu Ile Ala His
                 245                 250                 255

Asn Ala Gln Pro Leu Glu Lys Pro Ala Asn Thr Ala Phe Leu Ala Lys
                 260                 265                 270

Glu Thr Asp Gly Glu Arg Pro Val Ile Gly Ile Ala Leu Asp Glu Ala
             275                 280                 285

Phe Asn Phe Tyr Tyr His Asp Asn Leu Glu Leu Leu Gln Leu Ala Gly
 290                 295                 300

Ala Asp Leu Arg Tyr Phe Ser Pro Ile His Asp Gly Lys Leu Pro Asn
 305                 310                 315                 320

Val Asp Gly Leu Tyr Ile Gly Gly Tyr Pro Glu Leu Phe Ala Ala
             325                 330                 335

Glu Leu Glu Asp Asn Val Ser Met Arg Glu Asp Ile Leu Thr Ala Ser
                 340                 345                 350

Arg Ser Gly Leu Pro Ile Tyr Ala Glu Cys Gly Gly Leu Met Tyr Leu
             355                 360                 365

Thr Glu Lys Leu Thr Thr Gly Val Lys Gly Lys Ser Thr Tyr His Met
 370                 375                 380

Ala Glu Met Pro Glu Ser Thr His Glu Met Val Gly Ala Leu Pro Gly
 385                 390                 395                 400

His Thr Leu Met Gly His Lys Arg Val Val Ser Tyr Asn Ile Gly Ser
                 405                 410                 415

Leu Glu Met Asn Thr Val Ile Gly Lys Met Gly Asn Ser Phe Arg Gly
                 420                 425                 430

His Glu Phe His His Ser Glu Val Thr Asp Ile Pro Lys Asp Ala Lys
             435                 440                 445

Phe Ser Ile Lys Leu Ser Arg Gly Thr Gly Ile Ile Asp Gly Trp Asp
 450                 455                 460

Gly Leu Thr Val Asn Asn Thr Leu Gly Cys Tyr Ala His Leu Val Ala
```

```
                465                 470                 475                 480
Ser Ser Tyr Arg Glu Phe Ala Gly Ser Phe Val Glu Phe Met Glu Asn
                    485                 490                 495

Asn Pro Ile Asn Ser Leu
                500

<210> SEQ ID NO 44
<211> LENGTH: 447
<212> TYPE: PRT
<213> ORGANISM: Methanomassiliicoccus luminyensis B10

<400> SEQUENCE: 44

Met Ser Ile Pro Arg Val Val Leu Ala Gly Ala Gly Ser Gly Val Gly
1               5                   10                  15

Lys Thr Val Ile Ala Ala Gly Leu Met Ala Arg Leu Ser Lys Glu Arg
                20                  25                  30

Arg Val Gln Gly Phe Lys Val Gly Pro Asp Phe Ile Asp Pro Met Phe
            35                  40                  45

His Thr Ala Ala Thr Gly Arg Pro Ser Arg Asn Leu Asp Ser Phe Leu
        50                  55                  60

Leu Glu Lys Gly Thr Leu Gln Asn Val Phe Gly Trp Ala Ser Lys Asp
65                  70                  75                  80

Ala Asp Ile Ser Ile Val Glu Gly Val Arg Gly Leu Tyr Asp Gly Leu
                85                  90                  95

Thr Ser Thr Ala Asp Val Gly Ser Thr Ala Glu Ile Ala Lys Tyr Ile
            100                 105                 110

Asp Ala Pro Val Ile Leu Ile Val Asn Ala Arg Ser Leu Ala Lys Ser
        115                 120                 125

Ala Ala Ala His Val Leu Gly Phe Lys Met Leu Asp Pro Thr Val Asn
130                 135                 140

Ile Lys Gly Val Ile Leu Asn His Ile Ser Asn Asp Arg His Glu Gln
145                 150                 155                 160

Lys Ala Val Glu Ala Val Glu Ser Leu Thr Gly Thr Glu Val Ile Gly
                165                 170                 175

Val Ile Arg Gly Gln Lys Glu Lys Leu Pro Glu Arg His Leu Gly Leu
            180                 185                 190

His Thr Leu Glu Pro His Glu Ala Gly Pro Val Leu Arg Lys Ile Glu
        195                 200                 205

Asp Met Val Ala Gly Ile Asp Leu Asp Arg Leu Leu Ala Ile Ala Glu
210                 215                 220

Ser Ala Pro Glu Arg His Phe Asp Asp Ser Ser Pro Phe Pro Arg Arg
225                 230                 235                 240

Ser Pro Gln Gly Val Arg Ile Ala Val Pro Lys Asp Lys Ala Tyr Cys
                245                 250                 255

Phe Tyr Tyr Pro Glu Asn Leu Glu Ala Leu Lys Ala Ala Gly Ala Glu
            260                 265                 270

Ile Val His Phe Arg Pro Ala Asp Gly Glu Lys Leu Pro Asp Ala Asp
        275                 280                 285

Ala Ile Tyr Leu Gly Gly Gly Tyr Pro Glu Leu Tyr Leu Tyr Glu Leu
    290                 295                 300

Ser Thr Asn His Asp Phe Leu Glu Gly Val Lys Gln Met Ser Leu Glu
305                 310                 315                 320

Gly Arg Val Val Tyr Gly Glu Cys Gly Gly Leu Met Thr Leu Cys Arg
                325                 330                 335
```

```
Ala Ile Asp Asp Gly Ser Glu Ala Val Glu Met Val Gly Val Phe Asp
            340                 345                 350

Pro Val Ala Met Met Ala Ala Gly Arg Gln Gly Pro Thr Tyr Val Arg
            355                 360                 365

Ala Lys Gly Thr Pro Gln Asn Leu Ile Met Pro Gly Arg Glu Ile Arg
            370                 375                 380

Ala His Glu Phe His Tyr Ser Gln Leu Ser Pro Ala Pro Pro Gly Pro
385                 390                 395                 400

Tyr Ala Tyr Asp Val Ser Arg Gly Ile Gly Phe Gly Asn Gly Val Asp
                405                 410                 415

Gly Ala Met Val Arg Arg Thr Val Gly Thr Tyr Met His Gln His Ala
            420                 425                 430

Leu Ser Ser Pro Gly Trp Gly Glu Gly Phe Val Asn Leu Ile Glu
            435                 440                 445

<210> SEQ ID NO 45
<211> LENGTH: 458
<212> TYPE: PRT
<213> ORGANISM: Methanolacinia petrolearia DSM 11571

<400> SEQUENCE: 45

Met Lys Ser Phe Leu Ile Thr Gly Asp Arg Ser Gly Ser Gly Lys Thr
1               5                   10                  15

Ser Ile Thr Leu Ala Leu Ser Ser Ile Leu Ser Asp Asp Phe Thr Val
            20                  25                  30

Gln Thr Phe Lys Val Ala Met Asp Tyr Ile Asp Pro Ser Tyr Leu Thr
            35                  40                  45

Ala Val Thr Gly Arg Pro Cys Arg Asn Leu Asp Ser Phe Val Met Thr
        50                  55                  60

Pro Glu Gln Ile Arg Asp Ser Tyr Thr Asn Gly Cys Ile Gly Ala Glu
65                  70                  75                  80

Val Ala Val Ile Glu Gly Val Arg Gly Leu Phe Glu Gly Ser Glu Ala
                85                  90                  95

Leu Asn Asp Thr Gly Ser Thr Ala Ser Val Ala Lys Met Leu Gly Gln
            100                 105                 110

Asn Val Ile Leu Val Ile Asp Ala Arg Ser Ile Thr Arg Ser Ala Ala
            115                 120                 125

Ala Ile Val Met Gly Phe Leu Ala Tyr Asp Pro Asp Val Arg Ile Lys
        130                 135                 140

Gly Val Ile Leu Asn Gln Ile Ile Ser Glu Lys His Leu Asn Lys Ala
145                 150                 155                 160

Lys Ala Ala Ile Glu Ala Ala Thr Gly Ile Pro Val Ile Gly Ala Ile
                165                 170                 175

Pro Arg Arg Asp Glu Met Lys Leu Thr Met Arg His Leu Gly Leu Ile
            180                 185                 190

Pro Phe Leu Glu Gly Lys Lys Asp Asp Glu Phe Leu Lys Arg Val Asp
            195                 200                 205

Ala Val Lys Glu Ile Val Ser Arg Asn Val Asp Ile Asp Ala Leu Leu
        210                 215                 220

Asp Leu Ala Gly Glu Ser Pro Ala Pro Val Asp Val Pro Lys Ser Phe
225                 230                 235                 240

Val Gln Ala Lys Glu Lys Asp Val Lys Ile Gly Val Ala Val Asp Glu
                245                 250                 255

Ala Phe Asn Phe Tyr Tyr Asn Asp Val Phe Asp Ile Leu Gly Ala Lys
            260                 265                 270
```

```
Gly Ala Glu Ile Val Thr Phe Ser Pro Ile His Asp Ser Leu Pro Glu
        275                 280                 285

Ala Asp Gly Tyr Ile Leu Gly Gly Tyr Pro Glu Met Phe Ala Gly
        290                 295                 300

Glu Leu Glu Ala Asn Asp Arg Met Arg Glu Ala Val Leu Glu Val Ser
305                 310                 315                 320

Arg Asn Gly Thr Pro Ile Tyr Ala Glu Cys Gly Gly Leu Ile Tyr Leu
                325                 330                 335

Thr Gly Glu Leu Val Leu Lys Ser Gly Trp Asn Asp Leu Glu Ala Asp
        340                 345                 350

Lys Ser Tyr Gly Met Cys Gly Val Phe Asp Gly Lys Thr Val Met Pro
        355                 360                 365

Ser Lys Arg Val Ile Gly Tyr Val Lys Gly Val Ser Asp Ser Arg Ser
        370                 375                 380

Pro Leu Gly Glu Ala Val Phe Ser Gly His Glu Phe His His Thr Asp
385                 390                 395                 400

Val Arg Leu Pro Lys Asp Thr His Tyr Ser Tyr Arg Leu Ser Arg Gly
                405                 410                 415

Ser Gly Ile Ile Gly Gly Phe Asp Gly Ala Val Ala Asn Arg Thr Gln
        420                 425                 430

Gly Ser Tyr Thr His Leu His Pro Leu Ala Ser Ala Gly Met Ile Gly
        435                 440                 445

Asn Phe Val Glu Asn Cys Arg Lys Lys Glu
450                 455

<210> SEQ ID NO 46
<211> LENGTH: 490
<212> TYPE: PRT
<213> ORGANISM: Methanomethylovorans hollandica DSM 15978

<400> SEQUENCE: 46

Met Asn Thr Ser Thr His Ile Lys Pro Ala Ala Ser Gly Glu Gly Lys
1               5                   10                  15

His Ile Pro Arg Val Leu Ile Ser Ala Gly Ser Ser Ser Gly Lys
            20                  25                  30

Thr Thr Val Thr Ile Gly Leu Leu Ala Ala Leu Ser Lys Ala Gly Tyr
            35                  40                  45

Lys Val Gln Pro Phe Lys Val Gly Leu Asp Tyr Ile Asp Pro Ser Tyr
        50                  55                  60

Tyr Ser Asp Ile Thr Gly Arg Arg Ala Arg Asn Ile Asp Gly Tyr Leu
65                  70                  75                  80

Met Asp Glu Glu Arg Val Leu Asp Val Phe Leu His Gly Tyr Glu Val
                85                  90                  95

Asp Gly Glu Ala Asp Ile Ala Ile Ile Glu Gly Val Arg Gly Leu Tyr
            100                 105                 110

Glu Gly Leu Glu Ser Tyr Ser Asp Ile Gly Ser Thr Ala Gln Ile Ala
        115                 120                 125

Lys Ile Leu Asn Cys Ala Val Ile Leu Val Leu Asn Ala Arg Ser Ile
130                 135                 140

Thr Arg Ser Ala Ala Ala Ile Val Ser Gly Phe Lys Ala Phe Asp Pro
145                 150                 155                 160

Gln Val Asn Ile Ala Gly Val Ile Leu Asn Asn Ile Gly Gly Gln Arg
                165                 170                 175

His Ala Met Lys Ala Lys Glu Ala Ile Glu His Tyr Thr Gly Val Pro
```

```
            180                 185                 190
Val Ile Gly Ile Ile His Arg Asn Asn Glu Met Met Ile Ser Met Arg
            195                 200                 205

His Leu Gly Leu Val Pro Ala Ile Glu Glu Arg Arg Arg Ser Ala Asp
            210                 215                 220

Phe Asp Thr Arg Ile Asn Thr Ile Arg Asp Val Ile Ile Glu Gly Val
225                 230                 235                 240

Asp Ile Asp Lys Val Leu Asp Ile Ala Arg Gln Thr Ala Pro Leu Ser
            245                 250                 255

Arg Pro Ser Asp Thr Ile Phe Val Arg Arg Glu Ile Ser Gln Lys Pro
            260                 265                 270

Val Ile Gly Ile Ala Leu Asp Glu Ala Phe Asn Phe Tyr Tyr His Asp
            275                 280                 285

Asn Leu Glu Leu Leu Gln Leu Ala Gly Ala Lys Leu Gln Tyr Phe Ser
            290                 295                 300

Pro Val His Asp Lys His Leu Pro Asp Val Asp Gly Ile Tyr Ile Gly
305                 310                 315                 320

Gly Gly Tyr Pro Glu Leu Phe Ala Ala Glu Leu Glu Ala Asn Ile Ser
            325                 330                 335

Met Arg Glu Asp Met Lys Ala Ala Ser Glu Ala Gly Met Pro Ile Tyr
            340                 345                 350

Gly Glu Cys Gly Gly Leu Met Tyr Leu Thr Glu Lys Leu Thr Thr Gly
            355                 360                 365

Val Lys Asp Lys Gly Thr Tyr His Met Ala Glu Met Pro Glu Ser Thr
370                 375                 380

Tyr Asp Met Val Gly Ala Leu Pro Gly His Thr Leu Met Gly His Lys
385                 390                 395                 400

Arg Val Val Ser Tyr Asn Ile Gly Ser Leu Thr Leu Asp Thr Val Ile
            405                 410                 415

Gly Lys Ile Gly Asn Asp Phe Arg Ala His Glu Phe His His Ser Glu
            420                 425                 430

Val Thr Glu Leu Pro Glu Asp Ala Lys Phe Ala Ile Lys Leu Ser Arg
            435                 440                 445

Gly Thr Gly Ile Ile Glu Gly Trp Asp Gly Leu Thr Val Lys Asn Thr
            450                 455                 460

Leu Gly Cys Tyr Ala His Leu Val Ala Ser Ser Tyr Glu Glu Phe Ala
465                 470                 475                 480

Arg Ser Phe Val Glu Phe Ile Tyr Asn Thr
            485                 490

<210> SEQ ID NO 47
<211> LENGTH: 458
<212> TYPE: PRT
<213> ORGANISM: Methanomicrobium mobile BP

<400> SEQUENCE: 47

Met Lys Ser Phe Leu Ile Thr Gly Asp Arg Ser Ser Gly Lys Thr
1               5                   10                  15

Ser Ile Thr Leu Gly Ile Ser Ala Val Leu Ala Arg Glu Tyr Lys Val
            20                  25                  30

Gln Pro Phe Lys Val Ala Met Asp Tyr Ile Asp Pro Ser Tyr Leu Thr
            35                  40                  45

Gly Val Thr Gly Arg Met Cys Arg Asn Leu Asp Ser Tyr Val Met Ser
            50                  55                  60
```

Glu Glu Gln Leu Arg Ala Ser Tyr Asp Asn Arg Ala Asp Ala Asp
65                  70                  75                  80

Ile Ala Val Ile Glu Gly Val Arg Gly Leu Tyr Glu Gly Ser Glu Ala
            85                  90                  95

Leu Ser Asp Lys Gly Ser Thr Ala Glu Val Ala Lys Met Leu Asp Gln
            100                 105                 110

Asn Val Ile Met Val Leu Asn Ala Arg Ser Ile Thr Arg Ser Ala Ala
            115                 120                 125

Ala Ile Val Lys Gly Phe Cys Asp Phe Asp Pro Ala Ile Lys Ile Lys
    130                 135                 140

Gly Val Ile Leu Asn Gln Ile Ile Ser Asp Lys His Lys Glu Lys Ala
145                 150                 155                 160

Ser Ile Ala Ile Glu His Ser Thr Gly Ile Pro Val Ile Gly Ala Ile
                165                 170                 175

Pro Arg Asn Glu Glu Met Gly Leu Thr Met Arg His Leu Gly Leu Ile
            180                 185                 190

Pro Tyr Leu Glu Gly Lys Gly Asp Ala Glu Phe Leu Lys Arg Val Asn
        195                 200                 205

Lys Val Ala Asp Ile Val Glu Lys Asn Thr Asp Met Asp Ala Leu Leu
210                 215                 220

Ser Ile Ala Gly Glu Ile Pro Ala Pro Ser Glu Lys Pro Glu Ile Phe
225                 230                 235                 240

Arg Ala Lys Ser Asp Gly Cys Asp Leu Lys Val Gly Val Ala Val Asp
                245                 250                 255

Glu Ala Phe Asn Phe Tyr Tyr Asn Asp Ile Phe Asp Ile Leu Pro Ser
            260                 265                 270

Leu Gly Ala Glu Val Ile Lys Phe Ser Pro Ile His Asp Arg Leu Pro
    275                 280                 285

Asp Ala Asp Gly Tyr Ile Phe Gly Gly Gly Tyr Pro Glu Ile Phe Ala
    290                 295                 300

Lys Glu Leu Glu Ala Asn Asp Arg Met Arg Glu Ala Val Arg Glu Ile
305                 310                 315                 320

Ser Arg Asn Gly Thr Pro Ile Tyr Ala Glu Cys Gly Gly Leu Ile Tyr
            325                 330                 335

Leu Thr Glu Asn Ile Ile Leu Lys Glu Gly Trp Glu Gly Arg Thr Ala
            340                 345                 350

Asp Glu Ser Tyr Glu Leu Ala Gly Val Phe Lys Gly Lys Thr Arg Met
            355                 360                 365

Pro Thr Lys Arg Val Ile Gly Tyr Val Asp Gly Val Ser Asp Ser Arg
        370                 375                 380

Ser Pro Met Gly Ala Gly Ser Phe Ser Gly His Glu Phe His His Ser
385                 390                 395                 400

Asp Val Ile Leu Ser Asp Asp Thr His Tyr Ser Tyr Arg Leu Ser Arg
                405                 410                 415

Gly Asn Gly Ile Arg Asp Gly Leu Asp Gly Ala Val Ser His Asn Thr
            420                 425                 430

Leu Ala Ser Tyr Thr His Leu His Pro Val Ala Ser Tyr Gly Met Phe
                435                 440                 445

Arg Asn Phe Thr Glu Lys Met Arg Ser Gln
        450                 455

<210> SEQ ID NO 48
<211> LENGTH: 458
<212> TYPE: PRT

<213> ORGANISM: Methanoplanus limicola DSM 2279

<400> SEQUENCE: 48

```
Met Arg Ser Ile Leu Ile Thr Gly Asp Arg Ser Gly Ser Gly Lys Thr
1               5                   10                  15

Ser Ile Thr Leu Ala Ile Ser Ala Ile Leu Ala Arg Glu Tyr Lys Val
            20                  25                  30

Gln Pro Phe Lys Val Ala Met Asp Tyr Ile Asp Pro Ser Tyr Leu Thr
        35                  40                  45

Gly Val Thr Gly Arg Met Cys Arg Asn Leu Asp Ser Phe Val Met Asn
50                  55                  60

Pro Asp Glu Ile Ser Asp Ser Phe Thr His Ala Cys Lys Gly Ala Asp
65                  70                  75                  80

Ile Ala Val Ile Glu Gly Val Arg Gly Leu Tyr Glu Gly Ser Glu Ser
                85                  90                  95

Leu Ala Asp Thr Gly Ser Thr Ala Ser Ile Ala Lys Met Leu Asn Val
            100                 105                 110

Asn Val Ile Leu Val Ile Asp Ala Arg Ser Ile Thr Arg Ser Ala Ala
        115                 120                 125

Ala Ile Val Met Gly Phe Met Ala Phe Asp Pro Lys Val Arg Ile Lys
130                 135                 140

Gly Val Ile Leu Asn Gln Val Ile Ser Glu Lys His Thr Arg Lys Ala
145                 150                 155                 160

Lys Glu Ala Ile Glu Ser Ala Thr Gly Ile Pro Val Ile Gly Ala Ile
                165                 170                 175

Pro Arg Lys Glu Glu Met Lys Leu Thr Met Arg His Leu Gly Leu Ile
            180                 185                 190

Pro Tyr Met Glu Gly Arg Thr Lys Asp Glu Phe Thr Glu Lys Leu Lys
        195                 200                 205

Ala Val Thr Asp Ile Val Glu Glu His Val Asp Met Asp Ala Leu Leu
210                 215                 220

Ser Leu Thr Asn Asp Val Asp Ile Glu Lys Pro Glu Lys Thr Ile Phe
225                 230                 235                 240

Glu Met Gly Lys Ser Pro Asp Ile Lys Ile Gly Ile Ala Leu Asp Glu
                245                 250                 255

Ala Phe Asn Phe Tyr Tyr Asn Asp Leu Phe Asp Ile Leu Lys Gly Leu
            260                 265                 270

Asn Ala Glu Pro Val Phe Phe Ser Pro Val His Asp Arg Leu Pro Asp
        275                 280                 285

Ala Glu Gly Tyr Ile Phe Gly Gly Tyr Pro Glu Leu Phe Ala Gly
290                 295                 300

Glu Leu Glu Gly Asn Tyr Ala Met Arg Glu Ala Val Arg Glu Val Ser
305                 310                 315                 320

Ala Asn Gly Thr Pro Ile Tyr Ala Glu Cys Gly Gly Leu Ile Tyr Leu
                325                 330                 335

Thr Glu Lys Val Val Leu Lys Ala Gly Trp Ser Asp Leu Lys Glu Asp
            340                 345                 350

Glu Ser Tyr Ser Met Ala Gly Val Phe Lys Gly Arg Thr Glu Met Pro
        355                 360                 365

Val Gly Arg Val Val Ser Tyr Val Glu Gly Val Ser Ser Gly Gly Pro
370                 375                 380

Leu Gly Asp Gly Pro Phe Lys Gly His Glu Phe His His Thr Asp Val
385                 390                 395                 400
```

```
Thr Leu Asp Ser Asp Thr Lys Tyr Ser Tyr Leu Leu Ser Arg Gly Lys
                405                 410                 415

Gly Ile Lys Gly Asn Arg Asp Gly Ala Leu Ala Asp Asn Thr Leu Ala
            420                 425                 430

Ser Tyr Thr His Leu His Pro Ala Ala Ser Tyr Asp Lys Ile Ser Ser
        435                 440                 445

Phe Val Lys Ala Cys Arg Asn Phe Arg Asp
    450                 455

<210> SEQ ID NO 49
<211> LENGTH: 463
<212> TYPE: PRT
<213> ORGANISM: Methanopyrus kandleri AV19

<400> SEQUENCE: 49

Met Ile His Gly Asn Arg Gly Ala Leu Leu Pro Ile Pro Arg Ile Val
1               5                   10                  15

Leu Ala Gly Ser Ser Ala Cys Gly Lys Thr Met Ile Thr Ala Gly
            20                  25                  30

Ile Ile Gln Ala Leu Arg Ala Asp Gly Tyr Glu Val Gln Pro Phe Lys
            35                  40                  45

Val Gly Pro Asp Tyr Ile Asp Pro Ser Tyr His Trp Leu Ala Ser Gly
    50                  55                  60

Arg Pro Cys Gly Asn Leu Asp Thr Phe Leu Phe Arg Glu Lys His Val
65                  70                  75                  80

Arg Trp Leu Phe Glu His Arg Cys Glu Gly Ala Asp Leu Ala Val Val
                85                  90                  95

Glu Gly Val Arg Gly Leu Tyr Glu Gly Ile Gly Ala Val Gly Val Arg
            100                 105                 110

Gly Ser Thr Tyr His Val Ser Glu Val Leu Asn Ala Pro Val Val Leu
        115                 120                 125

Ile Val Asp Ala Arg Ser Leu Thr Lys Ser Val Ala Ala Leu Val Lys
    130                 135                 140

Gly Tyr Ala Glu Leu Glu Gly Ala Asn Ile Ala Gly Val Ile Leu Asn
145                 150                 155                 160

Arg Ile Arg Ser Glu Val His Tyr His Lys Val Arg Ala Leu Val
                165                 170                 175

Lys Tyr Thr Asp Val Lys Val Leu Gly Tyr Val Pro Arg Asp Arg Arg
            180                 185                 190

Leu Lys Val Glu Tyr Arg His Leu Gly Leu Val Pro Thr Pro Glu Arg
        195                 200                 205

Leu Glu Glu Met Arg Glu Arg Leu Arg Thr Val Ala Glu Val Ile Ser
    210                 215                 220

Glu His Val Asp Leu Asp Ala Leu Ile Asp Val Ala Glu Ala Ala Gly
225                 230                 235                 240

Pro Leu Gly Pro Gly Glu Arg Pro Trp Glu Val Asn Pro Thr Lys Cys
                245                 250                 255

Arg Ile Ala Val Ala Lys Asp Glu Ala Phe Asn Phe Tyr Tyr Pro Glu
            260                 265                 270

Asn Leu Glu Ala Leu Glu Glu Asn Gly Ala Lys Leu Leu Glu Phe Ser
        275                 280                 285

Pro Val Arg Asp Glu Asp Val Pro Pro Asp Ala Asp Ala Leu Tyr Ile
    290                 295                 300

Gly Gly Gly Tyr Pro Glu Leu Phe Ala Arg Gln Leu Glu Asp Ala Glu
305                 310                 315                 320
```

-continued

```
Ser Thr Arg Asn Ser Ile Arg Glu Leu Ala Glu Ser Gly Ala Pro Ile
                325                 330                 335

Tyr Ala Glu Cys Gly Gly Phe Met Tyr Leu Cys Arg Glu Leu Arg Trp
            340                 345                 350

Asn Glu Asp Arg Tyr Arg Trp Val Gly Val Phe Asp Val Ala Val Glu
        355                 360                 365

Met Thr Asp Arg Val Gln Gly Leu Ser Tyr Thr Val Ala Arg Ala Val
    370                 375                 380

Asp Asp Thr Pro Val Thr Arg Lys Gly Glu Thr Phe Lys Gly His Glu
385                 390                 395                 400

Phe His Tyr Ser Arg Leu Val Arg Pro Glu Gly Leu Glu Ser Ala Tyr
                405                 410                 415

Arg Ile Ile Arg Gly Gln Gly Trp Arg Gly Arg Glu Gly Phe Arg Pro
            420                 425                 430

Lys Asp Leu Pro Asn Val Leu Gly Thr Tyr Val His Val His Ala Ala
        435                 440                 445

Ser His Pro Thr Phe Ala Thr Asn Phe Thr Gly Ser Thr Gly Ser
    450                 455                 460

<210> SEQ ID NO 50
<211> LENGTH: 457
<212> TYPE: PRT
<213> ORGANISM: Methanoregula formicica SMSP

<400> SEQUENCE: 50

Met Lys Ala Val Leu Ile Thr Gly Asp Arg Ser Gly Ser Gly Lys Thr
1               5                   10                  15

Ser Ile Thr Leu Ala Leu Ala Ala Leu Leu Ser Lys Thr Asp Lys Val
                20                  25                  30

Gln Thr Phe Lys Val Gly Met Asp Tyr Ile Asp Pro Ser Tyr Leu Ala
            35                  40                  45

Ala Val Ser His Arg Pro Cys Arg Asn Leu Asp Thr Phe Thr Leu Asn
        50                  55                  60

Gly Ala Gln Val Gln Asp Ile Phe Arg Phe Gly Cys Arg Gly Ala Asp
65                  70                  75                  80

Ile Ala Leu Val Glu Gly Val Arg Gly Leu Tyr Glu Gly Ala Glu Ala
                85                  90                  95

Leu Gly Asp Thr Gly Ser Thr Ala Ala Ile Ala Lys Glu Leu Asp Leu
                100                 105                 110

Pro Val Val Leu Val Val Ser Ala Gln Ser Ile Thr Arg Ser Ala Ala
            115                 120                 125

Ala Ile Val Lys Gly Phe Gln Ser Phe Asp Pro Lys Ile Arg Ile Ala
        130                 135                 140

Gly Val Ile Leu Asn Asn Ile Lys Gly Gly Ser His Lys Ala Lys Ala
145                 150                 155                 160

Val Thr Ala Ile Glu His Tyr Cys Gly Val Pro Val Leu Gly Ala Ile
                165                 170                 175

Pro Arg Met Glu Glu Met Gln Leu Ala Met Arg His Leu Gly Leu Val
            180                 185                 190

Pro Tyr Arg Glu Gly Ala Gly Arg Gly Asp Phe Asp Ala Arg Ile Glu
        195                 200                 205

Thr Ile Thr Lys Met Ile Gly Gln Tyr Val Asp Leu Asp Lys Leu Arg
    210                 215                 220

Ser Leu Met Lys Glu Ile Pro Asp Asn Pro Ala Pro Thr Leu Phe Asp
```

```
              225                 230                 235                 240
        Ala Val Pro Ala Pro Asp Val Lys Ile Gly Val Ala Phe Asp Glu Ala
                        245                 250                 255

Phe Asn Phe Tyr Tyr Ala Asp Leu Phe Asp Ile Leu Lys Thr Cys Gly
                        260                 265                 270

Ala Glu Thr Val Pro Phe Ser Pro Val His Asp Arg Leu Pro Glu Ala
                        275                 280                 285

Asp Gly Tyr Ile Ile Gly Gly Tyr Pro Glu Leu Phe Thr Lys Glu
                        290                 295                 300

Leu Glu Ala Asn Asp Arg Met Arg Glu Ala Val Arg Glu Val Ser Arg
        305                 310                 315                 320

Asn Gly Thr Pro Val Tyr Ala Glu Cys Gly Leu Met Tyr Leu Thr
                        325                 330                 335

Glu Arg Met Val Leu Lys Lys Gly Trp Gln Gly Ser Asn Arg Asp Gln
                        340                 345                 350

Ser Thr Ala Met Cys Gly Val Phe Ser Gly Glu Thr Arg Met Pro Ala
                        355                 360                 365

Arg Arg Val Val Ser Tyr Val Glu Gly Lys Ser Ser Ala Asp Ser Pro
                        370                 375                 380

Met Gly Ser Ala Val Phe Arg Gly His Glu Phe His Tyr Ser Glu Val
        385                 390                 395                 400

Val Leu Asp Lys Ala Thr Arg Tyr Ala Tyr Thr Leu Ser Arg Gly Val
                        405                 410                 415

Gly Ile Arg Asp Asn Cys Asp Gly Ala Val Val Lys Asn Thr Leu Gly
                        420                 425                 430

Ser Tyr Thr His Leu His Pro Val Gly Ser Ala Gly Met Phe Arg His
                        435                 440                 445

Phe Val Glu Lys Cys Arg Gln Lys Met
                        450                 455

<210> SEQ ID NO 51
<211> LENGTH: 466
<212> TYPE: PRT
<213> ORGANISM: Methanosaeta concilii GP6

<400> SEQUENCE: 51

Met Gly Ile Lys Met Arg Ala Asp Cys Pro Arg Ile Leu Leu Ala Gly
        1               5                   10                  15

Asp Arg Ser Ser Ser Gly Lys Thr Thr Ile Val Ala Gly Leu Leu Ser
                        20                  25                  30

Ala Leu Arg Gly Arg Asn Leu Lys Val Gln Pro Phe Lys Val Ala Met
                        35                  40                  45

Asp Tyr Ile Asp Pro Ser Tyr His Thr Trp Ile Thr Gly Arg Ser Cys
                        50                  55                  60

Arg Asn Leu Asp Gly Tyr Leu Met Asn Glu Ala Ala Val Arg Glu Ile
        65                  70                  75                  80

Tyr Ala His Ala Ala Gln Gly Ala Asp Val Ala Ile Glu Gly Val
                        85                  90                  95

Arg Gly Leu Tyr Glu Gly Tyr Glu Gly Asp Leu Gly Ser Thr Ala Gln
                        100                 105                 110

Ile Ala Lys Met Leu Arg Val Pro Val Ile Phe Val Val Asp Ala Arg
                        115                 120                 125

Ser Ile Thr Arg Ser Cys Ala Ala Leu Val Lys Gly Tyr Met Asp Tyr
                        130                 135                 140
```

```
Asp Pro Ala Val Gln Phe Arg Gly Val Ile Leu Asn Lys Val Gly Ser
145                 150                 155                 160

Ala Arg His Ala Asp Lys Ala Thr Arg Glu Ile Glu Arg Tyr Ala Lys
                165                 170                 175

Val Glu Val Gly Thr Ile Arg Arg Asn Glu Asp Met His Leu Ala
            180                 185                 190

Met Arg His Leu Gly Leu Val Pro Val Met Glu Gly Lys Thr Arg His
        195                 200                 205

Glu Gly Phe Lys Glu Arg Val Asp Arg Ile Arg Gln Ile Val Glu Glu
    210                 215                 220

Gly Leu Asp Leu Asp Arg Ile Arg Glu Ile Ala Arg Glu Ala Glu Pro
225                 230                 235                 240

Leu Pro Glu Val Glu Pro Asp Leu Tyr Leu Lys Asn Asp Ser Gly Lys
                245                 250                 255

Asp Leu Ser Ile Gly Val Ala Gln Asp Glu Ala Phe Asn Phe Tyr Tyr
            260                 265                 270

Arg Asp Asn Leu Glu Leu Met Glu Leu Ala Gly Ala Arg Ile Val Pro
        275                 280                 285

Phe Ser Pro Val His Asp Ala Ser Leu Pro Glu Val Asp Gly Ile Tyr
    290                 295                 300

Ile Gly Gly Gly Tyr Pro Glu Ile Tyr Ala Arg Glu Leu Ser Glu Asn
305                 310                 315                 320

Gln Ser Phe Lys Ser Ser Ile Gln Lys Ala His Glu Lys Asp Ile Pro
                325                 330                 335

Ile Phe Gly Glu Cys Gly Gly Leu Met Tyr Leu Gly Arg Glu Ile Glu
            340                 345                 350

Trp Asp Gly Glu Arg Arg Glu Met Ala Gly Leu Ile Pro Gly Lys Ala
        355                 360                 365

Arg Arg Gly Ala Arg Arg Thr Val Ser Tyr Val His Gly His Leu Ala
370                 375                 380

Gln Ala Ser Pro Leu Gly Arg Ala Gly Glu Tyr Ile Met Gly His Glu
385                 390                 395                 400

Phe His His Ser Glu Met Leu Ile Asp Pro Lys Ala Arg Val Glu Tyr
                405                 410                 415

Ala Ile Arg Leu Glu Arg Gly Thr Gly Ile Ala Asp Gly Leu Asp Gly
            420                 425                 430

Ile His Ile Gly Asn Leu Val Ala Ser Tyr Ser His Ile His Ser Ala
        435                 440                 445

Ser Phe Arg Gly Phe Pro Ala Ser Phe Leu Ser Ala Cys Arg Asp Lys
    450                 455                 460

Arg Gln
465

<210> SEQ ID NO 52
<211> LENGTH: 500
<212> TYPE: PRT
<213> ORGANISM: Methanosalsum zhilinae DSM 4017

<400> SEQUENCE: 52

Met Asn Lys Leu Thr Leu Asn Glu Lys Tyr Phe Asp Asp Ser Lys Asp
1               5                   10                  15

Gln Ser Asp Asp Met Val Ser Val Pro Arg Ile Leu Leu Ser Ala Asp
                20                  25                  30

Arg Ser Ser Ser Gly Lys Thr Thr Ile Met Met Gly Ile Leu Ser Ala
            35                  40                  45
```

```
Leu Val Ser Arg Gly Tyr Ser Val Gln Pro Phe Lys Val Gly Leu Asp
     50                  55                  60

Tyr Ile Asp Pro Ser Tyr His Ser Asp Ile Thr Gly Arg Lys Ala Arg
 65                  70                  75                  80

Asn Ile Asp Gly Tyr Leu Met Asp Glu Thr Asp Ile Ile Asp Thr Phe
                 85                  90                  95

Val His Ala Cys Lys Ala Glu Gly Ala Asp Leu Ala Val Ile Glu
                100                 105                 110

Gly Val Arg Gly Leu Tyr Glu Gly Phe Asp Ser Leu Arg Asp Thr Gly
            115                 120                 125

Ser Thr Ala Gln Val Ala Lys Ile Leu Lys Cys Pro Val Ile Phe Val
        130                 135                 140

Ile Asn Ala Arg Ser Ile Thr Arg Ser Ala Ala Leu Val Asn Gly
145                 150                 155                 160

Tyr Arg Ser Phe Asp Pro Glu Ile Asn Ile Ala Gly Ile Ile Leu Asn
                165                 170                 175

Asn Val Gly Gly Glu Arg His Ala Lys Lys Ala Lys Glu Ala Ile Glu
            180                 185                 190

His Tyr Thr Gly Leu Pro Val Val Gly Ile Val Pro Arg Asp Pro Lys
        195                 200                 205

Met Gln Ile Ser Met Arg His Leu Gly Leu Ile Pro Ala Ile Glu Ser
    210                 215                 220

Gln Gln Lys Ile Thr Glu Tyr Asn Thr Arg Met Glu Tyr Ile Gln Asn
225                 230                 235                 240

Ala Ile Asn Lys Arg Ile Asp Val Asn Lys Leu Ile Glu Thr Ala Tyr
                245                 250                 255

Gln Ala Pro Pro Val Ile Arg Thr Gly Lys Ser Met Phe Lys Pro Ile
            260                 265                 270

Ser Thr Ser Gly Glu Gly Pro Val Ile Gly Val Ala Leu Asp Glu Ala
        275                 280                 285

Phe Asn Phe Tyr Tyr His Asp Asn Ile Glu Met Leu Gln Ala Ala Gly
    290                 295                 300

Ala Ser Ile Lys Tyr Phe Ser Pro Leu His Asp Ser Lys Ile Pro His
305                 310                 315                 320

Val Asp Gly Ile Tyr Ile Gly Gly Tyr Pro Glu Leu Phe Ala Ser
                325                 330                 335

Glu Leu Glu Lys Asn Thr Leu Ile Lys Asn Arg Ile Tyr Glu Leu Ser
            340                 345                 350

Ser Asp Asn Met Pro Ile Tyr Ala Glu Cys Gly Gly Leu Met Tyr Leu
        355                 360                 365

Thr Glu Lys Ile Thr Thr Gly Ala His Asn Ser Asn Asp Ser Ile Tyr
    370                 375                 380

Asn Met Thr Ser Met Glu Lys Ala Thr Tyr Glu Met Val Gly Ala Leu
385                 390                 395                 400

Pro Gly His Thr Leu Met Gly Asn Lys Arg Val Ser Tyr Asn Thr
                405                 410                 415

Gly Val Leu Asn Met Asp Thr Val Ile Gly Lys Ser Gly Asn Ile Phe
            420                 425                 430

Lys Gly His Glu Phe His His Ser Glu Ile Thr Asp Ile Pro Glu Gly
        435                 440                 445

Thr Lys Phe Ala Ile Asp Leu Ser Arg Gly Glu Gly Ile Val Asn Gly
    450                 455                 460
```

-continued

```
Lys Asp Gly Leu Thr Val Asn Asn Thr Ile Gly Ser Tyr Ala His Leu
465                 470                 475                 480

His Ala Val Ser Tyr Lys Glu Phe Ala Leu Ser Phe Val Asp Phe Met
                485                 490                 495

Ser Asn Leu Met
            500

<210> SEQ ID NO 53
<211> LENGTH: 497
<212> TYPE: PRT
<213> ORGANISM: Methanosarcina acetivorans C2A

<400> SEQUENCE: 53

Met Ser His Ser Lys Gln Ser Gly Thr Glu Ala Gly Ser Ile Pro Arg
1               5                   10                  15

Val Leu Ile Ser Ala Asp Arg Ser Ser Gly Lys Thr Thr Ile Ser
            20                  25                  30

Met Gly Leu Met Ala Ala Leu Val Ser Arg Gly Tyr Lys Val Gln Pro
            35                  40                  45

Phe Lys Val Ala Leu Asp Tyr Ile Asp Pro Ser Tyr His Thr Glu Ile
    50                  55                  60

Thr Gly Arg Phe Cys Arg Asn Leu Asp Gly Tyr Leu Met Asp Glu Asn
65                  70                  75                  80

Gly Ile Leu Asp Val Tyr Ser His Ala Cys Glu Thr Gly Ser Gly Ala
                85                  90                  95

Asp Ile Ala Ile Ile Glu Gly Val Arg Gly Leu Tyr Glu Gly Phe Glu
            100                 105                 110

Gly Leu Ser Asp Leu Gly Ser Thr Ala Gln Ile Ala Lys Ile Leu Lys
            115                 120                 125

Cys Pro Val Val Phe Val Ile Asn Ala Arg Ser Ile Thr Arg Ser Ala
    130                 135                 140

Ala Ala Leu Ile Ser Gly Tyr Lys Asn Phe Asp Pro Asp Val Glu Ile
145                 150                 155                 160

Ala Gly Val Ile Leu Asn Asn Ile Gly Gly Arg Arg His Ala Gln Lys
                165                 170                 175

Ala Lys Glu Ala Ile Glu His Tyr Thr Gly Val Pro Val Ile Gly Ile
            180                 185                 190

Ile Pro Arg Asp Pro Ser Met Gln Ile Ser Met Arg His Leu Gly Leu
        195                 200                 205

Met Pro Ala Leu Glu Gly Arg Arg Leu Gly Asp Gly Gly Phe Glu
    210                 215                 220

Asp Arg Leu Arg Gly Ile Glu Ile Ile Asn Lys Gly Ile Asp Val
225                 230                 235                 240

Asp Arg Phe Leu Glu Ile Ala Gly Ser Ala Lys Ser Leu Thr Ser Pro
                245                 250                 255

Glu Asn Ser Ile Phe Ser Pro Ala Ala Gly Ala Gly Ser Pro Arg Pro
            260                 265                 270

Arg Ile Gly Ile Ala Leu Asp Glu Ala Phe Asn Phe Tyr Tyr Arg Asp
        275                 280                 285

Asn Ile Asp Leu Leu Glu Leu Ala Gly Ala Glu Ile Val Tyr Phe Ser
    290                 295                 300

Pro Val Asn Asp Pro Glu Leu Pro Asp Val Asp Gly Leu Tyr Ile Gly
305                 310                 315                 320

Gly Gly Tyr Pro Glu Leu Phe Ala Ala Glu Leu Glu Ala Asn Glu Ser
                325                 330                 335
```

```
Met Arg Arg Ser Ile Lys Glu Ala Ser Ala Ala Gly Met Pro Ile Tyr
            340                 345                 350

Ala Glu Cys Gly Gly Leu Met Tyr Leu Thr Glu Lys Ile Ser Thr Gly
            355                 360                 365

Val Pro Gly Lys Gly Thr Tyr His Asp Ala Ser Met Pro Glu Ser Thr
370                 375                 380

Tyr Ile Met Val Gly Ala Leu Pro Gly His Thr Ile Met Gly Gln Thr
385                 390                 395                 400

Arg Val Val Ser Tyr Asn Ile Gly Thr Leu Asp Arg Asp Cys Leu Ile
                405                 410                 415

Gly Lys Glu Gly Asn Ser Phe Lys Gly His Glu Phe His His Ser Glu
            420                 425                 430

Ile Arg Glu Ile Pro Glu Tyr Ala Glu Phe Ala Ile Ala Leu Leu Arg
            435                 440                 445

Gly Thr Gly Ile Lys Gly Asp Arg Asp Gly Leu Ile Val Gly Asn Thr
            450                 455                 460

Leu Gly Ser Tyr Ala His Leu His Gly Val Ala Tyr Arg Glu Leu Ala
465                 470                 475                 480

Gly Ser Leu Val Glu Ala Ala Gly Lys Phe Arg Ala Ser Arg Ala Pro
                485                 490                 495

Arg
```

<210> SEQ ID NO 54
<211> LENGTH: 453
<212> TYPE: PRT
<213> ORGANISM: Methanosphaera stadtmanae DSM 3091

<400> SEQUENCE: 54

```
Met Lys Arg Val Val Leu Thr Gly Thr Gly Ser Gly Val Gly Lys Thr
1               5                   10                  15

Thr Ile Ala Thr Gly Ile Met Lys Ala Leu Ser Asp Glu His Lys Ile
            20                  25                  30

Gln Pro Phe Lys Val Gly Pro Asp Tyr Ile Asp Pro Ser Tyr His Asn
        35                  40                  45

Cys Ala Thr Gly Val Ser Ser Arg Asn Leu Asp Ser Phe Phe Met Ser
    50                  55                  60

Asp Gly Gln Ile Arg Gln Ser Phe Lys Asn Gly Met Thr Ser Ser His
65                  70                  75                  80

Ala Asp Tyr Gly Ile Ile Glu Gly Val Arg Gly Leu Tyr Glu Gly Ile
                85                  90                  95

Ser Pro Thr Asn Asp Ile Gly Ser Thr Ser Ser Ile Ala Lys Ala Leu
            100                 105                 110

Asn Ser Pro Val Ile Leu Ile Asn Ser Arg Ser Leu Val Arg Ser
            115                 120                 125

Ala Ala Ala Met Thr Leu Gly Phe Lys Ala Leu Asp Ser Arg Ile Asp
            130                 135                 140

Ile Glu Gly Val Ile Leu Asn Asn Val Lys Ser Gln Lys His Tyr Leu
145                 150                 155                 160

Lys Thr Lys Glu Ala Val Glu Lys Leu Ala Asn Thr Arg Val Leu Gly
                165                 170                 175

Gly Ile Glu Arg Asp Asn Ser Ile Ser Met Glu Gln Arg His Leu Gly
            180                 185                 190

Leu Ile Pro Ala Val Glu Gln Glu Arg Ile Ser Gly Leu Val Glu Lys
            195                 200                 205
```

```
Trp Gly Glu Leu Ile Arg Glu Asn Ile Asp Leu Asp Ala Leu Met Glu
            210                 215                 220

Ile Met Asp Asn Ser Asn Pro Ile Ile Asn Glu Tyr Glu Pro Ile Trp
225                 230                 235                 240

Ser Pro Asn Lys Thr Lys His Lys Thr Arg Ile Ala Val Pro Phe Asp
                245                 250                 255

Glu Ala Phe Asn Phe Tyr Tyr Lys Glu Asn Leu Glu Ala Leu Glu Tyr
            260                 265                 270

Asn Asn Ala Lys Ile Glu Tyr Phe Ser Pro Ile His Asp Glu Gln Leu
            275                 280                 285

Pro Ser Val Asp Ala Leu Tyr Ile Gly Gly Tyr Pro Glu Ile Phe
290                 295                 300

Lys Lys Glu Leu Ser Lys Asn Thr Thr Met Leu Glu Ser Ile Lys Glu
305                 310                 315                 320

Phe Ser Gln Asp Asn His Pro Ile Tyr Ala Glu Cys Gly Gly Leu Met
                325                 330                 335

Tyr Leu Cys Lys Thr Ile Asp Ser Leu Pro Met Val Asp Val Phe Pro
                340                 345                 350

Tyr His Ser Met Leu Thr Lys Arg Val Gln Gly Leu Ser Tyr Thr Ile
            355                 360                 365

Ala His Val Gln Arg Asp Asn Pro Ile Leu Lys Lys Asn Thr Thr Tyr
370                 375                 380

His Gly His Glu Phe His Tyr Ser Lys Val Glu Tyr Thr Gly Ser Asn
385                 390                 395                 400

Ser Asn Asp Phe Ala Phe Ser Met Arg Arg Gly Val Gly Ile Thr Gly
                405                 410                 415

Lys Tyr Asp Gly Leu Leu Lys Asn Asn Thr Leu Ala Ser Tyr Ile His
            420                 425                 430

Thr His Thr Ala Cys Leu Pro Asp Phe Gly Tyr Asn Phe Thr Gln Ser
            435                 440                 445

Ala Tyr Glu Asn Lys
450

<210> SEQ ID NO 55
<211> LENGTH: 460
<212> TYPE: PRT
<213> ORGANISM: Methanosphaerula palustris E1-9c

<400> SEQUENCE: 55

Met Lys Thr Leu Leu Ile Ala Gly Asp Arg Ser Gly Ser Gly Lys Thr
1               5                   10                  15

Ser Ile Thr Leu Ala Leu Ala Ala Leu Leu Arg Lys Arg Phe Ser Val
            20                  25                  30

Gln Thr Phe Lys Val Gly Met Asp Tyr Ile Asp Pro Ser Tyr Leu Thr
        35                  40                  45

Gly Val Thr Gly Arg Pro Cys Arg Asn Leu Asp Gly Tyr Val Met Thr
    50                  55                  60

Ala Asp Glu Ile Arg Gly Ile Tyr Asn His Gly Cys Gln Gly Ala Glu
65                  70                  75                  80

Val Ala Leu Val Glu Gly Val Arg Gly Leu Tyr Glu Gly Ala Glu Ala
                85                  90                  95

Leu Ser Asn Lys Gly Ser Thr Ala Glu Val Ala Arg Leu Leu Asp Leu
            100                 105                 110

Asn Val Val Leu Val Ile Asn Ala Arg Ser Ile Thr Arg Ser Ala Ala
```

```
            115                 120                 125
Ala Ile Val Lys Gly Phe Met Ala Phe Asp Pro Glu Val Lys Ile Cys
    130                 135                 140

Gly Val Ile Leu Asn Asn Val Met Gly Glu Arg His Lys Glu Lys Ala
145                 150                 155                 160

Ile Thr Ala Val Glu His Tyr Cys Gly Val Pro Val Ile Gly Ala Ile
                165                 170                 175

Pro Arg Leu Glu Glu Met His Leu Ala Met Arg His Leu Gly Leu Val
            180                 185                 190

Pro Phe Arg Glu Gly Glu Gly Ser Glu Phe Arg Asp Arg Ile Gln
        195                 200                 205

Ala Ile Thr Asp Leu Ile Gly Gln Tyr Val Ser Val Asp Arg Leu Leu
    210                 215                 220

Glu Leu Ala Gly Asp Val Thr Pro Ala Pro Ser Pro Glu Tyr Leu Arg
225                 230                 235                 240

Pro Ala Val Asn Arg Asp Leu Thr Ile Gly Val Ala Tyr Asp Glu Ala
                245                 250                 255

Phe Asn Phe Tyr Tyr Ala Glu Leu Phe Asp Ile Leu Ala Ala Gly Gly
            260                 265                 270

Ala Glu Val Val Arg Phe Ser Pro Val His Asp Ala Leu Pro Arg Ala
        275                 280                 285

Asp Gly Tyr Ile Phe Gly Gly Tyr Pro Glu Leu Phe Gly Ala Glu
    290                 295                 300

Leu Ala Ala Asn Thr Gln Met Arg Glu Ala Val Arg Ala Ala Ala Leu
305                 310                 315                 320

Ala Gly Thr Pro Ile Tyr Ala Glu Cys Gly Gly Leu Met Tyr Leu Thr
                325                 330                 335

Glu Ala Ile Val Leu Lys Gln Gly Trp Gln Gln Ser Thr Gln Glu Gln
            340                 345                 350

Thr Tyr Arg Met Cys Gly Val Tyr Ala Gly Arg Thr Val Met Pro Ala
        355                 360                 365

Ala Arg Val Val Thr Tyr Ile Glu Gly Ser Ser Ala Ala Asp Ser Pro
    370                 375                 380

Met Gly Ala Ser Arg Phe Arg Gly His Ala Phe His Tyr Ser Asp Val
385                 390                 395                 400

Asp Leu Thr Lys Glu Thr Arg Tyr Ala Tyr Thr Leu Thr Arg Gly Val
                405                 410                 415

Gly Ile Thr Gly Asp Ala Asp Gly Ala Leu Phe Asn Asn Thr Leu Gly
            420                 425                 430

Ala Tyr Cys His Leu His Pro Val Ser Ser Arg Glu Met Phe Ala Ala
        435                 440                 445

Phe Leu His Ala Cys Arg Ser Gly Arg Thr Glu Ala
    450                 455                 460

<210> SEQ ID NO 56
<211> LENGTH: 463
<212> TYPE: PRT
<213> ORGANISM: Methanospirillum hungatei JF-1

<400> SEQUENCE: 56

Met Lys Ala Phe Leu Ile Ser Gly Asp Arg Ser Gly Ser Gly Lys Thr
1               5                   10                  15

Ser Ile Thr Leu Ala Ile Ala Ala Leu Ala Lys Arg Cys Thr Val
            20                  25                  30
```

```
Gln Thr Phe Lys Val Gly Met Asp Tyr Ile Asp Pro Ser Tyr Leu Thr
             35                  40                  45
Gly Val Thr Gly Arg Pro Cys Arg Asn Leu Asp Ser Phe Val Met Asn
 50                  55                  60
Arg Asp Glu Met Thr Ala Val Phe Asn His Ala Cys Ile Gly Ala Asp
 65                  70                  75                  80
Ile Ala Ile Ile Glu Gly Val Arg Gly Leu Tyr Glu Gly Ala Asp Ser
                 85                  90                  95
Ile Ala Asp Ile Gly Ser Thr Ala Ser Ile Ala Lys His Phe His Val
            100                 105                 110
Pro Ile Ile Leu Val Ile Asp Ala Arg Ser Ile Thr Arg Ser Ala Ala
            115                 120                 125
Ala Leu Leu Tyr Gly Phe Met Lys Phe Asp Pro Asp Ile Gln Ile Ala
130                 135                 140
Gly Val Ile Leu Asn Asn Val Arg Gly Glu Lys His Ile Arg Lys Ala
145                 150                 155                 160
Thr Glu Ala Ile Arg His Tyr Cys Ser Ile Pro Val Ile Gly Ala Val
                165                 170                 175
Pro Arg Val Asp Asn Leu Asp Leu Thr Met Arg His Leu Gly Leu Val
            180                 185                 190
Pro Phe Glu Glu Gly Leu Lys Asp Gln Pro Phe Leu Asp Arg Val Ser
            195                 200                 205
Ser Ile Val Glu Met Ile Cys Ser His Leu Asp Ile Asp Ala Leu Leu
            210                 215                 220
Ser Leu Ser Arg Glu Met Lys Ser Ser Leu His Ile Pro Asp Leu Phe
225                 230                 235                 240
Ala Ser Val Glu Gln His His Arg Glu Arg Ile Ala Val Ala Arg Asp
                245                 250                 255
Glu Ala Phe Asn Phe Tyr Tyr Ala Asp Leu Phe Ser Leu Ile Glu Ala
                260                 265                 270
Arg Gly Tyr Asp Ile Val Tyr Phe Ser Pro Ile His Gly Asp Leu Pro
            275                 280                 285
Asp Ala Asp Gly Tyr Ile Leu Gly Gly Tyr Pro Glu Tyr Tyr Gly
290                 295                 300
Arg Glu Leu Ala Asp Asn Gln Ser Met Met Glu Asp Ile Arg Thr Ala
305                 310                 315                 320
Ala Gly Asp Glu Arg Pro Ile Leu Ala Glu Cys Gly Leu Met Tyr
                325                 330                 335
Leu Cys Arg Glu Ile Asp Val Leu His Asp Phe Ser Gly Leu Ser Ala
            340                 345                 350
Gly Thr Ser Phe Lys Met Ala Asp Val Leu Pro Ala Arg Cys Thr Ile
            355                 360                 365
Pro Lys Lys Arg Val Val Thr Tyr Val Ser Gly Lys Thr Thr Pro Asn
370                 375                 380
Phe Pro Phe Ala Glu Lys Pro Leu Pro Val Lys Gly His Ala Phe His
385                 390                 395                 400
Tyr Ser Thr Val His Pro Asp Lys Gly Ser Thr Phe Gly Tyr Glu Leu
                405                 410                 415
Asp Arg Gly Phe Gly Ile Asp Ala Thr His Asp Gly Met Val Leu Asn
            420                 425                 430
Lys Val Gly Ser Tyr Thr His Ile His Pro Val Pro Ser Arg Asp
            435                 440                 445
Leu Leu Tyr Ser Phe Leu Ser Ala Cys Leu Ser Asp Ser Ser Ile
```

-continued

```
            450             455             460
```

<210> SEQ ID NO 57
<211> LENGTH: 451
<212> TYPE: PRT
<213> ORGANISM: Methanothermobacter marburgensis str. Marburg

<400> SEQUENCE: 57

```
Met Arg Leu Val Leu Ala Gly Thr Gly Ser Ala Val Gly Lys Thr Thr
1               5                   10                  15

Ile Ala Thr Gly Ile Met Arg Ala Leu Ser Asp Arg Gly Ile Gln Pro
            20                  25                  30

Phe Lys Val Gly Pro Asp Tyr Ile Asp Pro Ser Tyr His Thr Met Ala
        35                  40                  45

Thr Gly Asn Val Ser Arg Asn Leu Asp Ser Phe Phe Met Thr Asp Ala
    50                  55                  60

Gln Ile Arg Glu Ala Phe Thr Arg Ala Met Lys Ile Ser Gly Ala Arg
65                  70                  75                  80

Met Gly Ile Ile Glu Gly Val Arg Gly Leu Tyr Glu Gly Ile Ser Ala
                85                  90                  95

Thr Gly Asp Thr Gly Ser Thr Ala Ser Val Ala Lys Ala Leu Lys Ala
            100                 105                 110

Pro Val Val Leu Ile Ile Asn Ser Arg Ser Leu Val Lys Ser Ala Ala
        115                 120                 125

Ala Met Val Leu Gly Phe Arg Ser Leu Asp Pro Glu Val Lys Ile Arg
    130                 135                 140

Gly Val Ile Leu Asn Gln Val Lys Asn Arg Arg His Tyr Leu Lys Thr
145                 150                 155                 160

Lys Glu Ala Ile Glu Lys Leu Thr Gly Thr Glu Val Val Gly Gly Ile
                165                 170                 175

Pro Arg Ser Ala Glu Leu Glu Val Gln Arg His Leu Gly Leu Val
            180                 185                 190

Pro Ala Val Glu Arg Glu Gln Ile Ala Ser Tyr Ile Glu Lys Trp Gly
        195                 200                 205

Ser Ala Met Glu Glu Tyr Leu Asp Leu Glu Ala Leu Glu Asp Ile Met
    210                 215                 220

Ala Ser Ala Gly Lys Ile Asp Gly Glu Arg Glu Pro Leu Trp Arg Arg
225                 230                 235                 240

Glu Asn Lys Arg Lys Val Lys Ile Gly Val Ala Phe Asp Glu Ala Phe
                245                 250                 255

Asn Phe Tyr Tyr Arg Glu Asn Ile Glu Ala Leu Glu Asp Asn Ala Ala
            260                 265                 270

Ser Val Val Tyr Phe Ser Pro Leu His Asp Glu Leu Pro Asp Val
        275                 280                 285

Asp Ala Val Tyr Ile Gly Gly Gly Tyr Pro Glu Val Phe Ala Gly Glu
    290                 295                 300

Leu Glu Ser Asn Arg Ser Met Arg Ile Ser Val Arg Lys Phe His Ala
305                 310                 315                 320

Asp Gly Arg Pro Ile Phe Gly Glu Cys Gly Gly Leu Met Tyr Leu Met
                325                 330                 335

Asn Ser Ile Asp Gly His Lys Met Cys Gly Val Phe Pro Tyr Ser Ala
            340                 345                 350

Glu Met Thr Lys Asn Val Gln Gly Leu Ser Tyr Val Ile Ser Glu Ala
        355                 360                 365
```

-continued

```
Val Ser Asp Asn Leu Ile Thr Glu Glu Gly Asp Val Phe Arg Gly His
    370                 375                 380

Glu Phe His Tyr Ser Arg Val Ser Val Thr Gly Asp Ala Gln Phe Ala
385                 390                 395                 400

Phe Arg Val Leu Arg Gly Arg Gly Ile Met Asp Ser Met Asp Gly Ile
                405                 410                 415

Thr Ser Gly Ser Ala Leu Ala Ser Tyr Val His Ile His Ala Ala Ser
                420                 425                 430

Cys Pro Thr Phe Ala Ala Asn Phe Thr Arg Asn Ala Trp Glu Leu Gln
                435                 440                 445

Asp Glu Val
    450

<210> SEQ ID NO 58
<211> LENGTH: 458
<212> TYPE: PRT
<213> ORGANISM: Methanothermococcus okinawensis IH1

<400> SEQUENCE: 58

Met Lys Asp Phe Lys Arg Val Val Leu Ala Gly Thr Ser Ser Met Val
1               5                   10                  15

Gly Lys Thr Thr Ile Ser Thr Gly Ile Met Lys Ala Leu Ser Lys Lys
                20                  25                  30

Tyr Asn Val Gln Pro Tyr Lys Ile Gly Pro Asp Tyr Ile Asp Pro Thr
            35                  40                  45

Tyr His Thr Leu Ala Thr Gly Asn Tyr Ser Arg Asn Leu Asp Ser Phe
        50                  55                  60

Phe Met Glu Asp Tyr Gln Ile Arg Glu Leu Phe Lys Arg Asn Ser Lys
65                  70                  75                  80

Asn Lys Asp Ile Ser Ile Ile Glu Gly Val Arg Gly Leu Tyr Glu Gly
                85                  90                  95

Ile Ser Pro Tyr Asn Asp Val Gly Ser Thr Ala Ser Val Ser Lys Ser
            100                 105                 110

Leu Asn Ala Pro Val Ile Leu Ile Met Asp Ala Arg Ser Leu Thr Arg
        115                 120                 125

Ser Ala Ala Ile Ile Lys Gly Phe Lys Ser Phe Asp Glu His Val
130                 135                 140

Asn Ile Gln Gly Val Ile Phe Asn Lys Ile Arg Gly Lys Asn His Tyr
145                 150                 155                 160

Lys Lys Leu Lys Asp Ala Val Lys His Tyr Ile Pro Asp Ile Glu Ile
                165                 170                 175

Ile Gly Ala Ile Pro Arg Asp Glu Lys Leu Glu Val Ser Gln Arg His
            180                 185                 190

Leu Gly Leu Val Pro Thr Pro Glu Asn Arg Asp Asn Ile Asn Lys Asn
        195                 200                 205

Ile Asp Met Trp Gly His Val Val Glu Glu Tyr Leu Asp Leu Asp Lys
    210                 215                 220

Ile Val Glu Ile Ser Glu Lys Ser Glu Asn Asn Glu Leu Gly Ser Asn
225                 230                 235                 240

Tyr Tyr Asn Asn Asn His Tyr Asn Asp Phe Leu Leu Trp Asn Val Asn
                245                 250                 255

Lys Asn Arg Cys Thr Ile Gly Ile Ala Tyr Asp Glu Val Phe Asn Phe
            260                 265                 270

Tyr Tyr Trp Asp Asn Phe Asp Ala Leu Glu Glu Asn Gly Ala Lys Leu
        275                 280                 285
```

```
Lys Phe Phe Ser Pro Leu Asn Asp Glu Ser Ile Pro Asn Cys Asp Ile
    290                 295                 300

Leu Tyr Phe Gly Gly Tyr Pro Glu Ile Phe Ala Asn Glu Leu Asn
305                 310                 315                 320

Lys Asn Lys Ser Met Ile Glu Ser Ile Arg Asn Phe Asp Gly Lys Ile
                325                 330                 335

Tyr Gly Glu Cys Gly Gly Leu Met Tyr Leu Thr Asn Ser Ile Asn Gly
                340                 345                 350

Ile Glu Met Leu Lys Met Leu Asn Cys Asp Ala Ile Met Thr Lys Asn
                355                 360                 365

Val Gln Gly Leu Ser Tyr Val Asn Gly Thr Phe Ile His Asp Cys Pro
    370                 375                 380

Thr Gly Lys Ile Gly Gly Lys Phe Arg Ala His Glu Phe His Tyr Ser
385                 390                 395                 400

Lys Leu Ile Asn Ile Lys Glu Lys Leu Phe Ala Tyr Lys Ile Asn Arg
                405                 410                 415

Gly Lys Gly Ile Ile Asn Asn Met Asp Gly Ile Leu Ser Asn Asn Gly
                420                 425                 430

Arg Ile Leu Gly Gly Tyr Ala His Gln His Cys Val Gly Asn Pro Tyr
                435                 440                 445

Phe Ala Ser Ser Ile Val Glu Asp Leu Lys
    450                 455

<210> SEQ ID NO 59
<211> LENGTH: 449
<212> TYPE: PRT
<213> ORGANISM: Methanothermus fervidus DSM 2088

<400> SEQUENCE: 59

Met Arg Val Val Leu Ala Gly Thr Gly Ser Ala Val Gly Lys Thr Thr
1               5                   10                  15

Ile Ser Thr Gly Ile Met Arg Ala Leu Ser Lys Glu Met Lys Val Gln
                20                  25                  30

Pro Phe Lys Val Gly Pro Asp Tyr Ile Asp Pro Thr Tyr His Tyr Leu
            35                  40                  45

Ala Thr Gly Val Pro Ser Arg Asn Leu Asp Ser Phe Phe Met Ser Asp
        50                  55                  60

Asp Gln Ile Arg Glu Ala Phe Cys Arg Gly Leu Glu Ile Ser Asn Ala
65              70                  75                  80

Lys Ala Gly Ile Ile Glu Gly Val Arg Gly Leu Tyr Glu Gly Ile Ser
                85                  90                  95

Pro Ile Ser Asp Val Gly Ser Thr Ser Ser Ile Ala Leu Ala Leu Asn
            100                 105                 110

Ser Pro Val Val Leu Ile Met Asn Thr Arg Ser Leu Val Lys Ser Ala
        115                 120                 125

Ala Ala Ile Ile Leu Gly Phe Glu Lys Leu Asp Pro Arg Val Lys Ile
    130                 135                 140

Glu Gly Val Ile Leu Asn Phe Ile Lys Asn Arg Arg His Tyr Leu Lys
145                 150                 155                 160

Thr Lys Lys Ala Ile Glu Ser Leu Thr Asp Val Lys Val Leu Gly Gly
                165                 170                 175

Ile Pro Arg Lys Lys Glu Leu Thr Val Lys Gln Arg His Leu Gly Leu
            180                 185                 190

Ile Pro Ala Val Glu Asn Lys Lys Ile Ile Glu Tyr Ile Asp Arg Trp
```

```
            195                 200                 205
Ala Lys Val Val Glu Asn Ile Asp Ile Asp Met Leu Lys Glu Ile
210                 215                 220

Met Lys Asp Ala Gly Lys Ile Pro Ser Ser Arg Glu Ser Leu Trp Val
225                 230                 235                 240

Lys Glu Asn Lys Lys Arg Val Lys Ile Gly Leu Ala Tyr Asp Lys Ala
                    245                 250                 255

Phe Thr Phe Tyr Tyr Gln Glu Asn Ile Glu Ala Leu Glu Asp Asn Asn
                260                 265                 270

Ala Lys Ile Ile Lys Phe Ser Pro Cys Glu Asp Glu Met Ile Pro Asp
                275                 280                 285

Val Asp Gly Ile Tyr Ile Gly Gly Tyr Pro Glu Ile Phe Ser Lys
290                 295                 300

Glu Leu Glu Arg Asn Ile Ser Met Arg Lys Ser Ile Lys Lys Phe His
305                 310                 315                 320

Met Asp Gly Arg Pro Ile Tyr Ala Glu Cys Gly Gly Leu Met Tyr Leu
                    325                 330                 335

Met Lys Ala Leu Asp Ser Ala Lys Met Cys Gly Ile Tyr Pro His Ile
                340                 345                 350

Ala Lys Met Thr Lys Asn Val Gln Gly Leu Ser Tyr Val Ile Ala Lys
                355                 360                 365

Val Glu Asn Asn Ile Ile Ser Ser Lys Gly Glu Ile Ile Lys Gly
370                 375                 380

His Glu Phe His Tyr Ser Lys Ile Lys Ile Thr Gly Asn Pro Lys Phe
385                 390                 395                 400

Ala Phe Arg Ile Met Arg Gly Arg Gly Ile Val Asn Ser Lys Asp Gly
                    405                 410                 415

Leu Ile Ser Asn Asn Thr Leu Ala Asn Tyr Met His Ile His Val Ala
                420                 425                 430

Ser Tyr Pro Lys Phe Ala Ala Asn Phe Thr Arg Ala Ala Leu Glu Cys
            435                 440                 445

Gly

<210> SEQ ID NO 60
<211> LENGTH: 443
<212> TYPE: PRT
<213> ORGANISM: Methanotorris igneus Kol 5

<400> SEQUENCE: 60

Met Arg Arg Val Val Ile Ala Gly Thr Ser Ser Met Val Gly Lys Thr
1               5                   10                  15

Thr Ile Ser Thr Gly Ile Met Lys Ala Leu Ser Lys Lys Tyr Asn Val
                20                  25                  30

Gln Pro Tyr Lys Val Gly Pro Asp Tyr Ile Asp Pro Thr Tyr His Thr
                35                  40                  45

Ile Ala Thr Asn Asn Lys Ser Arg Asn Leu Asp Ser Phe Phe Met Ser
            50                  55                  60

Gly Glu Gln Ile Lys Ala Leu Phe Lys Lys His Ser Lys Asp Lys Asp
65              70                  75                  80

Ile Ser Val Ile Glu Gly Val Arg Gly Leu Tyr Glu Gly Ile Ser Pro
                85                  90                  95

Tyr Asn Asp Ile Gly Ser Thr Ala Ser Val Ala Lys Ala Leu Asn Ala
                100                 105                 110

Pro Val Ile Leu Leu Met Asn Ala Arg Ser Leu Thr Arg Ser Ala Ala
```

```
            115                 120                 125
Ala Ile Ile Lys Gly Phe Arg Ala Phe Asp Ser Gln Val Asn Ile Lys
        130                 135                 140

Gly Val Ile Phe Asn Met Val Arg Gly Glu Lys His Ile Lys Lys Leu
145                 150                 155                 160

Glu Glu Ala Val Lys Tyr Tyr Ile Pro Asp Ile Glu Ile Ile Gly Ala
                165                 170                 175

Ile Pro Arg Asp Glu Ser Leu Asn Val Pro Gln Arg His Leu Gly Leu
        180                 185                 190

Ile Pro Thr Pro Glu Asn Lys Lys Ala Leu Glu Glu Lys Ile Asn Leu
        195                 200                 205

Trp Gly Glu Ile Val Glu Lys Tyr Leu Asp Leu Asp Lys Leu Val Glu
        210                 215                 220

Ile Ser Asp Val Asp Asp Phe Glu Val Asn Gly Gly Glu Leu Trp Glu
225                 230                 235                 240

Ile Asn Lys Asn Lys Cys Lys Ile Gly Val Ala Tyr Asp Glu Val Phe
                245                 250                 255

Asn Phe Tyr Tyr Trp Asp Asn Phe Asp Ala Leu Glu Glu Asn Gly Ala
            260                 265                 270

Lys Ile Glu Phe Phe Ser Pro Leu Asn Asp Asp Ile Pro Asn Cys
        275                 280                 285

Asp Ile Ile Tyr Ile Gly Gly Gly Tyr Pro Glu Glu Phe Ala Glu Lys
        290                 295                 300

Leu Ser Ser Asn Lys Asp Met Leu Asp Ala Ile Arg Asn Phe Asp Gly
305                 310                 315                 320

Lys Ile Tyr Gly Glu Cys Gly Gly Leu Met Tyr Leu Thr Asn Ser Ile
                325                 330                 335

Asn Gly Val Glu Met Leu Gly Leu Leu Asp Cys Asp Ala Val Met Thr
            340                 345                 350

Lys Asn Val Gln Gly Leu Ser Tyr Val Glu Gly Glu Phe Val Glu Asn
        355                 360                 365

Cys Val Ile Gly Lys Lys Gly Leu Lys Phe Arg Ala His Glu Phe His
        370                 375                 380

Tyr Ser Lys Leu Ile Asn Ile Arg Glu Lys Ile Phe Ala Tyr Lys Ile
385                 390                 395                 400

Asn Arg Gly Arg Gly Ile Ile Asn Ser Met Asp Gly Ile Lys Lys Gly
                405                 410                 415

Asn Val Leu Gly Gly Tyr Ala His Gln His Cys Val Ala Asn Pro Tyr
            420                 425                 430

Phe Ala Ser Thr Met Val Asn Ser Val Asp Glu
        435                 440
```

<210> SEQ ID NO 61
<211> LENGTH: 477
<212> TYPE: PRT
<213> ORGANISM: Methermicoccus shengliensis DSM 18856

<400> SEQUENCE: 61

```
Met Ser Ile Pro Arg Ile Leu Ile Ser Ala Asp Arg Ser Ser Ala Gly
1               5                   10                  15

Lys Thr Thr Ile Ala Met Gly Leu Gly Ser Leu Leu His Lys Arg Gly
            20                  25                  30

Ile Arg Val Gln Pro Phe Lys Val Ala Leu Asp Tyr Ile Asp Ser Ser
        35                  40                  45
```

```
Tyr His Thr Glu Leu Thr Gly Arg Pro Cys Arg Asn Leu Asp Gly Phe
 50              55                  60
Leu Met Ser Glu Asp Thr Ile Leu Glu Ser Phe Ser Arg Gly Val Lys
 65              70                  75                  80
Gly Ala Glu Leu Ala Leu Ile Glu Gly Val Arg Gly Leu Tyr Glu Gly
                 85                  90                  95
Leu Glu Ala Thr Ser Asp Val Gly Ser Thr Ala Gln Ile Ala Lys Leu
                100                 105                 110
Leu Arg Cys Pro Val Val Leu Val Ile Asn Ala Arg Ser Ile Thr Arg
            115                 120                 125
Ser Ala Ala Ala Ile Val Arg Gly Tyr Gln Glu Phe Asp Arg Lys Val
130                 135                 140
Asn Ile Arg Gly Val Ile Leu Asn Gln Ile Gly Ser Gln Ala His Ala
145                 150                 155                 160
Gln Lys Thr Ile Glu Ala Ile Glu Thr Tyr Thr Asp Val Lys Val Leu
                165                 170                 175
Gly Ala Ile Pro Arg Ser Ser Glu Met Arg Leu Val Met Arg His Leu
            180                 185                 190
Gly Leu Val Pro Ala Ile Glu Gly Lys Leu Thr Asp Arg Lys Gln Phe
        195                 200                 205
Glu Arg Arg Val Ser Thr Ile Glu Arg Met Leu Ser Glu His Val Asp
    210                 215                 220
Ile Asp Ala Leu Val Lys Ile Ala Arg Glu Ala Pro Pro Leu Lys Leu
225                 230                 235                 240
Pro Pro Val Pro Glu Gln Gly Glu Ser Pro Ser Asp Val Arg Val Gly
                245                 250                 255
Val Ala Met Asp Glu Ala Phe Asn Phe Tyr Tyr Pro Glu Asn Ile Glu
            260                 265                 270
Ser Leu Gln Gln Ala Gly Ala Gln Val Val Pro Phe Ser Pro Val Gly
        275                 280                 285
Asp Ser His Leu Pro Asp Val Asp Gly Leu Tyr Ile Gly Gly Gly Tyr
    290                 295                 300
Pro Glu Leu Phe Ala Glu Glu Leu Ser Ser Asn Trp Gly Met Arg Gln
305                 310                 315                 320
Asp Ile Leu Glu Ala Ser Arg Gly Gly Met Pro Ile Phe Ala Glu Cys
                325                 330                 335
Gly Gly Leu Leu Tyr Leu Ala Arg Ser Ile Ser Ile Asp Val Asp Gly
            340                 345                 350
Phe Leu Ala Ser Leu Glu Gly Lys Arg Val Glu Gln His Gly Glu Thr
        355                 360                 365
Tyr Glu Met Val Gly Val Val Pro Ala His Ala Thr Met Gly Glu Arg
    370                 375                 380
His Val Val Arg Tyr Thr Ala Gly Thr Leu Thr Arg Asp Thr Pro Ile
385                 390                 395                 400
Gly Ala Ala Gly Thr His Leu Lys Gly His Glu Phe His His Ser His
                405                 410                 415
Leu Glu Gly Leu Pro Gln Asp Ala Pro Leu Val Leu Ser Leu Ser Arg
            420                 425                 430
Gly Glu Gly Ile Asp Gly Ser Arg Asp Gly Phe Leu Ser Gly Gln Thr
        435                 440                 445
Leu Ala Gln Tyr Cys His Ile His Ala Leu Ser Tyr Arg Gly Phe Ala
450                 455                 460
Pro Ser Phe Val Arg Ala Cys Lys Ser Phe Lys Ile Gly
```

-continued

```
                465                 470                 475

<210> SEQ ID NO 62
<211> LENGTH: 479
<212> TYPE: PRT
<213> ORGANISM: Methanoperedens nitroreducens

<400> SEQUENCE: 62

Met Ile Asp Lys Leu Asp Ile Pro Arg Ile Leu Ile Ala Gly Asp Arg
1               5                   10                  15

Ser Ser Ala Gly Lys Thr Thr Ile Ser Ile Gly Ile Met Ser Val Leu
            20                  25                  30

Arg Asp Met Gly Tyr Lys Val Gln Pro Phe Lys Val Gly Leu Asp Phe
        35                  40                  45

Ile Asp Pro Ser Tyr His Thr Glu Val Thr Gly Arg Tyr Ser Arg Asn
    50                  55                  60

Leu Asp Gly Tyr Leu Met Pro Glu Arg Thr Val Ser Glu Val Phe Ser
65                  70                  75                  80

His Ala Val Glu Asp Ala Asp Ile Ala Val Ile Glu Gly Val Arg Gly
                85                  90                  95

Leu Phe Glu Gly Leu Glu Ala Thr Ser Asp Ile Gly Ser Thr Ala Gln
            100                 105                 110

Ile Ala Lys Leu Leu Arg Cys Pro Val Val Leu Val Ile Asn Ala Arg
        115                 120                 125

Ser Ile Thr Arg Ser Ala Ala Ala Val Val Ser Gly Tyr Arg Ser Phe
    130                 135                 140

Asp Pro Glu Val Asn Ile Ala Gly Val Ile Leu Asn Asn Ile Gly Ser
145                 150                 155                 160

Gln Arg His Ser Glu Lys Ala Arg Thr Ala Ile Glu Thr Tyr Thr Gly
                165                 170                 175

Ile Arg Val Ile Gly Glu Val Pro Arg Asn Ser Ser Met Lys Ile Ser
            180                 185                 190

Met Arg His Leu Gly Leu Ile Pro Ala Leu Glu Gly Arg Arg Arg Leu
        195                 200                 205

Ser Asp Phe Asp Glu Asn Leu Gly Lys Ile Lys Thr Ile Ile Asn Glu
    210                 215                 220

Asn Val Asp Ile Asp Arg Phe Leu Ser Leu Ala Lys Ser Ala Glu Pro
225                 230                 235                 240

Leu Pro Arg Pro Glu Lys Ser Ile Phe Asn Phe Lys Ala Arg Val Ser
                245                 250                 255

Glu Ser Ala Pro Arg Ile Gly Val Ala Tyr Asp Glu Ala Phe Asn Phe
            260                 265                 270

Tyr Tyr Arg Asp Asn Leu Glu Leu Leu Glu Leu Ala Gly Ala Glu Leu
        275                 280                 285

Val Tyr Phe Ser Pro Val Asn Asp Arg Ser Leu Pro Arg Val Asp Gly
    290                 295                 300

Leu Tyr Ile Gly Gly Gly Tyr Pro Glu Leu Phe Ala Gln Glu Leu Glu
305                 310                 315                 320

Asp Asn Ser Ser Met Arg Glu Ser Ile Lys Gln Val Ser Ser Glu Gly
                325                 330                 335

Leu Pro Val Tyr Ala Glu Cys Gly Gly Leu Met Tyr Leu Thr Arg Lys
            340                 345                 350

Ile Glu Met Asp Val Thr Gly Ser Gly Asn Tyr Asn Met Ala Gln Met
        355                 360                 365
```

```
Gln Gly Gly Thr Phe Ser Met Val Gly Ala Val Pro Gly Arg Thr Leu
    370                 375                 380

Met Gly His Lys Arg Val Val Ser Tyr Asn Ile Gly Arg Phe Val Lys
385                 390                 395                 400

Asp Asn Met Ile Gly Lys Ser Gly Asn Ser Phe Ile Gly His Glu Phe
                405                 410                 415

His His Ser Glu Val Leu Asp Leu Pro Asp Thr Thr Phe Ala Ile
            420                 425                 430

Arg Leu Asp Arg Gly Thr Gly Ile Arg Gly Glu Tyr Asp Gly Ile Leu
                435                 440                 445

Val Gly Asn Thr Met Ala Ala Tyr Ala His Leu His Ala Ala Ser Tyr
450                 455                 460

Thr Gly Phe Ala Arg Ser Phe Val Asp Ser Cys Ser Gly Gln Lys
465                 470                 475

<210> SEQ ID NO 63
<211> LENGTH: 264
<212> TYPE: PRT
<213> ORGANISM: Methanobacterium formicicum DSM 3637

<400> SEQUENCE: 63

Met Ser Ser Lys His Ile Ala Ile Tyr Gly Lys Gly Ile Gly Lys
1               5                   10                  15

Ser Thr Ile Val Ser Asn Leu Ala Ala Ala Tyr Ser Glu Asp Lys Asn
                20                  25                  30

Val Leu Val Ile Gly Cys Asp Pro Lys Ala Asp Thr Thr Arg Thr Leu
            35                  40                  45

Val Gly Arg Arg Ile Pro Thr Ile Leu Asp Ile Leu Lys Glu Lys Lys
50                  55                  60

Gly Ala Gln Glu Glu Asp Val Leu Phe Gln Gly Tyr Gly Asn Val Met
65                  70                  75                  80

Cys Val Glu Ser Gly Gly Pro Glu Pro Gly Val Gly Cys Ala Gly Arg
                85                  90                  95

Gly Val Ile Val Ala Met Lys Leu Leu Glu Asn Leu Glu Val Phe Ser
            100                 105                 110

Gln Asp Pro Glu Val Ile Ile Tyr Asp Val Leu Gly Asp Val Val Cys
        115                 120                 125

Gly Gly Phe Ala Val Pro Leu Arg Glu Asn Phe Ala Asp Glu Val Tyr
    130                 135                 140

Ile Val Thr Ser Gly Glu Tyr Met Ala Leu Tyr Ala Ala Asn Asn Ile
145                 150                 155                 160

Ser Lys Gly Ile Lys Lys Leu Lys Ser Asn Leu Gly Gly Ile Ile Cys
                165                 170                 175

Asn Cys Arg Gly Ile Asn Arg Glu Leu Glu Ile Val Glu Glu Phe Ala
            180                 185                 190

His Arg Ile Gly Ser Lys Val Ile Gly Val Ile Pro Arg Ser Glu Leu
        195                 200                 205

Val Gln Glu Ser Glu Ile Asp Ala Lys Thr Val Met Glu Lys Phe Pro
    210                 215                 220

Glu Ser Glu Gln Ala Gln Lys Tyr Arg Lys Leu Ser Ser Ala Ile Leu
225                 230                 235                 240

Asp Asn Gln Gly Phe Val Ile Pro Glu Pro Met Gly Ala Asp Glu Phe
                245                 250                 255

Asp Glu Phe Phe Arg Gly Phe Gln
            260
```

<210> SEQ ID NO 64
<211> LENGTH: 267
<212> TYPE: PRT
<213> ORGANISM: Methanobrevibacter ruminantium M1

<400> SEQUENCE: 64

Met Lys Arg Gln Lys Lys Ile Ala Ile Tyr Gly Lys Gly Gly Ile Gly
1               5                   10                  15

Lys Ser Thr Thr Val Ala Asn Ile Ala Ala Tyr Ser Glu Asp Asn
            20                  25                  30

Lys Lys Val Met Val Ile Gly Cys Asp Pro Lys Ser Asp Thr Thr Arg
        35                  40                  45

Thr Leu Cys Gly Lys Arg Ile Pro Thr Ile Val His Thr Leu Lys Asp
    50                  55                  60

Asn Lys Lys Pro Glu Leu Asp Asp Leu Val Phe Glu Gly Phe Asn Lys
65                  70                  75                  80

Ile Lys Cys Val Glu Ser Gly Gly Pro Glu Pro Gly Val Gly Cys Ala
                85                  90                  95

Gly Arg Gly Val Ile Val Ala Met Lys Arg Leu Glu Asn Leu Asn Ala
            100                 105                 110

Phe Glu Glu Glu Phe Asp Val Ile Leu Tyr Asp Val Leu Gly Asp Val
        115                 120                 125

Val Cys Gly Gly Phe Ser Val Pro Leu Arg Glu Asp Tyr Ala Asp Glu
    130                 135                 140

Val Phe Ile Val Ser Ser Gly Glu Tyr Met Ser Leu Tyr Ala Ala Asn
145                 150                 155                 160

Asn Ile Ser Arg Gly Ile Lys Lys Leu Lys Gly Asn Leu Gly Gly Ile
                165                 170                 175

Ile Cys Asn Cys Lys Gly Ile Asp Asn Glu Glu Ile Val Asn Ser
            180                 185                 190

Phe Ala Lys Glu Ile Gly Thr Gln Val Ile Gly Val Ile Gly Arg Ser
        195                 200                 205

Asn Leu Ile Gln Arg Ser Glu Leu Asp Ala Lys Thr Val Val Glu Tyr
    210                 215                 220

Ala Pro Glu Ser Ile Glu Ser Asp Ala Tyr Arg Lys Leu Ala Lys Asp
225                 230                 235                 240

Ile Phe Asp Asn Asp Asn Tyr Ser Thr Pro Gln Pro Met Glu Asp Glu
                245                 250                 255

Asp Phe Glu Asn Phe Phe Lys Ser Phe Ile Asp
            260                 265

<210> SEQ ID NO 65
<211> LENGTH: 279
<212> TYPE: PRT
<213> ORGANISM: Methanocaldococcus jannaschii DSM 2661

<400> SEQUENCE: 65

Met Arg Lys Phe Cys Val Tyr Gly Lys Gly Gly Ile Gly Lys Ser Thr
1               5                   10                  15

Thr Val Ser Asn Ile Ala Ala Ala Leu Ala Glu Asp Gly Lys Lys Val
            20                  25                  30

Leu Val Val Gly Cys Asp Pro Lys Ala Asp Thr Thr Arg Asn Leu Val
        35                  40                  45

Gly Arg Lys Ile Pro Thr Val Leu Asp Val Phe Arg Lys Lys Gly Ala
    50                  55                  60

```
Glu Asn Met Lys Leu Glu Asp Ile Val Phe Glu Gly Phe Gly Gly Val
 65                  70                  75                  80

Tyr Cys Val Glu Ser Gly Gly Pro Glu Pro Gly Val Gly Cys Ala Gly
                 85                  90                  95

Arg Gly Val Ile Thr Ala Val Asp Met Leu Asn Arg Leu Gly Ala Phe
            100                 105                 110

Glu Glu Leu Lys Pro Asp Val Val Ile Tyr Asp Ile Leu Gly Asp Val
        115                 120                 125

Val Cys Gly Gly Phe Ala Met Pro Leu Gln Lys His Leu Ala Asp Asp
130                 135                 140

Val Tyr Ile Val Thr Thr Cys Asp Pro Met Ala Ile Tyr Ala Ala Asn
145                 150                 155                 160

Asn Ile Cys Lys Gly Ile Lys Arg Tyr Ala Ser Arg Gly Lys Ile Ala
                165                 170                 175

Leu Gly Gly Ile Ile Tyr Asn Gly Arg Ser Val Ile Asp Ala Pro Glu
            180                 185                 190

Ile Val Lys Asp Phe Ala Lys Lys Ile Gly Thr Gln Val Ile Gly Lys
        195                 200                 205

Ile Pro Met Ser Asn Ile Ile Thr Arg Ala Glu Ile Tyr Lys Lys Thr
210                 215                 220

Val Ile Glu Tyr Ala Pro Asp Ser Glu Ile Ala Asn Thr Phe Arg Glu
225                 230                 235                 240

Ile Ala Lys Ala Ile Tyr Glu Asn Glu Asn Arg Val Ile Pro Asn Pro
                245                 250                 255

Leu Ser Glu Glu Leu Asp Glu Ile Thr Glu Lys Ile Asp Val Leu
            260                 265                 270

Leu Lys Glu Ser Val Lys Gly
        275

<210> SEQ ID NO 66
<211> LENGTH: 272
<212> TYPE: PRT
<213> ORGANISM: Methanocella arvoryzae MRE50

<400> SEQUENCE: 66

Met Lys Gln Ser Thr Ser Gln Lys Gln Leu Ala Val Tyr Gly Lys Gly
 1               5                  10                  15

Gly Ile Gly Lys Ser Thr Thr Ala Ser Asn Met Ala Ala Ala Leu Gly
             20                  25                  30

Glu Met Gly Lys Lys Val Met Leu Ile Gly Cys Asp Pro Lys Ser Asp
         35                  40                  45

Ser Ser Ile Thr Leu Leu Gly Gly Arg Arg Ile Pro Thr Ile Met Asp
     50                  55                  60

Thr Val Arg Glu Arg Lys Asn Lys Ile Asp Gly Ile Lys Glu Glu Asp
 65                  70                  75                  80

Val Val Phe Glu Gly Phe Gly Val Arg Cys Thr Glu Val Gly Gly
                 85                  90                  95

Pro Glu Pro Gly Ile Gly Cys Ala Gly Arg Gly Ile Ile Val Ala Val
            100                 105                 110

Asp Val Leu Met Lys Asn Ser Thr Phe Met Lys Glu Ala Asp Val Leu
        115                 120                 125

Ile Phe Asp Val Pro Gly Asp Ile Val Cys Gly Gly Phe Ala Val Pro
130                 135                 140

Ile Thr Lys Lys Met Val Ser Glu Ala Tyr Ile Ile Thr Ser Gly Glu
```

```
            145                 150                 155                 160
Tyr Met Pro Leu Tyr Ala Ala Asn Asn Ile Cys Arg Gly Leu Asn Thr
                165                 170                 175

Leu Arg Thr Pro Leu Gly Gly Ile Ile Cys Asn Glu Arg Glu Ala Ala
                180                 185                 190

Asp Glu Lys Glu Ile Val Gly Arg Phe Ala Asp Ala Leu Gly Val Pro
                195                 200                 205

Leu Leu Ser Tyr Ile Pro Arg Ser Arg Ile Val Gln Gln Cys Glu Arg
210                 215                 220

Glu Gly Lys Thr Val Ile Glu Ala Ser Pro Asp Ser Gly Thr Ala Ser
225                 230                 235                 240

Ile Tyr Arg Gly Leu Ala Ala Lys Val Leu Met Glu Lys Asp Asn Lys
                245                 250                 255

Val Pro Glu Ala Leu Glu Asp Ala Tyr Leu Arg Glu Leu Thr Leu Leu
                260                 265                 270

<210> SEQ ID NO 67
<211> LENGTH: 264
<212> TYPE: PRT
<213> ORGANISM: Methanococcoides methylutens MM1

<400> SEQUENCE: 67

Met Thr Ile Gln Lys Arg Ile Ala Ile Tyr Gly Lys Gly Gly Ile Gly
1               5                   10                  15

Lys Ser Ser Thr Ala Ser Asn Val Ala Ala Cys Ala Asp Glu Gly
                20                  25                  30

Tyr Lys Val Met Ile Ile Gly Cys Asp Pro Lys Ser Asp Ser Ser Ile
                35                  40                  45

Thr Leu Leu Gly Gly Lys Arg Ile Pro Thr Ile Leu Asp Leu Leu Arg
                50                  55                  60

Asp Gly Val Asp Val Lys Glu Asp Val Ile His Glu Gly Tyr Lys
65                  70                  75                  80

Gly Val Lys Cys Val Glu Val Gly Gly Pro Glu Pro Gly Ile Gly Cys
                85                  90                  95

Ala Gly Arg Gly Ile Ile Val Ala Ile Gln Thr Leu Lys Lys Ile Ser
                100                 105                 110

Lys Ser Leu Asn Glu Met Asp Leu Ile Ile Tyr Asp Val Pro Gly Asp
                115                 120                 125

Ile Val Cys Gly Gly Phe Val Ala Pro Ile Arg Lys Gly Leu Val Lys
130                 135                 140

Glu Ala Tyr Val Leu Thr Ser Gly Glu Tyr Met Pro Leu Tyr Ala Ala
145                 150                 155                 160

Asn Asn Ile Cys Arg Gly Leu Ala Lys Ile Asn Thr Pro Leu Ser Gly
                165                 170                 175

Ile Ile Cys Asn Ser Arg Ser Val Arg Glu Glu Ile Val Thr
                180                 185                 190

Lys Phe Ala Ser Glu Ile Gly Ser Glu Leu Met Ala Phe Ile Pro Lys
                195                 200                 205

Glu Gln Ile Val Gln Asp Cys Glu Arg Asp Gly Phe Ser Val Met Glu
                210                 215                 220

Lys Ala Pro Asp Ser Asn Val Ala Lys Val Tyr Arg Lys Leu Ala Gln
225                 230                 235                 240

Ala Ile Met Glu Arg Asp Ser Val Met Pro Glu Ala Leu Asp Asp
                245                 250                 255
```

Glu Arg Leu Arg Glu Leu Thr Lys
            260

<210> SEQ ID NO 68
<211> LENGTH: 292
<212> TYPE: PRT
<213> ORGANISM: Methanococcus maripaludis C7

<400> SEQUENCE: 68

Met Lys Gln Ile Ala Phe Tyr Gly Lys Gly Gly Ile Gly Lys Ser Thr
1               5                   10                  15

Thr Val Cys Asn Leu Ala Ala Ala Leu Ser Lys Ser Gly Lys Lys Val
            20                  25                  30

Ile Val Val Gly Cys Asp Pro Lys His Asp Cys Thr Ser Asn Leu Arg
        35                  40                  45

Arg Gly Glu Asp Ile Pro Thr Val Leu Asp Val Leu Arg Glu Lys Gly
    50                  55                  60

Ile Asp Lys Leu Gly Ile Glu Thr Ile Ile Arg Glu Asn Leu Leu Lys
65                  70                  75                  80

Lys Glu Asp Ile Ile Tyr Glu Gly Phe Asn Gly Ile Tyr Cys Val Glu
                85                  90                  95

Ala Gly Gly Pro Lys Pro Gly Tyr Gly Cys Ala Gly Arg Gly Val Ile
            100                 105                 110

Val Val Ile Asp Leu Leu Lys Lys Met Asn Val Phe Glu Glu Leu Gly
        115                 120                 125

Val Asp Ile Val Ile Tyr Asp Val Leu Gly Asp Val Val Cys Gly Gly
    130                 135                 140

Phe Ala Met Pro Leu Arg Met Gly Leu Ala Asp Gln Ile Tyr Val Val
145                 150                 155                 160

Thr Ser Ser Asp Tyr Met Ala Leu Tyr Ala Ala Asn Asn Ile Cys Asn
                165                 170                 175

Gly Ile Ser Gln Phe Val Lys Arg Gly Gly Ser Thr Leu Gly Gly Ile
            180                 185                 190

Val Tyr Asn Val Arg Gly Ser Met Asp Ala Phe Asp Ile Val Ser Glu
        195                 200                 205

Phe Ala Ser Gln Leu Asn Ala Asn Ile Ile Gly Lys Val Pro Asn Ser
    210                 215                 220

Ser Ile Ile Asn Glu Ala Glu Ile Asp Gly Gln Thr Ala Ile Glu Tyr
225                 230                 235                 240

Ala Pro Glu Glu Glu Ile Ser Lys Ile Tyr Met Glu Leu Ala Glu Thr
                245                 250                 255

Ile Tyr Lys Asn Asn Thr Gly Thr Thr Pro Lys Pro Leu Glu Asn Ala
            260                 265                 270

Gln Ile Met Gln Ile Gly Lys Met Ile Lys Glu Arg Ile Lys Lys Gln
        275                 280                 285

Lys Thr Val Glu
    290

<210> SEQ ID NO 69
<211> LENGTH: 268
<212> TYPE: PRT
<213> ORGANISM: Methanocorpusculum labreanum Z

<400> SEQUENCE: 69

Met Arg Gln Ile Ala Leu Tyr Gly Lys Gly Gly Ile Gly Lys Ser Thr
1               5                   10                  15

Thr Ser Ala Asn Leu Ser Ala Ala Phe Ser Glu Met Asp Leu Asp Val
            20                  25                  30

Met Gln Ile Gly Cys Asp Pro Lys His Asp Ser Thr Arg Met Leu Met
        35                  40                  45

His Gly Arg Trp Ile Pro Thr Val Leu Glu Gln Met Tyr Asp His Lys
    50                  55                  60

Glu Ile Lys Ser Glu Asp Ile Ile Tyr Gln Gly Phe Gly Asn Ile Arg
65                  70                  75                  80

Cys Val Glu Ala Gly Gly Pro Glu Pro Gly Ile Gly Cys Ala Gly Arg
                85                  90                  95

Gly Ile Ile Ala Thr Phe Gln Leu Leu Glu Lys Met Asp Ala Leu Tyr
            100                 105                 110

Gly Asp Val Val Val Tyr Asp Val Leu Gly Asp Val Val Cys Gly Gly
            115                 120                 125

Phe Ala Met Pro Met Arg Asp Gly Tyr Ala Gln Glu Val Tyr Leu Val
    130                 135                 140

Thr Ser Gly Glu Leu Met Ser Leu Tyr Ala Ala Asn Asn Ile Cys Lys
145                 150                 155                 160

Ala Ile Ala Arg Ile Ser Glu Arg Ser Thr Ala Lys Cys Arg Leu Gly
                165                 170                 175

Gly Val Ile Cys Asn Ala Lys Asn Met Asp Asn Glu Arg Glu Leu Val
            180                 185                 190

Glu Glu Phe Ala Lys Arg Ile Gly Ser Arg Leu Val Cys Tyr Ile Pro
        195                 200                 205

Arg Ser Lys Ser Val Arg Ala Ala Glu Val Asn Cys Met Thr Val Ile
    210                 215                 220

Glu His Asp Pro Thr Ser Glu Gln Ala Ala Val Tyr Arg Asp Cys Ala
225                 230                 235                 240

Lys Thr Ile Leu Glu Asn Thr Asp Leu Arg Ile Pro Thr Pro Leu Ala
                245                 250                 255

Leu Glu Glu Leu Glu Glu Leu Ala Arg His Tyr Leu
            260                 265

<210> SEQ ID NO 70
<211> LENGTH: 272
<212> TYPE: PRT
<213> ORGANISM: Methanoculleus bourgensis MS2

<400> SEQUENCE: 70

Met Lys Gln Ile Ala Leu Tyr Gly Lys Gly Gly Ile Gly Lys Ser Thr
1               5                   10                  15

Thr Ala Ala Asn Leu Ser Ala Ala Leu Ala Glu Glu Gly Leu Asp Ile
            20                  25                  30

Leu Gln Ile Gly Cys Asp Pro Lys His Asp Ser Thr Arg Met Leu Met
        35                  40                  45

His Gly Thr Trp Ile Pro Thr Val Leu Asp Leu Ile Arg Glu Arg Gly
    50                  55                  60

Asp Glu Asn Ile Thr Val Asp Asp Val Val Tyr Gln Gly Phe Arg Gly
65                  70                  75                  80

Val Arg Cys Val Glu Ala Gly Gly Pro Glu Pro Gly Ile Gly Cys Ala
                85                  90                  95

Gly Arg Gly Ile Ile Ala Thr Phe Gln Leu Leu Glu Arg Leu Asp Ala
            100                 105                 110

Leu Lys Gly Asp Val Ile Val Tyr Asp Val Leu Gly Asp Val Val Cys
            115                 120                 125

Gly Gly Phe Ala Met Pro Met Arg Glu Gly Tyr Ala Gln Glu Ile Tyr
            130                 135                 140

Leu Val Thr Ser Gly Glu Leu Met Ser Ile Tyr Ala Ala Asn Asn Ile
145                 150                 155                 160

Ala Lys Ala Ile Ala Arg Leu Ser Arg Arg Ala Arg Ser Arg Cys Thr
                165                 170                 175

Leu Gly Gly Val Ile Cys Asn Ala Lys Asn Ile Glu Gly Glu Arg Asp
            180                 185                 190

Leu Val Ala Glu Phe Ala Arg Arg Ile Asn Ser Arg Leu Ile Ala Tyr
        195                 200                 205

Ile Pro Arg Ser Arg Asp Val Gln Val Ala Glu Leu His Arg Gln Thr
    210                 215                 220

Val Val Glu Tyr Ala Pro Glu Ser Asp Gln Ala Ala Val Tyr Arg Glu
225                 230                 235                 240

Leu Gly Arg Thr Val Tyr Gly Asn Gln Lys Thr Ser Ile Pro Thr Pro
                245                 250                 255

Leu Glu Met Asp Glu Leu Glu Ser Phe Ala Phe Glu Phe Val Gln Val
            260                 265                 270

<210> SEQ ID NO 71
<211> LENGTH: 276
<212> TYPE: PRT
<213> ORGANISM: Methanofollis liminatans DSM 4140

<400> SEQUENCE: 71

Met Arg Asp Asp Met Lys Gln Ile Ala Leu Tyr Gly Lys Gly Gly Ile
1               5                   10                  15

Gly Lys Ser Thr Thr Ser Ala Asn Leu Ser Ala Ala Leu Gly Glu Thr
            20                  25                  30

Gly Leu Asp Ile Leu Gln Ile Gly Cys Asp Pro Lys His Asp Ser Thr
        35                  40                  45

Arg Met Leu Met His Gly Ala Trp Ile Pro Thr Val Leu Asp Leu Val
    50                  55                  60

Arg Glu Arg Gly Asp Ala Ala Ile Ala Thr Asp Asp Val Val Phe Asn
65                  70                  75                  80

Gly Tyr Ala Gly Val Arg Cys Val Glu Ala Gly Pro Glu Pro Gly
                85                  90                  95

Ile Gly Cys Ala Gly Arg Gly Ile Ile Ala Thr Phe Gln Leu Leu Glu
            100                 105                 110

Arg Leu Gly Ala Leu Asn Gly Asp Val Ile Val Tyr Asp Val Leu Gly
        115                 120                 125

Asp Val Val Cys Gly Gly Phe Ala Met Pro Met Arg Glu Gly Tyr Ala
    130                 135                 140

Glu Glu Val Tyr Leu Ile Thr Ser Gly Glu Leu Met Ser Leu Tyr Ala
145                 150                 155                 160

Ala Asn Asn Ile Ala Lys Ala Ile Ala Arg Leu Ala Lys Arg Ser Arg
                165                 170                 175

Gln Thr Cys Ala Leu Ala Gly Val Ile Cys Asn Ser Lys Asn Met Glu
            180                 185                 190

Gly Glu Glu Asp Leu Val Arg Glu Phe Ala Ala Arg Ile Asn Ser Ala
        195                 200                 205

Met Val Ala Tyr Ile Pro Arg Ser Arg Thr Val Thr Leu Ala Glu Leu
    210                 215                 220

Asn Arg Gln Thr Val Met Glu Tyr Ala Pro Glu Ser Glu Gln Ala Gly

```
            225                 230                 235                 240
Val Tyr Arg Arg Leu Ala Glu Asp Ile Met Lys Asn Thr Arg Thr Ser
                245                 250                 255
Ile Pro Thr Pro Leu Glu Ile Asp Glu Leu Glu Glu Leu Ala Arg Arg
                260                 265                 270
Phe Ala Gln Val
            275

<210> SEQ ID NO 72
<211> LENGTH: 293
<212> TYPE: PRT
<213> ORGANISM: Methanohalobium evestigatum Z-7303

<400> SEQUENCE: 72

Met Asn Asn Lys Thr Asn Asp Asn Asn Gln Lys Gln Lys Arg Ile Ala
1               5                   10                  15
Leu Tyr Gly Lys Gly Gly Ile Gly Lys Ser Ser Thr Ala Ser Asn Val
                20                  25                  30
Ala Ala Ala Cys Ala Asp Glu Gly Tyr Lys Val Met Ile Ile Gly Cys
                35                  40                  45
Asp Pro Lys Ser Asp Ser Ser Ile Thr Leu Leu Gly Gly Lys Arg Ile
            50                  55                  60
Pro Thr Ile Leu Asp Leu Leu Arg Asp Gly Glu Gly Leu Asn Glu Glu
65                  70                  75                  80
Asp Val Val Phe Glu Gly Tyr Asn Gly Val Lys Cys Val Glu Val Gly
                85                  90                  95
Gly Pro Glu Pro Gly Ile Gly Cys Ala Gly Arg Gly Ile Ile Val Ala
                100                 105                 110
Ile Asn Gln Leu Lys Arg Ile Ser Asp Ser Met Lys Glu Met Asp Leu
            115                 120                 125
Ile Ile Tyr Asp Val Pro Gly Asp Ile Val Cys Gly Gly Phe Val Ala
130                 135                 140
Pro Val Arg Lys Gly Met Val Asn Glu Ser Tyr Ile Ile Thr Ser Gly
145                 150                 155                 160
Glu Tyr Met Pro Met Tyr Ala Ala Asn Asn Ile Cys Ser Gly Leu Ser
                165                 170                 175
Lys Ile Asn Thr Pro Leu Asn Gly Ile Val Cys Asn Ser Arg Asp Val
                180                 185                 190
Thr Asn Glu Lys Glu Ile Val Glu Glu Phe Ala His Glu Ile Gly Ser
            195                 200                 205
Glu Leu Leu Ser Phe Ile Pro Lys Glu Gln Ile Val Gln Asp Cys Glu
        210                 215                 220
Arg Glu Gly Tyr Ser Val Met Asp Ile Ala Pro Asp Ser Lys Ile Ala
225                 230                 235                 240
Gln Val Tyr Arg Glu Leu Ala Gln Lys Ile Met Ser Lys Thr Glu Pro
                245                 250                 255
Asp Ser Val Leu Pro Asn Ser Met Asp Asp Glu Gln Leu Arg Glu Leu
                260                 265                 270
Ala Arg Lys Gln Ser Lys Gln Glu Thr Lys Ser Cys His Asn Lys Lys
            275                 280                 285
Thr Ile Arg Thr Glu
        290

<210> SEQ ID NO 73
<211> LENGTH: 265
```

<212> TYPE: PRT
<213> ORGANISM: Methanohalophilus mahii DSM 5219

<400> SEQUENCE: 73

Met Asn Pro Gln Lys Arg Ile Ala Ile Tyr Gly Lys Gly Gly Ile Gly
1               5                   10                  15

Lys Ser Ser Thr Ala Ser Asn Val Ala Ala Cys Ala Asp Glu Gly
            20                  25                  30

Tyr Asn Val Met Ile Ile Gly Cys Asp Pro Lys Ser Asp Ser Ser Ile
                35                  40                  45

Thr Leu Leu Gly Gly Lys Arg Ile Pro Thr Ile Leu Asp Leu Leu Arg
    50                  55                  60

Glu Gly Met Glu Ile Glu Glu Gly Asp Val Val Phe Glu Gly Tyr
65              70                  75                  80

Lys Ala Val Lys Cys Val Glu Val Gly Pro Glu Pro Gly Ile Gly
                85                  90                  95

Cys Ala Gly Arg Gly Ile Ile Val Ala Ile Gln Lys Leu Lys Lys Ile
            100                 105                 110

Ser Gln Ser Met Lys Glu Met Asp Leu Ile Ile Tyr Asp Val Pro Gly
        115                 120                 125

Asp Ile Val Cys Gly Gly Phe Val Ala Pro Ile Arg Lys Gly Leu Val
    130                 135                 140

Asn Glu Ala Tyr Val Leu Thr Ser Gly Glu Tyr Met Pro Leu Tyr Ala
145                 150                 155                 160

Ala Asn Asn Ile Cys Lys Gly Leu Ser Arg Ile Asn Thr Lys Leu Ser
                165                 170                 175

Gly Val Ile Cys Asn Ser Arg Ser Val Ser Arg Glu Lys Glu Ile Val
            180                 185                 190

Ser Lys Phe Ala Asn Glu Ile Gly Ser Glu Leu Val Ala Phe Ile Pro
        195                 200                 205

Lys Glu Gln Ile Val Gln Asp Cys Gly Arg Asp Gly Tyr Ser Val Leu
    210                 215                 220

Glu Lys Ala Gly Gly Thr Asp Ile Ala Glu Val Tyr Arg Ala Leu Ala
225                 230                 235                 240

Arg Asn Ile Met Ser Ser Asp Cys Ala Val Asp Pro Arg Ala Leu Thr
                245                 250                 255

Asp Glu Arg Leu Arg Glu Leu Thr Arg
            260                 265

<210> SEQ ID NO 74
<211> LENGTH: 274
<212> TYPE: PRT
<213> ORGANISM: Methanolacinia petrolearia DSM 11571

<400> SEQUENCE: 74

Met Lys Gln Ile Ala Leu Tyr Gly Lys Gly Gly Ile Gly Lys Ser Thr
1               5                   10                  15

Thr Ser Ala Asn Leu Ser Ala Ala Leu Ser Glu Lys Ser Leu Glu Ile
            20                  25                  30

Leu Gln Ile Gly Cys Asp Pro Lys His Asp Ser Thr Arg Met Leu Met
        35                  40                  45

His Gly Glu Trp Ile Pro Thr Val Leu Asp Leu Val Arg Lys Lys Gly
    50                  55                  60

Glu Ala Asn Ile Ala Val Asp Glu Ile Val Phe Lys Gly Tyr Asn Gly
65                  70                  75                  80

```
Ile Arg Cys Val Glu Ala Gly Gly Pro Glu Pro Gly Ile Gly Cys Ala
                85                  90                  95

Gly Arg Gly Ile Ile Ala Thr Phe Gln Leu Leu Glu Lys Leu Asn Ala
            100                 105                 110

Leu Tyr Gly Asp Val Ile Val Tyr Asp Val Leu Gly Asp Val Val Cys
            115                 120                 125

Gly Gly Phe Ala Met Pro Met Arg Glu Gly Tyr Ala Gln Glu Val Tyr
130                 135                 140

Leu Val Thr Ser Gly Asp Phe Met Ala Leu Tyr Ala Ala Asn Asn Ile
145                 150                 155                 160

Cys Lys Ala Ile Ala Arg Leu Ser Lys Arg Thr Lys Asn Arg Cys Thr
                165                 170                 175

Leu Gly Gly Val Ile Cys Asn Ser Ala Asn Ile Glu Asn Glu Tyr Glu
            180                 185                 190

Leu Val Lys Glu Phe Ala Glu Lys Ile Asn Ser Lys Leu Val Ala Tyr
            195                 200                 205

Ile Pro Arg Ser Pro Ile Val Arg Val Ser Glu Val Asn Arg Lys Thr
            210                 215                 220

Val Ile Glu Tyr Ala Pro Glu Ser Glu Gln Ala Asp Ile Tyr Arg Lys
225                 230                 235                 240

Leu Ala Asp Thr Ile Met Glu Asn Val Pro Asp Lys Asn Arg Ile Pro
                245                 250                 255

Val Pro Met Glu Met Asp Glu Leu Glu Ser Leu Ser Leu Lys Tyr Ile
                260                 265                 270

Lys Thr

<210> SEQ ID NO 75
<211> LENGTH: 264
<212> TYPE: PRT
<213> ORGANISM: Methanolobus psychrophilus R15

<400> SEQUENCE: 75

Met Lys Asp Gln Lys Arg Ile Ala Ile Tyr Gly Lys Gly Gly Ile Gly
1               5                   10                  15

Lys Ser Ser Thr Ala Ser Asn Val Ala Ala Ala Cys Ala Asp Glu Gly
            20                  25                  30

Tyr Lys Val Met Ile Ile Gly Cys Asp Pro Lys Ser Asp Ser Ser Ile
            35                  40                  45

Thr Leu Leu Gly Gly Lys Arg Ile Pro Thr Ile Leu Asp Leu Leu Lys
50                  55                  60

Gln His Leu Asp Val Asn Glu Lys Asp Ile Val Phe Glu Gly Tyr Gly
65                  70                  75                  80

Gly Val Lys Cys Val Glu Val Gly Gly Pro Glu Pro Gly Ile Gly Cys
                85                  90                  95

Ala Gly Arg Gly Ile Ile Val Ala Ile Gln Lys Leu Gln Lys Val Cys
            100                 105                 110

Pro Ser Met Asn Asp Met Asp Leu Ile Ile Tyr Asp Val Pro Gly Asp
            115                 120                 125

Ile Val Cys Gly Gly Phe Val Ala Pro Ile Arg Lys Gly Leu Val Thr
130                 135                 140

Glu Ala Tyr Ile Leu Thr Ser Gly Glu Tyr Met Pro Leu Tyr Ala Ala
145                 150                 155                 160

Asn Asn Ile Cys Lys Gly Leu Ala Lys Ile Asp Thr Pro Leu Ser Gly
                165                 170                 175
```

```
Ile Ile Cys Asn Ser Arg Ser Val Thr Arg Glu Glu Ile Val Arg
            180                 185                 190

Lys Phe Ser Glu Glu Ile Gly Ser Arg Leu Val Ala Phe Ile Pro Lys
        195                 200                 205

Glu Gln Val Val Gln Asp Cys Glu Arg Asp Gly Phe Ser Val Leu Glu
    210                 215                 220

Lys Ala Pro Lys Ser Asp Ile Ala Gln Val Tyr Arg Asp Leu Ala Lys
225                 230                 235                 240

Ser Ile Met Phe Asn Asp Gln Ser Ile Leu Pro Gly Ser Leu Asp Asp
                245                 250                 255

Glu Arg Leu Arg Glu Leu Thr Arg
            260
```

<210> SEQ ID NO 76
<211> LENGTH: 259
<212> TYPE: PRT
<213> ORGANISM: Methanomassiliicoccus luminyensis B10

<400> SEQUENCE: 76

```
Met Arg Gln Ile Ala Val Tyr Gly Lys Gly Gly Ile Gly Lys Ser Thr
1               5                   10                  15

Val Ser Ala Asn Val Cys Ala Ala Leu Ala Glu Ser Gly Leu Lys Val
            20                  25                  30

Trp Tyr Ile Gly Cys Asp Pro Lys Ser Asp Gly Ser Met Thr Leu Leu
        35                  40                  45

Gly Gly Arg Lys Ile Pro Thr Phe Leu Glu Gln Arg Lys Glu Gly Arg
    50                  55                  60

Thr Glu Ala Val Phe Glu Gly Phe His Gly Ile Lys Cys Val Glu Thr
65                  70                  75                  80

Gly Gly Pro Leu Ala Gly Val Gly Cys Ala Gly Arg Gly Ile Ile Val
                85                  90                  95

Ala Val Gly Glu Leu Ser Arg Ser Tyr Phe Arg Glu Ser Asp Asp Val
            100                 105                 110

Leu Ile Tyr Asp Val Pro Gly Asp Val Val Cys Gly Gly Phe Ala Ala
        115                 120                 125

Pro Leu Arg Glu Lys Phe Ala Asn Glu Val Tyr Ile Val Thr Ser Gly
    130                 135                 140

Glu Tyr Leu Ala Leu Tyr Ala Ala Asn Ile Ala Lys Gly Leu Ala
145                 150                 155                 160

Asn Leu Asp Val Pro Leu Gly Gly Ile Ile Cys Asn Ser Arg Glu Val
                165                 170                 175

Ala Asn Glu Glu Ala Ile Val Lys Glu Phe Ala Thr Arg Ile Gly Ser
            180                 185                 190

Gln Leu Ile Gly Phe Val Pro Arg Ser Ala Val Val Arg Glu Cys Glu
        195                 200                 205

Asn Gln Gly Met Thr Val Ile Glu His Ala Pro Asp Asp Ser Gln Ala
    210                 215                 220

Gly Ala Tyr Arg Arg Leu Gly Gly Ala Ile Met Ser Asn Arg Gln Leu
225                 230                 235                 240

Ala Val Pro Ser Pro Met Asp Pro Glu Asn Ile Arg Ala Leu Leu Arg
                245                 250                 255

Glu Met Ser
```

<210> SEQ ID NO 77
<211> LENGTH: 264

```
<212> TYPE: PRT
<213> ORGANISM: Methanomethylovorans hollandica DSM 15978

<400> SEQUENCE: 77
```

Met Lys Lys Gln Lys Arg Ile Ala Ile Tyr Gly Lys Gly Ile Gly
1               5                   10                  15

Lys Ser Ser Thr Ala Ser Asn Val Ala Ala Cys Ala Glu Glu Gly
            20                  25                  30

Tyr Lys Val Met Ile Ile Gly Cys Asp Pro Lys Ser Asp Ser Ser Ile
        35                  40                  45

Thr Leu Leu Gly Gly Arg Arg Ile Pro Thr Ile Leu Asp Leu Leu Arg
    50                  55                  60

Gln Gly Val Lys Val Lys Glu Glu Asp Ile Val Phe His Gly Tyr Arg
65                  70                  75                  80

Asn Val Arg Cys Val Glu Val Gly Gly Pro Glu Pro Gly Ile Gly Cys
                85                  90                  95

Ala Gly Arg Gly Ile Ile Val Ala Ile Lys Thr Leu Arg Asp Met Cys
            100                 105                 110

Lys Glu Met Asp Asp Met Asp Leu Ile Ile Tyr Asp Val Pro Gly Asp
        115                 120                 125

Ile Val Cys Gly Gly Phe Val Ala Pro Ile Lys Lys Gly Leu Val Asn
    130                 135                 140

Asp Ala Tyr Val Leu Thr Ser Gly Glu Tyr Met Pro Leu Tyr Ala Ala
145                 150                 155                 160

Asn Asn Ile Cys Lys Gly Leu Ser Lys Ile Asp Thr Arg Leu Ser Gly
                165                 170                 175

Val Ile Cys Asn Ser Arg Ser Val Thr Arg Glu Glu Ile Val Ser
            180                 185                 190

Arg Phe Ala Glu Glu Ile Gly Ser Lys Leu Val Ala Phe Ile Pro Lys
        195                 200                 205

Glu Gln Ile Val Gln Asp Cys Glu Arg Asp Gly Phe Ser Val Leu Glu
    210                 215                 220

Lys Ala Pro Val Ser Asp Ile Ala Gln Val Tyr Arg Asp Leu Ala Arg
225                 230                 235                 240

Thr Ile Met Ser Asn Ala Asp Ser Ser Leu Pro Lys Ser Leu Glu Asp
                245                 250                 255

Glu Arg Leu Arg Glu Leu Thr Arg
            260

```
<210> SEQ ID NO 78
<211> LENGTH: 273
<212> TYPE: PRT
<213> ORGANISM: Methanomicrobium mobile BP

<400> SEQUENCE: 78
```

Met Lys Gln Ile Ala Leu Tyr Gly Lys Gly Ile Gly Lys Ser Thr
1               5                   10                  15

Thr Ser Ala Asn Leu Ser Ala Ala Leu Ser Glu Lys Asn Leu Ser Ile
            20                  25                  30

Met Gln Ile Gly Cys Asp Pro Lys His Asp Ser Thr Arg Met Leu Met
        35                  40                  45

Gly Gly Arg Trp Ile Pro Thr Val Leu Asp Thr Ile Arg Asp Lys Gly
    50                  55                  60

Glu Glu Ile Asn Ala Asp Glu Ile Val Phe Ala Gly Tyr Asn Asn Ile
65                  70                  75                  80

```
Arg Cys Val Glu Ala Gly Gly Pro Glu Pro Gly Val Gly Cys Ala Gly
                85                  90                  95

Arg Gly Ile Ile Ala Thr Phe Gln Leu Leu Glu Lys Leu Asp Ala Leu
            100                 105                 110

Tyr Gly Asp Val Ile Val Tyr Asp Val Leu Gly Asp Val Val Cys Gly
            115                 120                 125

Gly Phe Ala Met Pro Met Arg Glu Gly Tyr Ala Arg Glu Val Tyr Leu
130                 135                 140

Val Thr Ser Gly Asp Phe Met Ala Leu Tyr Ala Ala Asn Asn Ile Ser
145                 150                 155                 160

Lys Ala Ile Ala Arg Leu Ser Asn Arg Ser Arg Asn Phe Cys Ser Leu
                165                 170                 175

Gly Gly Val Ile Cys Asn Ser Gln Asn Ile Glu Gly Glu Leu Glu Leu
            180                 185                 190

Val Ser Glu Phe Ala Gln Met Ile Asn Ser Gln Leu Ile Gly Phe Ile
            195                 200                 205

Pro Arg Ser Gln Ile Val Arg Val Ala Glu Val Asn Lys Lys Thr Val
            210                 215                 220

Leu Glu Tyr Ala Pro Glu Ser Glu Gln Ala Gly Ile Tyr Arg Thr Ile
225                 230                 235                 240

Ala Asp Arg Ile Met Gln Asn Ser Pro Asp Val Thr Lys Lys Pro Thr
                245                 250                 255

Pro Leu Thr Met Asp Glu Leu Glu Glu Leu Ala Gln Lys His Ile Lys
                260                 265                 270

Ala

<210> SEQ ID NO 79
<211> LENGTH: 274
<212> TYPE: PRT
<213> ORGANISM: Methanoplanus limicola DSM 2279

<400> SEQUENCE: 79

Met Lys Gln Ile Ala Leu Tyr Gly Lys Gly Gly Ile Gly Lys Ser Thr
1               5                   10                  15

Thr Ser Ala Asn Leu Ser Ala Ala Leu Ser Glu Lys Asn Leu Asp Ile
            20                  25                  30

Leu Gln Ile Gly Cys Asp Pro Lys His Asp Ser Thr Arg Met Leu Met
            35                  40                  45

Arg Gly Glu Trp Ile Pro Thr Val Leu Asp Leu Ile Arg Glu Asn Gly
50                  55                  60

Glu Asn Asn Leu Thr Thr Glu Glu Ile Val Tyr Lys Gly Tyr Asn Asn
65                  70                  75                  80

Ile Arg Cys Val Glu Ala Gly Gly Pro Glu Pro Gly Ile Gly Cys Ala
                85                  90                  95

Gly Arg Gly Ile Ile Ala Thr Phe Gln Leu Leu Glu Lys Leu Glu Ala
            100                 105                 110

Leu Tyr Gly Asp Ile Ile Val Tyr Asp Val Leu Gly Asp Val Val Cys
            115                 120                 125

Gly Gly Phe Ala Met Pro Met Arg Glu Gly Tyr Ala Gln Glu Val Tyr
130                 135                 140

Leu Val Thr Ser Gly Asp Phe Met Ala Leu Tyr Ala Ala Asn Asn Ile
145                 150                 155                 160

Cys Lys Ala Ile Ala Arg Leu Ser Lys Arg Ser Lys Asn Arg Cys Arg
                165                 170                 175
```

```
Leu Ala Gly Val Ile Cys Asn Ser Ala Asn Ile Glu Gly Arg Glu
            180                 185                 190

Leu Val Glu Glu Phe Ala Arg Ser Ile Asn Ser Glu Met Ile Ala Phe
        195                 200                 205

Ile Pro Arg Ser Lys Thr Val Arg Val Ser Glu Val Asn Lys Arg Thr
    210                 215                 220

Val Leu Glu Tyr Ala Pro Glu Ser Glu Gln Ala Glu Val Tyr Arg Glu
225                 230                 235                 240

Leu Ala Asp Lys Ile Ile Asn Asn Arg Pro Ala Ala Asp Lys Thr Pro
                245                 250                 255

Thr Pro Leu Glu Met Asp Glu Leu Glu Ala Leu Ala Leu Arg Tyr Ile
            260                 265                 270

Lys Ala

<210> SEQ ID NO 80
<211> LENGTH: 266
<212> TYPE: PRT
<213> ORGANISM: Methanopyrus kandleri AV19

<400> SEQUENCE: 80

Met Lys Arg Ile Ala Val Tyr Gly Lys Gly Gly Ile Gly Lys Ser Thr
1               5                   10                  15

Ile Ala Ala Asn Val Ala Ala Ala Leu Ala Glu Glu Gly Tyr Arg Val
            20                  25                  30

Met Leu Val Gly Cys Asp Pro Lys Ala Asp Ser Thr Leu Thr Leu Ala
        35                  40                  45

Gly Arg Arg Ile Pro Thr Val Met His Glu Tyr Arg Arg Lys Gly Glu
    50                  55                  60

Gly Leu Lys Leu Glu Asp Ile Ile Val Glu Gly Asp Phe Gly Val Leu
65                  70                  75                  80

Cys Val Glu Ser Gly Gly Pro Lys Pro Gly Val Gly Cys Ala Gly Arg
                85                  90                  95

Gly Val Leu Lys Ala Leu Glu Met Leu Thr Arg Met Gly Ala Phe Glu
            100                 105                 110

Asp Val Asp Val Val Ile Phe Asp Val Leu Gly Asp Val Val Cys Gly
        115                 120                 125

Gly Phe Ala Leu Pro Ile Arg Arg Gly Tyr Ala Asp Thr Val Phe Val
    130                 135                 140

Val Thr Ser Ser Glu Pro Met Ser Leu Tyr Ala Ala Asn Asn Ile Cys
145                 150                 155                 160

Arg Gly Ile Ala Glu Tyr Ala Asp Arg Gly Ala Lys Leu Gly Gly
                165                 170                 175

Val Ile His Asn Arg Arg Ser Arg Asp Ser Asp Ser Arg Val Val Thr
            180                 185                 190

Glu Phe Cys Arg Arg Ile Arg Ala Glu Leu Ile Tyr Asp Leu Phe Tyr
        195                 200                 205

Met Glu Glu Val Arg Lys Ala Glu Ser Arg Tyr Arg Thr Val Ile Arg
    210                 215                 220

Glu Phe Pro Asp Ser Asp Ala Ala Glu Ala Phe Arg Glu Leu Ala His
225                 230                 235                 240

Arg Met Leu Glu Thr Glu Gly Val Val Pro Gln Pro Leu Glu Glu Glu
                245                 250                 255

Glu Val Leu Arg Leu Ala Gly Val Arg Phe
            260                 265
```

```
<210> SEQ ID NO 81
<211> LENGTH: 270
<212> TYPE: PRT
<213> ORGANISM: Methanoregula formicica SMSP

<400> SEQUENCE: 81

Met Lys Gln Ile Ala Leu Tyr Gly Lys Gly Gly Ile Gly Lys Ser Thr
1               5                   10                  15

Thr Ser Ala Asn Leu Ser Ala Ala Leu Ser His Arg Asp Leu Ser Val
            20                  25                  30

Leu Gln Ile Gly Cys Asp Pro Lys Arg Asp Ser Thr Arg Met Leu Met
        35                  40                  45

Gln Gly Arg Phe Ile Pro Thr Val Met Asp Leu Val Arg Val Arg Gly
    50                  55                  60

Asp Ala Asn Val Ser Leu Lys Asp Val Val Phe Thr Gly Tyr Asn Gly
65                  70                  75                  80

Ile Arg Cys Val Glu Ala Gly Gly Pro Glu Pro Gly Val Gly Cys Ala
                85                  90                  95

Gly Arg Gly Ile Ile Ala Thr Phe Gln Leu Leu Glu Lys Phe Gly Ala
            100                 105                 110

Leu Asp Gly Asp Val Ile Val Tyr Asp Val Leu Gly Asp Val Val Cys
        115                 120                 125

Gly Gly Phe Ala Met Pro Met Arg Glu Gly Tyr Ala Gln Glu Ile Tyr
    130                 135                 140

Leu Val Thr Ser Gly Glu Leu Met Ser Leu Tyr Ala Ala Asn Asn Ile
145                 150                 155                 160

Cys Lys Ala Val Gln Arg Leu Ala Ser Arg Val Lys Ser Lys Cys Arg
                165                 170                 175

Leu Gly Gly Val Ile Cys Asn Ala Lys Gly Gln Pro Arg Glu Glu Glu
            180                 185                 190

Leu Val Ser Glu Phe Ala Arg Arg Val Asn Ser Thr Met Val Gln Tyr
        195                 200                 205

Ile Pro Arg Asp His Val Val Gln Gln Ala Glu Val Asn Arg Gln Thr
    210                 215                 220

Val Ile Glu Phe Ala Pro Asp Ser Pro Gln Ala Gly His Tyr Arg Ser
225                 230                 235                 240

Leu Ala Gly Arg Ile Val Glu Asn Thr Asn Leu Ser Ile Pro Thr Pro
                245                 250                 255

Leu Glu Thr Asp Asp Leu Glu Ser Leu Ala Arg Glu Phe Leu
            260                 265                 270

<210> SEQ ID NO 82
<211> LENGTH: 271
<212> TYPE: PRT
<213> ORGANISM: Methanosaeta concilii GP6

<400> SEQUENCE: 82

Met Ser Ser Ile Lys His Val Ala Ile Tyr Gly Lys Gly Gly Ile Gly
1               5                   10                  15

Lys Ser Cys Thr Ala Ser Asn Ile Ala Ala Ala Cys Ala Glu Glu Gly
            20                  25                  30

His Lys Val Leu Met Val Gly Cys Asp Pro Lys Ser Asp Ser Ser Ile
        35                  40                  45

Thr Leu Ile Gly Arg Arg Ile Pro Thr Met Met Asp Leu Ile Leu Lys
    50                  55                  60
```

```
Gly Gly Glu Phe Lys Glu Asp Val Val His Gln Gly Phe Arg Gly
65                  70                  75                  80

Val Arg Cys Ile Glu Val Gly Pro Glu Pro Gly Val Gly Cys Ala
                85                  90                  95

Gly Arg Gly Ile Ile Val Ala Ile Asp Phe Leu Arg Lys Val Ser Lys
            100                 105                 110

Ala Met Glu Glu Val Asp Leu Val Leu Tyr Asp Val Pro Gly Asp Ile
            115                 120                 125

Val Cys Gly Gly Phe Ser Ala Pro Ile Arg Lys Gly Leu Val Ser Gln
        130                 135                 140

Ala Tyr Ile Ile Thr Ser Gly Glu Tyr Met Pro Leu Tyr Ala Ala Asn
145                 150                 155                 160

Asn Ile Ser Lys Gly Leu Leu Arg Leu Asn Thr Pro Leu Ala Gly Val
                165                 170                 175

Ile Cys Asn Ser Arg Glu Ala Ala Gly Glu Arg Glu Arg Glu Ile Val
            180                 185                 190

Asn Gln Phe Ala Gln Glu Leu Asn Ser Arg Met Val Ala Phe Ile Pro
        195                 200                 205

Lys Glu Pro Ile Val Gln Gln Cys Glu Arg Arg Thr Val Thr Val Ile
    210                 215                 220

Glu Gly Ala Pro Asp Ser Lys Ile Ala Ala Val Tyr Arg Ala Leu Ala
225                 230                 235                 240

Arg Glu Ile Met Ser Gly Gly Glu Ala Arg Ile Pro Glu Pro Leu Ser
                245                 250                 255

Asp Glu Arg Leu Arg Glu Leu Ser Arg Asp Leu Gly Ser Glu Glu
            260                 265                 270

<210> SEQ ID NO 83
<211> LENGTH: 264
<212> TYPE: PRT
<213> ORGANISM: Methanosalsum zhilinae DSM 4017

<400> SEQUENCE: 83

Met Lys Asn Arg Lys Ile Ile Ala Ile Tyr Gly Lys Gly Gly Ile Gly
1               5                   10                  15

Lys Ser Ser Thr Ala Ser Asn Ile Ala Ala Ala Cys Ala Asp Glu Gly
                20                  25                  30

Tyr Lys Val Met Ile Ile Gly Cys Asp Pro Lys Ser Asp Ser Ser Ile
            35                  40                  45

Asn Leu Leu Gly Gly Gln Arg Ile Pro Thr Ile Met Gly Leu Leu Arg
        50                  55                  60

Glu Ser Val Asp Ile Gln Glu Asp Ile Ile Phe Glu Gly Tyr Asn
65                  70                  75                  80

Gly Val Lys Cys Val Glu Val Gly Pro Glu Pro Gly Ile Gly Cys
                85                  90                  95

Ala Gly Arg Gly Ile Ile Val Ala Ile Gln Lys Leu Lys Ser Val Ser
            100                 105                 110

Lys Ala His Gln Glu Met Asp Leu Ile Ile Tyr Asp Val Pro Gly Asp
        115                 120                 125

Ile Val Cys Gly Gly Phe Val Ala Pro Ile Lys Lys Gly Phe Val Asn
    130                 135                 140

Glu Ala Tyr Val Leu Thr Ser Gly Glu Tyr Met Pro Leu Tyr Ala Ala
145                 150                 155                 160

Asn Asn Ile Cys Arg Gly Leu Asn Lys Ile Asn Thr Pro Leu Ser Gly
                165                 170                 175
```

```
Val Ile Cys Asn Ser Arg Asp Val Ser Arg Glu Arg Glu Ile Val Lys
                180                 185                 190

Lys Phe Ser Glu Glu Leu Gly Ser Glu Leu Ile Ala Phe Ile Pro Lys
            195                 200                 205

Glu Gln Ile Val Gln Asp Cys Glu Arg Glu Gly Phe Ser Val Ile Glu
        210                 215                 220

Lys Glu Pro Asp Ser Ser Ile Ala Asp Val Tyr Arg Glu Leu Ala Arg
225                 230                 235                 240

Lys Ile Met Ser Gln Lys Lys Ala Ser Asn Pro Asp Pro Met Asp Asp
                245                 250                 255

Glu Lys Leu Arg Ser Leu Thr Arg
            260
```

<210> SEQ ID NO 84
<211> LENGTH: 265
<212> TYPE: PRT
<213> ORGANISM: Methanosarcina acetivorans C2A

<400> SEQUENCE: 84

```
Met Lys Lys Gln Lys Ile Val Ala Ile Tyr Gly Lys Gly Gly Ile Gly
1               5                   10                  15

Lys Ser Ser Thr Ala Ser Asn Val Ala Ala Cys Ala Glu Ala Gly
            20                  25                  30

Lys Lys Val Met Ile Ile Gly Cys Asp Pro Lys Ser Asp Ser Ser Ile
            35                  40                  45

Thr Leu Leu Arg Gly Lys Arg Ile Pro Thr Ile Leu Asp Leu Leu Arg
50                  55                  60

Glu Gly Val Asp Val Gln Glu Lys Asp Val Val Phe Glu Gly Tyr Ala
65                  70                  75                  80

Gly Val Lys Cys Val Glu Ala Gly Gly Pro Glu Pro Gly Ile Gly Cys
                85                  90                  95

Ala Gly Arg Gly Ile Ile Val Ala Ile Gln Lys Leu Lys Ser Ile Ser
            100                 105                 110

Gly Asp Leu Leu Lys Glu Gln Asp Leu Ile Ile Tyr Asp Val Pro Gly
        115                 120                 125

Asp Ile Val Cys Gly Gly Phe Val Ala Pro Val Arg Lys Gly Tyr Val
    130                 135                 140

Asn Glu Ala Tyr Val Leu Thr Ser Gly Glu Tyr Met Pro Leu Tyr Ala
145                 150                 155                 160

Ala Asn Asn Ile Cys Lys Gly Leu Ser Lys Ile Gly Met Pro Leu Ser
                165                 170                 175

Gly Val Ile Cys Asn Ser Arg Asn Ala Ser Arg Glu Glu Ile Val
            180                 185                 190

Arg Lys Phe Ser Glu Glu Ile Gly Ser Gln Leu Met Ala Phe Ile Pro
        195                 200                 205

Lys Arg Gln Ile Val Gln Asp Cys Glu Arg Glu Gly Tyr Ser Val Met
    210                 215                 220

Glu Lys Ala Pro Asp Ser Asp Ile Ala Glu Val Tyr Arg Gln Leu Gly
225                 230                 235                 240

Lys Ser Ile Leu Thr Asn Glu Lys Lys Val Met Ala Ser His Leu Ser
                245                 250                 255

Asp Glu Arg Leu Arg Glu Met Thr Lys
            260                 265
```

-continued

```
<210> SEQ ID NO 85
<211> LENGTH: 262
<212> TYPE: PRT
<213> ORGANISM: Methanosphaera stadtmanae DSM 3091

<400> SEQUENCE: 85
```

Met Val Leu Lys Lys Ile Ala Ile Tyr Gly Lys Gly Gly Ile Gly Lys
1               5                   10                  15

Ser Thr Thr Val Ser Asn Met Ala Ala Tyr Asp Asn Ser Thr Phe
                20                  25                  30

Val Ile Gly Cys Asp Pro Lys Ala Asp Thr Thr Arg Thr Leu Val Gly
                35                  40                  45

Lys Arg Ile Pro Thr Ile Leu Asp Thr Met Arg Asp Asn Thr Gln Pro
50                  55                  60

Glu Leu Glu Asp Ile Val Tyr Glu Gly Tyr Asn Asn Thr Leu Cys Val
65                  70                  75                  80

Glu Ser Gly Gly Pro Glu Pro Gly Val Gly Cys Ala Gly Arg Gly Val
                85                  90                  95

Ile Val Ala Met Asn Leu Leu Asp Lys Ile Gly Ala Phe Asp Asn Asp
                100                 105                 110

Pro Asp Leu Val Ile Tyr Asp Val Leu Gly Asp Val Val Cys Gly Gly
                115                 120                 125

Phe Ser Val Pro Leu Arg Glu Asp Tyr Ala Asp Glu Val Tyr Ile Val
130                 135                 140

Thr Ser Gly Glu Tyr Met Ser Leu Tyr Ala Ala Asn Ile Ala Lys
145                 150                 155                 160

Gly Ile Lys Lys Leu Asn Gly Lys Leu Gly Gly Ile Ile Cys Asn Cys
                165                 170                 175

Arg Asn Val Lys Asn Glu Val Glu Val Val Thr Glu Phe Ala Ser Leu
                180                 185                 190

Ile Ser Ser Lys Ile Met Gly Ile Ile Pro Arg Cys Glu Leu Val Gln
                195                 200                 205

Thr Ser Glu Tyr Lys Ala Ser Thr Val Val Glu Thr Phe Pro Asp Ser
210                 215                 220

Ser Gln Ser Lys Ile Tyr Ser Glu Leu Ile Asn Asn Ile Met Asn Asn
225                 230                 235                 240

Gln Glu Phe Ser Thr Pro Thr Pro Met Gly Ile Glu Glu Phe Glu Glu
                245                 250                 255

Phe Phe Tyr Ser Tyr Val
                260

```
<210> SEQ ID NO 86
<211> LENGTH: 272
<212> TYPE: PRT
<213> ORGANISM: Methanosphaerula palustris E1-9c

<400> SEQUENCE: 86
```

Met Lys Gln Ile Ala Leu Tyr Gly Lys Gly Gly Ile Gly Lys Ser Thr
1               5                   10                  15

Thr Ser Ala Asn Leu Ser Ala Ala Leu Ala Glu Gln Gly Leu Gly Val
                20                  25                  30

Leu Gln Ile Gly Cys Asp Pro Lys His Asp Ser Thr Arg Met Leu Met
                35                  40                  45

His Gly Thr Trp Ile Pro Thr Val Leu Asp Leu Ile Arg Glu Arg Gly
50                  55                  60

Gly Thr Asn Leu Thr Ile Asp Asp Val Val Tyr Thr Gly Tyr Arg Gly

```
                65                  70                  75                  80
Ile Arg Cys Val Glu Ala Gly Gly Pro Glu Pro Gly Ile Gly Cys Ala
                    85                  90                  95
Gly Arg Gly Ile Ile Ala Thr Phe Gln Val Leu Glu Lys Leu Glu Ala
                    100                 105                 110
Phe Ser Ala Asp Val Val Val Tyr Asp Val Leu Gly Asp Val Val Cys
                    115                 120                 125
Gly Gly Phe Ala Met Pro Met Arg Glu Gly Tyr Ala Glu Ile Tyr
                130                 135                 140
Leu Val Thr Ser Gly Glu Leu Met Ser Leu Tyr Ala Ala Asn Asn Ile
145                 150                 155                 160
Cys Lys Ala Ile Asn Arg Leu Ser Gln Arg Pro Lys Cys Thr Cys Arg
                    165                 170                 175
Leu Ala Gly Val Ile Cys Asn Ala Lys Asn Ile Asp Arg Glu Glu Asp
                    180                 185                 190
Leu Val Arg Glu Phe Ala Glu Arg Val Gly Ser Asn Leu Val Ala Tyr
                    195                 200                 205
Ile Pro Arg Asp Arg Ile Val Gln Leu Ala Glu Val His Lys Gln Thr
                    210                 215                 220
Val Leu Glu Tyr Ala Pro Asp Ser Ala Gln Ala Ala Thr Tyr Arg Thr
225                 230                 235                 240
Leu Ala Glu Val Val Leu Thr Asn Thr Thr Leu Thr Ile Pro Lys Pro
                    245                 250                 255
Leu Glu Leu Asp Glu Leu Glu Asp Leu Ala Phe Lys Tyr Ile Ser Ile
                    260                 265                 270

<210> SEQ ID NO 87
<211> LENGTH: 280
<212> TYPE: PRT
<213> ORGANISM: Methanospirillum hungatei JF-1

<400> SEQUENCE: 87

Met Lys Gln Ile Ala Leu Tyr Gly Lys Gly Gly Ile Gly Lys Ser Thr
1               5                   10                  15
Thr Ser Ala Asn Leu Ser Ala Ala Leu Val Asn Arg Gly Leu Ser Val
                    20                  25                  30
Met Gln Ile Gly Cys Asp Pro Lys Arg Asp Ser Thr Arg Met Leu Met
                    35                  40                  45
Lys Gly Ile Leu Ile Pro Thr Val Leu Asp Leu Ile Arg Glu Arg Gly
                50                  55                  60
Glu Glu Asn Leu Thr Leu Asp Asp Val Val Phe Thr Gly Tyr Lys Gly
65                  70                  75                  80
Val Arg Cys Val Glu Ala Gly Gly Pro Glu Pro Gly Val Gly Cys Ala
                    85                  90                  95
Gly Arg Gly Ile Ile Ala Thr Phe Gln Leu Leu Glu Arg Leu Ser Ala
                    100                 105                 110
Phe Asp Glu Asp Ile Ile Val Tyr Asp Val Leu Gly Asp Val Val Cys
                    115                 120                 125
Gly Gly Phe Ala Met Pro Met Arg Lys Gly Tyr Ala Gln Glu Ile Tyr
                130                 135                 140
Leu Val Thr Ser Gly Glu Leu Met Ser Leu Tyr Ala Ala Asn Asn Ile
145                 150                 155                 160
Cys Lys Ala Ile Ser Arg Ile Ser Gln Asn Val Arg Gln Val Cys Arg
                    165                 170                 175
```

```
Leu Gly Gly Val Ile Cys Asn Ser Arg Asn Leu Pro Asp Glu Lys
            180                 185                 190

Leu Val Gly Ala Phe Ala Ser Glu Val Gly Ser Lys Ile Ile Ala Tyr
        195                 200                 205

Ile Pro Arg Ser Gly Leu Val Gln Tyr Ala Glu Leu Asn Asn Gln Thr
    210                 215                 220

Val Ile Glu Phe Ala Pro Asp Ser Ser Leu Ser Ala Thr Tyr Gln Ser
225                 230                 235                 240

Leu Ala Glu Glu Ile Met Thr Asn Thr Asp Phe Val Ile Pro Lys Pro
                245                 250                 255

Leu Glu Ile Glu Glu Leu Glu Lys Leu Ala Arg Ser Tyr Leu Pro Thr
            260                 265                 270

Ile Asp His Gln Gly Ile Asn His
        275                 280

<210> SEQ ID NO 88
<211> LENGTH: 265
<212> TYPE: PRT
<213> ORGANISM: Methanothermobacter marburgensis str. Marburg

<400> SEQUENCE: 88

Met Lys Arg Ile Ala Ile Tyr Gly Lys Gly Ile Gly Lys Ser Thr
1               5                   10                  15

Ile Val Ser Asn Met Ala Ala Tyr Ser Ser His His Arg Val Leu
            20                  25                  30

Val Ile Gly Cys Asp Pro Lys Ala Asp Thr Thr Arg Thr Leu Tyr Gly
        35                  40                  45

Glu Arg Leu Pro Ala Val Leu Asp Val Leu Arg Glu Asn Arg Lys Pro
50                  55                  60

Asp Ala Ser Glu Val Ile His Glu Gly Phe Gly Gly Val Arg Cys Val
65                  70                  75                  80

Glu Ser Gly Gly Pro Glu Pro Gly Val Gly Cys Ala Gly Arg Gly Val
                85                  90                  95

Ile Val Ala Met Asn Leu Leu Glu Lys Leu Gly Val Phe Glu Glu Glu
            100                 105                 110

Ile Asp Val Ile Ile Tyr Asp Val Leu Gly Asp Val Val Cys Gly Gly
        115                 120                 125

Phe Ala Val Pro Leu Arg Glu Glu Phe Ala Asp Glu Val Tyr Ile Val
    130                 135                 140

Thr Ser Gly Glu Tyr Met Ser Leu Tyr Ala Ala Asn Asn Ile Ala Arg
145                 150                 155                 160

Gly Ile Arg Lys Leu Arg Gly Lys Leu Gly Gly Val Ile Cys Asn Cys
                165                 170                 175

Arg Gly Ile Arg Asn Glu Val Asp Ile Val Ser Glu Phe Ala Ser Arg
            180                 185                 190

Ile Gly Ser Arg Val Ile Gly Val Val Pro Arg Ser Ser Leu Val Gln
        195                 200                 205

Glu Ser Glu Ile Glu Ala Lys Thr Val Ile Glu Ser Phe Pro Glu Ser
    210                 215                 220

Glu Gln Ala Glu Val Tyr Arg Lys Leu Ala Asp Glu Val Tyr Leu Asn
225                 230                 235                 240

Thr Glu Phe Val Val Pro Glu Pro Met Asp Pro Glu Glu Phe Glu Glu
                245                 250                 255

Phe Phe Arg Lys Phe Arg Gly Asp Asp
            260                 265
```

<210> SEQ ID NO 89
<211> LENGTH: 280
<212> TYPE: PRT
<213> ORGANISM: Methanothermococcus okinawensis IH1

<400> SEQUENCE: 89

```
Met Val Arg Lys Phe Cys Ile Tyr Gly Lys Gly Ile Gly Lys Ser
1               5                   10                  15

Thr Thr Val Ser Asn Ile Ala Gly Ala Leu Ala Glu Ser Gly Lys Lys
            20                  25                  30

Val Met Val Ile Gly Cys Asp Pro Lys Ala Asp Ser Thr Arg Asn Leu
        35                  40                  45

Met Gly Arg Lys Ile Pro Thr Val Leu Asp Val Phe Arg Lys Lys Gly
    50                  55                  60

Asn Ala Ile Lys Leu Glu Asp Ile Val Phe Glu Gly Phe Cys Gly Thr
65                  70                  75                  80

Tyr Cys Ile Glu Ser Gly Gly Pro Glu Pro Gly Val Gly Cys Ala Gly
                85                  90                  95

Arg Gly Val Ile Thr Ala Ile Glu Val Leu Asn Arg Leu Gly Ala Phe
            100                 105                 110

Glu Thr Leu Asn Pro Asp Val Ile Ile Tyr Asp Ile Leu Gly Asp Val
        115                 120                 125

Val Cys Gly Gly Phe Ala Met Pro Leu Gln Lys His Leu Ala Asp Asp
    130                 135                 140

Val Tyr Ile Val Thr Thr Cys Asp Pro Met Ala Ile Tyr Ala Ala Asn
145                 150                 155                 160

Asn Ile Cys Lys Gly Ile Lys Arg Tyr Ala Lys Arg Gly Lys Val Ala
                165                 170                 175

Leu Gly Gly Ile Ile Tyr Asn Gly Arg Ser Val Ile Asn Glu Pro Ser
            180                 185                 190

Ile Val Glu Glu Phe Ala Ser Lys Ile Gly Thr Asn Val Met Gly Asn
        195                 200                 205

Val Pro Met Ser Asn Ile Ile Thr Lys Ala Glu Ile Tyr Lys Lys Thr
    210                 215                 220

Val Ile Glu Tyr Ala Pro Asp Ser Glu Ile Ala Asp Val Phe Arg Glu
225                 230                 235                 240

Leu Ala Asp Ala Ile Tyr Lys Asn Asp Lys Arg Val Ile Pro Thr Pro
                245                 250                 255

Leu Ser Glu Glu Glu Ile Asp Glu Ile Thr Glu Lys Ile Asp Asp Leu
            260                 265                 270

Leu Lys Glu Lys Ile Val Ile Val
        275                 280
```

<210> SEQ ID NO 90
<211> LENGTH: 270
<212> TYPE: PRT
<213> ORGANISM: Methanothermus fervidus DSM 2088

<400> SEQUENCE: 90

```
Met Lys Lys Arg Lys Gln Arg Arg Ile Ala Ile Tyr Gly Lys Gly Gly
1               5                   10                  15

Ile Gly Lys Ser Thr Ile Val Ser Asn Ile Ala Ala Ala Tyr Ser Asp
            20                  25                  30

Lys Tyr Lys Val Leu Val Ile Gly Cys Asp Pro Lys Ser Asp Thr Thr
        35                  40                  45
```

Arg Thr Leu Tyr Gly Ser Arg Ile Pro Thr Val Leu His Ile Leu Lys
        50                  55                  60

Glu Lys Lys Glu Pro Lys Val Glu Asp Val Val Tyr Val Gly Tyr Asn
65                  70                  75                  80

Gly Val Lys Cys Val Glu Ser Gly Gly Pro Glu Pro Gly Val Gly Cys
                85                  90                  95

Ala Gly Arg Gly Val Ile Val Ala Met Asn Leu Leu Glu Lys Leu Gly
            100                 105                 110

Val Phe Arg Glu Ser Leu Asp Ile Ile Ile Tyr Asp Val Leu Gly Asp
        115                 120                 125

Val Val Cys Gly Gly Phe Ala Val Pro Leu Arg Glu Asp Tyr Ala Asp
    130                 135                 140

Glu Val Tyr Ile Val Thr Ser Gly Glu Tyr Met Ser Leu Tyr Ala Ala
145                 150                 155                 160

Asn Asn Ile Cys Lys Gly Ile Lys Arg Leu Lys Gly Arg Leu Gly Gly
                165                 170                 175

Ile Ile Cys Asn Cys Arg Gly Ile Lys Asn Glu Val Glu Ile Val Glu
            180                 185                 190

Lys Phe Ala Lys Lys Ile Gly Ser Lys Val Val Gly Val Ile Pro Arg
        195                 200                 205

Ser Asp Leu Val Gln Lys Ser Glu Ile Glu Gly Lys Thr Val Ile Glu
    210                 215                 220

Lys Phe Pro Lys Ser Glu Gln Ala Lys Ile Tyr Arg Asp Leu Ala Lys
225                 230                 235                 240

Ser Ile Tyr Leu Asn Lys Asp Phe Val Glu Pro Lys Pro Met Ser Ile
                245                 250                 255

Asp Glu Leu Glu Lys Phe Ile Lys Asn Leu Tyr Asn Val Ser
            260                 265                 270

<210> SEQ ID NO 91
<211> LENGTH: 288
<212> TYPE: PRT
<213> ORGANISM: Methanotorris igneus Kol 5

<400> SEQUENCE: 91

Met Lys Gln Ile Ala Phe Tyr Gly Lys Gly Gly Ile Gly Lys Ser Thr
1               5                   10                  15

Thr Val Cys Asn Ile Ala Ala Ala Leu Ala Asp Glu Gly Lys Arg Val
                20                  25                  30

Met Val Val Gly Cys Asp Pro Lys His Asp Cys Thr Ser Asn Leu Arg
            35                  40                  45

Gly Gly Glu Glu Ile Pro Thr Val Leu Asp Thr Leu Arg Glu Lys Gly
        50                  55                  60

Met Glu Lys Met Ser Leu Ser Asp Ile Glu Lys Arg Ile Asp Ile Asp
65                  70                  75                  80

Glu Ile Val Tyr Lys Gly Tyr Lys Gly Ile Tyr Cys Ile Glu Ala Gly
                85                  90                  95

Gly Pro Lys Pro Gly Tyr Gly Cys Ala Gly Arg Gly Val Ile Val Ala
            100                 105                 110

Ile Asp Leu Leu Lys Lys Met Asn Val Phe Glu Glu Leu Gly Val Asp
        115                 120                 125

Val Val Leu Tyr Asp Val Leu Gly Asp Val Val Cys Gly Gly Phe Ala
    130                 135                 140

Met Pro Leu Arg Met Gly Leu Ala Glu Gln Ile Tyr Ile Val Thr Ser

```
           145                 150                 155                 160
Ser Asp Tyr Met Ala Met Tyr Ala Ala Asn Asn Ile Cys Arg Gly Met
                165                 170                 175
Lys Glu Phe Ala Lys Arg Gly Gly Ser Arg Leu Gly Gly Leu Ile Tyr
                180                 185                 190
Asn Val Arg Gly Ser Leu Asp Ala Glu Asp Ile Val Thr Glu Phe Ala
                195                 200                 205
Lys Lys Leu Gly Thr Glu Ile Ile Gly Lys Ile Pro Asn Ser Leu Leu
            210                 215                 220
Ile Ala Glu Ala Glu Ile Glu Gly Lys Thr Val Ile Glu Tyr Ala Pro
225                 230                 235                 240
Asp Ser Glu Ile Ala Ser Ile Tyr Arg Glu Leu Ala Lys Lys Ile Tyr
                245                 250                 255
Lys Asn Lys Asn Gly Val Ile Pro Asn Pro Leu Glu Asn Glu Glu Ile
                260                 265                 270
Met Gln Ile Gly Lys Arg Val Lys Glu Arg Ile Arg Ser Leu Arg Ser
                275                 280                 285

<210> SEQ ID NO 92
<211> LENGTH: 270
<212> TYPE: PRT
<213> ORGANISM: Methermicoccus shengliensis DSM 18856

<400> SEQUENCE: 92

Met Arg Gln Ile Ala Ile Tyr Gly Lys Gly Ile Gly Lys Ser Leu
1               5                   10                  15
Thr Cys Ala Asn Ile Ser Ala Ala Leu Ala Leu Met Gly Arg Arg Val
                20                  25                  30
Met Gln Val Gly Cys Asp Pro Lys His Asp Ser Thr Arg Leu Leu Leu
                35                  40                  45
Gly His Thr Cys Arg His Thr Val Leu Asp Leu Leu Arg Glu His Gly
            50                  55                  60
Pro Ser Gly Ile Arg Arg Glu Asp Val Val His Glu Gly Phe Gly Gly
65                  70                  75                  80
Val Leu Cys Val Glu Ala Gly Gly Pro Glu Pro Gly Val Gly Cys Ala
                85                  90                  95
Gly Arg Gly Ile Ile Ala Thr Phe Glu Val Leu Glu Arg Leu Gly Val
                100                 105                 110
Tyr Glu Glu Gly Leu Asp Tyr Cys Leu Tyr Asp Val Leu Gly Asp Val
                115                 120                 125
Val Cys Gly Gly Phe Ala Met Pro Ile Arg Glu Gly Tyr Ala Gln Glu
            130                 135                 140
Ile Tyr Ile Val Thr Ser Gly Glu Pro Met Ala Leu Tyr Ala Ala Asn
145                 150                 155                 160
Asn Ile Cys Lys Gly Ile Arg Arg Phe Glu Arg Thr Ser Ser Ala Arg
                165                 170                 175
Leu Ala Gly Ile Ile Ala Asn Leu Arg Gly Ile Glu His Glu Leu Asp
                180                 185                 190
Ile Val Glu Arg Phe Ala Ser Thr Met Gly Ser Arg Val Val Gly Val
                195                 200                 205
Val Pro Arg Asp Ala Ile Val Gln Arg Ala Glu Arg Ala Arg Lys Thr
            210                 215                 220
Val Val Glu Phe Ala Pro His Ser Gln Leu Ala Arg Thr Tyr Met Ala
225                 230                 235                 240
```

```
Leu Ala Gln Arg Ile Glu His Asn Thr Gln Arg Val Val Pro Ala Pro
            245                 250                 255

Leu Glu Leu Asp Ala Leu Glu Gln Leu Leu Glu Glu Arg Pro
        260                 265                 270

<210> SEQ ID NO 93
<211> LENGTH: 263
<212> TYPE: PRT
<213> ORGANISM: Methanoperedens nitroreducens

<400> SEQUENCE: 93

Met Ser Lys Gln Ile Ala Ile Tyr Gly Lys Gly Gly Ile Gly Lys Ser
1               5                   10                  15

Ser Thr Ala Ser Asn Val Ala Ala Cys Ala Asp Glu Gly Tyr Arg
            20                  25                  30

Val Thr Ile Ile Gly Cys Asp Pro Lys Ser Asp Ser Ile Thr Leu
        35                  40                  45

Leu Arg Gly Arg Arg Ile Pro Thr Ile Met Asp Leu Met Arg Gln Gly
    50                  55                  60

Val Asp Ile Glu Glu Asp Ile Val Phe Asp Gly Tyr Lys Gly Val
65                  70                  75                  80

Lys Cys Val Glu Ile Gly Gly Pro Glu Pro Gly Ile Gly Cys Ala Gly
                85                  90                  95

Arg Gly Ile Ile Val Ala Ile Ser Leu Leu Lys Lys Thr Ser Lys Ala
            100                 105                 110

Ile Glu Asp Thr Asp Leu Val Ile Tyr Asp Val Pro Gly Asp Ile Val
        115                 120                 125

Cys Gly Gly Phe Val Ala Pro Val Lys Lys Gly Leu Val Ser Glu Ala
    130                 135                 140

Tyr Val Leu Thr Ser Gly Glu Tyr Met Pro Leu Tyr Ala Ala Asn Asn
145                 150                 155                 160

Ile Cys Lys Gly Leu Ser Arg Leu Glu Met Pro Leu Asn Gly Val Ile
                165                 170                 175

Cys Asn Ser Arg Gly Ala Pro Asn Glu Glu Asn Ile Val Ser Glu Phe
            180                 185                 190

Ala Lys Glu Ile Gly Ser Gln Leu Leu Ala Phe Ile Pro Lys Asp Val
        195                 200                 205

Leu Val Gln Thr Cys Glu Arg Glu Gly Phe Ser Val Ile Glu Lys Glu
    210                 215                 220

Pro Gly Ser Ala Ile Ala Ala Val Tyr Arg Lys Leu Ala Arg Ser Ile
225                 230                 235                 240

Met Thr Lys Ser Asp Ala Arg Val Pro Glu Pro Leu Asp Asp Ala Arg
                245                 250                 255

Leu Arg Glu Leu Thr Lys Ile
            260

<210> SEQ ID NO 94
<211> LENGTH: 359
<212> TYPE: PRT
<213> ORGANISM: Methanobacterium formicicum DSM 3637

<400> SEQUENCE: 94

Met His Pro Arg Pro Ser Pro Ile Ala Ala Ser Leu Tyr Thr Leu Arg
1               5                   10                  15

Asp Leu Asn Ala Asp Val Ile Ile Leu His Gly Pro His Gly Cys Cys
            20                  25                  30
```

```
Phe Arg Thr Gly Arg Leu Leu Glu Asn Asp Gly Val Arg Val Val Thr
            35                  40                  45

Thr Ala Met Ser Glu Asn Asp Phe Ile Phe Gly Ala Ser Ala Lys Leu
 50                  55                  60

Glu Glu Thr Leu Arg Glu Ala Asp Glu Leu Phe His Pro Gln Leu Val
 65                  70                  75                  80

Gly Val Val Gly Thr Cys Ala Ser Met Ile Ile Gly Glu Asp Met Arg
                 85                  90                  95

Glu Ala Val Asn Asn Ala Gly Ile Pro Ala Lys Val Leu Thr Val Glu
                100                 105                 110

Ser His Gly Gly Leu Ser Glu Gly Asp Asn Thr Glu Gly Ala Ile Ala
                115                 120                 125

Val Leu Glu Ala Ala Gln Leu Glu Gly Val Ile Pro Pro Glu Glu Thr
130                 135                 140

Glu Arg Gln Ser Arg Met Leu Lys Lys Ala Thr Glu Ile Glu Lys Thr
145                 150                 155                 160

Arg Gly Met Ala Gln Gly Lys Tyr Ile Ala Pro Ser Tyr Gly Asp Asp
                165                 170                 175

Lys Glu Lys Val Ala Ser Leu Leu Glu Ala Phe Glu Lys Gly Asp
                180                 185                 190

Lys Ile Ala Phe Val Leu Asn Ala Lys Lys Glu Thr Ser Tyr Leu Phe
                195                 200                 205

Ala Asp Leu Leu Lys Ile Pro Phe Gln Glu Ile Tyr Pro Glu Asn Lys
                210                 215                 220

Pro Leu Ile Ile Ala Asn Leu Asp Leu Glu Thr Gly Leu Pro Arg Ile
225                 230                 235                 240

Arg Gln His Ala Gln Asn Ile Gln Glu Glu Leu Asn Glu Asn Arg Leu
                245                 250                 255

Gln Ile Asp Phe Ile Thr Gly Gly Leu Asp Glu Tyr Pro Ile Thr Gly
                260                 265                 270

Asp Asn Ala Val Glu Tyr Leu Glu Lys Glu Asp Tyr Asp Leu Val Val
                275                 280                 285

Val Ala Gly Val Pro His Ala Leu Pro Ile Glu Lys Leu Asn Ile Gln
290                 295                 300

Ser Val Ala Ile Thr Asp Gly Pro Arg Leu Val Glu Pro Leu Lys Lys
305                 310                 315                 320

Leu Gly Tyr Asn Trp Val Val Thr Glu Leu Asp Ala His Ala Lys Thr
                325                 330                 335

Leu Gly Asp Lys Ile Val Glu Ser Asp Phe Gly Thr Val Leu Arg
                340                 345                 350

Val Lys Ile Asp Glu Lys Arg
        355

<210> SEQ ID NO 95
<211> LENGTH: 372
<212> TYPE: PRT
<213> ORGANISM: Methanobrevibacter ruminantium M1

<400> SEQUENCE: 95

Met Met His Pro Arg Pro Ser Pro Ile Ala Ala Ser Leu Tyr Thr Leu
  1               5                  10                  15

Arg Asp Leu Asn Ala Asp Val Ile Ile Met His Gly Pro His Gly Cys
                 20                  25                  30

Cys Phe Arg Thr Gly Arg Leu Leu Glu Ser Asp Gly Val Arg Val Val
                 35                  40                  45
```

```
Thr Thr Ala Met Ala Glu Asn Asp Phe Ile Leu Gly Ala Ala Asp Lys
    50                  55                  60

Leu Glu Glu Thr Leu Gln Glu Ala Tyr Asp Thr Phe Asn Pro Lys Leu
65                  70                  75                  80

Ile Gly Ile Val Gly Thr Cys Ala Ser Met Ile Ile Gly Glu Asp Leu
                85                  90                  95

Lys Glu Pro Ile Glu Asn Leu Asn Leu Asp Ala Val Val Ile Pro Val
            100                 105                 110

Glu Ser His Gly Gly Phe Gly Glu Gly Asp Asn Thr Glu Gly Ala Ile
        115                 120                 125

Ala Val Leu Asn Ala Ala Val Glu Cys Gly Val Ile Pro Gln Glu Glu
    130                 135                 140

Ala Asp Arg Gln Asn Glu Met Leu Arg Leu Ala Thr Val Val Glu Lys
145                 150                 155                 160

Thr Arg Gly Met Ala Gln Gly Lys Tyr Ile Lys Pro Asn Phe Gly Asp
                165                 170                 175

Asn Lys Glu Lys Val Ala Lys Ile Val Val Lys Ala Val Lys Glu Gly
            180                 185                 190

Lys Asn Val Ala Phe Val Leu Asn Ala Lys Lys Glu Thr Ser Tyr Leu
        195                 200                 205

Phe Ala Asp Ile Leu Asn Cys Asp Phe Ser Lys Leu Phe Gln Asp Thr
    210                 215                 220

Asp Ser Asn Ile Lys Ser Asn Lys Asp Ile Glu Asn Leu His Phe Ile
225                 230                 235                 240

Ala Asn Leu Asp Glu Asn Ile Gly Leu Pro Arg Ile Arg Gln His Ala
                245                 250                 255

Val Asn Ile Thr Lys Glu Leu Asn Glu Thr Gly Ile Asp Ile Glu Cys
            260                 265                 270

Ile Thr Gly Gly Leu Asp Glu Tyr Pro Ile Thr Pro Arg Lys Ala Glu
        275                 280                 285

Glu Tyr Leu Asn Glu Leu Asn Pro Asp Leu Val Ile Val Ala Gly Val
    290                 295                 300

Pro His Ala Leu Tyr Val Glu Glu Leu Asp Cys Glu Thr Ile Ala Val
305                 310                 315                 320

Thr Asp Gly Pro Arg Leu Val Gln Pro Leu Asn Glu Leu Gly Tyr Ser
                325                 330                 335

His Val Ile Ala Glu Leu Asp Ala His Ser Lys Thr Leu Gly Val Asp
            340                 345                 350

Glu Ile Val Asp Ser Asp Phe Gly Met Met Ile Arg Ser Ala Ile Glu
        355                 360                 365

Trp Glu Leu Glu
    370

<210> SEQ ID NO 96
<211> LENGTH: 352
<212> TYPE: PRT
<213> ORGANISM: Methanocaldococcus jannaschii DSM 2661

<400> SEQUENCE: 96

Met Ile Phe His Pro Arg Pro Ser Pro Ile Ala Ala Ala Met Tyr Gln
1               5                   10                  15

Leu Arg Asp Leu Gly Val Asp Ala Ile Ile Leu His Gly Pro Ser Gly
            20                  25                  30

Cys Cys Phe Arg Thr Ala Arg Leu Leu Glu Leu Asp Gly Val Arg Val
```

```
                35                  40                  45
Phe Thr Ser Asn Ile Asp Glu Asn Ala Ile Val Phe Gly Ala Ser Glu
 50                  55                  60

Asn Leu Lys Lys Ala Leu Asp Tyr Ala Ile Glu Tyr Leu Lys Lys Glu
 65                  70                  75                  80

Leu Lys Lys Glu Arg Pro Met Ile Gly Ile Val Gly Thr Cys Ala Ser
                 85                  90                  95

Met Ile Ile Gly Glu Asp Leu Trp Glu Phe Val Asp Asp Arg Ala
            100                 105                 110

Ile Ile Ile Pro Val Glu Val His Ser Gly Ser Gly Asp Asn Thr Ile
            115                 120                 125

Gly Ala Ile Lys Ala Met Glu Ser Ala Leu Lys Leu Gly Ile Ile Asp
            130                 135                 140

Glu Lys Glu Phe Glu Arg Gln Lys Phe Leu Leu Lys Lys Ala Thr Glu
145                 150                 155                 160

Val Glu Lys Lys Arg Gly Met Ala Lys Lys Glu Tyr Ile Lys Pro Thr
                165                 170                 175

Tyr Asp Asp Asp Leu Asn Glu Ala Ile Lys Val Leu Lys Asp Leu Lys
            180                 185                 190

Glu Lys Asp Gly Lys Ile Ala Cys Val Leu Asn Ala Lys Lys Glu Thr
            195                 200                 205

Ala Tyr Leu Phe Ala His Pro Leu Ile Val Leu Asn Lys Tyr Phe Asn
210                 215                 220

Cys Val Asn Ile Ala Asn Leu Asp Ile Asn Lys Gly Leu Pro Lys Ile
225                 230                 235                 240

Arg Arg Asp Ala Gln Asn Ile Leu Arg Arg Phe Lys Ala Asp Tyr Ile
                245                 250                 255

Thr Gly Gly Leu Asp Glu Tyr Pro Ile Thr Gly Glu Arg Ala Val Glu
            260                 265                 270

Ile Leu Lys Asp Leu Asp Val Asp Ala Ile Val Val Ser Gly Val Pro
            275                 280                 285

His Ala Leu Pro Ile Glu Glu Ile Asp Lys Asp Ile Ile Lys Ile Gly
            290                 295                 300

Ile Ser Asp Gly Pro Arg Thr Tyr His Pro Ile Lys Glu Ile Tyr Asp
305                 310                 315                 320

Tyr Ala Ile Val Glu Leu Asp Ala His Ala Lys Val Leu Gly Lys Arg
                325                 330                 335

Asp Ile Val Lys Ser Arg Phe Gly Glu Ile Leu Asp Tyr Ala Leu Glu
            340                 345                 350

<210> SEQ ID NO 97
<211> LENGTH: 364
<212> TYPE: PRT
<213> ORGANISM: Methanocella arvoryzae MRE50

<400> SEQUENCE: 97

Met Glu Asp Asn Arg Ile Ile Gln Pro Arg Pro Ser Ala Ile Val Ala
 1               5                  10                  15

Ala Leu Tyr Thr Leu Arg Asp Leu Asp Val Asp Val Ala Val Leu His
                20                  25                  30

Gly Pro Pro Gly Cys Cys Phe Lys His Ser Arg Leu Leu Glu Glu Asp
            35                  40                  45

Gly Met Arg Val Val Thr Thr Ala Met Cys Asp Ser Asp Tyr Val Phe
 50                  55                  60
```

```
Gly Ala His Asp Val Leu Val Ser Val Leu Lys Val Ser Asp Arg
 65                  70                  75                  80

Phe Ser Pro Lys Thr Ile Gly Ile Val Gly Thr Cys Ala Ser Met Ile
                 85                  90                  95

Ile Gly Glu Asn Phe His Arg Ala Val Glu Asp Ala Glu Pro Gly Val
                100                 105                 110

Pro Val Val Glu Val Glu Ile His Ala Gly His Gly Asp Asn Thr Thr
            115                 120                 125

Gly Ala Ile Ala Thr Leu Glu Ala Ala His Ala Ala Gly Ile Leu Glu
        130                 135                 140

Lys Ala Glu Leu Asp Arg Gln Lys Gln Met Leu Leu Leu Ala Thr Glu
145                 150                 155                 160

Leu Glu Lys Lys Ala Gly Ala Ala Ser Ser Asp Tyr Ile Glu Pro Ser
                165                 170                 175

Arg Gly Asp Leu Lys Tyr Arg Ala Ala Ala Arg Leu Leu Glu Leu Met
            180                 185                 190

Arg Glu Asp Lys Lys Gly Ile Ser Ile Leu Asn Ala Lys Lys Glu Thr
        195                 200                 205

Ala Tyr Met Phe Ala Asp Ala Asn Met Ala Val Asn Glu Ala Ala Leu
    210                 215                 220

Arg Leu Gly Ala Pro Ala Pro Val Thr Ile Ala Asn Leu Asp Met Arg
225                 230                 235                 240

Ile Gly Leu Pro Arg Ile Arg Arg Tyr Ala Ser Thr Ile Thr Lys Ala
                245                 250                 255

Tyr Gly Glu Lys Gly Phe Ser Ile Asp His Ile Thr Gly Gly Leu Asp
            260                 265                 270

Glu Tyr Pro Leu Ala Gly Asp Arg Ala Ala Glu Ile Ile Lys Glu Lys
        275                 280                 285

Tyr Ser Asp Tyr Asp Tyr Ala Val Ile Thr Gly Val Pro His Gly Val
    290                 295                 300

Pro Phe Glu Ala Leu Gln Gly Met Glu Ile Phe Ser Ile Thr Asn Gly
305                 310                 315                 320

Pro Arg Gln Val Glu Pro Leu Arg Lys Ala Gly His Gln His Val Met
                325                 330                 335

Val Glu Ile Asp Leu His Pro Lys Thr Leu Gly Val Asp Asn Ile Val
            340                 345                 350

Glu Ser Glu Phe Gly Ala Thr Leu Arg Ser Met Leu
        355                 360
```

<210> SEQ ID NO 98
<211> LENGTH: 371
<212> TYPE: PRT
<213> ORGANISM: Methanococcoides methylutens MM1

<400> SEQUENCE: 98

```
Met Asp Asn Lys Asn Ile Ser Ile Ile His Pro Arg Pro Ser Ser Ile
  1               5                  10                  15

Val Ala Ala Leu Tyr Thr Leu Arg Asp Leu Asn Val Asp Val Ala Ile
                 20                  25                  30

Leu His Gly Pro Pro Gly Cys Ser Phe Lys His Ala Arg Leu Leu Glu
             35                  40                  45

Glu Asp Gly Ile His Val Val Thr Thr Ala Leu Asp Glu Ser Gly Phe
         50                  55                  60

Val Phe Gly Gly His Arg Glu Leu Val Asn Val Leu His Lys Val Asn
 65                  70                  75                  80
```

-continued

```
Asp Met Phe His Pro Lys Leu Ile Gly Val Val Gly Thr Cys Ala Ser
             85                  90                  95

Met Ile Ile Gly Glu Glu Met Arg Glu Pro Val Met Glu Ala Asn Leu
            100                 105                 110

Asp Val Pro Val Ile Glu Val Val His Ala Gly Tyr Arg Asn Asn
            115                 120                 125

Thr Lys Gly Val Leu Phe Ala Leu Glu Ser Ala Leu Asp Ala Gly Ile
        130                 135                 140

Ile Asp Arg Glu Glu Phe Ser Arg Gln Gln His Leu Leu Glu Glu Ala
145                 150                 155                 160

Thr Asn Val Glu Leu Arg His Gly Ala Ala Ser Lys Glu Tyr Leu Ala
                165                 170                 175

Pro Ser Arg Gly Asp Val Lys Tyr Lys Val Ala Gln Arg Ile Ile Glu
            180                 185                 190

Leu Leu Lys Glu Gly Lys Arg Gly Ile Thr Ile Met Asn Ala Lys Lys
        195                 200                 205

Glu Thr Gly Tyr Met Phe Ala Asp Ile Thr Val Ala Val Asn Glu Ile
    210                 215                 220

Ala Glu Gln Leu Gly Lys Ala Asp Asn Ile Ile Asn Met Ser Asn Thr
225                 230                 235                 240

Asp Val Gly Leu Gly Leu Pro Arg Val Arg His His Ala Glu Cys Ile
                245                 250                 255

Met Asn Asp Phe Glu Glu Lys Gly Ile Pro Ile His Glu Ile Ile Gly
            260                 265                 270

Gly Leu Asp Glu Tyr Pro Val Ala Gly Ala Thr Ile Asp Lys Leu Ile
        275                 280                 285

Glu Glu Lys Tyr Ser Asp Tyr Asp Phe Ala Val Ile Thr Gly Val Pro
    290                 295                 300

His Ala Ile Pro Met Asp His Leu Ser Asp Met Glu Ile Ile Ser Val
305                 310                 315                 320

Thr Asn Gly Pro Arg Gln Val Leu Pro Leu Lys Glu Leu Gly His Glu
                325                 330                 335

His Val Leu Val Glu Ile Asp Leu His Pro Lys Thr Leu Gly Val Asn
            340                 345                 350

His Ile Val Glu Ser Glu Phe Gly Ala Thr Leu Arg Glu Val Ala Lys
        355                 360                 365

Glu Ser Ile
    370
```

<210> SEQ ID NO 99
<211> LENGTH: 366
<212> TYPE: PRT
<213> ORGANISM: Methanococcus maripaludis C7

<400> SEQUENCE: 99

```
Met Ile Leu His Pro Arg Pro Ser Pro Ile Ala Ala Met Tyr Gln
1               5                  10                  15

Leu Arg Asp Ile Gly Val Asp Ala Ile Ile Leu His Gly Pro Ser Gly
            20                  25                  30

Cys Cys Phe Arg Thr Ala Arg Leu Leu Glu Ile Asp Gly Ile Arg Val
        35                  40                  45

Phe Thr Ser Ala Met Gly Glu Asn Asp Phe Ile Phe Gly Ala Met Asp
    50                  55                  60

Lys Leu Arg Asp Val Ile Asn Glu Val Leu Glu Tyr Leu Lys Lys Glu
```

```
               65                  70                  75                  80
Thr Pro Lys Asp Glu Lys Tyr Arg Ile Gly Ile Val Gly Thr Cys Ala
                    85                  90                  95

Ser Met Ile Ile Gly Glu Asp Leu Glu Ser Leu Ile Asp Asp Phe Asp
                    100                 105                 110

Asp Ile Ile Ile Pro Val Asp Ile His Ser Gly Leu Val Asp Asn Thr
                    115                 120                 125

Val Gly Ala Ile Arg Ala Met Asp Gly Ala Leu Asn Ala Gly Leu Ile
        130                 135                 140

Asp Tyr Ser Glu Tyr Glu Arg Gln Lys Lys Met Leu Val Ala Ala Thr
145                 150                 155                 160

Asp Val Glu Lys Lys Arg Gly Met Ala Lys Asn Arg Tyr Leu Lys Pro
                    165                 170                 175

Thr Tyr Glu Asp Asp Leu Glu Asn Phe Ile Thr Val Leu Lys Glu Thr
                    180                 185                 190

Asp Glu Lys Ile Lys Gln Gly Asn Glu Val Lys Ile Ala Cys Val Leu
                    195                 200                 205

Asn Ala Lys Lys Glu Thr Ala Tyr Leu Phe Ser Asp Pro Leu Leu Glu
        210                 215                 220

Ile Asn Arg His Phe Lys Cys Ile Asn Ile Ala Asn Leu Asp Glu Asn
225                 230                 235                 240

Ile Gly Phe Asp Lys Val Arg Asn Asp Ala Lys Asn Ile Leu Lys Glu
                    245                 250                 255

Phe Asn Glu Asn Gly Phe Lys Ile Asp Tyr Ile Thr Gly Gly Leu Asp
                    260                 265                 270

Glu Tyr Pro Ile Thr Gly Glu Lys Ala Leu Ser Tyr Leu Lys Glu Ile
                    275                 280                 285

Asn Pro Asp Ile Val Val Ser Gly Val Pro His Ala Leu Leu Ile
        290                 295                 300

Glu Asn Leu Lys Glu Ile Asn Pro Asp Val Ile Thr Val Gly Ile Ser
305                 310                 315                 320

Asp Gly Pro Arg Leu Tyr His Pro Ile Lys Glu Val Tyr Asn Tyr Gly
                    325                 330                 335

Ile Ile Glu Leu Asp Ala His Ala Lys Val Leu Gly Lys Lys Asn Ile
                    340                 345                 350

Val Lys Ser Arg Phe Gly Glu Ile Leu Ser Phe Met Thr Phe
                    355                 360                 365

<210> SEQ ID NO 100
<211> LENGTH: 353
<212> TYPE: PRT
<213> ORGANISM: Methanocorpusculum labreanum Z

<400> SEQUENCE: 100

Met Arg Tyr Val Gln Pro Arg Pro Ser Ser Ile Val Ala Ala Leu Tyr
1               5                   10                  15

Thr Leu Arg Asp Leu Asn Val Asp Leu Ala Ile Leu His Gly Pro Ser
                    20                  25                  30

Gly Cys Ser Phe Lys His Ala Arg Leu Leu Glu Glu Asp Gly Ile Arg
                    35                  40                  45

Val Leu Thr Thr Ser Leu Gly Asp Glu Glu Phe Ile Phe Gly Gly Gln
        50                  55                  60

Lys Ile Leu Glu Asp Val Leu Gln Tyr Ala Glu Lys Glu Phe Ser Pro
65                  70                  75                  80
```

Arg Arg Ile Ala Val Val Gly Thr Cys Val Ser Met Ile Ile Gly Glu
            85                  90                  95

Asp Leu Asp Ala Ala Ile Glu Ala Ser Gly Ile Thr Thr Pro Ala Ile
        100                 105                 110

Gly Val Ser Ile His Ala Gly Phe Arg Glu Asn Ile Asp Gly Val Ile
        115                 120                 125

Ala Thr Leu Glu Pro Ala Ala Lys Ile Gly Trp Ile Ser Glu Glu Glu
        130                 135                 140

Phe Glu Arg Gln Lys Leu Val Leu Ala Ser Ala Asn Lys Thr Glu Arg
145                 150                 155                 160

Glu Arg Gly Ala Ala Cys Lys Thr Tyr Ile Ala Pro Ser Arg Gly Asp
                165                 170                 175

Leu Lys His Val Ala Ala Ala Glu Leu Ala Glu Leu Leu Arg Ser Gly
                180                 185                 190

Lys Lys Gly Met Ala Ile Met Asn Ala Lys Lys Glu Thr Ala Tyr Met
            195                 200                 205

Phe Ala Asp His Leu Cys Ala Val His Glu Cys Ala Pro Asp Ala Asn
210                 215                 220

Val Thr Phe Val Ala Asn Leu Glu Ala Arg Gly Leu Pro Lys Val Arg
225                 230                 235                 240

Gly Asp Ala Ala Met Ile Leu Ala Glu Leu Asn Glu Arg Gly Ile His
                245                 250                 255

Pro Glu Leu Ile Gly Ala Leu Asp Glu Tyr Gly Gly Asn Gly Pro Arg
                260                 265                 270

Ile Ala Glu Arg Ile Ala Glu Val Lys Pro Glu Phe Leu Leu Leu Val
            275                 280                 285

Gly Val Pro His Ala Val Ser Pro Glu Ala Leu Ala Gly Ile Lys Val
        290                 295                 300

Phe Ser Val Thr Asn Gly Pro Arg Gln Val Leu Pro Leu Lys Glu Gln
305                 310                 315                 320

Gly His Ala His Val Met Val Glu Val Asp Leu His Pro Lys Thr Leu
                325                 330                 335

Gly Val His Asn Ile Val Glu Ser Glu Phe Gly Ala Val Leu Arg Ser
                340                 345                 350

Met

<210> SEQ ID NO 101
<211> LENGTH: 354
<212> TYPE: PRT
<213> ORGANISM: Methanoculleus bourgensis MS2

<400> SEQUENCE: 101

Met Gln Tyr Ile Gln Pro Arg Pro Ser Ser Ile Val Ala Ala Leu Tyr
1               5                   10                  15

Thr Ala Arg Asp Leu Gly Val Asp Val Ala Ile Leu His Gly Pro Ser
            20                  25                  30

Gly Cys Ser Phe Lys His Ala Arg Leu Leu Glu Glu Asp Gly Met Arg
        35                  40                  45

Val Leu Thr Thr Ser Leu Ala Asp Asn Glu Phe Ile Phe Gly Gly His
    50                  55                  60

Asp Pro Leu Val Arg Val Leu Arg His Ala Glu Glu Phe Ser Pro
65                  70                  75                  80

His Arg Ile Ala Val Val Gly Thr Cys Val Ala Met Ile Ile Gly Glu
                85                  90                  95

```
Asp Leu Glu Ser Ala Ile His Asp Ala Gly Val Thr Thr Pro Thr Ile
                100                 105                 110

Ala Val Asp Ile His Ala Gly Phe Arg Glu Asn Ile Asp Gly Val Leu
            115                 120                 125

Ala Thr Leu Glu Pro Ala Ala Ala Gly Trp Ile Ser Asp Asp Glu
        130                 135                 140

Leu Glu Arg Gln Arg Tyr His Leu Gly Lys Ala Asn Glu Val Glu Arg
145                 150                 155                 160

Leu Arg Gly Ala Ala Ser Arg Ser Tyr Ile Glu Pro Ser Arg Gly Asp
                165                 170                 175

Leu Lys His Ile Ala Ala Lys Arg Leu Val Glu Leu Ala Asp Glu Gly
            180                 185                 190

Ala Arg Gly Val Ala Val Met Asn Ala Lys Lys Glu Thr Ala Tyr Met
        195                 200                 205

Phe Ala Asp Glu Leu Ile Gly Leu His Asp Ala Cys Pro Asp Ala Ala
210                 215                 220

Ile Thr Tyr Leu Ala Asn Leu Glu Asp Arg Gly Leu Pro Lys Val Arg
225                 230                 235                 240

Glu Asp Ala Ala Arg Ile Leu Ala Gly Met Arg Glu Arg Gly Val Asp
                245                 250                 255

Pro Glu Leu Ile Gly Ala Leu Asp Glu Tyr Gly Ala Asn Gly Thr Ala
            260                 265                 270

Val Gly Glu Arg Ile Arg Glu Leu Ala Pro Asp Phe Ala Leu Ile Val
        275                 280                 285

Gly Val Pro His Ala Val Pro Pro Glu Tyr Met Lys Gly Ile Glu Cys
290                 295                 300

Phe Ser Val Thr Asn Gly Pro Arg Gln Val Glu Pro Leu Arg Glu Met
305                 310                 315                 320

Gly His Arg His Val Met Val Glu Ile Asp Leu His Pro Lys Thr Leu
                325                 330                 335

Gly Val Arg Glu Ile Val Glu Ser Glu Phe Gly Ala Val Leu Arg Ser
            340                 345                 350

Met Arg

<210> SEQ ID NO 102
<211> LENGTH: 357
<212> TYPE: PRT
<213> ORGANISM: Methanofollis liminatans DSM 4140

<400> SEQUENCE: 102

Met Asp Tyr Ile Gln Pro Arg Pro Ser Ser Ile Val Ala Ala Leu Tyr
1               5                   10                  15

Thr Ala Arg Asp Leu Glu Val Glu Val Ala Ile Leu His Gly Pro Ser
            20                  25                  30

Gly Cys Ser Phe Lys His Ala Arg Leu Leu Glu Glu Asp Gly Met Arg
        35                  40                  45

Val Leu Thr Thr Ser Leu Ala Asp Asn Glu Phe Ile Phe Gly Gly Gln
    50                  55                  60

Ala Val Leu Glu Arg Val Leu Lys Gly Ala Glu Lys Asp Phe Ala Pro
65                  70                  75                  80

Lys Arg Met Ala Val Val Gly Thr Cys Val Ser Met Ile Ile Gly Glu
                85                  90                  95

Asp Leu Gln Ala Ala Ile Asp Ala Ser Gly Val Glu Thr Pro Thr Ile
            100                 105                 110
```

Ala Ile Asp Ile His Ala Gly Phe Arg Glu Asn Ile Gln Gly Val Leu
            115                 120                 125

Ala Ala Leu Glu Pro Ala Ala Ile Gly Trp Ile Ser Ala Asp Glu
        130                 135                 140

Leu Glu Arg Gln Arg Arg Leu Leu Ala Ala Asn Glu Val Glu His
145                 150                 155                 160

Leu Arg Gly Ala Ala Ser Arg Ser Tyr Ile Glu Pro Ser Arg Gly Asp
                165                 170                 175

Leu Lys His Val Ala Ala Arg Arg Leu Ile Asp Leu Ala Arg Glu Gly
            180                 185                 190

Lys Arg Gly Ile Ala Val Met Asn Ala Lys Lys Glu Thr Ala Tyr Met
        195                 200                 205

Phe Ala Asp Glu Leu Leu Ala Leu His Asp Ala Cys Pro Asp Ala Glu
    210                 215                 220

Ile Thr Tyr Ile Ala Asn Leu Glu Asp Arg Gly Leu Pro Lys Val Arg
225                 230                 235                 240

Ala Asp Ala Ala Arg Val Leu Gln Gly Met Arg Glu Ala Gly Leu Glu
                245                 250                 255

Pro Glu Leu Leu Gly Ala Leu Asp Glu Tyr Gly Ala Asn Gly Asp Ala
            260                 265                 270

Ile Gly Glu Arg Ile Arg Glu Ile Glu Pro Asp Phe Ala Leu Ile Val
        275                 280                 285

Gly Val Pro His Ala Val Pro Pro Glu Tyr Thr Ala Gly Val Glu Val
    290                 295                 300

Val Ser Val Thr Asn Gly Pro Arg Gln Val Ala Pro Leu Arg Glu Met
305                 310                 315                 320

Gly His Ala Ala Val Val Glu Val Asp Leu His Pro Lys Thr Leu
                325                 330                 335

Gly Val Arg Ser Ile Val Glu Ser Glu Phe Gly Ala Val Val Arg Ser
            340                 345                 350

Ile Ala Arg Gly Glu
        355

<210> SEQ ID NO 103
<211> LENGTH: 373
<212> TYPE: PRT
<213> ORGANISM: Methanohalobium evestigatum Z-7303

<400> SEQUENCE: 103

Met Ser Thr Asn Pro Lys Thr Lys Glu Leu Ser Ile Ile His Pro Arg
1               5                   10                  15

Pro Ser Ser Ile Val Ala Ala Leu Tyr Thr Leu Arg Asp Leu Asn Val
                20                  25                  30

Asp Val Ala Ile Leu His Gly Pro Pro Gly Cys Ser Phe Lys His Ala
            35                  40                  45

Arg Leu Leu Glu Glu Asp Gly Ile His Val Leu Thr Thr Ala Leu Asp
        50                  55                  60

Glu Asn Cys Phe Val Phe Gly Gly His Asp Glu Leu Val Asn Val Ile
65                  70                  75                  80

Asn Lys Ala Val Asp Leu Phe Asn Pro Gly Leu Ile Gly Ile Val Gly
                85                  90                  95

Thr Cys Ala Ser Met Ile Ile Gly Glu Asp Leu His Glu Pro Val Leu
            100                 105                 110

Asp Ala Asn Leu Asp Ile Pro Val Ile Glu Val Glu Val His Ala Gly
        115                 120                 125

-continued

```
Tyr Ser Asp Asn Thr Lys Gly Val Leu Phe Ala Leu Glu Ser Ala Leu
        130                 135                 140

Asp Ala Gly Ile Ile Asp Arg Thr Glu Phe Glu Arg Gln Lys Tyr Leu
145                 150                 155                 160

Leu Glu Glu Ala Thr Ser Val Glu Lys Arg Tyr Gly Ala Ala Ser Lys
                165                 170                 175

Gln Tyr Leu Glu Pro Ser Arg Gly Asp Val Lys Tyr Arg Val Gly Lys
            180                 185                 190

Arg Ile Ile Glu Leu Leu Lys Glu Gly Lys Arg Gly Ile Thr Ile Met
        195                 200                 205

Asn Ala Lys Lys Glu Thr Gly Tyr Met Phe Ala Asp Ile Thr Leu Ala
    210                 215                 220

Val Asn Gln Val Ala Ser Lys Leu Gly Lys Glu Ser Asn Ile Val Asn
225                 230                 235                 240

Met Ala Asn Thr Asn Asp Asn Val Gly Leu Pro Arg Val Arg Gln His
                245                 250                 255

Ala Gln Asn Ile Met Asp Asp Phe Asn Glu Asn Asp Val Asp Val His
            260                 265                 270

Glu Leu Ile Gly Gly Met Asp Glu Tyr Pro Ile Thr Gly Asp Glu Ile
        275                 280                 285

Asn Arg Leu Ile Glu Glu Lys Tyr Ser Asp Tyr Asp Phe Ala Val Ile
    290                 295                 300

Ser Gly Val Pro His Ala Ile Pro Met Asp Asn Leu Ser Asp Met Glu
305                 310                 315                 320

Ile Val Ser Val Thr Asn Gly Pro Arg Gln Val Phe Pro Leu Lys Asp
                325                 330                 335

Met Gly His Asp His Val Ile Val Glu Val Asp Leu His Pro Lys Thr
            340                 345                 350

Leu Gly Val Asp Tyr Ile Val Glu Ser Glu Phe Gly Ala Thr Leu Arg
        355                 360                 365

Glu Ile Ile Asn Glu
    370
```

<210> SEQ ID NO 104
<211> LENGTH: 369
<212> TYPE: PRT
<213> ORGANISM: Methanohalophilus mahii DSM 5219

<400> SEQUENCE: 104

```
Met Gln Gln Lys Asn Leu Ser Ile Met His Pro Arg Pro Ser Ser Ile
1               5                   10                  15

Val Ala Ala Leu Tyr Thr Leu Arg Asp Leu Asn Val Glu Val Ala Ile
                20                  25                  30

Leu His Gly Pro Pro Gly Cys Ser Phe Lys His Ala Arg Leu Leu Glu
            35                  40                  45

Glu Asp Gly Ile Arg Val Val Thr Thr Ala Leu Asp Glu Asn Gly Phe
        50                  55                  60

Val Phe Gly Gly His Asp Arg Leu Val Asp Met Leu Gln Lys Val Glu
65                  70                  75                  80

Glu Arg Phe Ser Pro Lys Arg Ile Gly Val Val Gly Thr Cys Val Ser
                85                  90                  95

Met Ile Ile Gly Glu Glu Leu His Glu Ala Val Met Glu Ala Asn Leu
            100                 105                 110

Asp Ala Pro Val Ile Glu Val Glu Val His Ala Gly Tyr Asn Asp Asn
```

```
            115                 120                 125
Thr Lys Gly Val Leu Phe Ala Leu Glu Ser Ala Leu Asp Val Gly Ile
    130                 135                 140
Ile Asp Arg Gln Glu Phe Glu Arg Gln Gln His Leu Leu Asn Glu Ala
145                 150                 155                 160
Thr Asn Val Glu Lys Lys Tyr Gly Ala Ala Ser Lys Glu Tyr Leu Glu
                165                 170                 175
Pro Ser Arg Gly Asp Val Lys Tyr Thr Val Ala Lys Arg Val Ile Glu
            180                 185                 190
Met Leu Lys Ala Gly Lys Lys Gly Ile Cys Ile Leu Asn Ala Lys Lys
                195                 200                 205
Glu Thr Ala Tyr Met Phe Ala Asp Ile Thr Val Ala Leu Gln Glu Val
    210                 215                 220
Ala Glu Lys Leu Gly Val Glu Asp Asn Ile Val Asn Phe Ala Asn Leu
225                 230                 235                 240
Asp Thr Gly Leu Gly Leu Pro Arg Val Arg Gln His Ala Glu His Ile
                245                 250                 255
Leu Ala Asp Met His Asp Asn Val Lys Ile Asp Glu Ile Ile Gly Gly
            260                 265                 270
Leu Asp Glu Tyr Pro Ile Ala Gly Gln Gln Val Arg Gln Leu Ile Glu
        275                 280                 285
Ala Lys Tyr Lys Asp Phe Asp Phe Ala Val Ile Ala Gly Val Pro His
    290                 295                 300
Ala Ile Pro Met Glu Ser Leu Glu Gly Met Glu Leu Ile Ser Ile Thr
305                 310                 315                 320
Asn Gly Pro Arg Gln Val His Pro Leu Lys Asp Met Gly His Glu His
                325                 330                 335
Val Leu Val Glu Ile Asp Leu His Pro Lys Thr Leu Gly Val Thr Asn
            340                 345                 350
Ile Val Glu Ser Glu Phe Gly Ala Thr Val Arg Gln Leu Ala Arg Glu
        355                 360                 365
Glu

<210> SEQ ID NO 105
<211> LENGTH: 353
<212> TYPE: PRT
<213> ORGANISM: Methanolacinia petrolearia DSM 11571

<400> SEQUENCE: 105

Met Asn Tyr Ile Gln Pro Arg Pro Ser Ser Ile Val Ala Ala Leu Tyr
1               5                   10                  15
Thr Val Arg Asp Leu Gly Val Asp Leu Ala Ile Leu His Gly Pro Ser
                20                  25                  30
Gly Cys Ser Phe Lys His Ala Arg Leu Leu Glu Glu Asp Gly Leu Arg
            35                  40                  45
Val Leu Thr Thr Ser Leu Ala Asp Asn Glu Phe Ile Phe Gly Gly Gln
        50                  55                  60
Gln Val Leu Glu Asp Val Leu Arg Tyr Ala Lys Glu Phe Lys Pro
65                  70                  75                  80
Glu Arg Ile Ala Val Gly Thr Cys Val Ser Met Ile Ile Gly Glu
                85                  90                  95
Asp Met Glu Ala Ala Ile Ile Asp Ser Gly Ile Glu Thr Pro Ala Ile
            100                 105                 110
Ala Val Asp Ile His Ala Gly Phe Arg Glu Asn Ile Asp Gly Val Ile
```

```
            115                 120                 125
Ala Ala Leu Glu Pro Ala Ala Glu Ala Gly Trp Ile Asp Glu Asp Glu
        130                 135                 140

Leu Glu Arg Gln Lys Gly Leu Leu Lys Ala Ala Asn Glu Val Glu Arg
145                 150                 155                 160

Lys Arg Gly Ala Ala Tyr Lys Pro Tyr Val Gln Pro Ser Arg Gly Asp
                165                 170                 175

Leu Lys His Val Val Ala Gly Ser Leu Val Glu Ser Ala Cys Ser Gly
            180                 185                 190

Arg Lys Gly Ile Ala Ile Leu Asn Ala Lys Lys Glu Thr Ala Tyr Met
        195                 200                 205

Phe Ala Asp Val Leu Ile Ala Leu His Glu Arg Cys Pro Asp Ala Asp
        210                 215                 220

Ile Thr Tyr Val Val Asn Leu Glu Asn Arg Gly Leu Pro Lys Ile Arg
225                 230                 235                 240

Arg Asp Ala Glu Thr Ile Leu Ser Gly Ile Arg Ser Ala Gly Ile Asp
                245                 250                 255

Pro Val Leu Cys Gly Ala Leu Asp Glu Tyr Gly Ala Asn Gly Asp Arg
            260                 265                 270

Ile Gly Glu Ile Ile Asn Glu Ile Lys Pro Asp Phe Ala Leu Ile Ala
        275                 280                 285

Gly Val Pro His Ala Ile Pro Pro Glu Tyr Leu Glu Gly Ile Glu Val
        290                 295                 300

Phe Ser Val Thr Asn Gly Pro Arg Gln Val Glu Pro Leu Lys Glu Phe
305                 310                 315                 320

Gly His Asp His Val Val Glu Ile Asp Leu His Pro Lys Thr Leu
                325                 330                 335

Gly Val Arg Glu Ile Val Pro Ser Glu Phe Gly Asp Thr Ile Arg Ser
            340                 345                 350

Ile

<210> SEQ ID NO 106
<211> LENGTH: 373
<212> TYPE: PRT
<213> ORGANISM: Methanolobus psychrophilus R15

<400> SEQUENCE: 106

Met Ile Gly Lys Asn Leu Ser Ile Met His Pro Arg Pro Ser Ser Ile
1               5                   10                  15

Val Ala Ala Leu Tyr Thr Leu Arg Asp Leu Asn Val Asp Val Ala Ile
                20                  25                  30

Leu His Gly Pro Pro Gly Cys Ser Phe Lys His Ala Arg Leu Leu Glu
            35                  40                  45

Glu Asp Gly Ile Arg Val Val Thr Thr Ala Leu Asp Glu Asn Gly Phe
        50                  55                  60

Val Phe Gly Gly Arg Gln Glu Leu Ser Ser Leu Leu Val Lys Val Asn
65                  70                  75                  80

Glu Met Phe Lys Pro Lys Leu Ile Gly Val Val Gly Thr Cys Ala Ser
                85                  90                  95

Met Ile Ile Gly Glu Glu Leu Arg Glu Pro Val Glu Asp Ala Asn Leu
            100                 105                 110

Asp Val Pro Val Ile Glu Val Glu Val His Ala Gly Tyr Pro Asp Asn
        115                 120                 125

Thr Lys Gly Val Leu Ile Thr Leu Glu Ser Ala Phe Glu Val Gly Val
```

```
                130               135               140
Ile Gly Lys Glu Glu Leu Glu Arg Gln Lys Val Leu Leu Arg Glu Ala
145                 150                 155                 160

Thr Leu Val Glu Lys Arg His Gly Ala Ala Ser Lys Glu Tyr Leu Glu
                165                 170                 175

Pro Ser Arg Gly Asp Val Lys Tyr Lys Val Ala Glu Lys Val Val Arg
                180                 185                 190

Leu Leu Gln Glu Gly Lys Lys Gly Ile Thr Ile Met Asn Ala Lys Lys
                195                 200                 205

Glu Thr Gly Tyr Met Phe Ala Asp Val Ser Ala Ala Val Asn Glu Val
                210                 215                 220

Ala Leu Ala Leu Gly Lys Gly Asn Val Val Asn Met Ala Asn Ile
225                 230                 235                 240

Asp Asp Ser Leu Gly Leu Pro Arg Val Arg His His Ala Lys Cys Ile
                245                 250                 255

Thr Ala Asp Leu Gln Glu Arg Gly Ile Thr Val His Glu Val Ile Gly
                260                 265                 270

Gly Met Asp Glu Tyr Pro Val Thr Gly Glu Lys Val Gly Glu Leu Ile
                275                 280                 285

Lys Gln Lys Tyr Ser Asp Tyr Asp Phe Ala Ile Ile Thr Gly Val Pro
                290                 295                 300

His Ala Ile Pro Met Glu Ala Leu Glu Gly Met Glu Ile Ile Ser Val
305                 310                 315                 320

Thr Asn Gly Pro Arg Gln Val Leu Pro Leu Lys Glu Met Gly His Gln
                325                 330                 335

His Val Ile Val Glu Ile Asp Leu His Pro Lys Thr Leu Gly Val Asn
                340                 345                 350

His Ile Val Glu Ser Glu Phe Gly Ala Thr Leu Arg Glu Val Ala Lys
                355                 360                 365

Asp Val Leu Gly Arg
    370

<210> SEQ ID NO 107
<211> LENGTH: 368
<212> TYPE: PRT
<213> ORGANISM: Methanomassiliicoccus luminyensis B10

<400> SEQUENCE: 107

Met His Gln Gly Gly Leu Pro Leu Ile Asp Val Leu His Pro Arg Pro
1                 5                  10                  15

Asn Pro Ile Ile Ala Ala Met Tyr Thr Met Arg Asp Leu Glu Ala Asp
                20                  25                  30

Ile Val Leu Met His Gly Pro Ala Gly Cys Gly Phe Met Ala Ala Arg
                35                  40                  45

Arg Leu Glu Glu Ala Gly Val Arg Val Met Thr Thr Gly Met Asn Glu
                50                  55                  60

Asp Asp Leu Ile Phe Gly Ala Asn Asp Lys Leu Ala Arg Ile Leu Lys
65                  70                  75                  80

Ser Val Asp Glu Arg Tyr Arg Pro Lys Leu Ile Gly Val Val Gly Thr
                85                  90                  95

Cys Ala Ser Met Ile Ile Gly Glu Asp Leu Asp Ala Ala Val Lys Lys
                100                 105                 110

Ala Gly Val Arg Ala Thr Val Leu Pro Val Asp Val His Gly Cys Ser
                115                 120                 125
```

```
Gly Pro Asn Thr Ala Gly Ala Ile Arg Thr Leu Glu Val Ala Ala Glu
            130                 135                 140

Lys Arg Val Ile Ser Tyr Glu Arg Asp Arg Gln Lys Ser Met Leu
145                 150                 155                 160

Thr Lys Ala Thr Leu Leu Glu Lys Glu Arg Gly Leu Thr Ser Arg Glu
                165                 170                 175

Tyr Leu Glu Pro His Pro Gly Ser Thr Lys Leu Ser Ala Gly Leu Arg
                180                 185                 190

Ile Val Asn Thr Leu Arg Glu Gly Lys Val Ala Val Ala Leu Asn
                195                 200                 205

Ala Lys Lys Glu Thr Ala Tyr Gly Phe Ala Asp Val Met Arg Ala Val
            210                 215                 220

Glu Tyr Ala Arg Ser Lys Val Gly Gly Thr Ala Thr Tyr Ile Gly Asn
225                 230                 235                 240

Leu Asp Pro Glu Val Gly Leu Pro Arg Ile Arg Arg Tyr Ser Ser Asp
                245                 250                 255

Ile Leu Arg Asp Leu Asp Glu Ala Gly Val Ala Val Asp Val Ile Thr
                260                 265                 270

Gly Gly Leu Asp Glu Tyr Pro Val Thr Gly Asp Lys Ala Ala Ala
            275                 280                 285

Leu Asp Ala Ser Ala Ala Asp Leu Arg Val Ile Ala Gly Leu Pro His
            290                 295                 300

Ala Val Pro Gly Leu Arg Lys Asp Asp Val Leu Val Thr Asp Gln Pro
305                 310                 315                 320

Arg Glu Leu Arg Asn Tyr Ile Asp Gln Gly Tyr His Met Ser Val Gly
                325                 330                 335

Glu Ile Thr Thr His Ala Asp Val Met Gly Thr Ser Lys Val Leu Tyr
                340                 345                 350

Asn Glu Leu Gly Asn Thr Ile Arg Glu Ile Thr Asp Lys Gly Trp Thr
                355                 360                 365

<210> SEQ ID NO 108
<211> LENGTH: 375
<212> TYPE: PRT
<213> ORGANISM: Methanomethylovorans hollandica DSM 15978

<400> SEQUENCE: 108

Met Ala Ala Asn Asp Ile Ser Ile Ile His Pro Arg Pro Ser Ser Ile
1               5                   10                  15

Val Ala Ala Leu Tyr Thr Leu Arg Asp Leu Asn Val Asp Val Ala Ile
                20                  25                  30

Leu His Gly Pro Pro Gly Cys Ser Phe Lys His Ala Arg Leu Leu Glu
            35                  40                  45

Glu Asp Gly Ile His Val Val Thr Thr Ala Leu Asp Glu Asn Gly Phe
    50                  55                  60

Val Phe Gly Gly Arg Arg Glu Leu Ser Ser Val Leu Gln Lys Val Asn
65                  70                  75                  80

Glu Met Phe His Pro Lys Leu Ile Gly Val Val Gly Thr Cys Ala Ser
                85                  90                  95

Met Ile Ile Gly Glu Glu Leu His Glu Pro Val Met Asp Ala Asp Leu
            100                 105                 110

Glu Val Pro Val Ile Glu Val Glu Val His Ala Gly Tyr Ala Asn Asn
                115                 120                 125

Thr Lys Gly Val Leu Ile Thr Leu Glu Ser Ala Leu Glu Ile Gly Val
            130                 135                 140
```

Ile Asp Arg Glu Glu Phe Glu Arg Gln Lys Val Leu Met Glu Glu Ala
145                 150                 155                 160

Thr Glu Val Glu Lys Arg His Gly Ala Ala Ser Lys Glu Tyr Leu Ala
            165                 170                 175

Pro Ser Arg Gly Asp Leu Lys Tyr Lys Val Ala Gln Arg Ile Ile Glu
            180                 185                 190

Leu Leu Lys Glu Gly Lys Lys Gly Leu Val Ile Met Asn Ala Lys Lys
        195                 200                 205

Glu Thr Gly Tyr Met Phe Ala Asp Ile Asn Val Ala His Glu Val
    210                 215                 220

Ala Ser Gln Leu Gly Val Ala Ala Asn Val Asn Met Ala Asn Leu
225                 230                 235                 240

Asp Glu Ser Leu Gly Leu Pro Arg Val Arg Asp His Ala Arg Asn Ile
            245                 250                 255

Met His Asp Leu Lys Glu Arg Gly Val Gln Val His Glu Ile Thr Gly
            260                 265                 270

Gly Leu Asp Glu Tyr Pro Ile Ala Gly Asn Val Val Asp Glu Leu Ile
        275                 280                 285

Ala Lys Lys Tyr Ala Asn Tyr Asp Phe Ala Val Ile Thr Gly Val Pro
290                 295                 300

His Ala Ile Pro Met Asp His Ile Ser Asn Met Glu Ile Ile Ser Val
305                 310                 315                 320

Thr Asn Gly Pro Arg Gln Val Leu Pro Leu Lys Glu Met Gly His Arg
            325                 330                 335

His Val Val Val Glu Ile Asp Leu His Pro Lys Thr Leu Gly Val Lys
        340                 345                 350

His Ile Val Glu Ser Glu Met Gly Ala Thr Leu Arg Glu Met Val Lys
        355                 360                 365

Glu Met His Glu Ser Phe Val
    370                 375

<210> SEQ ID NO 109
<211> LENGTH: 361
<212> TYPE: PRT
<213> ORGANISM: Methanomicrobium mobile BP

<400> SEQUENCE: 109

Met Glu Tyr Ile Gln Pro Arg Pro Ser Ser Ile Val Ala Gly Leu Tyr
1               5                   10                  15

Thr Val Arg Asp Leu Gly Val Asp Val Ala Ile Leu His Gly Pro Ser
            20                  25                  30

Gly Cys Ser Phe Lys His Ala Arg Leu Leu Glu Glu Asp Gly Leu Arg
        35                  40                  45

Val Leu Thr Thr Ser Leu Ala Asp Asn Glu Phe Ile Phe Gly Gly His
    50                  55                  60

Asp Ile Leu Val Lys Val Leu Lys Phe Ala Glu Lys Glu Phe Lys Pro
65                  70                  75                  80

Arg Arg Ile Ala Val Val Gly Thr Cys Val Ala Met Ile Ile Gly Glu
                85                  90                  95

Asp Met Gln Ala Ala Ile Asp Asp Ser Gly Ile Ser Thr Pro Ala Ile
            100                 105                 110

Ala Val Asn Ile His Ala Gly Phe Arg Glu Asn Ile Asp Gly Val Ile
        115                 120                 125

Ala Ala Leu Glu Pro Ala Ala Asp Ala Gly Trp Ile Asp Glu Asp Glu

```
                  130                 135                 140
Leu Glu Arg Gln Lys Val Leu Arg Ala Ala Asn Gln Val Glu Arg
145                 150                 155                 160

Ala Arg Gly Ala Ala Tyr Lys Pro Tyr Val Gln Pro His Arg Gly Asp
                    165                 170                 175

Leu Lys His Val Val Ala Lys Arg Leu Leu Glu Leu Ala Lys Glu Gly
                    180                 185                 190

Lys Lys Gly Val Ala Ile Leu Asn Ala Lys Lys Glu Thr Ala Tyr Met
                195                 200                 205

Phe Ala Asp Val Leu Thr Ala Phe Arg Glu Ala Cys Pro Asp Ala Asp
                210                 215                 220

Val Gln Tyr Ile Ala Asn Leu Glu Ala Arg Gly Leu Pro Lys Val Arg
225                 230                 235                 240

Glu Asp Ala Lys Asn Ile Leu Leu Gly Leu Glu Lys Ala Gly Ile Ala
                    245                 250                 255

Glu Gly Lys Asn Leu Lys Leu Ile Gly Ala Leu Asp Glu Tyr Gly Ala
                    260                 265                 270

Asn Gly Glu Lys Leu Gly Ala Ala Leu Lys Glu Ile Lys Pro Asp Phe
                275                 280                 285

Ala Ile Ile Ser Gly Val Pro His Ala Ile Ala Pro Glu Tyr Leu Glu
                290                 295                 300

Gly Ile Glu Val Phe Ser Val Thr Asn Gly Pro Arg Gln Tyr Gln Pro
305                 310                 315                 320

Leu Lys Glu Phe Gly His Asp His Val Val Glu Ile Asp Leu His
                    325                 330                 335

Pro Lys Thr Leu Gly Val Arg Glu Ile Val Pro Ser Glu Phe Gly Asp
                340                 345                 350

Val Ile Arg Ser Leu Lys Asp Glu Ser
                355                 360

<210> SEQ ID NO 110
<211> LENGTH: 356
<212> TYPE: PRT
<213> ORGANISM: Methanoplanus limicola DSM 2279

<400> SEQUENCE: 110

Met His Tyr Ile Gln Pro Arg Pro Ser Ser Ile Val Ala Ala Leu Tyr
1               5                   10                  15

Thr Val Arg Asp Leu Gly Val Asp Leu Ala Ile Leu His Gly Pro Ser
                20                  25                  30

Gly Cys Ser Phe Lys His Ala Arg Leu Leu Glu Glu Asp Gly Leu Arg
            35                  40                  45

Val Leu Thr Thr Ser Leu Ala Asp Asn Glu Phe Ile Phe Gly Gly Gln
        50                  55                  60

Asn Ile Leu Glu Asp Val Leu Arg Tyr Ala Glu Ser Glu Phe Ser Pro
65                  70                  75                  80

Lys Arg Ile Ala Val Val Gly Thr Cys Val Ser Met Ile Ile Gly Glu
                85                  90                  95

Asp Met Gln Ala Ala Ile Glu Asp Ser Gly Ile Lys Thr Pro Ala Ile
                100                 105                 110

Ala Ile Asp Ile His Ala Gly Phe Arg Glu Asn Ile Asp Gly Val Ile
            115                 120                 125

Ala Ala Leu Glu Pro Ala Ala Glu Ala Gly Trp Ile Asp Ala Glu Glu
        130                 135                 140
```

Leu Glu Arg Gln Lys Trp Val Leu Lys Glu Ala Asn Arg Val Glu Lys
145                 150                 155                 160

Glu Arg Gly Ala Ala Tyr Lys Lys Tyr Val Gln Pro Ser Arg Gly Asp
            165                 170                 175

Leu Lys His Leu Val Ala Glu Arg Leu Val Glu Thr Ala Thr Ser Gly
                180                 185                 190

Lys Lys Gly Val Ala Val Met Asn Ala Lys Lys Glu Thr Ala Tyr Met
        195                 200                 205

Phe Ala Asp Glu Leu Val Ala Leu His Glu Val Cys Pro Asp Ala Asp
210                 215                 220

Ile Thr Tyr Ile Val Asn Leu Glu Glu Arg Gly Leu Pro Lys Val Arg
225                 230                 235                 240

Gln Asp Ala Glu Asn Val Leu Lys Gly Ile Lys Asp Ala Gly Ile Ile
            245                 250                 255

Pro Val Leu Lys Gly Ala Leu Asp Glu Tyr Gly Ala Asn Gly Asp Ile
                260                 265                 270

Leu Gly Glu Ala Ile Arg Lys Leu Lys Pro Asp Phe Ala Leu Ile Ala
        275                 280                 285

Gly Val Pro His Ala Ile Pro Pro Glu Tyr Leu Lys Gly Ile Glu Leu
290                 295                 300

Phe Ser Val Thr Asn Gly Pro Arg Gln Val Glu Pro Leu Lys Asp Phe
305                 310                 315                 320

Gly His Glu His Val Val Glu Ile Asp Leu His Pro Lys Thr Leu
            325                 330                 335

Gly Val Lys Asn Ile Val Pro Gly Glu Phe Gly Asp Val Leu Arg Ser
                340                 345                 350

Phe Lys Arg Ser
        355

<210> SEQ ID NO 111
<211> LENGTH: 349
<212> TYPE: PRT
<213> ORGANISM: Methanopyrus kandleri AV19

<400> SEQUENCE: 111

Met Ser Thr Trp His Pro Arg Pro Gly Pro Ile Pro Ala Ala Met Tyr
1               5                   10                  15

Thr Leu Arg Asp Leu Leu Ala Asp Ala Val Val Leu His Gly Pro Lys
            20                  25                  30

Gly Cys Cys Phe Arg Thr Ala Arg Leu Leu Glu Lys Asp Gly Val Arg
        35                  40                  45

Val Phe Val Thr Gly Met Glu Glu Asp Asp Phe Val Phe Gly Ala Leu
50                  55                  60

Glu Lys Leu Val Glu Leu Glu Tyr Val Glu Arg Leu Glu Pro
65                  70                  75                  80

Glu Leu Ile Gly Val Val Gly Thr Cys Val Ser Ser Ile Ile Gly Glu
            85                  90                  95

Asp Leu Glu Ala Ala Val Glu Glu Ala Asp Val Asp Ala Thr Val Val
            100                 105                 110

Thr Val Glu Val His Asn Gly Met Gly Pro Asn Thr Glu Gly Val Ile
            115                 120                 125

Arg Thr Leu Glu Arg Ala Ala Glu Ala Gly Val Ile Pro Glu Gly Glu
        130                 135                 140

Val Glu Arg Gln Lys Arg Leu Met Arg Ala Ala Ala Glu Leu Glu Arg
145                 150                 155                 160

Arg Arg Gly Met Ala Ser Arg Glu Tyr Leu Glu Pro Trp Ser Gly His
            165                 170                 175

Asp Pro Ser Glu Val Ala Arg Val Leu Leu Ser Ser Glu Asp Val Leu
        180                 185                 190

Ala Ile Leu Asn Ala Lys Lys Glu Thr Ala Tyr Leu Phe Ala Asp Pro
        195                 200                 205

Val Leu Glu Val Gly Lys Arg Gly Ala Trp Val Leu Ala Asn Leu Ser
    210                 215                 220

Pro Glu Ser Gly Leu Pro Lys Val Arg Arg Asp Ala Glu Val Ile Gly
225                 230                 235                 240

Ser Ile Phe Arg Glu Glu Gly Ile Glu Phe Glu Val Thr Gly Ser Leu
                245                 250                 255

Asp Glu Tyr Ala Val Thr Gly Glu Leu Leu Ala Glu Lys Ile Glu Glu
            260                 265                 270

Phe Asp Pro Asp Ser Val Leu Ile Thr Gly Ile Pro His Ala Val Ala
        275                 280                 285

Pro Glu Glu Leu Asp Val Asp Ala Thr Phe Val Ala Val Thr Asp Gly
    290                 295                 300

Leu Arg Glu Ala Ser Ala Leu Arg Glu Leu Gly Tyr Asp Tyr Val Val
305                 310                 315                 320

Val Glu Glu Glu Ala His Ala Arg Val Leu Gly Arg Arg Glu Ile Val
                325                 330                 335

Pro Ser Asp Leu Gly Glu Ala Ile Arg Gln Leu Ser Ala
            340                 345

<210> SEQ ID NO 112
<211> LENGTH: 354
<212> TYPE: PRT
<213> ORGANISM: Methanoregula formicica SMSP

<400> SEQUENCE: 112

Met Lys Tyr Met His Pro Arg Pro Ser Ser Ile Val Ala Ala Leu Tyr
1               5                   10                  15

Thr Ala Arg Asp Leu Asn Val Asp Val Ala Ile Leu His Gly Pro Ser
            20                  25                  30

Gly Cys Ser Phe Lys His Ala Arg Leu Leu Glu Glu Asp Gly Met Arg
        35                  40                  45

Thr Leu Thr Thr Ser Leu Ala Asp Asn Glu Phe Ile Phe Gly Gly Gln
    50                  55                  60

Lys Pro Leu Glu Asp Val Leu Arg Tyr Ala Glu Glu Met Phe His Pro
65                  70                  75                  80

Lys Arg Met Ala Val Ile Gly Thr Cys Val Ala Met Ile Ile Gly Glu
                85                  90                  95

Asp Leu Gln Ser Ala Ile Asp Gly Ala Gly Ile Thr Thr Pro Thr Ile
            100                 105                 110

Ala Val Asp Ile His Ala Gly Tyr Leu Glu Asn Ile Ala Gly Val Leu
        115                 120                 125

Ser Thr Leu Glu Ala Ala Ala Glu Ala Gly Trp Ile Thr Gln Glu Glu
    130                 135                 140

Leu Ala Arg Gln Arg Gln Met Met Arg Ala Asn Glu Val Glu Arg
145                 150                 155                 160

Leu Arg Gly Ala Ala Ser Gln Ser Tyr Ile Glu Ala Ser Arg Gly Asp
                165                 170                 175

Leu Lys His Val Ala Ala Gln Glu Leu Leu Arg Leu Ala Arg Ser Gly

|   |   |   | 180 |   |   |   |   | 185 |   |   |   |   | 190 |   |
|---|---|---|-----|---|---|---|---|-----|---|---|---|---|-----|---|

Lys Lys Gly Val Ala Ile Leu Asn Ala Lys Lys Glu Thr Ala Tyr Met
                  195               200                  205

Phe Val Asp Ala Leu Ile Ala Phe His Asp Lys Cys Pro Asp Ala Asp
    210                    215              220

Ile Thr Tyr Ile Ala Asn Leu Glu Gln Arg Gly Leu Pro Lys Thr Arg
225                    230               235                  240

Gly Asp Ala Glu Arg Ile Ala Thr Glu Leu Ala Glu Arg Gly Val Asn
               245               250                255

Ala Glu Leu Ile Gly Ala Leu Asp Glu Tyr Gly Ala Asn Gly Asn Arg
          260               265                270

Leu Gly Arg Arg Ile Arg Glu Ile Arg Pro Asp Phe Ala Leu Ile Thr
       275                280              285

Gly Val Pro His Ala Ile Pro Pro Glu Tyr Thr Lys Gly Val Glu Cys
    290                  295              300

Phe Ser Ile Thr Asn Gly Pro Arg Gln Val Ala Pro Leu Arg Ala Ile
305                    310               315                320

Gly His Gln His Val Met Val Glu Ile Asp Leu His Pro Lys Thr Leu
               325               330               335

Gly Val Arg Ser Ile Val Glu Ser Glu Phe Gly Ala Val Leu Arg Ser
          340               345                350

Leu Pro

<210> SEQ ID NO 113
<211> LENGTH: 369
<212> TYPE: PRT
<213> ORGANISM: Methanosaeta concilii GP6

<400> SEQUENCE: 113

Met Ala Ser Glu Met Gln Asn Leu Asn Val Leu His Pro Arg Pro Ser
1                   5                  10               15

Ser Ile Val Ala Ala Leu Tyr Thr Leu Arg Asp Leu Gly Ala Asp Val
               20               25                30

Val Ile Leu His Gly Pro Ser Gly Cys Cys Phe Lys His Ala Arg Leu
          35               40                45

Leu Glu Glu Asp Gly Val Arg Val Leu Thr Thr Ala Leu Asp Glu Ala
  50                   55               60

Gly Phe Val Phe Gly Gly His Lys Pro Leu Thr Ala Leu Leu Lys Lys
65                  70               75                  80

Ala Val Glu Leu Phe Asn Pro Arg Leu Met Ala Ile Ser Gly Thr Cys
               85               90                95

Ser Ser Met Ile Ile Gly Asp Asp Leu His Gln Ala Val Leu Glu Ala
          100               105               110

Asp Leu Asp Ile Pro Val Leu Glu Val Glu Val His Ala Gly Tyr Arg
        115               120              125

Asp Asn Thr Lys Gly Val Ile Ile Thr Leu Glu Ala Ala Arg Asp Lys
    130                  135             140

Gly Ile Ile Asp Glu Ala Glu Phe Val Arg Gln Lys Thr Leu Leu Glu
145                 150               155                160

Lys Ala Thr Glu Val Glu Arg Leu Arg Gly Ala Ala Ser Ala Glu Tyr
               165              170                175

Leu Ala Pro Glu Arg Gly Asp Leu Lys Tyr Gln Ala Ala Glu Arg Leu
            180              185              190

Leu Glu Leu Ile Gln Gln Gly Lys Arg Gly Leu Asn Ile Leu Asn Ala

```
                195                 200                 205
Lys Lys Glu Thr Ala Tyr Met Phe Ala Asp Ile Thr Ala Ala Val Ala
    210                 215                 220

Glu Val Ala Gly Gly Gln Val Asp Thr Leu Ala Asn Leu Asn Asp Gln
225                 230                 235                 240

Leu Gly Leu Pro Lys Val Arg Arg Asp Ala Val Asn Val Ala Gly Asp
                245                 250                 255

Leu Arg Gly Arg Gly Val Gln Phe Ser Ile Ile Gly Gly Leu Asp Glu
            260                 265                 270

Tyr Pro Val Thr Gly Asp Val Ile Ala Gln Arg Ala Gln Glu Gly Gly
        275                 280                 285

Tyr Asp Phe Ala Val Val Ser Gly Val Pro His Ala Leu Thr Ala Ser
    290                 295                 300

Ala Leu Gln Gly Leu Glu Ile Phe Ser Ile Thr Asn Gly Pro Arg Gln
305                 310                 315                 320

Val Lys Pro Leu Arg Asp Leu Gly His Gln His Val Met Val Glu Ile
                325                 330                 335

Asp Leu His Pro Lys Thr Met Gly Val Thr Ser Ile Val Glu Ser Glu
            340                 345                 350

Phe Gly Ala Thr Leu Arg Ala Met Asn Lys Ala Arg Ala Lys Gln Asp
        355                 360                 365

Gly
```

<210> SEQ ID NO 114
<211> LENGTH: 382
<212> TYPE: PRT
<213> ORGANISM: Methanosalsum zhilinae DSM 4017

<400> SEQUENCE: 114

```
Met Lys Thr Asp Gln Ile Ser Ile Ile His Pro Arg Pro Ser Ser Ile
1               5                   10                  15

Val Ala Ala Leu Tyr Thr Leu Arg Asp Leu Asp Val Asp Val Ala Ile
                20                  25                  30

Leu His Gly Pro Ala Gly Cys Ser Phe Lys His Ala Arg Leu Leu Glu
            35                  40                  45

Glu Asp Gly Val His Val Leu Thr Thr Ala Leu Asp Glu Asn Gly Phe
        50                  55                  60

Val Phe Gly Gly His Asp Glu Leu Val Ser Leu Ile Lys Lys Ala Ala
65                  70                  75                  80

Asp Met Phe Asn Pro Gly Ser Met Ala Val Val Gly Thr Cys Ala Ser
                85                  90                  95

Met Ile Ile Gly Glu Glu Leu His Asp Ala Val Glu Glu Ala Gly Leu
            100                 105                 110

Asn Ile Pro Val Ile Glu Val Glu Val His Ala Gly Tyr Arg Asp Asn
        115                 120                 125

Thr Lys Gly Val Leu Leu Ala Leu Glu Ser Ala Ala Asp Ala Gly Leu
    130                 135                 140

Ile Ser Asp Thr Glu Tyr Gln Arg Gln Ile Ile Leu Lys Glu Ala
145                 150                 155                 160

Thr Glu Ile Glu Lys Lys His Gly Ala Ala Ser Lys Ser Tyr Leu Ala
                165                 170                 175

Pro Ser Arg Gly Asp Val Lys Tyr Ser Val Ala Lys Arg Val Met Asn
            180                 185                 190

Leu Leu Lys Glu Gly Lys Lys Gly Ile Ile Ile Met Asn Ala Lys Lys
```

```
                195                 200                 205
Glu Thr Gly Tyr Met Phe Ala Asp Val Ile Leu Ala Val Asn Glu Ile
210                 215                 220
Ala Glu Gln Met Lys Val Glu Ser Asn Ile Val Asn Met Ala Asn Ile
225                 230                 235                 240
Asp Gln Thr Leu Gly Leu Pro Arg Val Arg Ser His Ala Arg Asn Ile
            245                 250                 255
Met Ser Asp Phe Lys Lys His Gly Thr Gln Ile His Glu Ile Ile Gly
            260                 265                 270
Gly Met Asp Glu Tyr Ala Ile Thr Gly Lys Tyr Ile Thr Lys Ala Ile
            275                 280                 285
Arg Glu Lys Tyr Ser Asn Tyr Asp Phe Ala Ile Ile Ala Gly Val Pro
            290                 295                 300
His Ala Ile Pro Ala Asp Val Ile Ser Gly Met Glu Ile Ile Ser Ile
305                 310                 315                 320
Thr Asn Gly Pro Arg Gln Val Leu Pro Leu Lys Glu Met Gly His Glu
                325                 330                 335
His Val Val Val Glu Ile Asp Leu His Pro Arg Thr Leu Gly Val Ser
            340                 345                 350
Ser Ile Val Glu Ser Glu Phe Gly Ala Thr Leu Arg Glu Ile Gly Lys
            355                 360                 365
Glu Leu Asn Ser Gln Lys Asn Gly Ser Leu Leu His Glu Lys
            370                 375                 380

<210> SEQ ID NO 115
<211> LENGTH: 370
<212> TYPE: PRT
<213> ORGANISM: Methanosarcina acetivorans C2A

<400> SEQUENCE: 115

Met Thr Gln Lys Glu Ile Ser Ile Ile His Pro Arg Pro Ser Ser Ile
1                   5                   10                  15
Val Ala Ala Leu Tyr Thr Leu Arg Asp Leu Asn Val Asp Val Ala Ile
                20                  25                  30
Leu His Gly Pro Pro Gly Cys Ser Phe Lys His Ala Arg Leu Leu Glu
            35                  40                  45
Glu Asp Gly Ile His Val Val Thr Thr Gly Leu Asp Glu Asn Gly Phe
        50                  55                  60
Val Phe Gly Gly His Asp Arg Leu Val Glu Val Ile Asn Lys Ser Ile
65                  70                  75                  80
Glu Leu Phe Asn Pro Lys Ile Leu Gly Val Val Gly Thr Cys Ala Ser
                85                  90                  95
Met Ile Ile Gly Glu Glu Met His Asp Ala Val Leu Glu Ala Asn Pro
            100                 105                 110
Asp Ile Pro Val Ile Glu Val Glu Val His Ala Gly Tyr His Asn Asn
            115                 120                 125
Thr Arg Gly Val Leu Phe Ala Leu Glu Ser Ala Leu Asp Ala Gly Ile
            130                 135                 140
Ile Asp Arg Lys Glu Phe Glu Arg Gln Glu Tyr Leu Leu Ile Lys Ala
145                 150                 155                 160
Thr Glu Val Glu Lys Arg Phe Gly Ala Ala Ser Lys Glu Tyr Leu Ala
                165                 170                 175
Pro Ser Arg Gly Asp Leu Lys Tyr Lys Val Ala Lys Arg Leu Ile Glu
            180                 185                 190
```

Leu Leu Lys Glu Gly Lys Lys Gly Leu Val Ile Met Asn Ala Lys Lys
            195                 200                 205

Glu Thr Gly Tyr Met Phe Ala Asp Ile Thr Leu Ala Val Ser Glu Val
        210                 215                 220

Ala Ala Ala Leu Gly Lys Lys Glu Asn Leu Val Asn Met Ala Asn Ile
225                 230                 235                 240

Asp Pro Glu Leu Gly Leu Pro Arg Val Arg Gln His Ala Gln Tyr Ile
                245                 250                 255

Met Arg Asp Phe Ile Ala His Gly Val Glu Ile His Glu Ile Ile Gly
            260                 265                 270

Gly Met Asp Glu Tyr Pro Ile Ala Gly Glu Lys Val Ser Glu Leu Ile
        275                 280                 285

Lys Glu Lys Tyr Ser Asp Tyr Asp Phe Ala Val Ile Thr Gly Val Pro
    290                 295                 300

His Ala Ile Pro Met Glu Asn Leu Gln His Met Glu Leu Ile Ser Ile
305                 310                 315                 320

Thr Asn Gly Pro Arg Gln Val Leu Pro Leu Lys Glu Met Gly His Glu
                325                 330                 335

His Val Leu Val Glu Ile Asp Leu His Pro Lys Thr Leu Gly Val Ser
            340                 345                 350

Glu Ile Val Glu Ser Glu Phe Gly Ala Thr Leu Arg Glu Val Ala Lys
        355                 360                 365

Glu Ala
    370

<210> SEQ ID NO 116
<211> LENGTH: 354
<212> TYPE: PRT
<213> ORGANISM: Methanosphaera stadtmanae DSM 3091

<400> SEQUENCE: 116

Met Ile His Pro Arg Pro Ser Pro Ile Ala Ala Leu Tyr Thr Leu
1               5                   10                  15

Arg Asp Leu Glu Val Asp Val Ile Ile Met His Gly Pro Ala Gly Cys
            20                  25                  30

Cys Phe Arg Thr Gly Arg Leu Leu Glu Asp Glu Gly Ile Arg Val Ile
        35                  40                  45

Thr Thr Ala Met Ser Glu Asn Asp Phe Ile Phe Gly Ala Gly Glu Lys
    50                  55                  60

Leu Ser Lys Thr Ile Arg Glu Val Tyr Glu Thr Phe Lys Pro Glu Asn
65                  70                  75                  80

Ile Gly Val Val Gly Thr Cys Ala Ser Met Ile Ile Gly Glu Asn Met
                85                  90                  95

Lys Lys Val Val Lys Glu Ala Asp Val Asp Ser Asn Ile Ile Val Val
            100                 105                 110

Glu Thr His Gly Gly Phe Asp Ser Gly Asp Asn Thr Ala Gly Ala Ile
        115                 120                 125

Leu Thr Leu Lys Ala Ala Asn Lys Ala Glu Leu Ile Asp Glu Asp Glu
    130                 135                 140

Val Lys Arg Gln Thr Gln Met Leu Gln Lys Ala Thr Gln Leu Glu Lys
145                 150                 155                 160

Thr Arg Gly Met Ala Lys Gly Glu Tyr Ile Gln Pro Asn Tyr Gly Asp
                165                 170                 175

Asn Lys Val Lys Val Ala Asn Met Ile Ile Asp Ala Leu Asn Val Asn
            180                 185                 190

```
Lys Lys Val Ser Ile Val Leu Asn Ala Lys Lys Glu Thr Ser Tyr Leu
            195                 200                 205

Phe Ala Asp Ile Met Ser Val Pro Trp Ser Lys Tyr Tyr Pro Asp Asn
210                 215                 220

Leu Pro Val Phe Ile Ala Asn Thr Asp Glu Asn Ile Gly Leu Pro Tyr
225                 230                 235                 240

Ile Lys His His Ala Thr Val Val Asn Ser Asn Val Asp Lys Lys Met
            245                 250                 255

Asp Tyr Ile Thr Gly Gly Leu Asp Glu Tyr Pro Val Thr Gly Ile Lys
            260                 265                 270

Ala Gln Thr Ile Leu Glu Asp Glu Asp Cys Asp Val Thr Ile Val Leu
            275                 280                 285

Gly Val Pro His Ala Val Asp Ile Thr Lys Val Pro Gly Lys Thr Ile
            290                 295                 300

Ala Val Thr Asp Gly Pro Arg Leu Val Lys Pro Leu Met Asp Met Gly
305                 310                 315                 320

Tyr Asp Tyr Val Ile Thr Glu Leu Asp Ala His Ser Lys Thr Leu Gly
                    325                 330                 335

Ala Lys Asn Ile Val Glu Ser Glu Phe Ala Ser Thr Leu Arg Gly Leu
            340                 345                 350

Leu Glu

<210> SEQ ID NO 117
<211> LENGTH: 352
<212> TYPE: PRT
<213> ORGANISM: Methanosphaerula palustris E1-9c

<400> SEQUENCE: 117

Met Asp Tyr Ile Gln Pro Arg Pro Ser Ser Ile Val Ala Ala Leu Tyr
1               5                   10                  15

Thr Ala Arg Asp Leu Lys Val Asp Val Ala Ile Leu His Gly Pro Ser
            20                  25                  30

Gly Cys Ser Phe Lys His Ala Arg Leu Leu Glu Glu Asp Gly Met Arg
        35                  40                  45

Val Leu Thr Thr Ser Leu Ala Asp Asn Glu Phe Ile Phe Gly Gly Gln
50                  55                  60

Glu Ala Leu Glu Arg Val Leu Ile Arg Ala Glu Glu Thr Phe His Pro
65                  70                  75                  80

Lys Arg Met Ala Val Ile Gly Thr Cys Val Ser Met Ile Ile Gly Glu
                85                  90                  95

Asp Leu Gln Ser Ala Leu His Ala Thr Thr Val Pro Ser Ile Ala Val
            100                 105                 110

Asp Val His Ala Gly Phe Lys Glu Asn Ile Glu Gly Val Ile Leu Thr
        115                 120                 125

Leu Val Ala Ala Ala Glu Ala Gly Trp Ile Ser Gly Glu Glu Leu Glu
130                 135                 140

Arg Gln Arg Arg Leu Leu Ala Ala Asn Glu Val Glu Arg Leu Arg
145                 150                 155                 160

Gly Ala Ala Ser Arg Thr Tyr Ile Glu Pro Glu Arg Gly Asp Leu Lys
                165                 170                 175

His Thr Ala Ala Gln Arg Leu Leu Glu Leu Ala Arg Ser Gly Ala Arg
            180                 185                 190

Gly Met Ala Val Met Asn Ala Lys Lys Glu Thr Ala Tyr Met Phe Ala
        195                 200                 205
```

Asp Glu Leu Leu Ala Leu His Glu Val Ala Pro Asp Ala Pro Val Arg
210                 215                 220

Tyr Leu Ala Asn Leu Glu Gln Arg Gly Leu Pro Lys Val Arg Leu Asp
225                 230                 235                 240

Ala Glu Arg Ile Leu Gln Gly Leu Glu Ala Gly Gly Leu Thr Pro Glu
                245                 250                 255

Leu Val Gly Ala Leu Asp Glu Tyr Gly Ala Leu Gly Asp Gln Ile Gly
            260                 265                 270

Glu Glu Ile Ile Lys Thr Asp Pro Glu Phe Ile Leu Leu Val Gly Val
        275                 280                 285

Pro His Ala Val Pro Ala Arg Tyr Thr Glu Gly Arg Glu Val Phe Ser
290                 295                 300

Ile Thr Asn Gly Pro Arg Gln Val Ala Pro Leu Arg Glu Leu Gly His
305                 310                 315                 320

Gln His Val Leu Val Glu Val Asp Leu His Pro Lys Thr Leu Gly Val
                325                 330                 335

Arg Ser Ile Val Glu Ser Glu Phe Gly Ala Val Leu Arg Ser Leu Arg
            340                 345                 350

<210> SEQ ID NO 118
<211> LENGTH: 354
<212> TYPE: PRT
<213> ORGANISM: Methanospirillum hungatei JF-1

<400> SEQUENCE: 118

Met Lys Tyr Val Gln Pro Arg Pro Ser Ser Ile Val Ala Ala Leu Tyr
1               5                   10                  15

Thr Ala Arg Asp Leu Glu Val Asp Val Ala Val Leu His Gly Pro Ser
            20                  25                  30

Gly Cys Ser Phe Lys His Ala Arg Leu Leu Glu Glu Asp Gly Met Arg
        35                  40                  45

Val Leu Thr Thr Ser Leu Ala Glu Asn Glu Phe Val Phe Gly Gly Gln
    50                  55                  60

Gly Arg Leu Glu Asp Val Ile Leu Tyr Ala Glu Glu Lys Phe Ala Pro
65                  70                  75                  80

Lys Arg Met Ala Val Met Gly Thr Cys Val Ser Met Ile Gly Glu
                85                  90                  95

Asp Leu Gln Ala Ala Ile Asp Asn Ser Gly Val Ser Thr Glu Thr Ile
            100                 105                 110

Ala Val Asp Ile His Ala Gly Phe Thr Glu Asn Ile Asp Gly Val Ile
        115                 120                 125

Ala Thr Leu Lys Pro Ala Ala Glu Ile Gly Trp Ile Ser Leu Asp Glu
    130                 135                 140

Leu Val Arg Gln Gln Glu Leu Leu Lys Ala Ala Asn Gln Val Glu Arg
145                 150                 155                 160

Leu Arg Gly Ala Ala Val Arg Glu Tyr Ile Glu Pro Ser Arg Gly Asp
                165                 170                 175

Leu Lys His Lys Val Ala Glu Arg Leu Val Asp Ile Ile Gln Glu Gly
            180                 185                 190

Lys Lys Gly Val Ala Ile Met Asn Ala Lys Lys Glu Thr Ala Tyr Met
        195                 200                 205

Phe Ala Asp Gly Leu Thr Ala Leu His Glu Leu Ala Pro Asp Ala Pro
    210                 215                 220

Ile Val Tyr Ser Val Asn Leu Glu Met Arg Gly Leu Pro Lys Val Arg

```
                225                 230                 235                 240
Arg Asp Ala Glu Arg Ile Ile Ala Asp Leu Asp Ala Thr Gly Leu Ser
                    245                 250                 255

Tyr Val Lys Gln Gly Ala Leu Asp Glu Tyr Gly Ala Thr Gly Asp Met
                    260                 265                 270

Leu Gly Arg Trp Ile Gln Asp Glu Asn Pro Asp Phe Ala Phe Ile Thr
                    275                 280                 285

Gly Val Pro His Ala Ile Pro Arg Glu Tyr Thr Asp Gly Ile Glu Cys
                290                 295                 300

Phe Ser Val Thr Asn Gly Pro Arg Gln Val Ala Pro Leu Lys Asp Leu
305                 310                 315                 320

Gly His Glu His Val Val Glu Ile Asp Leu His Pro Arg Thr Leu
                    325                 330                 335

Gly Val Arg Ser Ile Val Glu Ser Glu Phe Gly Ala Val Ile Arg Ser
                    340                 345                 350

Phe Leu

<210> SEQ ID NO 119
<211> LENGTH: 359
<212> TYPE: PRT
<213> ORGANISM: Methanothermobacter marburgensis str. Marburg

<400> SEQUENCE: 119

Met His Pro Arg Pro Ser Pro Ile Ala Ala Ser Leu Tyr Thr Leu Arg
1               5                   10                  15

Asp Leu Asp Ala Asp Val Ile Ile Leu His Gly Pro His Gly Cys Cys
                20                  25                  30

Phe Arg Thr Gly Arg Leu Leu Glu Thr Asp Gly Val Arg Val Leu Thr
            35                  40                  45

Thr Ala Met Ser Glu Gln Asp Phe Ile Phe Gly Ala Ser Asp Lys Leu
        50                  55                  60

Ala Glu Thr Leu Arg Lys Ala Asn Glu Met Phe Ser Pro Glu Leu Val
65                  70                  75                  80

Gly Val Val Gly Thr Cys Ala Ser Met Ile Ile Gly Glu Asp Leu Arg
                85                  90                  95

Glu Ala Val Gln Arg Ala Asp Ile Pro Ala Arg Val Leu Thr Val Glu
            100                 105                 110

Ser His Gly Gly Phe Gly Glu Gly Asp Asn Thr Glu Gly Ala Ile Ile
        115                 120                 125

Val Leu Glu Ala Ala Ala Glu Gln Gly Ile Ile Pro His Glu Glu Ala
    130                 135                 140

Glu Arg Gln Ile Glu Met Leu Arg Leu Ala Thr Glu Ile Glu Lys Thr
145                 150                 155                 160

Arg Gly Met Ala Gln Gly Asp Tyr Ile Arg Pro Ser Tyr Gly Asp Asp
                165                 170                 175

Lys Asp Glu Val Ala Leu Arg Val Ile Glu Ala Ile Lys Asp Gly Glu
            180                 185                 190

Arg Val Ala Phe Val Leu Asn Ala Lys Lys Glu Thr Ser Tyr Leu Phe
        195                 200                 205

Ala Asp Pro Leu Lys Leu Pro Phe His Ser Val Asn Pro Asp Asn His
    210                 215                 220

Pro Leu Ile Ile Ala Asn Leu Asp Arg Asn Thr Gly Leu Pro Arg Ile
225                 230                 235                 240

Arg Arg His Ala Val Asn Ile Leu Ala Glu Ile Glu Asp Ala Gly Asn
```

```
                    245                 250                 255
Arg Val Asp Tyr Ile Thr Gly Gly Leu Asp Glu Tyr Pro Val Thr Gly
                260                 265                 270

Glu Arg Ala Ala Glu Ile Leu Arg Asp Glu Lys Ile Glu Phe Ala Val
            275                 280                 285

Val Ser Gly Val Pro His Ala Leu Pro Val Glu Glu Leu Glu Leu Glu
        290                 295                 300

Ser Val Ala Val Thr Asp Gly Pro Arg Leu Val Glu Pro Leu Arg Lys
305                 310                 315                 320

Leu Gly Tyr Thr His Val Val Ala Glu Leu Asp Ala His Ala Arg Thr
                325                 330                 335

Leu Gly Gln Ser Thr Thr Val Ala Ser Asp Phe Gly Asp Ala Leu Arg
            340                 345                 350

Arg Asn Ile Glu Lys Val Ile
            355

<210> SEQ ID NO 120
<211> LENGTH: 406
<212> TYPE: PRT
<213> ORGANISM: Methanothermococcus okinawensis IH1

<400> SEQUENCE: 120

Met Ile Met His Pro Arg Pro Ser Pro Ile Ala Ala Ser Met Tyr Gln
1               5                   10                  15

Leu Arg Asp Ile Gly Val Asp Ala Ile Ile Met His Gly Pro Ser Gly
            20                  25                  30

Cys Cys Phe Arg Thr Ala Arg Leu Leu Glu Leu Asp Gly Val Arg Val
        35                  40                  45

Phe Thr Thr Ala Met Asp Glu Asn Asp Phe Ile Phe Gly Ala Gln Glu
    50                  55                  60

Lys Leu Ser Asn Thr Ile Ala Asp Val Ile Asp Tyr Leu Lys Lys Asn
65                  70                  75                  80

Lys Ser Glu Lys Asn Lys Tyr Leu Ile Gly Ile Val Gly Thr Cys Val
                85                  90                  95

Ser Met Ile Ile Gly Glu Asp Leu Tyr Ala Pro Val Asp Tyr Asn
            100                 105                 110

Asp Asn Arg Asp Val Val Ile Ile Pro Val Glu Val His Ser Gly Met
        115                 120                 125

Asn Asp Asn Thr Ile Gly Ala Ile Lys Thr Met Glu Ser Cys Leu Asn
    130                 135                 140

Leu Gly Ile Ile Asp Glu Lys Glu Phe Asn Arg Gln Lys Glu Met Leu
145                 150                 155                 160

Ile Lys Ala Thr Glu Val Glu Lys Thr Arg Gly Met Ala Lys Ser Lys
                165                 170                 175

Tyr Ile Lys Pro Thr Tyr Glu Asp Leu Asp Glu Val Ile Asn Leu
            180                 185                 190

Ile Thr Glu Tyr Ile Asn Lys Tyr Asn Asn Ile Asn Ser Ser Asn
        195                 200                 205

Asn Ile Asn Asn Asn Asn Asn Asn Ser Asn Asn Leu Lys Ile
    210                 215                 220

Ala Cys Val Leu Asn Ala Lys Lys Glu Thr Ala Tyr Leu Phe Ala His
225                 230                 235                 240

Pro Leu Val Glu Ile Asn Lys Ile Ile Asn Lys Ile Lys Asn Asn Ile
                245                 250                 255
```

Asp Lys Asn Lys Lys Asn Ile Asn Ile Glu Asn Ile Asp Ile Asn
                260                 265                 270

Ile Val Asn Leu Asp Lys Asn Ile Gly Phe Lys Val Arg Lys Asp
            275                 280                 285

Ala Glu Asn Ile Leu Asn Glu Tyr Ser Lys Asn Asn Ile Asn Ile Asp
        290                 295                 300

Tyr Ile Thr Gly Gly Leu Asp Glu Tyr Pro Ile Thr Gly Lys Arg Ala
305                 310                 315                 320

Val Asn Ile Leu Lys Glu Ile Asn Pro Asp Ile Val Ile Val Ser Gly
                325                 330                 335

Val Pro His Ala Leu Pro Ile Glu Glu Leu Lys Glu Ile Asn Lys Asp
            340                 345                 350

Val Ile Thr Ile Gly Ile Ser Asp Gly Pro Arg Leu Tyr Tyr Pro Ile
        355                 360                 365

Lys Glu Ile Tyr Asp Tyr Ala Ile Ile Glu Leu Asp Ala His Ala Lys
370                 375                 380

Val Leu Gly Lys Arg Ala Ile Val Lys Ser Arg Phe Gly Glu Val Leu
385                 390                 395                 400

Asn Tyr Ala Leu Asn Lys
                405

<210> SEQ ID NO 121
<211> LENGTH: 355
<212> TYPE: PRT
<213> ORGANISM: Methanothermus fervidus DSM 2088

<400> SEQUENCE: 121

Met His Pro Arg Pro Ser Pro Ile Ala Ala Leu Tyr Thr Leu Arg
1               5                   10                  15

Asp Leu Asp Val Asp Leu Ile Val Leu His Gly Pro Lys Gly Cys Cys
            20                  25                  30

Phe Arg Thr Ala Arg Leu Leu Glu Gln Asp Gly Val Arg Val Val Thr
        35                  40                  45

Thr Gly Met Ser Glu Lys Asp Phe Val Phe Gly Ala Glu Glu Lys Leu
50                  55                  60

Thr Lys Thr Leu Lys Lys Ala Tyr Lys Met Phe Ser Pro Lys Leu Ile
65                  70                  75                  80

Gly Val Val Gly Thr Cys Ala Ser Met Ile Ile Gly Glu Asn Leu Lys
                85                  90                  95

Arg Ala Val Glu Asn Ala Lys Val Pro Ala Lys Val Leu Ile Val Glu
            100                 105                 110

Ser His Gly Gly Phe Gly Glu Gly Asp Asn Thr Glu Gly Ala Ile Ala
        115                 120                 125

Val Leu Glu Val Ala Ala Lys Glu Arg Leu Ile Ser Glu Asp Glu Ala
    130                 135                 140

Arg Arg Gln Ile Lys Met Leu Arg Met Ala Thr Ala Ile Glu Lys Thr
145                 150                 155                 160

Arg Gly Met Ala Gln Gly Lys Tyr Ile Pro Pro Leu Glu Gly Asp Asn
                165                 170                 175

Lys Lys Lys Val Ala Lys Ile Val Ile Asn Ala Phe Lys Asn Gly Lys
            180                 185                 190

Lys Val Ala Met Val Leu Asn Ala Lys Lys Glu Thr Ala Tyr Leu Phe
        195                 200                 205

Ala Asp Val Leu Arg Leu Pro Tyr Ser Lys Leu Asn Gly Asn Pro Val
    210                 215                 220

Val Ile Ala Asn Leu Asp Glu Asn Ile Gly Leu Pro Arg Ile Arg Asn
225                 230                 235                 240

His Ala Lys Asn Ile Lys Lys Glu Leu Lys Asp Asn Gly Val Asn Ile
            245                 250                 255

Asn Tyr Ile Thr Gly Gly Leu Asp Glu Tyr Pro Val Thr Gly Lys Lys
            260                 265                 270

Ala Met Glu Ile Leu Glu Lys Glu Glu Ile Asp Phe Ala Val Val Ser
        275                 280                 285

Gly Ile Pro His Ala Leu Pro Ile Glu Lys Tyr Asn Asn Ile Glu Met
        290                 295                 300

Val Ala Val Thr Asp Gly Pro Arg Leu Val Glu Pro Leu Lys Asn Ile
305                 310                 315                 320

Gly Tyr Lys Tyr Val Val Leu Glu Leu Asp Ala His Ala Lys Thr Leu
                325                 330                 335

Gly Lys Arg Arg Ile Val Asn Ser Gly Phe Gly Asn Ile Ile Arg Ser
            340                 345                 350

Glu Ile Ser
        355

<210> SEQ ID NO 122
<211> LENGTH: 355
<212> TYPE: PRT
<213> ORGANISM: Methanotorris igneus Kol 5

<400> SEQUENCE: 122

Met Ile Leu His Pro Arg Pro Ser Pro Ile Ala Ala Met Tyr Gln
1               5                   10                  15

Leu Arg Asp Val Gly Val Asp Ala Ile Ile Leu His Gly Pro Ala Gly
            20                  25                  30

Cys Cys Phe Arg Thr Ala Arg Leu Leu Glu Leu Asp Gly Val Arg Val
        35                  40                  45

Phe Thr Ser Ala Met Asp Glu Asn Asp Phe Ile Phe Gly Ala Met Asp
    50                  55                  60

Lys Leu Arg Arg Thr Ile Glu Glu Val Ile Glu Tyr Leu Lys Glu His
65                  70                  75                  80

Lys Asn Asp Gly Asn Tyr Met Ile Gly Ile Val Gly Thr Cys Ala Ser
                85                  90                  95

Met Ile Ile Gly Glu Asp Ile Trp Ser Val Val Asp Glu Tyr Asp Ala
            100                 105                 110

Thr Leu Ile Pro Val Glu Val His Ser Gly Leu Asn Asp Asn Thr Ile
        115                 120                 125

Gly Ala Ile Asn Ala Met Glu Ser Cys Leu Lys Leu Gly Leu Ile Asp
    130                 135                 140

Glu Lys Glu Phe Glu Arg Gln Lys Tyr Met Leu Lys Lys Ala Thr Glu
145                 150                 155                 160

Ile Glu Lys Lys Arg Gly Met Ala Lys Ser Lys Tyr Ile Lys Pro Thr
                165                 170                 175

Tyr Glu Asp Asp Leu Lys Asp Val Ile Glu Leu Phe Lys Asn Asn Met
            180                 185                 190

Asn Lys Asn Pro Lys Val Ala Cys Val Leu Asn Ala Lys Lys Glu Thr
        195                 200                 205

Ala Tyr Leu Phe Ala His Pro Leu Ile Lys Ile Asn Glu Ile Phe Asn
    210                 215                 220

Asn Cys Ile Asn Ile Gly Asn Leu Asp Glu Asn Ile Gly Leu Lys Lys

```
             225                 230                 235                 240
Ile Arg Glu Asp Ala Lys Asn Ile Leu Arg Glu Phe Lys Val Asp Tyr
                245                 250                 255
Ile Thr Gly Gly Leu Asp Glu Tyr Pro Val Thr Gly Glu Lys Ala Val
                260                 265                 270
Glu Ile Leu Lys Glu Ile Lys Pro Asp Ile Val Val Ser Gly Val
                275                 280                 285
Pro His Ala Leu Pro Ile Glu Glu Leu Lys Glu Val Asp Cys Ile
            290                 295                 300
Thr Ile Gly Val Ser Asp Gly Pro Arg Leu Tyr Tyr Pro Ile Lys Glu
305                 310                 315                 320
Tyr Tyr Asp Tyr Ala Val Ile Glu Leu Asp Ala His Ala Lys Val Leu
                325                 330                 335
Gly Lys Arg Glu Val Val Lys Ser Arg Phe Gly Glu Ile Leu Glu Tyr
                340                 345                 350
Ala Leu Lys
        355

<210> SEQ ID NO 123
<211> LENGTH: 362
<212> TYPE: PRT
<213> ORGANISM: Methermicoccus shengliensis DSM 18856

<400> SEQUENCE: 123

Met Ala Ala Glu Ile Leu His Pro Arg Pro Ser Ser Ile Val Ala Ala
1               5                   10                  15
Leu Tyr Thr Leu Arg Asp Leu Asp Val Asp Val Val Leu His Gly
                20                  25                  30
Pro Pro Gly Cys Ser Phe Lys His Ala Arg Leu Leu Glu Glu Asp Gly
            35                  40                  45
Ile Lys Val Leu Thr Thr Ser Leu Asp Asp Thr Ala Phe Ile Phe Gly
    50                  55                  60
Gly Ala Glu Arg Leu Lys Glu Val Leu Arg His Ala Lys Glu Arg Phe
65                  70                  75                  80
Asn Pro Ser Ala Ile Gly Val Val Gly Thr Cys Ala Ser Met Ile Ile
                85                  90                  95
Gly Glu Asp Met Ser Ala Ala Val Arg Glu Ala Glu Leu Asp Val Pro
                100                 105                 110
Val Val Val Val Asn Val His Ala Gly Tyr Pro Asp Asn Thr Thr Gly
                115                 120                 125
Val Ile Met Thr Leu Glu Ala Ala Arg Asp Ala Gly Leu Leu Ser Asp
            130                 135                 140
Glu Glu Leu Glu Arg Gln Arg Thr Leu Met Leu Arg Ala Ser Glu Ile
145                 150                 155                 160
Glu Arg Glu His Gly Ala Ala Ser Arg Asp Tyr Leu Pro Pro Ser Arg
                165                 170                 175
Gly Asp Leu Lys His Glu Ala Ala Arg Leu Leu Ser Leu Met Arg
            180                 185                 190
Asp Arg Lys Arg Gly Val Val Val Leu Asn Ala Lys Lys Glu Thr Ala
            195                 200                 205
Tyr Ser Phe Ala Asp Ile Val Leu Ala Leu Asn Glu Val Ala Ser Lys
    210                 215                 220
Thr Ser Ala Arg Val Val Asn Ile Ala Asn Leu Arg Ser Asp Val Gly
225                 230                 235                 240
```

```
Leu Ser Arg Ile Arg Arg Tyr Ala Leu Asp Ile Thr Arg Glu Leu Gln
                245                 250                 255

Glu Cys Gly Val His Ile His His Leu Thr Gly Gly Leu Asp Glu Tyr
            260                 265                 270

Ala Val Ala Gly Glu Val Ala Ser Arg Val Ile Ser Glu Arg Tyr Cys
        275                 280                 285

Asp Tyr Asp Tyr Ala Val Val Cys Gly Val Pro His Ala Leu Asp Val
    290                 295                 300

Gly Met Leu Asp Met Glu Leu Phe Ala Ile Thr Asn Gly Pro Arg Gln
305                 310                 315                 320

Val Glu Pro Leu Arg Glu Met Gly Tyr His His Val Met Val Glu Ile
                325                 330                 335

Asp Leu His Pro Arg Thr Leu Gly Val Asn His Ile Val Pro Ser Glu
            340                 345                 350

Leu Gly Glu Cys Leu Arg Ala Leu Ala Pro
        355                 360

<210> SEQ ID NO 124
<211> LENGTH: 370
<212> TYPE: PRT
<213> ORGANISM: Methanoperedens nitroreducens

<400> SEQUENCE: 124

Met Pro Val Lys Glu Lys Glu Pro Met Ile Met His Pro Arg Pro Ser
1               5                   10                  15

Ser Ile Val Ala Ala Leu Tyr Thr Leu Arg Asp Leu Asp Thr Asp Val
            20                  25                  30

Val Ile Leu His Gly Pro Pro Gly Cys Cys Phe Lys His Ala Arg Leu
        35                  40                  45

Leu Glu Glu Asp Gly Met Arg Val Val Thr Thr Ser Leu Asp Glu Ser
    50                  55                  60

Gly Phe Val Phe Gly Gly His Asp Ser Leu Val Glu Val Leu Glu Lys
65                  70                  75                  80

Val Ile Arg Arg Phe Asn Pro Lys Arg Ile Gly Ile Val Gly Thr Cys
                85                  90                  95

Ala Ser Met Ile Ile Gly Glu Glu Leu His Glu Ala Val Met Asp Val
            100                 105                 110

Gln Pro Asp Val Pro Val Ile Glu Val Glu Val His Ala Gly Tyr Arg
        115                 120                 125

Asp Asn Thr Lys Gly Val Ile Ile Ala Leu Glu Ser Ala Leu Ala Ala
    130                 135                 140

Gly Ile Ile Ser Glu Ala Glu Phe Glu Arg Gln Lys Ser Leu Leu Lys
145                 150                 155                 160

Glu Ala Thr Met Val Glu Lys Arg His Gly Ala Ala Ser Lys Glu Tyr
                165                 170                 175

Leu Glu Pro Asn Arg Gly Asp Leu Lys Phe Lys Val Ala Gly Arg Leu
            180                 185                 190

Leu Glu Leu Met Lys Gln Gly Lys Arg Gly Leu Asn Ile Leu Asn Ala
        195                 200                 205

Lys Lys Glu Thr Ala Phe Met Phe Ala Asp Ile Asn Leu Ala Val Asn
    210                 215                 220

Gln Ile Ala Glu Lys Leu Gly Ser Pro Ile Ile Asn Met Ala Asn Leu
225                 230                 235                 240

Asn Glu Asp Val Gly Leu Pro Lys Asn Arg Arg Asn Ala Arg Glu Ile
                245                 250                 255
```

```
Lys Glu Glu Leu Lys Asn Arg Gly Met Asp Ile His His Ile Thr Gly
            260                 265                 270
Gly Leu Asp Glu Tyr Pro Val Ala Gly Asn Ser Ala Asn Gln Ile Ile
        275                 280                 285
Gly Glu Lys Tyr Ser Asp Tyr Asp Phe Ala Val Ile Thr Gly Val Pro
    290                 295                 300
His Ala Leu Pro Met Asp Asn Ile Asn Asn Met Glu Leu Phe Ser Ile
305                 310                 315                 320
Thr Asn Gly Pro Arg Gln Val Ile Pro Leu Lys Glu Met Gly His Arg
                325                 330                 335
His Val Met Val Glu Ile Asp Leu His Pro Arg Thr Leu Gly Ile Asn
            340                 345                 350
His Ile Val Glu Ser Glu Phe Gly Ala Thr Leu Arg Glu Met Ala Lys
        355                 360                 365
Asp Val
    370

<210> SEQ ID NO 125
<211> LENGTH: 475
<212> TYPE: PRT
<213> ORGANISM: Methanobacterium formicicum DSM 3637

<400> SEQUENCE: 125

Met Arg Ile Leu Val Asp Met Thr His Gly Gly Thr Ile Leu Ala
1               5                   10                  15
Ser Glu Phe Ser Lys Arg Lys Asp Cys Lys Val Phe Ala Trp Asp Ile
            20                  25                  30
Tyr Gln Thr Leu Ser Glu Glu Asp Lys Ser Leu Leu Glu Ala Gln Gly
        35                  40                  45
Ile Glu Leu Val Gly Glu Ser Phe Tyr Glu Ser Tyr Phe His Glu Asn
    50                  55                  60
Ile Val Leu Glu Asn Asp Met Ser Arg Ser Ser Leu Lys Asn Asp Lys
65                  70                  75                  80
Ser Asn Leu Met Val Val Ala Pro Val His Cys Asn Leu Pro Gln Pro
                85                  90                  95
Pro His Met Thr His His Gln Ala Val Gly Phe Leu Leu Lys Asp Gln
            100                 105                 110
Ile Asn Val Pro Val Ile Glu Ile Thr Gly Val Lys Gly Lys Thr Ser
        115                 120                 125
Thr Thr Ala Met Leu Lys Glu Ile Tyr Arg Asp Glu Asn Pro Leu Ile
    130                 135                 140
Leu Ser Ser Leu Gly Val Lys Val Val Glu Asp Gly Gln Glu Ile Thr
145                 150                 155                 160
Leu Gln Lys Asp Ile Ser Ile Thr Pro Ala Ser Ile Ile Thr Ala Trp
                165                 170                 175
Gln Leu Ser Gln Lys Phe Tyr Lys Asn Lys Val His Asn Val Gly Ile
            180                 185                 190
Cys Ile Phe Glu Ser Ser Leu Gly Gly Thr Gly Leu Ala Asp Val Gly
        195                 200                 205
Val Ile Thr Asn Ile Ala Glu Asp Tyr Ser Ile Ala Arg Gly Ser Ser
    210                 215                 220
Ser Ala Ser Lys Ala Lys Leu Gln Met Phe Lys Ser Lys Val Thr Val
225                 230                 235                 240
Cys Asp Asn Glu Ser Tyr Gln Lys Thr Tyr Ser His His Tyr Ser Leu
```

```
                245                 250                 255
Asn His Lys Pro Asn Thr Phe Ser Ile Asp Gly Ile Gly Asp Asn Val
            260                 265                 270

Asn Val Lys Ala His Ile Ile Asn Tyr Gly Leu His Lys Thr Val Phe
        275                 280                 285

Gln Val Lys Val Ile Asp Leu Ile Thr Ile Asn Gly Thr Ser Ile Asn
    290                 295                 300

Thr Ser Phe Glu Val Ser Thr Phe Ala Pro Ala Gln His His Leu Glu
305                 310                 315                 320

Asn Thr Leu Ser Ala Ile Thr Ala Ser Leu Ser Met Gly Thr Pro Ile
            325                 330                 335

Glu Ser Ile Ser Asn Gly Leu Lys Asn Phe Thr Gly Leu Pro Gly Arg
        340                 345                 350

Thr Ser Leu Ser Lys Val Gly Asp Met Val Ile Glu Glu Ile Asn
    355                 360                 365

Pro Gly Ile Asn Val Thr Ala Val Lys Lys Ala Val Asn Met Ile Lys
370                 375                 380

Gly Tyr Glu Lys Pro Val Leu Ile Val Gly Ser Tyr Gly Val Thr
385                 390                 395                 400

Cys Glu Glu Ile Asp Glu Thr Ser Leu Ser Asn Phe Leu Ala Asp Gln
            405                 410                 415

Ser Asp Glu Val Phe Met Ile Leu Thr Gly Asp Leu Gly Leu Ser Leu
        420                 425                 430

Trp Lys Gln Met Glu Lys Gln Tyr Asn Tyr Cys Asn Ser Ile Glu Leu
    435                 440                 445

Ala Leu Asn Lys Ser Lys Lys Val Gly Ala Lys Asn Ile Leu Leu Ile
450                 455                 460

Tyr Arg Ser Asn Phe Ser Glu Leu Gly Arg Arg
465                 470                 475

<210> SEQ ID NO 126
<211> LENGTH: 544
<212> TYPE: PRT
<213> ORGANISM: Methanobrevibacter ruminantium M1

<400> SEQUENCE: 126

Met Asn Val Phe Leu Val Asp Leu Thr His Gly Gly Val Lys Ile Ser
1               5                   10                  15

Ser Glu Leu Ser Lys Ser Lys Arg Phe Glu Lys Val Phe Ala Tyr Asp
            20                  25                  30

Leu Tyr Ser Thr Leu Lys Glu Glu Asp Glu His Leu Leu Lys Thr Tyr
        35                  40                  45

Asp Val Thr Ile Leu Lys Asp Phe Asp Ser Phe Lys Glu Glu Leu Lys
    50                  55                  60

Glu Asn Ser Lys Glu Leu Leu Lys Ser Glu Lys Glu Lys Glu Asn Asn
65                  70                  75                  80

Ser Lys Asp Leu Ile Ile Asn Pro Ile His Ser Ser Leu Asn Ile Lys
            85                  90                  95

Asp Leu Leu Asn Gln Ile Thr Glu Glu Ile Asn Pro Asn Asn Asp Leu
        100                 105                 110

Thr His Leu Tyr Glu Ile Ile Asn His His Gln Ala Thr Lys Leu Val
    115                 120                 125

Leu Glu Asn Trp Lys Glu Glu Thr Lys Lys His Asp Ile Lys Thr Ile
        130                 135                 140
```

Glu Ile Thr Gly Val Lys Gly Lys Thr Ser Thr Ala Phe Leu Leu Lys
145                 150                 155                 160

Glu Ile Phe Leu Glu Asn Asn Gln Asn Thr Leu Leu Leu Ser Ser Leu
            165                 170                 175

Gly Ala Tyr Leu Phe Arg Lys Asn Gln Asp Lys Glu Met Glu Leu Ile
        180                 185                 190

Leu Gln Lys Asn Ile Ser Ile Thr Pro Ala Asn Ile Ile Asn Thr Ile
    195                 200                 205

Gln Leu Ala Lys Lys Ile Ala Asn Pro Lys Cys Ser Tyr Phe Pro Lys
210                 215                 220

Cys Ala Ala Asn Lys Asn Lys Gln Glu Glu Asn Glu Leu Phe Glu Glu
225                 230                 235                 240

Tyr Asn Asn Asn Pro Tyr His Asn Leu Asn Tyr Asp Ile Ala Ile Phe
                245                 250                 255

Glu Asn Ser Leu Gly Val Cys Gly Leu Gly Asp Ile Gly Ile Leu Thr
            260                 265                 270

Asn Leu Val Glu Asn Tyr Pro Ile Ala Lys Gly Ser Ser Asn Ala Met
        275                 280                 285

Glu Ala Lys Arg Gln Val Phe Asp Cys Ser Leu Val Ile Ile Glu Tyr
    290                 295                 300

Glu Thr Leu Asn Glu Phe Tyr Lys Gly Glu Ser Glu Tyr Lys Asp
305                 310                 315                 320

Lys Ile Asn Ser Phe Ser Leu Asn Asn Lys Ala Asn Val Phe Cys
                325                 330                 335

Lys Asn Ile Asp Phe Asp Ile Asp Asn Thr Gln Ile Lys Ile Thr Tyr
            340                 345                 350

Gln Asp Phe Lys Thr Arg Asn Lys Asn Thr Ile Asn Gly Glu Phe Thr
        355                 360                 365

Leu Asn Cys Phe Ala Pro Gly Pro His His Val Leu Asn Ile Leu Thr
    370                 375                 380

Ala Val Ser Thr Ala Leu Ala Leu Glu Ile Asp Glu Lys Thr Ile Ile
385                 390                 395                 400

Ala Gly Ile Ser Lys Phe Asn Gly Ile Asp Gly Arg Thr Gln Val Lys
                405                 410                 415

Thr Val Glu Asn Ser Ile Ile Glu Glu Ile Asn Pro Gly Ile Asn
            420                 425                 430

Thr Lys Ala Ile Glu Ser Ser Ile Asn Met Ile Lys Asp Ile Asp Asn
        435                 440                 445

Tyr Tyr Ile Ile Ile Gly Gly Lys Tyr Gly Val Thr Cys Glu Glu Ile
    450                 455                 460

Asp Glu Glu Lys Leu Ser Asn Tyr Leu Asn Asn Tyr Leu Thr Asp Asn
465                 470                 475                 480

Pro Asn Thr Lys Leu Ile Leu Thr Asp Glu Val Gly Lys Ser Leu Lys
                485                 490                 495

Glu Lys Leu Asp Leu Leu Asn Asp Lys Asp Glu Tyr Glu Ile Met Phe
            500                 505                 510

Ile Glu Asn Tyr Glu Glu Ala Arg Asp Leu Ala Ile Asn Glu Asn Lys
        515                 520                 525

Asn Ile Leu Phe Ile Tyr Arg Ser Asn Tyr Ser Gln Val Ser Lys Arg
    530                 535                 540

<210> SEQ ID NO 127
<211> LENGTH: 404
<212> TYPE: PRT

<213> ORGANISM: Methanocaldococcus jannaschii DSM 2661

<400> SEQUENCE: 127

Met Val Phe Phe Met Leu Ile Ile Asp Val Asn His Gly Ala Leu Thr
1               5                   10                  15

Leu Ala Glu Glu Tyr Leu Asn Leu Gly Tyr Glu Val Asp Val Trp Asp
            20                  25                  30

Ile Tyr Gln Lys Ile Lys Lys Ser Glu Asp Phe Lys Val Lys Tyr Gln
        35                  40                  45

Lys Leu Lys Glu Lys Phe Gly Asn Lys Leu Asn Leu Phe Phe Glu Gln
    50                  55                  60

Pro Asn Phe Glu Lys Tyr Asp Arg Val Ile Ala Pro Ile His Cys Pro
65                  70                  75                  80

Ile Asp Val Asp Phe Ile Pro Phe Thr Asp Ala Val Ser Lys Ile Leu
                85                  90                  95

Lys Glu Lys Phe Gly Asn Ile His Lys Lys Ile Ile Asn Val Thr Gly
            100                 105                 110

Val Lys Gly Lys Thr Thr Thr Thr Ser Leu Ile Asn His Ile Leu Lys
        115                 120                 125

Asp Lys Tyr Ser Thr Tyr Leu His Asn Ser Asn Phe Gly Ser Ile Ala
    130                 135                 140

Pro Pro Thr Ile Leu Lys Val Leu Asn Ser Leu Asp Ile Asp Lys Tyr
145                 150                 155                 160

Asp Phe Phe Ile Phe Glu Thr Ser Leu Gly Leu Ile Lys Cys Lys Tyr
                165                 170                 175

Gly Ala Ile Thr Asn Val Leu Glu Asn Tyr Lys Ile Ala Gly Gly Arg
            180                 185                 190

Lys Asp Ala Leu Thr Ala Lys Phe Ser Ser Leu Lys Asn Ala Glu Leu
        195                 200                 205

Ser Phe Ile Asn Lys Arg Asp Ile Asn Arg Tyr Asp Leu Asn Ile Asn
    210                 215                 220

His Lys Cys Leu Asn Val Val Asp Val Asp Arg Ala Lys Ile Leu Asp
225                 230                 235                 240

Lys Tyr Pro Leu Lys Phe Lys Tyr Phe Asp Glu Ile Phe Glu Phe Ser
                245                 250                 255

Lys Asn Ile Phe Gly Leu His Phe Val Glu Asn Ser Leu Phe Ala Ile
            260                 265                 270

Glu Ile Cys Lys Asn Leu Val Asp Met Glu Glu Ile Arg Tyr Arg Leu
        275                 280                 285

Lys Thr Phe Thr Ile Lys Asn Arg Met Glu Ile Lys Glu Ile Asn Lys
    290                 295                 300

Lys Ile Leu Val Lys Asn Ile Asn Pro Gly Leu Asp Val Lys Ala Ile
305                 310                 315                 320

Ser Tyr Ala Ile Lys Asp Phe Leu Glu Val Phe Gly Gly Asp Ile Tyr
                325                 330                 335

Ile Gly Gly Asp Phe Gly Ile Val Cys Glu Glu Ile Asp Val Lys Lys
            340                 345                 350

Leu Ser Glu Val Leu Lys Arg Phe Asn Cys Arg Tyr Ile Phe Val Gly
        355                 360                 365

Glu Ile Gly Lys Glu Leu Leu Asn Tyr Leu Asn Gly Gly Tyr Ile Lys
    370                 375                 380

Ser Tyr Asp Glu Asn Lys Ile Lys Arg Asp Ser Leu Val Ile Leu Arg
385                 390                 395                 400

Glu Lys Ile Lys

<210> SEQ ID NO 128
<211> LENGTH: 424
<212> TYPE: PRT
<213> ORGANISM: Methanocella arvoryzae MRE50

<400> SEQUENCE: 128

```
Met Glu Leu Asn Ala Ser Arg Ile Ala Ile Leu Asp Val Asn His Gly
1               5                   10                  15

Gly Leu Val Leu Ala Arg Glu Leu Gln Ser Leu Gly Tyr Asp Thr Phe
                20                  25                  30

Ala Val Asp Val Tyr Gly Ser Gly Lys Glu Ser Glu Asp Ile Arg Ile
            35                  40                  45

Val Gln Ala Asp Glu Ala Pro Ala Phe Asp Met Leu Val Ala Pro Val
50                  55                  60

His Met Ala Pro Tyr Lys Leu Leu Tyr Asp Ala Val Arg Arg Gly Met
65                  70                  75                  80

Pro Val Leu Thr His Arg Met Ala Gly Met Leu Ile Glu Ala Thr
                85                  90                  95

Gly Arg Leu Lys Gly Val Lys Ser Val Glu Val Thr Gly Thr Tyr Gly
                100                 105                 110

Lys Thr Thr Ala Cys Ala Leu Leu Gly Arg Met Leu Gln Ala Lys Gly
            115                 120                 125

Glu His Val Leu Val His Ala Ser Met Gly Leu Thr Phe Asp Gly Met
130                 135                 140

Pro Val Gly Glu Arg Leu Ser Ile Thr Pro Ala Asn Met Leu Arg Ala
145                 150                 155                 160

Leu Asp Cys Ala Lys Lys Ala Gly Leu His Pro Thr Ala Cys Val Phe
                165                 170                 175

Glu Val Ser Leu Gly Gly Cys Gly Thr Ala Asp Val Gly Ile Ile Thr
            180                 185                 190

Thr Leu Asp Arg Asp Tyr Pro Val Ala Gly Gly Thr Lys Arg Ser Tyr
195                 200                 205

Met Ala Lys Met Gln Met Ile Glu His Ala Lys Pro Arg Ser Thr Ile
210                 215                 220

Val His Gln Ala Thr Tyr Arg Leu Thr Gly Gly Arg Asp Glu Ile Thr
225                 230                 235                 240

Phe Gly Glu Gly Gly Asp Leu Phe Tyr Gly Lys Ala Gly Met Ile Glu
                245                 250                 255

Gly Pro Leu Leu Glu Gly Glu Thr Ile Tyr Pro Ala Phe Ala Pro Gly
            260                 265                 270

Leu Asp Leu Glu Ser Tyr Gly Asp Pro Ala Leu Cys Ala Ala Ala
275                 280                 285

Ala Leu Ser Met Gly Thr Ser Pro Glu Ala Val Ser Asp Ala Leu Ala
290                 295                 300

Gly Phe Asp Gly Ile Pro Gly Arg Met Lys Arg Gly Ile Ile Gln Gly
305                 310                 315                 320

Arg Glu Leu Leu Asp Asn Ser Cys Ser Gly Leu Ser Ile Asp Gly Val
                325                 330                 335

Leu Arg Ala Leu Glu Lys Ser Gly Gly His Pro Gly Arg Lys Val Leu
            340                 345                 350

Val Leu Gly Glu Glu Lys Tyr Asn Val Cys Glu Gly Leu Asp Pro Ala
355                 360                 365
```

```
Glu Ala Ala Arg Ile Ala Glu Ala Trp Ala Gly Glu Val Val Leu Val
    370                 375                 380

Gly Asp Arg Leu Leu Ser Val Ser Gly Val His Ala Ala Ser Leu Lys
385                 390                 395                 400

Glu Gly Leu Arg Glu Ala Leu Ser Arg Thr Ala Pro Gly Asp Met Ile
                405                 410                 415

Ile Ser Cys Val Lys Thr Trp Arg
                420

<210> SEQ ID NO 129
<211> LENGTH: 462
<212> TYPE: PRT
<213> ORGANISM: Methanococcoides methylutens MM1

<400> SEQUENCE: 129

Met Thr Ala Gly Gln Arg Asn Ala Val Val Leu Asp Leu Thr His Ala
1               5                   10                  15

Gly Ile Pro Ile Ala Lys Glu Met Val Arg Leu Gly Tyr Asn Val Arg
                20                  25                  30

Ala Ile Asp Val Tyr Asp Thr Leu Asp Asp Glu Thr Ile Ser Asp Leu
            35                  40                  45

Gln Gln Ile Phe Pro Val Leu Ser Ser Gly Glu Ala Phe Glu Leu Lys
    50                  55                  60

Thr Thr Glu Thr Val Val Ala Pro Val His Leu Asn Pro Glu Phe His
65                  70                  75                  80

Val Leu Lys Ser Ala Arg Glu Lys Gly Asn Thr Ile Ile Ser His His
                85                  90                  95

Thr Met Val Gly Lys Leu Ile Leu Glu Ser Gly Arg Leu Ser Thr Ser
            100                 105                 110

Lys Val Ile Glu Leu Thr Gly Thr Lys Ala Lys Thr Ser Thr Ala Ser
    115                 120                 125

Ile Leu Ala Asp Ile Leu Ser Arg Ser Met Asp Val Val Leu His Thr
130                 135                 140

Ser Arg Gly Leu Glu His Trp Asn Asn Gly Val Ala Thr Ile Val His
145                 150                 155                 160

Lys Gly Leu Ser Ile Ala Pro Gly Ser Ile Leu Ser Ala Ile Glu Lys
                165                 170                 175

Thr Glu Glu Ala Asn Ile Arg Pro Glu Val Phe Ile Leu Glu Thr Ser
            180                 185                 190

Ile Gly Gly Thr Gly Cys Ala Asp Ile Gly Val Ile Thr Ser Leu Glu
    195                 200                 205

Gln Asp Tyr Arg Ile Ala Asn Asn Thr Ala Leu Ala Ser Asp Ala Lys
210                 215                 220

Leu Gln Met Leu Asp Asn Ala Lys Glu Gly Ser Ile Val Ile Val Asn
225                 230                 235                 240

Cys Asp Ala Arg Lys Ala Leu Gln Arg Ala Ala Glu Lys Asp Leu Glu
                245                 250                 255

Ile Ile Thr Phe Ser Asp Lys Asn Glu Glu Asp Ala Asp Phe Ser Leu
            260                 265                 270

Glu Ile Asn Gly Asn Asn Val Val Ile Ser Ser Lys Asp Gln Thr Ile
    275                 280                 285

Glu Thr Leu Met Glu Glu Gly Phe Asp Leu Ser Ala Tyr Arg Thr Ala
290                 295                 300

Phe Ser Ala Ala Ala Ala Ile Ser Ile Thr Met Gly Ile Glu Glu Lys
305                 310                 315                 320
```

```
Gln Ile Val Gly Thr Leu Gln Asn Phe Arg Gly Leu Thr Gly Arg Met
                325                 330                 335

Val Lys Asp Glu Leu Glu Gly Arg Thr Leu Ile Asp Asn Ser Asn Ser
            340                 345                 350

Gly Met Asp Ile Arg Ser Val Lys Lys Ala Leu Asp Tyr Thr Ser Ala
        355                 360                 365

Ile Ala Ser Asp Ile Asn Ser Asp Ser Thr Glu Arg Glu Ile Val Met
    370                 375                 380

Val Leu Gly Glu Glu Ala Glu Gln Val Cys Glu Gly Leu Pro Pro Glu
385                 390                 395                 400

Asp Val Ser Asp Phe Leu Met Lys Asn Gly Lys Lys Leu Asn Lys Ile
                405                 410                 415

Val Leu Val Gly Ser Arg Met Arg Ala Ile Lys Tyr Asp Asp Ala Tyr
            420                 425                 430

Tyr Glu Gly Ser Leu Glu Gly Leu Ser Ser Ala Leu Arg Cys Thr
        435                 440                 445

Asn Ile Gly Asp Ile Ile Ile Leu Cys Val Lys Cys Phe Arg
    450                 455                 460

<210> SEQ ID NO 130
<211> LENGTH: 400
<212> TYPE: PRT
<213> ORGANISM: Methanococcus maripaludis C7

<400> SEQUENCE: 130

Met Leu Ile Ile Asp Ile Asn His Gly Ala Leu Asp Leu Ala Val Glu
1               5                   10                  15

Tyr Glu Lys Ser Gly Lys Asn Pro Val Ile Trp Asp Ile Tyr Gly Lys
                20                  25                  30

Leu Glu Arg Asp Glu Lys Phe Lys Glu Cys Asn Lys Asn Ile Leu Ser
            35                  40                  45

Lys Phe Lys Ile Ile Ser Lys Lys Glu Met Pro Asp Phe Ser Asn Tyr
    50                  55                  60

Thr Glu Val Ile Ala Pro Val His Cys Pro Ile Asp Val Glu Phe Lys
65                  70                  75                  80

Thr Phe His Asp Ala Val Ser Glu Ile Ser Lys Lys Tyr Pro Gly
                85                  90                  95

Val Ile Glu Lys Met Ile Thr Val Thr Gly Val Lys Gly Lys Thr Thr
                100                 105                 110

Thr Thr Glu Leu Leu Lys His Ile Leu Ser Glu Glu Tyr Thr Val Tyr
            115                 120                 125

Cys His Asn Ser Asn Asp Gly Ser Ile Thr Pro Ile Thr Val Leu Asn
    130                 135                 140

Ile Leu Asn Asn Leu Ser Asp Glu Arg Lys Leu Gln Ile Tyr Asp Phe
145                 150                 155                 160

Phe Ile Phe Glu Ile Ser Leu Gly Ile Val Ser Ser Tyr Ser Ile
                165                 170                 175

Leu Thr Asn Ile Leu Glu Asn Tyr Lys Ile Ala Arg Gly Met Arg Ser
            180                 185                 190

Ala Ser Ile Lys Ile Asp Ser Leu Lys Asn Ser Lys Ile Ala Ile Ile
    195                 200                 205

Asn Asp Asp Val Ile Asn Ile Phe Asp Val Asn His Lys Asn Leu Lys
    210                 215                 220

Val Val Lys Asn Ala Asn Ile Ile Ser Lys Tyr Pro Leu Lys Phe Asn
```

```
                225                 230                 235                 240
Tyr Leu Lys Asn Asp Phe Glu Phe Asn Glu Ser Ile Leu Gly Ser His
                245                 250                 255

Phe Ile Glu Asn Ser Ile Phe Ala Ile Glu Leu Cys Ser Asn Phe Leu
                260                 265                 270

Ser Phe Glu Lys Ile Lys Asn Ser Leu Lys Lys Phe Lys Ile Glu Asn
                275                 280                 285

Arg Met Asn Val Glu Lys Glu Glu Tyr Thr Ile Val Lys Asn Ile
290                 295                 300

Asn Pro Gly Leu Asp Leu Lys Ala Ile Asp Tyr Ala Ile Ser Asp Phe
305                 310                 315                 320

Leu Ser Leu Phe Glu Asn Gly Met Val Ile Val Gly Asp Phe Gly
                325                 330                 335

Cys Thr Cys Glu Glu Ile Asn Ile Glu Lys Leu Ala Glu Leu Ile Asn
                340                 345                 350

Gln Tyr Leu Lys Lys Gly Val Lys Ile Thr Ile Ala Gly Asp Val Gly
                355                 360                 365

Ile Tyr Leu Lys Lys Tyr Val Asn Leu Glu Met Val Asp Ile Lys Asn
                370                 375                 380

Tyr Glu Phe Lys Asp Asn Thr Leu Val Val Tyr Arg Ser Lys Leu Cys
385                 390                 395                 400
```

<210> SEQ ID NO 131
<211> LENGTH: 381
<212> TYPE: PRT
<213> ORGANISM: Methanocorpusculum labreanum Z

<400> SEQUENCE: 131

```
Met Lys Val Leu Val Leu Asp Thr Ile His Gly Gly Thr Ile Leu Ala
1               5                   10                  15

Glu Ala Leu Leu Arg Asn Gly Asp Asp Val Asp Ala Leu Asp Val Tyr
                20                  25                  30

Arg Gly Val Gly Leu Thr Pro Glu Glu Ala Ala Ser Arg Gln Tyr Asp
                35                  40                  45

Leu Ile Thr Ser Pro Val His Leu Asp Pro Ala Tyr Pro Leu Leu Asn
                50                  55                  60

Thr Lys Thr Pro Val Ile Ser His His Glu Met Thr Arg Arg Leu Ala
65                  70                  75                  80

Gly Asp Leu Pro Glu Thr Val Ile Glu Val Thr Gly Ala Lys Gly Lys
                85                  90                  95

Thr Thr Thr Ser Phe Ala Val Ala Ser Leu Phe Thr Thr Lys Gly Val
                100                 105                 110

Leu His Thr Ser Arg Gly Thr Tyr Val Tyr Pro Glu Gly Thr Phe Leu
                115                 120                 125

Trp Lys Lys Ser Ile Thr Pro Ala Ser Val Leu Leu Ala Ala Gly Gly
                130                 135                 140

Ala Lys Thr His Asp Ala Lys Trp Leu Val Ala Glu Val Ser Ala Gly
145                 150                 155                 160

Val Thr Gly Ile Gly Thr Leu Gly Ile Leu Thr Ser Ala Asp Asp Tyr
                165                 170                 175

Ser Ile Ala Ala Gly Lys Lys Ser Ala Leu Ala Lys Leu Glu Ser
                180                 185                 190

Leu Ala Lys Cys Lys Thr Val Leu Val Pro Arg Gly Val Thr Leu Lys
                195                 200                 205
```

```
Glu Gly Trp His Val Ile Asp Asp Leu Val Ser Val Glu Gly Asp Val
        210                 215                 220
Leu Ser Phe Asp Gly Gly Ser Phe Lys Asn Pro Leu Leu Thr Leu Ala
225                 230                 235                 240
Gly Tyr Arg Glu Pro Leu Lys Cys Ala Ala Ala Gly Leu Leu Leu
            245                 250                 255
Gly Leu Asp Pro Ser Arg Leu Ala Gly Phe Thr Ala Ile Glu Gly Arg
            260                 265                 270
Met Gln Tyr Tyr Leu Glu Asp Gly Val Pro Phe Leu Asp Asn Ala Asn
            275                 280                 285
Ser Gly Thr Thr Arg Glu Thr Thr Leu Asp Ala Ala Tyr Leu Arg
        290                 295                 300
Arg Leu Val Pro Asp Lys Glu Ile Val Leu Ile Gly Glu Glu His
305                 310                 315                 320
Lys Ala Val Cys Glu Gly Phe Gln Asp Asp Ala Ile Arg Gln Thr Ile
                325                 330                 335
Glu Asp Ile Ala Pro Ile Gln Thr Ile Ser Val Ser Lys Lys Gly Gly
            340                 345                 350
Leu Asn Phe Ala Ala Ser Lys Ala Gln Ala Leu Ser Leu Ala Lys Glu
            355                 360                 365
His Asn Ala Ala Val Leu Leu Ala Val Lys Thr Trp Arg
        370                 375                 380

<210> SEQ ID NO 132
<211> LENGTH: 386
<212> TYPE: PRT
<213> ORGANISM: Methanoculleus bourgensis MS2

<400> SEQUENCE: 132

Met Gln Ile Leu Val Leu Asp Thr Ile His Gly Gly Ala Glu Leu Ala
1               5                   10                  15
Arg Ala Leu Arg Gly Ser Gly His Gln Val Asp Glu Val Asp Val Tyr
            20                  25                  30
Arg Gly Lys Ala Gly Ile Pro Val Glu Glu Ala Leu Glu Arg Ser Tyr
        35                  40                  45
Asp Leu Val Thr Ala Pro Val His Leu Asp Pro Ala His Pro Leu Leu
    50                  55                  60
Gln Arg His Gly Pro Ala Val Ser His His Glu Met Val Gly Trp Val
65                  70                  75                  80
Ile Arg Gly Arg Arg Thr Pro His Pro Phe Ile Glu Ile Thr Gly Ala
                85                  90                  95
Arg Gly Lys Thr Thr Thr Ala His Ala Leu Ala Ser Leu Leu Pro Gly
            100                 105                 110
Pro Gly Ile Leu His Thr Ser Thr Gly Thr Tyr Arg Tyr Pro Glu Arg
        115                 120                 125
Glu Arg Leu Trp Lys Arg Ser Ile Thr Pro Ala Ser Leu Ile Pro Ala
    130                 135                 140
Ala His Glu Ala Arg Arg Ile Gly Gly Trp Leu Ile Ala Glu Glu Ser
145                 150                 155                 160
Leu Gly Val Thr Gly Ala Gly Asp Val Ala Val Leu Thr Ser Pro Glu
                165                 170                 175
Asp Tyr Pro Val Ala Ala Gly Arg Lys His Ala Ile Thr Glu Lys Cys
            180                 185                 190
Arg Gln Leu Ala Arg Ala Arg Ile Val Val Leu Pro Pro Gly Ile Asp
        195                 200                 205
```

```
Leu Ala Gly Arg Thr Val Ala Gly Asp Ile Val Ser Phe Asp Gly
    210                 215                 220

Ala Val Cys Arg Tyr Ala Trp Gly Arg Ile Thr Gly Thr Phe Glu Asn
225                 230                 235                 240

Pro Leu Cys Thr Leu Glu Gly Tyr Arg Thr Pro Leu Ala Leu Ala Ala
                245                 250                 255

Ala Thr Ala Cys Val Leu Gly Ile Asp Pro Ala Pro Leu Ala Gly Phe
            260                 265                 270

Ala Ala Leu Pro Gly Arg Met Ala Ser Arg Arg Glu Gly Asn Leu Leu
        275                 280                 285

Ile Val Asp Asn Ala Asn Ser Gly Thr Asn Val Glu Thr Thr Val Glu
    290                 295                 300

Ala Ala Arg Tyr Ala Arg Ala Leu Ala Gly Asn Gly Ala Leu Thr Leu
305                 310                 315                 320

Val Ile Gly Glu Glu Ala Arg Ala Ile Cys Glu Gly Phe Ser Pro Glu
                325                 330                 335

Asp Ile Ala Arg Ala Val Ser Ala Val Gly Pro Thr Ala Thr Val Tyr
            340                 345                 350

Val Gly Glu Gly His Glu Ala Ala Thr Leu Asp Glu Gly Leu Thr Gln
        355                 360                 365

Ala Arg Asn Ile Thr Pro Ser Gly Ala Ile Val Leu Ala Val Lys Thr
    370                 375                 380

Trp Arg
385

<210> SEQ ID NO 133
<211> LENGTH: 390
<212> TYPE: PRT
<213> ORGANISM: Methanofollis liminatans DSM 4140

<400> SEQUENCE: 133

Met Lys Ile Leu Val Leu Asp Thr Ile His Gly Gly Ala Ala Leu Ala
1               5                   10                  15

Glu Ala Leu Lys Arg Ala Gly His Ala Val Asp Met Val Asp Val Tyr
            20                  25                  30

Arg Gly Arg Glu Gly Ile Pro Ala Gly Glu Ala Ala Arg Arg Tyr
        35                  40                  45

Asp Leu Val Ala Ala Pro Val His Leu Asp Pro Ala His Pro Leu Leu
    50                  55                  60

Cys Ala Ala Pro Arg Arg Ile Thr His His Glu Ala Val Arg Met Leu
65                  70                  75                  80

Leu Val Gly Asn Arg Pro Ala Arg Met Ile Glu Ile Thr Gly Ala Arg
                85                  90                  95

Gly Lys Thr Thr Thr Ala Thr Ala Leu Ala Ser Val Leu Pro Gly Pro
            100                 105                 110

Gly Ile Leu His Thr Ser Met Gly Thr Val Arg Tyr Pro Glu Gly Val
        115                 120                 125

Thr Leu Trp Lys Arg Ser Ile Thr Pro Ala Ser Val Leu Pro Ala Ala
    130                 135                 140

Ala Glu Ala Ala Arg Ile Gly Gly Trp Leu Val Ala Glu Glu Ser Leu
145                 150                 155                 160

Gly Val Thr Gly Ala Gly Asp Leu Ala Ile Leu Thr Ala Thr Gly Asp
                165                 170                 175

Tyr Thr Ile Ala Ala Gly Lys Arg Arg Ala Leu Ala Glu Lys Ile Arg
```

```
            180                 185                 190
Ser Met Ser Gly Cys Ala Glu Val Leu Ile Pro Pro Gly Thr Asp Leu
            195                 200                 205

Pro Gly Ala Cys Ala Ala Asp Thr Ile Ala Val Val Thr Gly Thr Leu
            210                 215                 220

Cys Arg Tyr Arg Trp Lys Gly Ile Glu Gly Ala Phe Glu Asn Pro Leu
225                 230                 235                 240

Leu Ala Leu Pro Gly Tyr Arg Thr Pro Leu Gln Met Ala Ala Ala
                245                 250                 255

Ala Cys Leu Leu Gly Ala Asp Pro Ala Ala Leu Ala Ala Phe Ala Pro
            260                 265                 270

Leu Glu Gly Arg Met Ala Val Ala Arg Arg Asp Gly Lys Val Ile Val
            275                 280                 285

Asp Asn Ala Asn Ser Gly Thr Cys Arg Glu Thr Ala Val Gly Ala Ala
            290                 295                 300

Ala Tyr Ala Arg Ala Leu Ala Gly Gly Gly Pro Leu Thr Leu Val Ile
305                 310                 315                 320

Gly Thr Glu Gly Gln Thr Ile Cys Glu Gly Phe Pro Ala Asp Glu Val
                325                 330                 335

Lys Arg Thr Ile Asp Asp Ile Arg Pro Asp Arg Val Val Leu Val Gly
                340                 345                 350

Asp Tyr Pro Glu Ile Glu Gly Ile Thr Ala Gly Asp Leu Ala Glu Gly
                355                 360                 365

Ala Gly Ile Ala Glu Glu Ile Ala Asn Asp Gly Gly Ala Val Val Leu
            370                 375                 380

Ala Val Lys Thr Trp Arg
385                 390

<210> SEQ ID NO 134
<211> LENGTH: 463
<212> TYPE: PRT
<213> ORGANISM: Methanohalobium evestigatum Z-7303

<400> SEQUENCE: 134

Met Ile Ser Gly Ala Cys Lys Tyr Lys Asn Ile Ala Val Leu Asp Leu
1               5                   10                  15

Thr His Gly Gly Ala Ile Ile Ala Arg Lys Leu Ser Glu Leu Gly Tyr
            20                  25                  30

Asn Val His Ala Val Asp Val Tyr Asn Thr Glu Asp Asp Thr Leu
        35                  40                  45

Ser Asn Leu Lys Ile Asn Asn Ile Ser Thr Tyr Lys Lys Pro Phe Pro
50                  55                  60

Val Asp Tyr Leu Asp Leu Leu Ile Thr Pro Ile His Leu Asp Pro Glu
65                  70                  75                  80

Tyr Pro Met Leu Lys Gln Ala Ile Ala Lys Asn Val Asp Ile Ala Thr
                85                  90                  95

His His Trp Ile Val Gly Lys Ile Leu Ser Asp Asp Lys Arg Leu Glu
            100                 105                 110

Asp Lys Thr Ile Ile Glu Val Thr Gly Thr Arg Ala Lys Thr Ser Thr
            115                 120                 125

Ser Ser Leu Leu Ala Asp Ile Leu Ser Arg Lys Leu Asp Val Val Leu
        130                 135                 140

His Ser Ser Arg Gly Val Glu Tyr Trp Lys Glu Gly Leu Pro Glu Thr
145                 150                 155                 160
```

```
Ile Tyr Asp Gly Leu Ser Ile Thr Pro Gly Asn Ile Leu Gln Val Met
            165                 170                 175

Asp Arg Ser Phe Ser Glu Lys Leu Asn Pro Asp Ala Tyr Ile Phe Glu
        180                 185                 190

Val Ser Leu Gly Gly Thr Gly Ile Ala Asp Phe Asn Ile Ile Thr Thr
    195                 200                 205

Leu Glu Gln Asp Tyr Lys Ile Ala Lys Glu Asn Arg Trp Ala Ser Ser
210                 215                 220

Ala Lys Thr Gln Met Ile Asn Tyr Ala Lys Gly Ser Lys Leu Leu
225                 230                 235                 240

Ile Asn Thr Asp Thr Lys Gly Leu Ile Asn His Ser Ala Lys Lys Phe
                245                 250                 255

Asn Ser Ile Phe Glu Phe Asn Asp Gly Lys Tyr Pro Asp Ser Gln Gly
        260                 265                 270

Asp Leu Asn Leu Ile Leu Asp Asn Asn Asp Ile Ile Ile Arg Leu Pro
    275                 280                 285

Asn Glu Thr Ile Ser Ile Asn Thr Gly Tyr Ser Tyr Asp Ile Glu Ser
290                 295                 300

Tyr Thr Thr Ala Ile Ala Ala Ala Val Ser Thr Ala Tyr Asn Ile Gly
305                 310                 315                 320

Val Glu Leu Ser Val Ile Lys Lys Thr Leu Val Glu Phe Ser Gly Leu
                325                 330                 335

Gln Gly Arg Met Arg Glu Gln Thr Phe Asn Asn Cys Ile Leu Ile Asp
        340                 345                 350

Asn Ser Asn Ser Gly Thr Asp Val Thr Ser Ala Asp Lys Ser Leu Asp
    355                 360                 365

Tyr Ala Leu Asp Lys Lys Cys Ser Gly Lys Val Val Met Val Met Gly
370                 375                 380

Glu Glu Ser Ala Gln Val Cys Glu Gly Leu Ser Leu Lys Lys Thr Tyr
385                 390                 395                 400

Asp Phe Val Asn Leu Arg Ser Ser Asp Ile Gln Leu Ile Leu Val
                405                 410                 415

Gly Asp Arg Leu His Asn Ile Lys Leu Lys Asp Ala Tyr His Thr Ser
        420                 425                 430

Thr Leu Asp Glu Gly Leu Lys Val Ala Phe Glu Ile Val Asn Ser Ser
    435                 440                 445

His Val Ser Asp Asn Leu Ile Ile Ser Asn Val Lys Cys Phe Arg
450                 455                 460

<210> SEQ ID NO 135
<211> LENGTH: 444
<212> TYPE: PRT
<213> ORGANISM: Methanohalophilus mahii DSM 5219

<400> SEQUENCE: 135

Met Thr Ala Gly Gln Arg His Phe Ile Val Leu Asp Leu Asn His Gly
1               5                   10                  15

Gly Leu Leu Ile Ser Ser Lys Leu Ala Gly His Gly Tyr Arg Val Thr
            20                  25                  30

Ala Val Asp Val Tyr Gly Thr Leu Pro Lys Glu Ala Phe Ser Asp Leu
        35                  40                  45

Pro Ala Gly Ile Glu Val Val Ser Lys Pro Pro Leu Pro Ala Lys Asn
    50                  55                  60

Ala Ile Ile Val Thr Pro Val His Leu Asp Pro Ala Tyr Pro Val Leu
65                  70                  75                  80
```

Glu Lys Ala Arg Thr Gln Gly Asn Thr Ile Tyr Ser His His Ala Ile
                85                  90                  95

Thr Gly Gln Ile Leu Arg Glu Gly Ile Phe Asp Gln Ala Lys Val
            100                 105                 110

Ile Glu Ile Thr Gly Val Lys Ala Lys Thr Ser Thr Val Thr Leu Leu
            115                 120                 125

Ala Arg Ile Leu Ala Leu Lys Glu Lys Val Ile Leu His Thr Thr Arg
130                 135                 140

Gly Ile Glu Tyr Leu Ser Glu Asn Gln His Ile Met Leu His Lys Gly
145                 150                 155                 160

Leu Ser Ile Thr Pro Ala Ser Ile Leu Glu Val Ile Asn Ile Val Lys
                165                 170                 175

Gly Gln Glu Ile Asp Pro Ser Val Tyr Val Leu Glu Glu Ser Leu Gly
            180                 185                 190

Thr Thr Gly Ile Gly Glu Ile Gly Ile Phe Thr Thr Leu Thr Pro Asp
            195                 200                 205

Tyr Arg Ile Ala Ser Asn Ser Lys Trp Ala Ser Glu Ala Lys Met Gln
210                 215                 220

Ile Met Ser His Leu Val Val Ile Met Asn His Gln Asp Thr Arg Leu
225                 230                 235                 240

Ile Glu Asn Asn Arg Asn Thr Glu Ile Ile Thr Phe Ala Ser Asp Asn
                245                 250                 255

Gln Lys Ala Asp Leu Ile Ser Arg Ile Ser Gly Glu Asn Ile Ser Ile
            260                 265                 270

Ile Ser Asp Gly Lys Thr Ile Glu Cys Lys Leu Gln His Gly Tyr Asn
            275                 280                 285

Pro Glu Glu Tyr Ala Ile Ala Phe Ala Ala Ser Ala Cys Ala Gly Leu
290                 295                 300

Gln Ala Gly Ala Asp Pro Asp Asp Ile Arg Lys Thr Phe Glu Glu Phe
305                 310                 315                 320

Arg Gly Ile Glu Gly Arg Met Arg Leu Thr Lys Phe Arg Gln Arg Arg
                325                 330                 335

Leu Ile Asp Asn Ser Ser Ser Gly Leu Asn Ile Asp Ser Ala Arg Ser
            340                 345                 350

Ala Ile Glu Met Gly Leu Asp Lys Ser Ala Lys Asn Val Leu Ile Ile
            355                 360                 365

Gly Glu His Ala Ala Gln Val Cys Glu Gly Phe Pro Pro Gln Asn Val
370                 375                 380

Gln Ile Leu Leu Ser Glu Tyr Lys Gln Phe Leu Asp His Val Ile Leu
385                 390                 395                 400

Ile Gly Lys Arg Met Glu Asn Leu Ser Ser Gln Asn Ile Ile His Arg
                405                 410                 415

Lys Asn Leu Gln Glu Gly Leu Glu Cys Ala Leu Ser Leu Thr Asp Ser
            420                 425                 430

Gly Asp Thr Ile Ile Ser Cys Val Lys Cys Phe Arg
435                 440

<210> SEQ ID NO 136
<211> LENGTH: 405
<212> TYPE: PRT
<213> ORGANISM: Methanolacinia petrolearia DSM 11571

<400> SEQUENCE: 136

Met Lys Ile Leu Val Leu Asp Thr Ile His Gly Gly Lys Thr Leu Ala

-continued

```
1               5                   10                  15
Glu Tyr Leu Lys Arg Ala Gly His Val Val Asp Thr Val Asp Val Tyr
                20                  25                  30

Arg Gly Arg Asp Gly Ser Val Ser Glu Asp Glu Ala Ala Gly Lys Val
                35                  40                  45

Tyr Asp Leu Ile Ala Ala Pro Val His Leu Asp Pro Asp Tyr Arg Leu
        50                  55                  60

Leu Asn Thr Gly Thr Asp Val Ile Ser His His Glu Ala Val Ala Val
65                  70                  75                  80

Ala Ala Ser Val Pro Glu Asp Thr Leu Leu Ile Glu Ile Thr Gly Ala
                    85                  90                  95

Arg Gly Lys Thr Thr Ala His Ala Leu Leu His Leu Met Glu Lys
                100                 105                 110

Asp Gly Cys Gly Ile Leu His Thr Ser Lys Gly Thr Val Arg Tyr Pro
                115                 120                 125

Glu Lys Asp Leu Ile Phe Lys Arg Ser Ile Thr Pro Ala Thr Leu Val
            130                 135                 140

Glu Val Leu Ser Ala Ala Gly Glu Lys Glu Cys Arg Trp Ile Ile
145                 150                 155                 160

Ala Glu Glu Ser Val Gly Val Thr Gly Leu Gly Asp Leu Gly Val Leu
                    165                 170                 175

Thr Ser Gly Thr Asp Tyr Pro Ile Ala Asn Gly Lys Lys Ser Ala Leu
                180                 185                 190

Asp Glu Lys Ile Arg Leu Leu Lys Gly Cys Lys Lys Ile Leu Leu Ala
            195                 200                 205

Pro Gly Val Glu Ala Asp Ile Pro Gly Ala Tyr Tyr Ser Asp Asp Ile
210                 215                 220

Val Val Val Glu Asp Asp Val Cys Arg Phe Gly Tyr Ala Gly Ile Lys
225                 230                 235                 240

Gly Glu Phe Ser Asn Lys Leu Leu Thr Val Glu Gly Tyr Lys Glu Ala
                245                 250                 255

Leu Met Thr Ala Ala Ala Gly Cys Ile Leu Gly Lys Asp Pro Ser
                260                 265                 270

Gly Leu Gly Ser Phe Ser Ala Leu Glu Gly Arg Leu Ser Tyr Ser Thr
            275                 280                 285

Arg Asp Gly Lys Gly Ile Ile Asp Asn Ser Asn Ser Gly Ala Asn Arg
            290                 295                 300

Lys Thr Ala Leu Thr Ala Ser Ala Tyr Ala His Arg Phe Ser Pro Gly
305                 310                 315                 320

Gln Glu Gln Val Leu Val Ile Gly Ile Glu Ala Glu Asn Ile Cys Glu
                325                 330                 335

Gly Phe Pro Asp Asp Glu Ile Ala Gly Ala Ile Ser Asp Ile Met Pro
            340                 345                 350

Tyr Ala Ala Val Val Ser Lys Asp Pro Glu Asn Val Arg Lys Ile
                355                 360                 365

Ile Pro Pro Gly Ile Glu Phe Glu Thr Ala Ser Ser Leu Glu Glu Gly
            370                 375                 380

Ala Glu Lys Ala Met Lys Tyr Gly Thr Asn Arg Ile Ile Ile Leu Ser
385                 390                 395                 400

Val Lys Thr Trp Arg
                405

<210> SEQ ID NO 137
```

<211> LENGTH: 469
<212> TYPE: PRT
<213> ORGANISM: Methanolobus psychrophilus R15

<400> SEQUENCE: 137

| | | | | | | | | | | | | | | |
|---|---|---|---|---|---|---|---|---|---|---|---|---|---|---|
| Met | Asn | Gly | Ile | Ser | Cys | Ile | Ser | Asn | Thr | Phe | Ser | Ala | Lys | Cys | Lys |
| 1 | | | | 5 | | | | | 10 | | | | | 15 | |
| Val | Ala | Val | Leu | Asp | Leu | Thr | His | Ala | Gly | Ile | Ile | Ala | Arg | Lys |
| | | 20 | | | | | 25 | | | | | 30 | | |
| Leu | Ala | Glu | Met | Gly | Phe | Asp | Val | Thr | Ala | Val | Asp | Tyr | Asn | Thr |
| | | 35 | | | | | 40 | | | | | 45 | | |
| Ile | Ala | Glu | Asp | Val | Leu | Leu | Ser | Met | Gln | Glu | Asp | Phe | Gly | Ile | Thr |
| 50 | | | | | 55 | | | | | 60 | | | | | |
| Val | Ser | Arg | Ser | Pro | Val | Pro | Val | Gly | Pro | Phe | Asp | Ile | Ile | Val | Ser |
| 65 | | | | | 70 | | | | | 75 | | | | | 80 |
| Pro | Val | His | Leu | Glu | Pro | Gly | Tyr | Gln | Met | Leu | Thr | Glu | Ala | Arg | Glu |
| | | | | 85 | | | | | 90 | | | | | 95 | |
| Gln | Gly | Lys | Glu | Leu | Ile | Ser | His | His | Arg | Ala | Val | Gly | Met | Ile | Leu |
| | | | 100 | | | | | 105 | | | | | 110 | | |
| Ser | Thr | Ser | Lys | Val | Leu | Gly | Glu | Val | Lys | Val | Ile | Glu | Ile | Thr | Gly |
| | | | 115 | | | | | 120 | | | | | 125 | | |
| Ser | Lys | Ala | Lys | Thr | Ser | Thr | Ala | Ser | Leu | Leu | Ala | Asp | Met | Leu | Ser |
| 130 | | | | | 135 | | | | | 140 | | | | | |
| Arg | Thr | Met | Val | Val | Val | Leu | His | Thr | Thr | Arg | Gly | Leu | Glu | Leu | Trp |
| 145 | | | | | 150 | | | | | 155 | | | | | 160 |
| Thr | Cys | Gly | Lys | Ala | Arg | Ile | Leu | His | Leu | Gly | Leu | Ser | Ile | Ala | Pro |
| | | | | 165 | | | | | 170 | | | | | 175 | |
| Gly | Ser | Ile | Leu | His | Ala | Val | Asp | Ile | Leu | Lys | Ser | Leu | Asp | Ile | His |
| | | | 180 | | | | | 185 | | | | | 190 | | |
| Pro | Asp | Cys | Cys | Ile | Phe | Glu | Val | Ser | Ile | Gly | Gly | Thr | Gly | Tyr | Ala |
| | | | 195 | | | | | 200 | | | | | 205 | | |
| Asp | Ile | Gly | Met | Ile | Thr | Thr | Leu | Glu | Pro | Asp | Tyr | Thr | Ile | Ala | Lys |
| | 210 | | | | | 215 | | | | | 220 | | | | |
| Ser | Thr | Ser | Gln | Ala | Ser | Asp | Ala | Lys | Leu | Arg | Met | Leu | Asp | Tyr | Gly |
| 225 | | | | | 230 | | | | | 235 | | | | | 240 |
| Lys | Glu | Gly | Ser | Val | Phe | Val | Leu | Asn | Ser | Gln | Asp | Ser | Arg | Ser | Val |
| | | | | 245 | | | | | 250 | | | | | 255 | |
| Ser | Lys | Ala | Arg | Glu | Ser | Gly | Arg | Asp | Phe | Phe | Thr | Phe | Thr | Asp | Ser |
| | | | 260 | | | | | 265 | | | | | 270 | | |
| Gly | Ser | Gln | Glu | Thr | Gln | Ala | Asp | Leu | Arg | Leu | Ala | Phe | Asn | Gly | Lys |
| | | | 275 | | | | | 280 | | | | | 285 | | |
| Ser | Val | Thr | Leu | Asn | Ala | Gly | Lys | Ile | Ser | Ile | Cys | Ala | Asp | Val | Asp |
| | 290 | | | | | 295 | | | | | 300 | | | | |
| Ser | Ser | Tyr | Asn | Thr | Ser | Ser | Tyr | Ser | Leu | Ala | Phe | Ala | Ala | Ala | Gly |
| 305 | | | | | 310 | | | | | 315 | | | | | 320 |
| Ala | Ala | Ala | Leu | His | Met | Gly | Val | Ser | Gly | Glu | Ala | Ile | Ala | Glu | Val |
| | | | | 325 | | | | | 330 | | | | | 335 | |
| Ile | Ser | Gly | Phe | Thr | Gly | Leu | Gln | Gly | Arg | Met | Gln | Glu | Lys | Asp | Ile |
| | | | 340 | | | | | 345 | | | | | 350 | | |
| Asn | Gly | Arg | Leu | Leu | Ile | Asp | Asn | Ser | Asn | Ser | Gly | Met | Asp | Ile | Thr |
| | | | 355 | | | | | 360 | | | | | 365 | | |
| Ser | Ala | Glu | Arg | Ala | Leu | Asp | Tyr | Gly | Phe | Ser | Arg | Ala | Val | Gly | Arg |
| | 370 | | | | | 375 | | | | | 380 | | | | |
| Lys | Ser | Gly | Lys | Val | Leu | Met | Val | Leu | Gly | Glu | Glu | Ala | Ala | Gln | Val |

```
                385                 390                 395                 400
Cys Glu Gly Leu Pro Pro Glu Lys Val Ala Glu Phe Val Val Arg Arg
                    405                 410                 415

Ile Cys Asp Ile Asp His Leu Val Leu Val Gly Glu Arg Met Lys Asp
                420                 425                 430

Ile Arg Asn Glu Lys Val Ser His Ala Leu His Leu Glu Asp Gly Leu
                435                 440                 445

Ala Leu Ala Leu Gly Met Ser Glu Gly Asp Leu Val Ile Ser Cys
450                 455                 460

Val Lys Cys Phe Arg
465

<210> SEQ ID NO 138
<211> LENGTH: 429
<212> TYPE: PRT
<213> ORGANISM: Methanomassiliicoccus luminyensis B10

<400> SEQUENCE: 138

Met Ser Gln Lys Val Leu Val Asp Leu Thr His Gly Gly Glu Val
1               5                   10                  15

Leu Ala Tyr Glu Tyr Ala Glu Arg Gly Asp Gln Val Thr Ile Val Asp
                20                  25                  30

Ile Tyr His Thr Gly Lys Pro Glu Leu Lys Ser Glu Leu Ile Ala Ala
                35                  40                  45

Gly Ile Arg Val Ala Glu Ala Ala Pro Ala Glu Thr Phe Asp Leu Gly
            50                  55                  60

Ile Val Pro Ile His Cys Pro Asp His Phe Ile Gly Glu Ala Lys Met
65                  70                  75                  80

Ala Arg Arg Ile Thr Ala His Gln Ala Thr Gly Glu Leu Ala Lys Phe
                85                  90                  95

Pro Tyr Pro Thr Val Glu Phe Thr Gly Thr Arg Gly Lys Thr Ser Ala
                100                 105                 110

Cys His Val Leu Ala His Met Leu Ala Gln Glu Gly Gln Lys Val Ala
                115                 120                 125

Leu Leu Thr Ser Lys Gly Leu Ser Ile Val Glu Glu Cys Thr Gly Ala
            130                 135                 140

Ile Leu Lys Asp Lys Val Ser Ile Ala Pro Pro Ser Val Leu Ser Val
145                 150                 155                 160

Ala Lys Met Asp Leu Gln Val Asp Ile Gly Val Phe Glu Val Ser Ile
                165                 170                 175

Gly Gly Thr Gly Leu Ala Asp Val Ser Val Val Thr Gly Leu Asp Asp
                180                 185                 190

Tyr Pro Ile Ala Ala Gly Thr Arg Lys Ala Phe Asp Gly Lys Val Gln
                195                 200                 205

Met Ile Glu Ser Ala Lys Ser Ala Ala Val Tyr Pro Gln Ala Glu Ala
            210                 215                 220

Gly Leu Trp Glu Lys His Val Pro Gln Gly Thr Asp Val Ile Thr Phe
225                 230                 235                 240

Gly Pro Gly Gly Asp Val Ser Ala Thr Leu Pro Lys Gln Leu Lys Leu
                245                 250                 255

Gly Lys Ala Val Pro Leu Asn Val Glu Ile Tyr Gly Asp Ala Phe Lys
                260                 265                 270

Thr Lys Leu Pro Gly Thr Phe Leu Val Pro Ser Tyr Lys Thr Ala Phe
            275                 280                 285
```

```
Asn Ser Ala Ile Ala Ala Val Ala Leu Gly Met Asp Met Asp Ala
    290                 295                 300

Ala Ile Gly Ser Leu Ser Ser Phe Gly Val Pro Gly Arg Gly Glu
305                 310                 315                 320

Val Ser Lys Glu Lys Gly Trp Tyr Leu Ile Ser Glu Arg Asn Pro Gly
                325                 330                 335

Val Ser Ala Gly Ser Ile Glu Trp Asn Val Ser Val Leu Glu Arg Tyr
                340                 345                 350

Tyr Gly Gln Glu Asp Ile Gly Val Ala Val Asp Pro Val Asn Gln Lys
                355                 360                 365

Val Cys Glu Lys Leu Val Leu Asp Asp Val Arg Glu Ala Leu Ser Lys
370                 375                 380

His Pro Ala Val Lys Gly Gln Tyr Val Ile Asn Met Pro Gly Phe Glu
385                 390                 395                 400

Pro Ser Gly Phe Arg Arg Ile Asp Ser Phe Val Asp Val Arg Gly Arg
                405                 410                 415

His Lys Val Leu Met Gln Cys Ile Lys Glu Gly Tyr Leu
                420                 425

<210> SEQ ID NO 139
<211> LENGTH: 468
<212> TYPE: PRT
<213> ORGANISM: Methanomethylovorans hollandica DSM 15978

<400> SEQUENCE: 139

Met His Arg Tyr Leu Ser Asp Pro Ser Val Lys Ser Val Ala Val Leu
1               5                   10                  15

Asp Met Thr His Gly Gly Ile Ile Ala His Arg Leu Lys Glu Leu
                20                  25                  30

Gly Phe Asn Val Thr Gly Val Asp Val Tyr Gly Thr Ile Ser Pro Glu
                35                  40                  45

Gln Cys Asn Ser Met Glu Met Asp Gly Ile Arg Val Ser Glu Lys Asn
    50                  55                  60

Cys Ser Val Glu Asp Leu Asp Leu Ile Ile Ser Pro Val His Leu Tyr
65                  70                  75                  80

Pro Asp His Ile Met Leu Gln Gln Ala Glu Glu Lys His Ile Pro Val
                85                  90                  95

Ile Ser His Arg Ala Val Gly Glu Ile Leu Asn Ile Lys Asp Thr
                100                 105                 110

Gly Asp His Thr Leu Met Ile Glu Val Thr Gly Thr Lys Ala Lys Thr
                115                 120                 125

Ser Thr Ala Ser Leu Leu Ala Asp Met Ile Ser Arg Lys Leu Thr Val
    130                 135                 140

Leu Leu His Thr Ser Arg Gly Leu Glu Met Trp Glu Asp Gly Val Cys
145                 150                 155                 160

Arg Leu Leu His Lys Gly Leu Ser Ile Ala Pro Gly Ser Ile Leu Gln
                165                 170                 175

Ala Met Asp Ile Ala Gly Ser Leu Asn Lys Glu Ile Glu Ala Tyr Ile
                180                 185                 190

Phe Glu Ile Ser Leu Gly Val Thr Gly Cys Gly Ser Val Gly Ile Ile
                195                 200                 205

Thr Thr Leu Asp Met Asp Tyr Met Ile Ala Gly Lys Thr Ser Met Ala
    210                 215                 220

Ser Glu Ala Lys Val Lys Ser Leu Met Ser Tyr Pro Glu Asp Val Pro
225                 230                 235                 240
```

```
Leu Val Leu Asn Asp Asn Tyr Lys Gly Ile Ser Gln Gln Leu Lys Pro
                245                 250                 255

Ala Leu Met Ser Lys His Ile Arg Thr Phe Ser Thr Pro Asp Lys Ser
            260                 265                 270

Glu Gly Leu Asn Ser Asp Ala Asp Tyr Arg Ile Ser Met His Glu Asn
        275                 280                 285

Ser Leu Ser Ile Ala Cys Ala Gly Glu Glu Ile Lys Ile Arg Leu Asp
    290                 295                 300

Thr Gly Tyr Asp Ala Trp Ser Tyr Arg Thr Ala Phe Ala Ala Ser Cys
305                 310                 315                 320

Ala Thr Ala Gln Glu Ile Asp Ile Pro Trp Lys Thr Val Lys Glu Val
                325                 330                 335

Ile Gln Asn Phe Arg Gly Leu Gln Gly Arg Met Gln Glu Ile Ile Gln
            340                 345                 350

Glu Asp Ile Thr Ile Leu Asp Asn Ser Asn Ser Gly Met Asp Ile Phe
        355                 360                 365

Ser Val Glu Lys Ala Leu Ser Leu Cys Leu Lys Arg Asn Gln Lys Val
    370                 375                 380

Ile Met Val Leu Gly Glu Glu Ala Ala Gln Val Cys Glu Gly Leu Pro
385                 390                 395                 400

Pro Glu Asp Val Ala Asp Met Leu Arg Ser Arg Leu Gln Asp Met Asp
                405                 410                 415

Glu Leu Ile Leu Val Gly Glu Arg Met Lys Pro Leu Ala Thr Gly Asn
            420                 425                 430

Ile Tyr Tyr Ala Glu Ser Phe Asp Met Gly Lys Thr Arg Ala Met Glu
        435                 440                 445

Phe Ala Arg Lys Lys Ser Asp Asp Lys Val Ile Ala Leu Cys Val
    450                 455                 460

Lys Cys Phe Arg
465

<210> SEQ ID NO 140
<211> LENGTH: 460
<212> TYPE: PRT
<213> ORGANISM: Methanomicrobium mobile BP

<400> SEQUENCE: 140

Met Asn Ile Leu Val Leu Asp Thr Ile His Gly Gly Lys Thr Ile Ala
1               5                   10                  15

Gly Tyr Leu Thr Ala Ser Gly Cys Ile Cys Asp Thr Val Asp Val Tyr
            20                  25                  30

Arg His Glu Ser Gly Ile Ser Glu Asp Glu Ala Val Arg Asn Leu Thr
        35                  40                  45

Leu Lys Arg Tyr Asp Phe Val Cys Ala Pro Val His Leu Ser Pro Gly
    50                  55                  60

His Cys Ile Leu Lys Ser Ala Ala Ala Glu Gly Ile Pro Val Ile Ser
65                  70                  75                  80

His His Glu Val Val Ser Leu Ile Val Ser Gly Leu Ser Asp Thr Asp
                85                  90                  95

Ser Asn Ser Glu Asn Thr Lys Pro Ile Ile Glu Ile Thr Gly Thr Arg
            100                 105                 110

Gly Lys Thr Thr Thr Ala Tyr Ala Leu Ser His Met Leu Ser Arg Val
        115                 120                 125

Ile Pro Gln Lys Asn Lys Thr Asn Asp Ser Glu Thr Gly Glu Ser Gly
```

```
                130                 135                 140
Ile Leu His Thr Ser Arg Glu Thr Val Thr Val Pro Asp Gly Arg Val
145                 150                 155                 160

Leu Gln Arg Val Ser Ile Thr Pro Ala Ser Ile Met Pro Ala Leu
                165                 170                 175

Tyr Ala Leu Lys Asn Asn Leu Trp Leu Val Ala Glu Glu Ser Leu Gly
                180                 185                 190

Val Cys Gly Phe Gly Asn Leu Ala Val Leu Thr Ser Thr Glu Asp Tyr
                195                 200                 205

Pro Cys Ala Asp Lys Lys Arg Ser Ala Leu Ala Val Lys Leu Ala Ser
                210                 215                 220

Met Ala Lys Cys Gly Arg Val Leu Val Gly Tyr Gly Ala Asp Lys Arg
225                 230                 235                 240

Lys Val Leu Glu Thr Ile Glu Ser Leu Pro Gln Ser Gln Arg Ile Pro
                245                 250                 255

Glu Glu Arg Leu Phe Phe Ala Ser Asp Ala Val Arg Val Glu Asp Gly
                260                 265                 270

Val Cys Gly Tyr Gly Asn Gly Ser Gly Gly Phe Ser Asn Pro Leu Leu
                275                 280                 285

Tyr Leu Glu Gly Tyr Lys Gln Ala Ile Ala Thr Ala Ala Ala Ala
                290                 295                 300

Cys Leu Leu Gly Tyr Asn Pro Asp Ser Leu Ser Gly Phe Thr Ser Val
305                 310                 315                 320

Pro Gly Arg Leu Ser Leu Thr Arg Glu Asn Gly Ile Thr Val Ile Asp
                325                 330                 335

Asn Ser Asn Ser Gly Thr Asn Arg Asn Thr Ser Val Ile Ala Ala Glu
                340                 345                 350

Tyr Ala Arg Arg Thr Glu Asn Ala Gly Ile Ile Leu Val Ile Gly Ile
                355                 360                 365

Glu Ser Glu Thr Val Cys Glu Gly Phe Pro Lys Glu Asp Val Thr Ser
370                 375                 380

Ala Ile Thr Glu Ile Lys Pro Glu Cys Ala Val Val Gly Asp Ser
385                 390                 395                 400

Leu Lys Gly Ile Val Gln Glu Asp Phe Asp Asn Thr Ser Asp Asn Thr
                405                 410                 415

Ile Ile Tyr His Ala Asp Asn Leu Glu Ser Gly Arg Lys Arg Ala Leu
                420                 425                 430

Glu Ile Ala Arg Val Ser Gly Asn Glu Ala Lys Gln Gly Asp Cys Gly
                435                 440                 445

Gly Lys Thr Val Val Leu Cys Val Lys Thr Trp Arg
450                 455                 460

<210> SEQ ID NO 141
<211> LENGTH: 404
<212> TYPE: PRT
<213> ORGANISM: Methanoplanus limicola DSM 2279

<400> SEQUENCE: 141

Met Asn Ile Leu Val Leu Asp Thr Ile His Gly Gly Asp Glu Ile Ser
1               5                   10                  15

Arg Arg Leu Ile Ser Leu Gly His Asn Thr Asp Thr Val Asp Val Tyr
                20                  25                  30

Arg His Lys Ser Gly Ile Ser Glu Gly Ser Ala Leu Leu Lys Asn Tyr
                35                  40                  45
```

```
Asp Leu Thr Ala Ser Pro Val His Leu Asp Pro Glu Tyr Pro Leu Leu
 50                  55                  60

Lys Lys Glu Cys Arg Ile Ile Ser His His Gln Ala Ala Met Ile
 65                  70                  75                  80

Ile Gly Asp Lys Lys Pro Glu Leu Met Ile Glu Ile Thr Gly Ala Lys
                 85                  90                  95

Gly Lys Thr Thr Thr Ala His Ala Leu Ala His Val Leu Arg Thr His
            100                 105                 110

Asn Asn Arg Leu Leu Leu His Thr Ser Lys Gly Thr Val Glu Phe Pro
        115                 120                 125

Gly Gly Lys Thr Leu Trp Lys Lys Ser Ile Thr Pro Ala Ser Val Ile
130                 135                 140

Asp Ala Ala Leu Tyr Ala His Glu Asn Gly Leu Trp Leu Ile Ala Glu
145                 150                 155                 160

Glu Ser Leu Gly Val Thr Gly Ala Gly Asp Ile Ala Ile Leu Thr Ser
                165                 170                 175

Lys Glu Asp Tyr Pro Ile Ala Ser Gly Lys Lys Ser Ala Ile Lys Ala
            180                 185                 190

Lys Leu Gly Ser Met Lys Asn Ser Gly Thr Val Ile Thr Ala Pro Gly
        195                 200                 205

Glu Asp Pro Gly Gly Asn Thr Gly Ala Tyr His Ser Glu Asp Ile Thr
210                 215                 220

Glu Val Lys Asn Gly Val Cys Arg Tyr Ser Tyr Lys Gly Ile Asn Gly
225                 230                 235                 240

Ser Phe Arg Asn Pro Leu Leu Glu Ile Ser Gly Tyr Lys Lys Ala Leu
                245                 250                 255

Gln Thr Ala Ala Ala Thr Ala Cys Ile Leu Gly Ile Asp Pro Ala Cys
            260                 265                 270

Leu Lys Asp Phe Leu Ala Leu Glu Gly Arg Met Ser Ser Gly Lys Arg
        275                 280                 285

Gly Ser Asn Ile Ile Ile Asp Asn Ser Asn Ser Gly Val Asn Lys Gln
290                 295                 300

Thr Thr Leu Asp Ala Val Arg Tyr Ala Arg Lys Val Ser Pro Lys Glu
305                 310                 315                 320

Asn Leu Thr Leu Val Ile Gly Leu Glu Ala Asn Asn Ile Cys Glu Gly
                325                 330                 335

Phe Pro Ala Glu Asp Ile Leu Asp Ala Ile Arg Gln Ser Gly Ala Asp
            340                 345                 350

Lys Val Val Leu Ala Gly Glu Ala Ala Arg Leu Lys Glu Glu Ala Glu
        355                 360                 365

Gly Leu Thr Gly Tyr Val Thr Leu Ser Ser Gly Leu Ser Asp Gly Arg
370                 375                 380

Glu Thr Ala Glu Lys Ile Thr Asp Asp Gly Leu Ile Val Leu Ser Val
385                 390                 395                 400

Lys Thr Trp Arg

<210> SEQ ID NO 142
<211> LENGTH: 366
<212> TYPE: PRT
<213> ORGANISM: Methanopyrus kandleri AV19

<400> SEQUENCE: 142

Met Ser Asp Glu Leu His Gly Ile Gly His Glu Val Val Leu Val Asp
1               5                   10                  15
```

```
Ile Tyr Gly Thr Cys Asp Glu Ala Arg Pro Tyr Pro Ile Leu Arg Arg
            20                  25                  30

Ala Phe Gly Arg Phe Asp Phe Ile Ala Val Pro Val His Cys Gly Val
        35                  40                  45

Asp Phe Gly Thr Val Glu Gly Pro Arg Val Thr His His Ala Leu Ala
    50                  55                  60

Gly Ala Leu Ala Ala Arg Tyr Lys Gln Asp Phe Leu Phe Glu Val Thr
65                  70                  75                  80

Gly Val Arg Gly Lys Thr Thr Thr Ala Thr Tyr Leu Ala Trp Ile Leu
                85                  90                  95

Glu Glu Ala Gly His Arg Pro Ala Leu Ser Thr Thr Asp Glu Ser Pro
            100                 105                 110

Val Gly Arg Pro Ser Val Thr Pro Ala Arg Val Val Glu Val Val Arg
        115                 120                 125

Glu Thr Ser Gly Pro Tyr Val Cys Glu Val Ser Leu Gly Val Thr Ser
    130                 135                 140

Ala Ala Asp Tyr Ala Val Phe Thr Gly Ala Pro Tyr Asp Tyr Pro Ile
145                 150                 155                 160

Ala Gly Gly Ser Ser Ala Leu Arg Ala Lys Lys Thr Leu Leu
                165                 170                 175

Glu Ser Gly Ala Glu Val Met Ile Glu Tyr Arg Glu Ala Val Lys Leu
            180                 185                 190

Ser Leu Val Gly Pro Lys Val His Arg Val His Thr Ser Asp Gly Thr
        195                 200                 205

Val Lys Cys Asp Asp Ile Cys Val Glu Phe Glu Ala Phe Asp Ile Pro
    210                 215                 220

Phe His Asp Arg Cys Phe Gly Leu Ala Ala Thr Ala Leu Thr Ser
225                 230                 235                 240

Gly Leu Ala Asp Arg Glu Asp Val Glu Ala Arg Ala Arg Gly Pro
                245                 250                 255

Val Pro Ser Arg Leu Glu Leu Arg Arg Asn Glu Leu Val Asp Ala His
            260                 265                 270

Ser Ala Val Asn Glu Gln Thr Val Arg Tyr Ala Leu Ser Val Ala Ser
        275                 280                 285

Asp Leu Trp Gly Arg Tyr Gly Ala Val Ile Gly Gly Thr Leu Gly Gly
    290                 295                 300

Tyr Cys Glu Gly Val Asp Pro Glu Ala Val Ala Glu Val Leu Gln Glu
305                 310                 315                 320

Arg Ile Glu Arg Gly Glu Leu Val Ala Leu Lys Leu Lys Gly Glu Leu
                325                 330                 335

Gly Arg Glu Val Glu Arg His Leu Glu Asn Val Asp Leu Pro Glu Pro
            340                 345                 350

Gly Pro Asp Thr Pro Ile Val Arg Ile Val Arg Lys Gly Asp
        355                 360                 365

<210> SEQ ID NO 143
<211> LENGTH: 406
<212> TYPE: PRT
<213> ORGANISM: Methanoregula formicica SMSP

<400> SEQUENCE: 143

Met Asn Ile Leu Val Leu Asp Ser Ile His Gly Gly Gln Pro Ile Ala
1               5                   10                  15

Ala Ala Phe Val Ser Arg Gly Asp Gln Val Asp Leu Val Asp Val Tyr
            20                  25                  30
```

Arg Gly Thr Gly Pro Val Ser Val Glu Val Ala Arg Ser Arg Lys Tyr
        35                  40                  45

Asp Leu Ile Val Ala Pro Val His Leu Asp Pro Asp His Pro Leu Ile
 50                  55                  60

Arg Thr Ala Lys Ala Pro Val Ile Thr His His Glu Ala Ile Arg Gln
 65                  70                  75                  80

Leu Leu Gly Ser Tyr Val Pro Gly Ile Met Val Glu Ile Thr Gly Ala
                 85                  90                  95

Arg Gly Lys Thr Thr Thr Ala His Ala Leu Ala Ser Leu Leu Pro Gly
                100                 105                 110

Pro Gly Ile Leu His Thr Ser Ser Gly Thr Phe Arg Tyr Pro Glu Lys
                115                 120                 125

Glu Phe Ile Ser Arg Ser Ser Ile Thr Pro Gly Ser Val Leu Glu Ala
            130                 135                 140

Val Arg Leu Ala Lys Glu Thr Gly Gly Trp Leu Ile Ala Glu Glu Ser
145                 150                 155                 160

Leu Gly Leu Thr Cys Ala Gly Thr Leu Gly Ile Ile Thr Ser Ala Gly
                165                 170                 175

Asp Phe Arg Phe Ala Ala Gly Lys Lys Ser Ala Leu Ser Ala Lys Leu
            180                 185                 190

Ala Ser Ala Arg Ser Cys Lys Asn Leu Leu Leu Ala Glu Gly Ile Thr
            195                 200                 205

Glu Asn Pro Leu Asn Asn Val Met His Leu Glu Asn Thr Ala Ser Cys
        210                 215                 220

Thr Gly Thr Glu Cys Thr Ile Ser Leu Gly Thr Thr Thr Arg Arg Phe
225                 230                 235                 240

Ile Asn Pro Leu Ile Ala Leu Pro Ala Tyr Arg Asp Ser Leu Ala Leu
                245                 250                 255

Ala Ala Thr Ala Ala Val Met Leu Gly Ile Asp Pro Ser Pro Leu Ser
            260                 265                 270

Gly Phe Thr Ala Leu Thr Gly Arg Met Glu Ala Arg Tyr Val Gly Gly
            275                 280                 285

Ile Leu Val Val Asp Asn Ala Asn Ser Gly Thr Asn Phe Arg Thr Thr
        290                 295                 300

Ile Asp Ala Ala Gln Tyr Ala Arg Asn Val Ala Gly Arg Asn Glu Ile
305                 310                 315                 320

Thr Leu Val Ile Gly Gln Gln Glu Gly Asp Gly Ala Val Cys Glu Gly
                325                 330                 335

Phe Ala Phe Asp Gln Ile Leu Ala Ala Met Glu Ala Ile Arg Pro Ser
            340                 345                 350

Ser Leu Ile Trp Val Gly Arg Phe Pro Glu Pro Gly Thr Pro Asp His
            355                 360                 365

Ala Ala Leu Ile Pro Leu Ala Pro Val Arg Ala Ala Thr Phe Glu Glu
        370                 375                 380

Gly Tyr Ile Leu Ala Arg Gln Lys Thr Val Gln Gly Ser Ile Val Leu
385                 390                 395                 400

Ala Val Lys Thr Trp Arg
                405

<210> SEQ ID NO 144
<211> LENGTH: 386
<212> TYPE: PRT
<213> ORGANISM: Methanosaeta concilii GP6

<400> SEQUENCE: 144

```
Met Val Glu Cys Gly Ile Gln Ala Glu Pro Leu Glu Val Tyr His His
1               5                   10                  15

Thr Ala Ser Leu Asp Ala Phe Asp Glu Val Ala Pro Val His Leu
            20                  25                  30

Pro Pro Asp Asn Pro His Leu Ile Gln Ala Lys Gly Leu Gly Lys Arg
            35                  40                  45

Ile Ile Ser His His Gln Ala Ala Gly Glu Leu Met Gly Ser Ile Asp
        50                  55                  60

Asp Asp Val Val Lys Ile Glu Val Thr Gly Thr His Ser Lys Thr Thr
65                  70                  75                  80

Thr Ala Leu Leu Leu Ala Met Ile Leu Ser Arg Gln Lys Arg Val Leu
                85                  90                  95

Ser His Thr Thr Arg Gly Leu Glu Ile Trp Ser Gly Arg Pro Gln
            100                 105                 110

Leu Leu Lys Glu Gly Leu Ser Ile Thr Pro Ala Asn Val Ile Leu Ala
            115                 120                 125

Ala Gln Glu Ala Leu Ala Gln Gly Ala Glu Ala Leu Ile Cys Glu Ile
130                 135                 140

Ser Leu Gly Gly Thr Gly Leu Ala Gln Leu Gly Ile Leu Thr Ser Phe
145                 150                 155                 160

Thr Asn Asp Tyr Arg Ile Ala Gly Gly Thr Lys Trp Ala Ser Thr Ala
                165                 170                 175

Lys Leu Gln Met Leu Ser Leu Ala Arg Arg Gly Ser Arg Leu Ala Ala
            180                 185                 190

Asn Ala Asp Cys Arg Ile Ser Pro Asp Ile Ser Phe Ala Lys Gly Gly
            195                 200                 205

Leu Val Arg Ala Leu Pro Asp Gly Leu Ile Tyr Gly Glu Glu Arg Leu
210                 215                 220

Gly Leu Tyr Leu Gly Glu Asp Leu Asp Phe Ala Ser Tyr Gln Thr Ala
225                 230                 235                 240

Ile Ser Gly Ala Ala Ala Ala Glu Leu Leu Glu Leu Glu Arg Glu
                245                 250                 255

Asp Thr Ile Arg Ala Leu Glu Gly Phe Gly Gly Phe Ser Gly Arg Met
            260                 265                 270

Lys Ile Glu Arg Leu Gly Gly Arg Thr Val Phe Asp Ser Ser Asn Ser
            275                 280                 285

Gly Leu Lys Val Ser Asp Ile Glu Arg Ala Met Asp Lys Ala Arg Gly
290                 295                 300

Pro Asn Leu Val Ala Val Gly Glu Asp Ala Gln Thr Val Cys Glu
305                 310                 315                 320

Gly Leu Asp Ile Pro Arg Leu Ala Glu Leu Arg Arg Arg Ser
                325                 330                 335

Glu Ile Glu Asp Leu Val Leu Val Gly Glu Arg Leu Arg Pro Leu Ala
            340                 345                 350

Arg Glu Leu Gly Ala Glu Thr Ala Gln Asp Leu Val Glu Gly Leu Glu
355                 360                 365

Lys Ala Glu Ser Thr Arg Pro Lys Arg Leu Leu Ser Ala Val Lys Cys
370                 375                 380

Phe Arg
385
```

<210> SEQ ID NO 145

<211> LENGTH: 461
<212> TYPE: PRT
<213> ORGANISM: Methanosalsum zhilinae DSM 4017

<400> SEQUENCE: 145

```
Met Asn Glu Thr Gly Lys Asn Ile Ala Val Leu Asp Leu Thr His Gly
1               5                   10                  15

Gly Ile Ala Ile Ala Lys Lys Leu Ser Leu Leu Gly Phe Gly Val Tyr
            20                  25                  30

Ala Val Asp Val Tyr Gln Thr Val Thr Asp Ser Val Lys Ser Glu Leu
        35                  40                  45

Leu Ser Ile Tyr Asn Ile Gly Val Ser Ser Asp Pro Pro Asp Ile Glu
    50                  55                  60

Asn Ile Asp Thr Val Val Ser Pro Val His Leu Asp Pro Asp Tyr Ile
65                  70                  75                  80

Leu Leu Lys Gln Ala Lys Ala Gly Lys Lys Ile Ile Ser His His
                85                  90                  95

Arg Ile Val Ala Glu Ile Leu Ala Glu Glu Lys Lys Leu Glu Lys Ala
                100                 105                 110

Thr Val Ile Glu Ile Thr Gly Ala Gln Ala Lys Thr Ser Thr Ser Thr
            115                 120                 125

Met Leu Ala Asp Ile Leu Ser Arg Gln Gly Asp Val Ile Leu His Thr
130                 135                 140

Ser Arg Gly Leu Glu Tyr Trp Thr Ser Gly Asn Cys Lys Val Ile His
145                 150                 155                 160

Lys Gly Leu Ser Ile Thr Pro Ala Ser Ile Leu Glu Ala Val Asp Ile
                165                 170                 175

Ser Ile Ser Asn Asn Phe Ile Pro Asp Ile Tyr Ile Phe Glu Val Ser
            180                 185                 190

Ile Gly Gly Thr Gly Tyr Ser Asp Leu Gly Ile Leu Thr Thr Thr His
        195                 200                 205

Pro Asp Tyr Lys Ile Ala Ala Gly Lys Lys Gln Ala Ser Ser Ala Lys
    210                 215                 220

Met Gln Ile Ile Glu Asn Ala Cys Cys Arg Lys Lys Arg Val Leu Cys
225                 230                 235                 240

Ile Asn Asn Ala Ala Leu Asp Thr Val Lys Cys Thr Glu Ile Ser Asn
                245                 250                 255

Gly Ser Cys Gln Glu Met Ile Thr Phe Ser Thr Thr Tyr Asp Gln Lys
            260                 265                 270

Ala Asp Ala Asn Ile Tyr Leu Gln Asp Asn Arg Ile Ile Ile Asn Tyr
        275                 280                 285

Leu Asp Gln His Tyr Leu Thr Ile Pro Val Gln Gly Gly Tyr Asp Pro
    290                 295                 300

Ser Ser Tyr Thr Ile Ala Met Ala Ala Ile Thr Ala Ser Ile Ala
305                 310                 315                 320

Met Gly Ile Glu Ser Lys Met Ile Gln Leu Cys Ile Ser Gly Phe Ser
                325                 330                 335

Gly Ile Ser Gly Arg Met Gln Lys Tyr Asp Leu Asp Gly Arg Thr Leu
            340                 345                 350

Ile Asp Asn Ser Asn Ser Gly Met Asn Ile Val Leu Ala Glu Lys Ala
        355                 360                 365

Leu Arg Tyr Ala Leu Gly Ile Lys Asn Lys Asn Ile Val Met Leu
    370                 375                 380

Leu Gly Glu Glu Ser Ala Gln Val Cys Glu Gly Leu Asp Pro Glu Asp
```

```
                385                 390                 395                 400
Val Ser Lys Phe Ile Lys Arg His Gly Asn Met Ile Asp Lys Leu Ile
                    405                 410                 415

Leu Ile Gly Gly Arg Met Met Pro Val Asp His Lys Asp Val Ile Tyr
                420                 425                 430

Val Leu Gly Phe Glu Glu Gly Leu Asn Glu Ala Ser Arg Ile Ser Asp
                435                 440                 445

Asp Gly Asp Ile Ile Val Ser Cys Val Lys Cys Phe Arg
    450                 455                 460

<210> SEQ ID NO 146
<211> LENGTH: 472
<212> TYPE: PRT
<213> ORGANISM: Methanosarcina acetivorans C2A

<400> SEQUENCE: 146

Met Asp Leu Phe Arg Lys Lys Leu Ala Val Leu Asp Leu Thr His Gly
1               5                   10                  15

Gly Ile Pro Ile Ala Arg Lys Leu Ala Ala Leu Gly Asn Asp Val Ser
                20                  25                  30

Gly Val Asp Val Tyr Gly Thr Val Asp Gln Ala Leu Leu Gly Glu Leu
            35                  40                  45

Glu Glu Lys Tyr Gly Ile Arg Cys Ser Lys Ala Pro Leu Pro Val Ser
        50                  55                  60

Asp Phe Asp Leu Leu Ile Ala Pro Val His Leu Asp Pro Ala Tyr Pro
65                  70                  75                  80

Met Leu Ile Lys Ala Arg Ser Glu Gly Lys Thr Val Leu Ser His His
                85                  90                  95

Glu Ala Val Gly Lys Ile Leu Gln Ala Asp Pro Arg Leu Ser Glu Ile
            100                 105                 110

Lys Ile Val Glu Ile Thr Gly Val Lys Ala Lys Thr Ser Thr Ala Ser
        115                 120                 125

Leu Leu Ala Asp Met Leu Ser Arg Ser Phe Lys Val Val Leu His Thr
130                 135                 140

Ser Arg Gly Leu Glu Ala Trp Lys Ala Gly Ile Pro Phe Leu Ile His
145                 150                 155                 160

Arg Gly Leu Ser Ile Thr Pro Gly Ser Ile Leu Ile Ala Val Glu Lys
                165                 170                 175

Ser Leu Glu Gln Glu Ile Arg Pro Glu Phe Phe Ile Phe Glu Ile Ser
            180                 185                 190

Ile Gly Ala Thr Gly Thr Ala Asp Leu Gly Ile Leu Thr Thr Leu Ser
        195                 200                 205

Pro Asp Tyr Gly Ile Ala Asn Asn Thr Ser Leu Ala Ser Asp Ala Lys
    210                 215                 220

Leu Gln Leu Val Leu Asn Ala Arg Pro Gly Ser Thr Leu Leu Leu Asn
225                 230                 235                 240

Ala Gly Ala Glu Lys Ala Leu Glu Ala Ala Lys Gly Ser Leu Ala Lys
                245                 250                 255

Val Leu Thr Phe Lys Asp Pro Phe Cys Ser Asp Ser Tyr Leu Lys Leu
            260                 265                 270

Ala Asp Ala Pro Asp Phe Val Leu Glu Thr Glu Ser Gly Ala Glu Lys
        275                 280                 285

Asn Leu Thr Leu His Phe Leu Arg Arg Gly Glu Glu Leu Phe Ser Ala
    290                 295                 300
```

Ser Leu Cys Pro Gly Tyr Asn Ser Ser Ala Tyr Arg Thr Ala Phe Val
305                 310                 315                 320

Ala Ala Ser Ala Ala Ala Leu Glu Leu Gly Val Gly Leu Glu Ala Ile
            325                 330                 335

Val Ser Val Leu Glu Glu Phe Arg Gly Leu Ser Gly Arg Met Gln Glu
            340                 345                 350

Lys Glu Leu Asn Gly Val Val Leu Val Asp Asn Ser Asn Ser Gly Met
            355                 360                 365

Asp Ile Leu Ser Ala Glu Lys Ala Leu Glu Tyr Ala Leu Leu Lys Lys
        370                 375                 380

Lys Asp Glu Lys Lys Gly Asn Ile Ile Leu Ile Leu Gly Glu Glu Ala
385                 390                 395                 400

Ser Gln Val Cys Glu Gly Leu Pro Pro Gly Ser Val Gln Gly Phe Leu
            405                 410                 415

Glu Lys Phe Gly Thr Lys Cys Arg His Ile Ile Leu Val Gly Glu Arg
            420                 425                 430

Met Glu Ala Val Ala Ala Glu Asn Ala Ser Tyr Ala Gly Ser Leu Pro
            435                 440                 445

Glu Gly Leu Gln Lys Ala Ser Glu Leu Ala Gly Thr Glu Asp Ile Ile
        450                 455                 460

Leu Ser Ser Val Lys Cys Phe Arg
465                 470

<210> SEQ ID NO 147
<211> LENGTH: 448
<212> TYPE: PRT
<213> ORGANISM: Methanosphaera stadtmanae DSM 3091

<400> SEQUENCE: 147

Met Lys Asn Ile Leu Ile Ser Asp Ala Asn His Gly Gly Leu Thr Leu
1               5                   10                  15

Leu Glu Glu Tyr Ser Lys Tyr Thr Lys Asn Asn Leu Phe Phe Tyr Asp
            20                  25                  30

Thr Tyr Asn Lys Leu Asn Leu Asp Met Lys Glu Phe Tyr Lys Lys Lys
        35                  40                  45

Tyr Asn Val Glu Phe Leu Ser Leu Asp Asp Ile Arg Lys Asn Glu Asp
    50                  55                  60

Lys Tyr Ile Thr Ile Ser Pro Ile His Met Lys Pro Leu Phe Arg Cys
65                  70                  75                  80

Asp Tyr Thr His His Glu Phe Thr Gly Tyr Leu Ile Lys Lys His Glu
            85                  90                  95

Glu Cys Tyr Gly Trp Asn Phe Lys Ile Ile Glu Ile Thr Gly Val Lys
            100                 105                 110

Gly Lys Thr Thr Thr Ala Asn Leu Ile Met Glu Val Leu Lys Asn Lys
        115                 120                 125

Asn Leu Leu Val Leu Thr Ser His Asn Leu Leu Tyr Lys Ser Cys Glu
    130                 135                 140

Arg Glu Ile Val Leu Asp Lys Thr Leu Ser Ile Thr Pro Ala Ser Ile
145                 150                 155                 160

Ile His Ala Leu Asn Arg Ala Lys Asp Met Asn Leu Leu Ser Ser Ile
            165                 170                 175

Asp Tyr Cys Ile Phe Glu Val Ser Leu Gly Ile Thr Thr Asn Thr Asp
            180                 185                 190

Ile Gly Ile Leu Thr Asn Ile Leu Glu Asp Tyr Pro Ile Ala Asp Asn
        195                 200                 205

```
Ser Gln Ser Ala Ser Ser Ala Lys Lys Ser Val Phe Lys Ser Lys Lys
    210                 215                 220

Val Ile Cys Asp Arg Thr Thr Leu Lys Lys Tyr Tyr Pro His Met Asp
225                 230                 235                 240

Lys Asn Ile Ile Thr Val Ser Leu Asp Asp Lys Thr Ala Asp Ile Tyr
                245                 250                 255

Thr Thr Glu Ile Asp Tyr Asn Ile Lys Ser Thr Ser Ile Arg Ile Lys
            260                 265                 270

Tyr Cys Asp Tyr Glu Phe Arg Val Asn Cys Phe Ala Leu Cys Asp Phe
        275                 280                 285

Tyr Ile Asn Asn Ile Leu Tyr Ala Val Cys Val Gly Leu Leu Leu Asp
    290                 295                 300

Ile Pro Ile Lys Thr Ile Thr Ser Asn Ile Lys Asp Thr Leu Pro Ile
305                 310                 315                 320

Glu Gly Arg Gly Ser Ile Lys Tyr Ile Glu Asp Lys Ile Val Leu Glu
                325                 330                 335

Asp Ile Asn Pro Gly Leu Asn Thr Thr Ser Ile Ser Lys Cys Ile Ser
            340                 345                 350

Asn Leu Glu Arg Tyr Ser Asn Asn Tyr Val Leu Ile Val Gly Gly Asp
        355                 360                 365

Tyr Gly Ile Thr Cys Glu Glu Ile Asp Glu Glu Lys Leu Ser Lys Tyr
    370                 375                 380

Ile Ser Thr Ile Asp Ser Pro Ile Val Leu Thr Gly Asp Val Gly Tyr
385                 390                 395                 400

Asn Leu Leu Lys Lys Leu Asp Lys Asp Tyr Glu Phe Tyr His Glu Leu
                405                 410                 415

Thr Asp Ala Phe Asn Tyr Leu Leu Lys Lys Asp Tyr Asp Val Ile Gln
            420                 425                 430

Ile Ile Tyr Arg Ser Glu Tyr Ala Arg Asn Ile Thr Tyr Leu Pro Asn
        435                 440                 445

<210> SEQ ID NO 148
<211> LENGTH: 401
<212> TYPE: PRT
<213> ORGANISM: Methanosphaerula palustris E1-9c

<400> SEQUENCE: 148

Met Arg Leu Leu Val Leu Asp Thr Ile His Gly Gly Val Ile Ala
1               5                   10                  15

Ala Ala Leu Ala Ala Gln Gly His Gln Val Asp Ala Val Asp Val Tyr
                20                  25                  30

Arg Gly Glu Gly Gly Val Pro Glu Glu Val Ala Met Glu Gln Gln Tyr
            35                  40                  45

Asp Leu Leu Ile Ala Pro Val His Leu Asp Pro Thr His Pro Leu Leu
    50                  55                  60

His His His Arg Cys Pro Ala Ile Thr His Gln Ala Val Arg Trp
65                  70                  75                  80

Ile Leu Gly Asn Gln Val Pro His Pro Phe Ile Glu Val Thr Gly Ala
                85                  90                  95

Gln Gly Lys Thr Thr Thr Ala Thr Ala Leu Ala Phe Leu Met Lys Gly
            100                 105                 110

Pro Gly Ile Leu His Thr Ser Thr Gly Thr Tyr Gln Tyr Pro Glu Lys
        115                 120                 125

Lys Leu Leu Phe Gln Ser Ser Ile Thr Pro Ala Ser Glu Ile Ala Ala
```

```
              130                 135                 140
Ala Glu Ala Ala Leu Ala Ile Asp Gly Trp Met Ile Ala Glu Val Ser
145                 150                 155                 160

Leu Gly Val Thr Gly Ala Gly Asp Leu Ala Ile Leu Thr Ser Gly Asn
                165                 170                 175

Asp Tyr Arg Cys Ala Ala Gly Thr Arg Ser Ala Leu Glu Glu Lys Ile
                180                 185                 190

Arg Ser Val Ala Thr Ala Ser Ile Val Val Ala Pro Leu Asp Val Gln
                195                 200                 205

Thr Ala His Pro His Gln Val Ser Val Asp Gln Ala Thr Thr Ile Arg
                210                 215                 220

Asp Asp Gln Cys Gln Phe Thr Tyr Gln Arg Thr Thr Gly His Phe Lys
225                 230                 235                 240

Asn Thr Leu Leu Leu Leu Pro Ala Tyr His Ser Pro Leu Ala Leu Ala
                245                 250                 255

Thr Thr Ala Ala Leu Ile Leu Gly Leu Asp Pro Ser Gly Leu Gly Gly
                260                 265                 270

Phe Glu Pro Leu Asp Gly Arg Met Lys Ile Ser Thr Arg Gly Gln Thr
                275                 280                 285

Leu Ile Val Asp Asn Ala Asn Ser Gly Val Ser Arg Val Thr Thr Arg
                290                 295                 300

Glu Ala Val Asn Thr Ala Arg Ser Met Asn Pro Lys Met Pro Val Thr
305                 310                 315                 320

Leu Val Ile Gly Glu Glu Ala His Ala Val Cys Glu Gly Phe Ser Pro
                325                 330                 335

Arg Glu Ile Arg Ala Ala Ile Ala Glu Thr Trp Pro Ala Ser Val Val
                340                 345                 350

Leu Val Gly Glu Lys Ala Arg Ala Leu Leu Ser Gly Leu Pro Asp Asp
                355                 360                 365

Gln Phe Leu Ala Ala Glu Thr Leu Ala Glu Ala Val Pro Met Ala Glu
                370                 375                 380

Lys Leu Thr Pro Gln Gly Gly Ser Ile Val Leu Ala Val Lys Met Trp
385                 390                 395                 400

Arg

<210> SEQ ID NO 149
<211> LENGTH: 404
<212> TYPE: PRT
<213> ORGANISM: Methanospirillum hungatei JF-1

<400> SEQUENCE: 149

Met Arg Ile Leu Val Leu Asp Ser Ile His Gly Gly Lys Val Ile Val
1               5                   10                  15

Asp His Leu Ser Ala His Gly His Val Thr Asp Leu Ile Asp Val Tyr
                20                  25                  30

Arg Asn Gln Glu Gly Ile Ser Pro Asp Leu Ala Arg Thr Arg Val Tyr
                35                  40                  45

Asp Leu Ile Ile Ala Pro Val His Leu Asp Pro Asp Tyr Ser Leu Leu
                50                  55                  60

Gln Asp Leu Arg Ile Pro Val Ile Ser His Ala Ala Val Arg Trp
65                  70                  75                  80

Leu Phe Thr Asp His Ala Val Ser Ser Val Ile Glu Ile Thr Gly Lys
                85                  90                  95

Gln Gly Lys Ser Thr Thr Ala Ala Ala Leu Ala Ser Ile Met Pro Gly
```

```
                    100                 105                 110
        Glu Gly Leu Leu His Thr Ser Ala Gly Val Val Arg Tyr Pro Ser Leu
                        115                 120                 125

Glu His Leu Gly Arg Tyr Ser Ile Thr Pro Ala Ser Ile Leu Gln Val
        130                 135                 140

Leu Ser Glu Gln Phe Ser Asp Gly Trp Leu Ile Ser Glu Val Ser Leu
        145                 150                 155                 160

Gly Phe Cys Gly Ile Gly Thr Leu Gly Ile Leu Thr Ser Phe Leu Asp
                        165                 170                 175

Tyr Pro Val Ala Gln Gly Lys Arg Arg Ala Leu Ala Leu Lys Thr Glu
                        180                 185                 190

Gln Ala His Leu Val Lys Gln Val Leu Ile Pro Pro Gly Gly Glu Leu
                        195                 200                 205

Val His Asp Gly Cys Ile Pro Val Ser Asp Leu Val Ser Val Ser Gly
                        210                 215                 220

Thr Arg Ala Cys Tyr Arg Tyr Gly Asp Leu Ser Gly Ser Phe Val Asn
        225                 230                 235                 240

Pro Leu Leu Leu Pro Gly Tyr Lys Thr Pro Leu Met Leu Ala Ala
                        245                 250                 255

Gly Ala Ala Leu Leu Leu Gly Val Asp Pro Ala Gly Leu Ser Asp Phe
                        260                 265                 270

Ser Ala Leu Pro Gly Arg Met Glu Val Thr Lys Asp Thr Gly Tyr Thr
                        275                 280                 285

Ile Ile Asp Asn Ala Asn Ser Gly Thr Cys His Ser Thr Thr Leu Asp
                        290                 295                 300

Ala Tyr Arg Tyr Gly Arg Glu Ile Ala Lys Asn Glu Pro Val Thr Leu
        305                 310                 315                 320

Ile Ile Gly Gln Glu Ser Ala Ser Val Cys Glu Asn Phe Ser Thr His
                        325                 330                 335

Glu Ile Cys Ala Ser Ile Ser Asp Ile Asn Pro Arg Asp Val Ile Leu
                        340                 345                 350

Ile Pro Gly Asp Glu Arg Ile Met Lys Glu Glu Ile Ile Gln Tyr Cys
                        355                 360                 365

Ala Asn Thr Gly Ile Thr Cys Ile Cys Ala Asn Ser Thr Glu Glu Gly
                        370                 375                 380

Ile Arg Arg Ala Lys Thr Leu Asn Asn Thr Leu Ile Leu Leu Ser Val
        385                 390                 395                 400

Lys Arg Trp Lys

<210> SEQ ID NO 150
<211> LENGTH: 440
<212> TYPE: PRT
<213> ORGANISM: Methanothermobacter marburgensis str. Marburg

<400> SEQUENCE: 150

Met Thr Lys Asp Leu Lys Asn Val Ser Lys Pro Leu Val Val Asp Leu
        1               5                   10                  15

Thr His Gly Gly Val Thr Ile Ala Arg Glu Leu Lys Lys Ile Ala Asp
                        20                  25                  30

His Val Leu Ala Trp Asp Ile Tyr Gly Thr Leu Lys Gly Ser Asp His
                        35                  40                  45

Glu Met Leu Leu Glu Met Gly Ile Asp Glu Val Asp Gly Pro Val Thr
                        50                  55                  60

Gly Ser Thr Val Ile Ala Pro Val His Cys Pro Val Lys Ala Asp Ile
```

```
            65                  70                  75                  80
Thr His His Glu Ile Thr Gly Leu Leu Leu Gly Pro Trp Lys Glu Ala
                    85                  90                  95
Arg Gly Ile Pro Val Val Glu Val Thr Gly Val Lys Gly Lys Thr Ser
                    100                 105                 110
Ala Val Trp Ile Leu Arg Lys Ile Met Glu Asn Leu Asn Pro Leu Ile
                    115                 120                 125
Leu Ser Ser Leu Gly Ser Tyr Ala Gly Ser Glu Leu Leu Arg Arg Asp
                    130                 135                 140
Ile Ser Ile Thr Pro Ala Ser Met Ile Glu Thr Val Lys Leu Ala Gly
145                 150                 155                 160
Pro Arg Asp Tyr Gly Ser Ala Ile Phe Glu Val Ser Leu Gly Gly Thr
                    165                 170                 175
Gly Leu Ala Asp Val Gly Val Leu Thr Asn Ile Ala Glu Asp Tyr Thr
                    180                 185                 190
Ile Arg Arg Gly Thr Ser Arg Ala Ser Ser Ala Lys Arg Gln Ile Phe
                    195                 200                 205
Lys Ser Arg Met Val Cys Cys Asp Leu Gln Ala Phe Asn Arg Tyr Tyr
                    210                 215                 220
Arg Asn Phe Gly Asp Lys Thr Asn Thr Phe Ser Val Asp Ala Gly Ala
225                 230                 235                 240
Ser Val His Ala Thr Asp Ile Arg Tyr Gly Leu Asp Ser Thr Val Ala
                    245                 250                 255
Ser Val Ser Val Glu Asp Leu Lys Thr Ile Asp Gly Asp Arg Ile Asn
                    260                 265                 270
Thr Glu Phe Gly Ile Glu Thr Phe Ala Pro Ala Glu His His Leu Ser
                    275                 280                 285
Asn Val Leu Ala Ala Val Ser Ala Ala Leu Thr Leu Asn Leu Asp Val
                    290                 295                 300
Arg Asp Ile Arg Arg Val Lys Gly Phe Gln Gly Ile Pro Gly Arg
305                 310                 315                 320
Thr Ser Ile Arg Lys Leu Asp Gly Ser Ile Ile Glu Glu Val Asn
                    325                 330                 335
Pro Gly Leu Asn Val Lys Ala Val Glu Tyr Thr Leu Lys Met Ala Glu
                    340                 345                 350
Asp Leu Pro Asp Pro Ala Val Ile Ile Gly Gly Arg Tyr Gly Val Thr
                    355                 360                 365
Cys Glu Asp Ile Asp Glu Asp Arg Leu Ser Gly Val Leu Arg Glu Phe
                    370                 375                 380
Ser Asp Leu Asn Ile Met Phe Thr Asp Glu Leu Gly Tyr Ser Ile Met
385                 390                 395                 400
Arg Lys Thr Arg Lys Asn Ser Pro Tyr Phe Lys Ser Pro Asp Asp Ala
                    405                 410                 415
Leu Lys Ala Ala Leu Glu His Glu Thr Val Ile Leu Ile Tyr Arg Ser
                    420                 425                 430
Glu Tyr Arg Asp Leu Ser Arg Arg
                    435                 440

<210> SEQ ID NO 151
<211> LENGTH: 434
<212> TYPE: PRT
<213> ORGANISM: Methanothermococcus okinawensis IH1

<400> SEQUENCE: 151
```

```
Met Leu Ile Ile Asp Val Asn His Gly Ala Leu Asp Ile Ala Lys Glu
1               5                   10                  15

Tyr Ile Asn Leu Gly Tyr Asn Val Ser Val Trp Asp Ile Tyr Gly Lys
            20                  25                  30

Leu Glu Lys Asp Lys Asp Ile Leu Lys Asn Leu Asn Tyr Ser Met Glu
        35                  40                  45

His Ile Asn Leu Ile Ser Ser Lys Glu Lys Pro Asp Phe Glu Lys Tyr
    50                  55                  60

Asp Asn Ile Ile Ala Pro Ile His Cys Pro Ile Asp Cys Asn Phe Ile
65                  70                  75                  80

Ser Phe His Asp Ala Ile Ser Glu Leu Tyr Lys Lys Tyr Gly Asn
                85                  90                  95

Ile His Lys Lys Phe Ile Glu Ile Thr Gly Val Lys Gly Lys Thr Thr
                100                 105                 110

Thr Thr Glu Leu Leu Tyr Tyr Ile Leu Lys Asp Glu Tyr Asn Ile Phe
        115                 120                 125

Leu Asn Asn Ser Asn Ser Gly Ser Ile Thr Pro Val Ser Val Leu Asn
    130                 135                 140

His Ile Asn Arg Leu Asn Glu Glu Asn Lys Leu Asp Leu Tyr Asn Leu
145                 150                 155                 160

Phe Ile Phe Glu Val Ser Leu Gly Ile Thr Ser Cys Lys Tyr Gly Ala
                165                 170                 175

Leu Thr Asn Val Val Glu Asn Tyr Pro Ile Gly Lys Gly Arg Arg Asn
                180                 185                 190

Ala Leu Asn Ala Lys Leu Tyr Thr Leu Lys Asn Ala Asp Arg Ile Tyr
        195                 200                 205

Ile Asn Lys Asn Ile Leu Asp Asn Tyr Gly Tyr Asp Asn Asn Asn Leu
        210                 215                 220

Asp Leu Val Asn Asn Ile Lys Tyr Lys Tyr Ile Asp Asn Lys Tyr
225                 230                 235                 240

Val Asp Asn Lys Asn Asn Asp Asn Leu Lys Lys Leu Thr Ala Ile Ser
                245                 250                 255

Pro Glu Asp Ala Glu Ile Ile Ser Lys Tyr Pro Leu Lys Tyr Lys Tyr
        260                 265                 270

Asn Asn Lys Ile Ile Glu Phe Ser Lys Tyr Ile Phe Gly Ala His Tyr
    275                 280                 285

Ile Glu Asp Ser Leu Phe Ala Leu Asn Ile Cys Lys Asn Phe Val Asn
        290                 295                 300

Cys Glu Tyr Ile Ile Asp Lys Ile Lys Thr Phe Glu Ile Lys Asn Arg
305                 310                 315                 320

Met Asn Ile Lys Glu Ile Asn Asn Arg Tyr Met Ile Glu Asn Ile Asn
                325                 330                 335

Pro Gly Leu Asn Val Lys Ser Ile Asp Tyr Ala Ile Lys Asp Phe Ser
        340                 345                 350

Glu Ile Phe Asp Gly Ile Val Ile Gly Gly Asp Phe Gly Cys Thr
        355                 360                 365

Cys Glu Glu Leu Asn Val Arg Arg Leu Ser Asn Ile Ile Asn Lys Tyr
    370                 375                 380

Lys Asn Lys Ser Asn Ile Lys Phe Ile Leu Thr Gly Ala Leu Gly Lys
385                 390                 395                 400

Lys Leu Lys Lys Tyr Val Asn Tyr Pro Tyr Val Glu Asn Tyr Asn Phe
                405                 410                 415

Lys Ser Thr Glu Leu Asp Lys Asn Ile Leu Ile Ile Tyr Arg Lys Ala
```

420             425             430

Ile Asn

<210> SEQ ID NO 152
<211> LENGTH: 437
<212> TYPE: PRT
<213> ORGANISM: Methanothermus fervidus DSM 2088

<400> SEQUENCE: 152

Met Asp Val Leu Val Asp Leu Thr His Gly Gly Ile Thr Leu Ala
1               5                   10                  15

Lys Glu Leu Lys Lys Tyr Phe Asp Asn Val Phe Val Trp Asp Ile Tyr
            20                  25                  30

Asn Thr Val Pro Lys Glu Lys Lys Phe Leu Ser Lys Tyr Phe Lys
            35                  40                  45

Phe Val Asp Thr Val Pro Lys Arg Lys Asn Ile Lys Ile Ala Pro
    50                  55                  60

Val His Cys Pro Leu Asn Ile Thr Pro Asp Phe Thr His His Glu Ala
65                  70                  75                  80

Val Asn Phe Ile Leu Gln Asp Trp Lys Asn Lys Arg Asp Ile Pro Ile
            85                  90                  95

Ile Glu Val Thr Gly Val Lys Gly Lys Thr Ser Val Val Trp Met Leu
            100                 105                 110

Lys Glu Ile Leu Ser His Lys Asn Pro Leu Ile Leu Ser Ser Ile Gly
            115                 120                 125

Ile Phe Leu Lys Asp Lys Val Leu Lys Asp Val Ser Ile Thr Pro
130                 135                 140

Ala Asn Ile Ile Lys Ala Ile Lys Leu Gly Lys Asp Lys Phe Gly Val
145                 150                 155                 160

Cys Ile Phe Glu Val Ser Leu Gly Gly Thr Gly Leu Ala Asp Val Gly
            165                 170                 175

Val Leu Thr Asn Ile Val Glu Asp Tyr Leu Ile Ala Gly Gly Lys Arg
            180                 185                 190

Lys Ala Ser Glu Ala Lys Lys Gln Ile Phe Arg Ser Lys Ile Thr Cys
            195                 200                 205

Cys Asp Tyr Lys Thr Leu Lys Lys Phe Tyr Lys Glu Tyr Ile Gly Glu
    210                 215                 220

Ala Asn Thr Phe Ser Ile Asn Tyr His Asp Asp Val Asn Val Trp Thr
225                 230                 235                 240

Ser Ser Ile Lys Tyr Asp Phe Glu Lys Thr Ser Phe Lys Val Asn Val
            245                 250                 255

Asp Gly Leu Lys Thr Leu Lys Gly Glu Phe Cys Gly Asn Ile Arg Ile
            260                 265                 270

Glu Thr Phe Ala Pro Thr Ser His Tyr Leu Leu Asn Val Leu Ala Ala
            275                 280                 285

Ile Ser Ala Ala Leu Ser Leu Gly Val Lys Thr Lys Tyr Ile Lys Lys
            290                 295                 300

Gly Leu Tyr Asn Phe Arg Gly Leu Lys Gly Arg Ser Ser Ile Lys Arg
305                 310                 315                 320

Lys Asn Ser Cys Arg Ile Ile Glu Glu Ile Asn Pro Gly Ile Asn Thr
                325                 330                 335

Lys Thr Ile Glu Asn Ser Leu Glu Ile Ala Lys Asn Leu Lys Asn Ser
            340                 345                 350

Val Val Ile Ile Gly Gly Gln Tyr Gly Val Thr Cys Glu Glu Leu Asn

```
                  355                 360                 365
Glu Glu Arg Val Ala Lys Ile Ile Asp Asn Asn Arg Asp Val Asn Val
        370                 375                 380

Ala Leu Val Asp Glu Val Gly Lys Ser Leu Leu Lys Lys Ile Lys Arg
385                 390                 395                 400

Lys Val Glu Tyr Ala Asp Asn Pro Asn Lys Leu Leu Lys Ser Phe Ile
                405                 410                 415

Glu Arg Gly Phe Lys Asn Ile Val Phe Val Tyr Arg Ser Lys Tyr Ser
                420                 425                 430

Asp Leu Ser Lys Arg
        435

<210> SEQ ID NO 153
<211> LENGTH: 409
<212> TYPE: PRT
<213> ORGANISM: Methanotorris igneus Kol 5

<400> SEQUENCE: 153

Met Leu Ile Val Asp Val Asn His Gly Ala Leu Asp Leu Ala Arg Glu
1               5                   10                  15

Tyr Ile Glu Leu Gly Tyr Ser Val Asp Val Trp Asp Ile Tyr Gly Lys
            20                  25                  30

Leu Glu Lys Asp Lys Asp Phe Ala Lys Asn Tyr Lys Asp Ile Ile Ser
        35                  40                  45

Lys Val Lys Ile Ile Lys Lys Asp Glu Asn Ile Asn Phe Asp Asn Tyr
    50                  55                  60

Asp Lys Ile Ile Ala Pro Ile His Cys Pro Ile Glu Asp Phe Ile
65                  70                  75                  80

Ser Phe His Asp Ala Val Ser Glu Ile Val Lys Glu Lys Tyr Gly Asn
                85                  90                  95

Ile His Lys Lys Phe Ile Glu Val Thr Gly Val Lys Gly Lys Thr Thr
            100                 105                 110

Thr Thr Glu Met Ile Asn Phe Ile Leu Lys Asp Asp Tyr Glu Val Phe
        115                 120                 125

Leu His Asn Ser Asn Lys Gly Ser Ile Ala Pro Thr Ser Ile Leu Asn
130                 135                 140

Val Leu Arg Glu Cys Asn Val Asp Asp Ile Asp Tyr Phe Ile Phe Glu
145                 150                 155                 160

Val Ser Leu Gly Ile Thr Ser Cys Gly Tyr Gly Val Ile Thr Asn Ile
                165                 170                 175

Val Glu Asn Tyr Pro Ile Ala Lys Gly Lys Arg Asn Ala Leu Ile Ala
            180                 185                 190

Lys Ile Ser Thr Leu Lys Asn Ala Asp Lys Lys Tyr Ile Asn Met Lys
        195                 200                 205

Ile Leu Glu Glu Tyr Gly Leu Lys Leu Asn Leu Glu Asn Leu Phe Val
    210                 215                 220

Ile Asp Thr Asn Lys Glu Ile Ile Ser Lys Tyr Pro Leu Lys Tyr Lys
225                 230                 235                 240

Phe Asp Asp Tyr Ile Val Glu Phe Asn Lys Asn Val Phe Gly Met His
                245                 250                 255

Leu Val Glu Asn Ser Ile Phe Ala Ile Lys Val Cys Glu Asn Phe Ile
            260                 265                 270

Asn Thr Glu Asp Ile Ile Glu Lys Ile Lys Asn Phe Arg Ile Asn Ser
        275                 280                 285
```

```
Arg Met Ser Val Glu Lys Ile Lys Asn Arg Tyr Ile Val Lys Asn Ile
    290                 295                 300

Asn Pro Gly Leu Asp Val Lys Ala Ile Asp Tyr Ala Ile Lys Asp Phe
305                 310                 315                 320

Leu Glu Val Phe Gly Val Lys Gln Asn Pro Ser Glu Pro His Ile Lys
                325                 330                 335

Asp Val Val Ile Ile Gly Gly Asp Phe Gly Ile Thr Cys Glu Glu Ile
                340                 345                 350

Asp Val Lys Arg Leu Ala Lys Val Ile Glu Lys Tyr Asn Ala Asn Phe
                355                 360                 365

Ile Phe Val Gly Asp Ile Gly Lys Glu Leu Lys Asn Leu Asp Lys
370                 375                 380

Tyr Pro Phe Tyr Ser Lys Ile Asp Leu Asp Glu Leu Asp Gly Asn Val
385                 390                 395                 400

Leu Val Ile Ile Arg Ser Ala Ile Ser
                405

<210> SEQ ID NO 154
<211> LENGTH: 432
<212> TYPE: PRT
<213> ORGANISM: Methermicoccus shengliensis DSM 18856

<400> SEQUENCE: 154

Met Gly Cys Ile Ala Val Leu Asp Leu Thr His Gly Gly Asp Val Leu
1               5                   10                  15

Ala Arg Trp Leu Ser Ser Met Gly Glu Arg Val Val Gly Ile Asp Val
                20                  25                  30

Tyr His Thr Leu Ser Asp His Glu Arg Gly Glu Leu Glu Asp Asn Gly
                35                  40                  45

Ile Pro Val Leu Glu Arg Met Pro Asp Glu Cys Thr Leu Val Val Ala
50                  55                  60

Pro Val His Leu Pro Pro Ile Pro Ile Leu Arg Glu Ala Glu Arg Arg
65                  70                  75                  80

Gly Ile His Arg Val Thr His His Glu Met Val Arg Arg Leu Ala Leu
                85                  90                  95

Glu Cys Phe Pro Glu Val Cys Glu Arg Cys Ile Glu Ile Thr Gly Thr
                100                 105                 110

Arg Gly Lys Thr Thr Thr Ser Val Leu Leu Ala Arg Leu Leu Ser Cys
            115                 120                 125

Glu Gly Lys Val Val Cys His Thr Thr Met Gly Val Asp Val Leu Glu
        130                 135                 140

Arg Gly Val Arg Thr Gln His Trp Lys Arg Leu Ser Ile Thr Pro Ala
145                 150                 155                 160

Ser Val Leu Asp Val Leu Lys Lys Ala Glu Gln Thr Arg Ala Glu His
                165                 170                 175

Val Val Leu Glu Val Ser Leu Gly Val Cys Gly Leu Arg Arg Gly Leu
                180                 185                 190

Leu Thr Thr Leu Glu Gly Glu Tyr Ser Ile Ala Gly Gly Thr Leu Thr
            195                 200                 205

Ser Thr His Ala Lys Thr Met Val Leu Ser His Pro Pro Glu Gly Phe
        210                 215                 220

Val Met Ala Val Pro Asp Glu Asp Val Pro Gln Ala Arg Cys Thr Leu
225                 230                 235                 240

Lys Tyr Leu His Asp Gly Leu Arg Val Arg Leu Leu Asp Gly Ser Gly
                245                 250                 255
```

```
Gly Ser Gly Gly Ser Gly Gly Ser Gly Gly Arg Gly Gly Glu Val Ala
            260                 265                 270

Thr Val Tyr Leu Asp Gly Ala Lys Glu Arg Leu Glu Ser Met Leu Asp
        275                 280                 285

Gly Thr Met Tyr Thr Arg Ala Leu Ala Arg Ala Ala Val Gly Gly Val
    290                 295                 300

Leu Cys Gly Leu Ser Pro Thr Thr Ile Glu His Tyr Leu Pro Arg Leu
305                 310                 315                 320

Gln Leu Asp Val Glu Gly Arg Met Ser Val Tyr Cys Ile Gly Asp Ala
                325                 330                 335

Arg Ile Val Asp Cys Ser Gly Ser Gly Leu Arg Ala Glu Asp Ile Ala
            340                 345                 350

Arg Ala Ile Glu Leu Ala Ile Gln Arg Phe Gly Arg Val Asp Val Leu
        355                 360                 365

Val Val Gly Gly Ser Arg Thr Val Cys Glu Gly Leu Asp Gly Pro Glu
    370                 375                 380

Leu Glu Ser Val Leu Ser Trp Ala Ser Glu Arg Val Gly Lys Val Ile
385                 390                 395                 400

His Leu Lys Gly Asn Glu Ser Tyr Glu Val Ala Leu Arg Cys Ala Leu
                405                 410                 415

Ser Ala Ala Pro Ser Gly Val Val Leu Leu Cys Ile Lys Cys Phe Arg
            420                 425                 430

<210> SEQ ID NO 155
<211> LENGTH: 464
<212> TYPE: PRT
<213> ORGANISM: Methanoperedens nitroreducens

<400> SEQUENCE: 155

Met Tyr Ile Asn Ser Ser Arg Val Ala Val Leu Asp Leu Thr His
1               5                   10                  15

Gly Gly Ile Val Leu Ser Arg Lys Leu Lys Leu Val Arg Ser Val
                20                  25                  30

Thr Ala Ile Asp Val Tyr Asn Thr Ile Thr Glu Val Leu Asp Glu Leu
            35                  40                  45

Glu Asn Glu Gly Ile Thr Thr Ala Gln Ser Pro Leu Asn Val Asp Asp
    50                  55                  60

Phe Asp Val Leu Ile Ala Pro Val His Leu Asp Pro Asp Tyr Pro Met
65                  70                  75                  80

Leu Arg Asp Ala Val Asn Lys Asn Ile Pro Val Leu Ser His His Ala
                85                  90                  95

Ala Ala Gly Gln Ile Leu Ser Ala Phe Ser Ser Ala Pro Gln Ser Asn
            100                 105                 110

Tyr Asp Leu Arg Asp Lys Thr Ile Ile Glu Ile Thr Gly Thr Lys Ala
        115                 120                 125

Lys Thr Ser Thr Ser Ile Leu Leu Ala Glu Met Leu Ser Arg Glu Lys
    130                 135                 140

Lys Val Ile Ser His Thr Ser Gln Gly Val Lys Asp Trp Ser Thr Gly
145                 150                 155                 160

Arg Ile Ile Lys Lys Gly Leu Ser Ile Thr Pro Ala Ser Thr Leu Ser
                165                 170                 175

Ala Leu Asp Ala Val Leu Glu Ala Gly Ile Glu Pro Glu Val Val Ile
            180                 185                 190

Phe Glu Ile Ser Leu Gly Gly Thr Gly Phe Ala Asn Ile Gly Val Ile
```

```
                195                 200                 205
Thr Thr Val Ala Asn Asp Tyr Pro Ile Ala Asn Asn Thr Arg Met Ala
210                 215                 220

Ser Glu Ala Lys Arg Gln Met Ile Leu Asn Ala Lys Thr Gly Ser Ser
225                 230                 235                 240

Leu Val Val Asn Tyr Asp Ala Leu Arg Leu Phe Gly Ala Cys Arg Arg
                245                 250                 255

Asp Ile Asn Ile Ile Ser Phe Thr Asp Thr Val Asn Ala Ser Cys Asn
            260                 265                 270

Val Tyr Tyr Glu Asp Ile Ser Ser Lys Gly Val Ile Ala Tyr Tyr
        275                 280                 285

Leu Gly Lys Arg Gln Gly Arg Ile His Ile Pro Glu Asn Pro Gly Tyr
290                 295                 300

Asp Ile Asp Ser Tyr Lys Thr Ala Phe Val Cys Ala Thr Ala Val Ala
305                 310                 315                 320

Leu Ala Met Asp Ile Asp Asp Ala Ile Asp Arg Ser Ile Arg Glu
                325                 330                 335

Phe Arg Gly Ala Glu Gly Arg Met Arg Lys Thr Ser Leu Gln Gly Arg
                340                 345                 350

Val Leu Ile Asp Asn Ser Asn Ser Gly Met Asp Ile His Thr Ala Glu
        355                 360                 365

Lys Ala Leu Leu Tyr Ser Lys Pro Glu Gly Arg Ile Val Met Val
370                 375                 380

Leu Gly Glu Glu Ala Gln Gln Val Cys Glu Gly Leu Asp Pro Gly Gly
385                 390                 395                 400

Val Ala Asp Phe Ile Asp Arg His Gln Ser Glu Leu Arg Ala Leu Val
                405                 410                 415

Leu Val Gly Glu Arg Met Leu Pro Phe Val Gln Asp Asn Val Lys Ser
                420                 425                 430

Ile Tyr Tyr Ala Asp Asn Leu Ser Cys Gly Ile Glu Leu Ala Ile Gln
        435                 440                 445

Leu Thr Asn Glu Lys Asp Ile Ile Leu Ser Cys Val Lys Cys Phe Arg
450                 455                 460

<210> SEQ ID NO 156
<211> LENGTH: 497
<212> TYPE: PRT
<213> ORGANISM: Methanosarcina acetivorans C2A

<400> SEQUENCE: 156

Met Ser His Ser Lys Gln Ser Gly Thr Glu Ala Gly Ser Ile Pro Arg
1               5                   10                  15

Val Leu Ile Ser Ala Asp Arg Ser Ser Gly Lys Thr Thr Ile Ser
            20                  25                  30

Met Gly Leu Met Ala Ala Leu Val Ser Arg Gly Tyr Lys Val Gln Pro
        35                  40                  45

Phe Lys Val Ala Leu Asp Tyr Ile Asp Pro Ser Tyr His Thr Glu Ile
    50                  55                  60

Thr Gly Arg Phe Cys Arg Asn Leu Asp Gly Tyr Leu Met Asp Glu Asn
65                  70                  75                  80

Gly Ile Leu Asp Val Tyr Ser His Ala Cys Glu Thr Gly Ser Gly Ala
                85                  90                  95

Asp Ile Ala Ile Ile Glu Gly Val Arg Gly Leu Tyr Glu Gly Phe Glu
            100                 105                 110
```

-continued

```
Gly Leu Ser Asp Leu Gly Ser Thr Ala Gln Ile Ala Lys Ile Leu Lys
            115                 120                 125

Cys Pro Val Val Phe Val Ile Asn Ala Arg Ser Ile Thr Arg Ser Ala
130                 135                 140

Ala Ala Leu Ile Ser Gly Tyr Lys Asn Phe Asp Pro Asp Val Glu Ile
145                 150                 155                 160

Ala Gly Val Ile Leu Asn Asn Ile Gly Gly Arg Arg His Ala Gln Lys
                165                 170                 175

Ala Lys Glu Ala Ile Glu His Tyr Thr Gly Val Pro Val Ile Gly Ile
            180                 185                 190

Ile Pro Arg Asp Pro Ser Met Gln Ile Ser Met Arg His Leu Gly Leu
195                 200                 205

Met Pro Ala Leu Glu Gly Arg Arg Leu Gly Asp Gly Gly Phe Glu
210                 215                 220

Asp Arg Leu Arg Gly Ile Glu Glu Ile Ile Asn Lys Gly Ile Asp Val
225                 230                 235                 240

Asp Arg Phe Leu Glu Ile Ala Gly Ser Ala Lys Ser Leu Thr Ser Pro
                245                 250                 255

Glu Asn Ser Ile Phe Ser Pro Ala Ala Gly Ala Gly Ser Pro Arg Pro
            260                 265                 270

Arg Ile Gly Ile Ala Leu Asp Glu Ala Phe Asn Phe Tyr Tyr Arg Asp
275                 280                 285

Asn Ile Asp Leu Leu Glu Leu Ala Gly Ala Glu Ile Val Tyr Phe Ser
290                 295                 300

Pro Val Asn Asp Pro Glu Leu Pro Asp Val Asp Gly Leu Tyr Ile Gly
305                 310                 315                 320

Gly Gly Tyr Pro Glu Leu Phe Ala Ala Glu Leu Glu Ala Asn Glu Ser
                325                 330                 335

Met Arg Arg Ser Ile Lys Glu Ala Ser Ala Ala Gly Met Pro Ile Tyr
            340                 345                 350

Ala Glu Cys Gly Gly Leu Met Tyr Leu Thr Glu Lys Ile Ser Thr Gly
355                 360                 365

Val Pro Gly Lys Gly Thr Tyr His Asp Ala Ser Met Pro Glu Ser Thr
370                 375                 380

Tyr Ile Met Val Gly Ala Leu Pro Gly His Thr Ile Met Gly Gln Thr
385                 390                 395                 400

Arg Val Val Ser Tyr Asn Ile Gly Thr Leu Asp Arg Asp Cys Leu Ile
                405                 410                 415

Gly Lys Glu Gly Asn Ser Phe Lys Gly His Glu Phe His His Ser Glu
            420                 425                 430

Ile Arg Glu Ile Pro Glu Tyr Ala Glu Phe Ala Ile Ala Leu Leu Arg
435                 440                 445

Gly Thr Gly Ile Lys Gly Asp Arg Asp Gly Leu Ile Val Gly Asn Thr
450                 455                 460

Leu Gly Ser Tyr Ala His Leu His Gly Val Ala Tyr Arg Glu Leu Ala
465                 470                 475                 480

Gly Ser Leu Val Glu Ala Ala Gly Lys Phe Arg Ala Ser Arg Ala Pro
                485                 490                 495

Arg
```

<210> SEQ ID NO 157
<211> LENGTH: 265
<212> TYPE: PRT
<213> ORGANISM: Methanosarcina acetivorans C2A

<400> SEQUENCE: 157

```
Met Lys Lys Gln Lys Ile Val Ala Ile Tyr Gly Lys Gly Gly Ile Gly
1               5                   10                  15

Lys Ser Ser Thr Ala Ser Asn Val Ala Ala Ala Cys Ala Glu Ala Gly
            20                  25                  30

Lys Lys Val Met Ile Ile Gly Cys Asp Pro Lys Ser Asp Ser Ser Ile
        35                  40                  45

Thr Leu Leu Arg Gly Lys Arg Ile Pro Thr Ile Asp Leu Leu Arg
50                  55                  60

Glu Gly Val Asp Val Gln Glu Lys Asp Val Val Phe Glu Gly Tyr Ala
65                  70                  75                  80

Gly Val Lys Cys Val Glu Ala Gly Pro Glu Pro Gly Ile Gly Cys
                85                  90                  95

Ala Gly Arg Gly Ile Ile Val Ala Ile Gln Lys Leu Lys Ser Ile Ser
                100                 105                 110

Gly Asp Leu Leu Lys Glu Gln Asp Leu Ile Ile Tyr Asp Val Pro Gly
            115                 120                 125

Asp Ile Val Cys Gly Gly Phe Val Ala Pro Val Arg Lys Gly Tyr Val
        130                 135                 140

Asn Glu Ala Tyr Val Leu Thr Ser Gly Glu Tyr Met Pro Leu Tyr Ala
145                 150                 155                 160

Ala Asn Asn Ile Cys Lys Gly Leu Ser Lys Ile Gly Met Pro Leu Ser
                165                 170                 175

Gly Val Ile Cys Asn Ser Arg Asn Ala Ser Arg Glu Glu Ile Val
                180                 185                 190

Arg Lys Phe Ser Glu Glu Ile Gly Ser Gln Leu Met Ala Phe Ile Pro
            195                 200                 205

Lys Arg Gln Ile Val Gln Asp Cys Glu Arg Glu Gly Tyr Ser Val Met
210                 215                 220

Glu Lys Ala Pro Asp Ser Asp Ile Ala Glu Val Tyr Arg Gln Leu Gly
225                 230                 235                 240

Lys Ser Ile Leu Thr Asn Glu Lys Lys Val Met Ala Ser His Leu Ser
                245                 250                 255

Asp Glu Arg Leu Arg Glu Met Thr Lys
            260                 265
```

<210> SEQ ID NO 158
<211> LENGTH: 370
<212> TYPE: PRT
<213> ORGANISM: Methanosarcina acetivorans C2A

<400> SEQUENCE: 158

```
Met Thr Gln Lys Glu Ile Ser Ile Ile His Pro Arg Pro Ser Ser Ile
1               5                   10                  15

Val Ala Ala Leu Tyr Thr Leu Arg Asp Leu Asn Val Asp Val Ala Ile
            20                  25                  30

Leu His Gly Pro Pro Gly Cys Ser Phe Lys His Ala Arg Leu Leu Glu
        35                  40                  45

Glu Asp Gly Ile His Val Val Thr Thr Gly Leu Asp Glu Asn Gly Phe
    50                  55                  60

Val Phe Gly Gly His Asp Arg Leu Val Glu Val Ile Asn Lys Ser Ile
65                  70                  75                  80

Glu Leu Phe Asn Pro Lys Ile Leu Gly Val Val Gly Thr Cys Ala Ser
                85                  90                  95
```

```
Met Ile Ile Gly Glu Glu Met His Asp Ala Val Leu Glu Ala Asn Pro
            100                 105                 110
Asp Ile Pro Val Ile Glu Val Glu Val His Ala Gly Tyr His Asn Asn
            115                 120                 125
Thr Arg Gly Val Leu Phe Ala Leu Glu Ser Ala Leu Asp Ala Gly Ile
        130                 135                 140
Ile Asp Arg Lys Glu Phe Glu Arg Gln Glu Tyr Leu Leu Ile Lys Ala
145                 150                 155                 160
Thr Glu Val Glu Lys Arg Phe Gly Ala Ala Ser Lys Glu Tyr Leu Ala
                165                 170                 175
Pro Ser Arg Gly Asp Leu Lys Tyr Lys Val Ala Lys Arg Leu Ile Glu
            180                 185                 190
Leu Leu Lys Glu Gly Lys Lys Gly Leu Val Ile Met Asn Ala Lys Lys
        195                 200                 205
Glu Thr Gly Tyr Met Phe Ala Asp Ile Thr Leu Ala Val Ser Glu Val
            210                 215                 220
Ala Ala Ala Leu Gly Lys Lys Glu Asn Leu Val Asn Met Ala Asn Ile
225                 230                 235                 240
Asp Pro Glu Leu Gly Leu Pro Arg Val Arg Gln His Ala Gln Tyr Ile
                245                 250                 255
Met Arg Asp Phe Ile Ala His Gly Val Glu Ile His Glu Ile Ile Gly
            260                 265                 270
Gly Met Asp Glu Tyr Pro Ile Ala Gly Glu Lys Val Ser Glu Leu Ile
        275                 280                 285
Lys Glu Lys Tyr Ser Asp Tyr Asp Phe Ala Val Ile Thr Gly Val Pro
            290                 295                 300
His Ala Ile Pro Met Glu Asn Leu Gln His Met Glu Leu Ile Ser Ile
305                 310                 315                 320
Thr Asn Gly Pro Arg Gln Val Leu Pro Leu Lys Glu Met Gly His Glu
                325                 330                 335
His Val Leu Val Glu Ile Asp Leu His Pro Lys Thr Leu Gly Val Ser
            340                 345                 350
Glu Ile Val Glu Ser Glu Phe Gly Ala Thr Leu Arg Glu Val Ala Lys
        355                 360                 365
Glu Ala
    370

<210> SEQ ID NO 159
<211> LENGTH: 83
<212> TYPE: PRT
<213> ORGANISM: Methanosarcina acetivorans C2A

<400> SEQUENCE: 159

Met Gln Phe Val Pro Ser Lys Ile Leu Phe Pro Ala Leu Gly Asn Trp
1               5                   10                  15
Gln Glu Phe Arg Val Trp Pro Arg Asp Phe Cys Arg Lys Phe Met Ile
            20                  25                  30
Gln Phe Tyr Ile Gly Ser Ser Asn Leu Tyr Ser Phe Pro Leu Leu Leu
        35                  40                  45
Thr Phe Asn Leu Ser Cys Phe Arg Ile Pro Ser Ser Arg Ser Gly Gly
    50                  55                  60
Val His Ser Pro Ala Gly Phe Arg Asn Leu Pro Gly Glu Thr Arg Ile
65                  70                  75                  80
Thr Phe Val
```

<210> SEQ ID NO 160
<211> LENGTH: 472
<212> TYPE: PRT
<213> ORGANISM: Methanosarcina acetivorans C2A

<400> SEQUENCE: 160

```
Met Asp Leu Phe Arg Lys Lys Leu Ala Val Leu Asp Leu Thr His Gly
1               5                   10                  15

Gly Ile Pro Ile Ala Arg Lys Leu Ala Leu Gly Asn Asp Val Ser
            20                  25                  30

Gly Val Asp Val Tyr Gly Thr Val Asp Gln Ala Leu Leu Gly Glu Leu
        35                  40                  45

Glu Glu Lys Tyr Gly Ile Arg Cys Ser Lys Ala Pro Leu Pro Val Ser
    50                  55                  60

Asp Phe Asp Leu Leu Ile Ala Pro Val His Leu Asp Pro Ala Tyr Pro
65                  70                  75                  80

Met Leu Ile Lys Ala Arg Ser Glu Gly Lys Thr Val Leu Ser His His
                85                  90                  95

Glu Ala Val Gly Lys Ile Leu Gln Ala Asp Pro Arg Leu Ser Glu Ile
            100                 105                 110

Lys Ile Val Glu Ile Thr Gly Val Lys Ala Lys Thr Ser Thr Ala Ser
        115                 120                 125

Leu Leu Ala Asp Met Leu Ser Arg Ser Phe Lys Val Val Leu His Thr
    130                 135                 140

Ser Arg Gly Leu Glu Ala Trp Lys Ala Gly Ile Pro Phe Leu Ile His
145                 150                 155                 160

Arg Gly Leu Ser Ile Thr Pro Gly Ser Ile Leu Ile Ala Val Glu Lys
                165                 170                 175

Ser Leu Glu Gln Glu Ile Arg Pro Glu Phe Phe Ile Phe Glu Ile Ser
            180                 185                 190

Ile Gly Ala Thr Gly Thr Ala Asp Leu Gly Ile Leu Thr Thr Leu Ser
        195                 200                 205

Pro Asp Tyr Gly Ile Ala Asn Asn Thr Ser Leu Ala Ser Asp Ala Lys
    210                 215                 220

Leu Gln Leu Val Leu Asn Ala Arg Pro Gly Ser Thr Leu Leu Leu Asn
225                 230                 235                 240

Ala Gly Ala Glu Lys Ala Leu Glu Ala Ala Lys Gly Ser Leu Ala Lys
                245                 250                 255

Val Leu Thr Phe Lys Asp Pro Phe Cys Ser Asp Ser Tyr Leu Lys Leu
            260                 265                 270

Ala Asp Ala Pro Asp Phe Val Leu Glu Thr Glu Ser Gly Ala Glu Lys
        275                 280                 285

Asn Leu Thr Leu His Phe Leu Arg Arg Gly Glu Glu Leu Phe Ser Ala
    290                 295                 300

Ser Leu Cys Pro Gly Tyr Asn Ser Ser Ala Tyr Arg Thr Ala Phe Val
305                 310                 315                 320

Ala Ala Ser Ala Ala Ala Leu Glu Leu Gly Val Gly Leu Glu Ala Ile
                325                 330                 335

Val Ser Val Leu Glu Glu Phe Arg Gly Leu Ser Gly Arg Met Gln Glu
            340                 345                 350

Lys Glu Leu Asn Gly Val Val Leu Val Asp Asn Ser Asn Ser Gly Met
        355                 360                 365

Asp Ile Leu Ser Ala Glu Lys Ala Leu Glu Tyr Ala Leu Leu Lys Lys
```

```
                    370                 375                 380
Lys Asp Glu Lys Lys Gly Asn Ile Ile Leu Ile Leu Gly Glu Ala
385                 390                 395                 400

Ser Gln Val Cys Glu Gly Leu Pro Pro Gly Ser Val Gln Gly Phe Leu
                405                 410                 415

Glu Lys Phe Gly Thr Lys Cys Arg His Ile Ile Leu Val Gly Glu Arg
                420                 425                 430

Met Glu Ala Val Ala Ala Glu Asn Ala Ser Tyr Ala Gly Ser Leu Pro
                435                 440                 445

Glu Gly Leu Gln Lys Ala Ser Glu Leu Ala Gly Thr Glu Asp Ile Ile
            450                 455                 460

Leu Ser Ser Val Lys Cys Phe Arg
465                 470

<210> SEQ ID NO 161
<211> LENGTH: 130
<212> TYPE: PRT
<213> ORGANISM: Methanosarcina acetivorans C2A

<400> SEQUENCE: 161

Met Thr Glu Lys Leu Gly Ile Leu Ala Ile Gly His Gly Ser Lys Leu
1               5                   10                  15

Pro Tyr Asn Lys Glu Val Val Ser Gln Ile Ala Asp Tyr Ile Ala Gln
                20                  25                  30

Lys His Ser Asp Val Val Arg Ala Gly Phe Met Glu Asn Ser Glu
            35                  40                  45

Pro Thr Leu Glu Glu Ala Ile Ala Gly Phe Ala Gly Thr Gly Val Thr
        50                  55                  60

Lys Ile Ala Ala Val Pro Val Phe Leu Ala Ser Gly Val His Ile Thr
65                  70                  75                  80

Lys Asp Ile Pro Gly Ile Leu Ser Leu Asp Glu Lys Gly Cys Gly Ile
                85                  90                  95

Leu Asn Ile Asp Gly Lys Asp Val Pro Leu Cys Tyr Ala Lys Pro Leu
            100                 105                 110

Gly Ala Asp Glu Leu Ile Ala Asp Leu Val Phe Lys Arg Val Gln Glu
        115                 120                 125

Ala Leu
    130

<210> SEQ ID NO 162
<211> LENGTH: 326
<212> TYPE: PRT
<213> ORGANISM: Methanosarcina acetivorans C2A

<400> SEQUENCE: 162

Met Glu Ile Arg Cys Arg Cys Gly Asp Thr Cys Ile Ile Pro Val Ser
1               5                   10                  15

Glu Val Leu Lys Asp Leu Glu Leu Phe Tyr Lys Pro Cys Asn Asp Cys
                20                  25                  30

Lys Thr Glu Lys Ile Arg Lys Phe Ser Pro Leu Ala Glu Gln Ile Asn
            35                  40                  45

Leu Asp Glu Ile Asp Asn His Phe Gly Ser Cys Lys Cys Gly Lys Arg
        50                  55                  60

Gln Leu Asp Ile Val Met Ala His Val Leu Lys Val Met Ile Asp Glu
65                  70                  75                  80

Gly Ile Lys Asn Lys Lys Ala Asn Leu Arg Asn Ala Cys Val Pro Leu
```

```
                    85                  90                  95
Val Thr Pro Gly Tyr Pro Thr Asp Ser Val Pro Tyr Leu Pro Glu Asn
                100                 105                 110

Ser Ile Val Ile Leu Ser Asp Arg Val Asp Lys Lys Cys Ala Glu Arg
            115                 120                 125

Ile Val Lys Glu Val Gly Glu Val Lys Gly Val Leu Lys Gly Asp Ala
        130                 135                 140

Arg Lys Thr Val Gly Ile Lys Asp Ser Asp Ser Asn Ser His Val Tyr
145                 150                 155                 160

Glu Leu Ala Gly Cys Asp Leu Arg Cys Asp Ile Ile Gln Thr Pro
                165                 170                 175

Tyr Gly Ala Leu Gly Ile Tyr Lys Tyr Gln His Glu Ile His Ile Glu
                180                 185                 190

Phe Pro Thr Val Glu Ser Pro Lys Ile Glu Arg Leu Lys Glu Ala Leu
            195                 200                 205

Lys Asp Tyr Asp Arg Pro Ala Val Leu Asp Cys Thr Cys Gly Pro Gly
        210                 215                 220

Thr Leu Gly Ile Ala Cys Leu Lys Ala Gly Ala Gln Lys Val Val Phe
225                 230                 235                 240

Asn Asp Ile Trp Lys Pro Ala Ile Glu Thr Thr Leu Ile Asn Leu Glu
                245                 250                 255

Thr Asn Gly Phe Pro Val Lys Leu Ser Gly Ser Gly Glu Glu Leu Ile
            260                 265                 270

Ala Ser Gly Glu Lys Phe Glu Ile Tyr Ser Met Asp Val Arg Glu Leu
        275                 280                 285

Ala Asn Cys Leu Asp Glu Lys Phe Asp Ile Cys Ile Ile Asp Thr Phe
290                 295                 300

Pro Gly Val Asp Thr Ala Glu Phe Val Glu Ala Ala Gly Lys Leu Gly
305                 310                 315                 320

Arg Lys Val Val Val Ile
                325

<210> SEQ ID NO 163
<211> LENGTH: 411
<212> TYPE: PRT
<213> ORGANISM: Methanosarcina acetivorans C2A

<400> SEQUENCE: 163

Met Glu Val Val Asp Val Gly Gly Asn Pro Gly Val Asp Cys Lys
1               5                   10                  15

Gly Phe Cys Lys Tyr Cys Tyr Phe Lys Val Lys Asp Ile Gln Pro
            20                  25                  30

Leu Gly Cys Lys Tyr Cys Leu Pro Phe Lys Lys Gly Cys Asp Tyr Cys
        35                  40                  45

Thr Arg Ser Val Lys Glu Ser Tyr Ser Gly Phe Lys Ser Leu Gln Met
50                  55                  60

Val Leu Glu Glu Thr Ala Asn Lys Leu Tyr Phe Thr Ser Gly Glu Val
65                  70                  75                  80

Lys Lys Phe Thr Val Ser Gly Gly Asp Leu Ser Cys Tyr Pro Glu
            85                  90                  95

Leu Lys Ser Leu Ile Thr Phe Leu Ser Gln Phe Asn Thr Pro Ile His
            100                 105                 110

Leu Gly Tyr Thr Ser Gly Lys Gly Phe Ser Lys Pro Asp Asp Ala Leu
        115                 120                 125
```

```
Phe Tyr Ile Asp Asn Gly Val Thr Glu Val Ser Phe Thr Val Phe Ala
    130                 135                 140

Thr Asp Pro Ala Leu Arg Ala Glu Tyr Met Lys Asp Pro Glu Pro Glu
145                 150                 155                 160

Ala Ser Ile Gln Val Leu Arg Asp Phe Cys Thr His Cys Glu Val Tyr
                165                 170                 175

Gly Ala Ile Val Leu Pro Gly Ile Asn Asp Gly Glu Val Leu Glu
            180                 185                 190

Lys Thr Leu Cys Asp Leu Glu Asn Met Gly Ala Lys Gly Ala Ile Leu
                195                 200                 205

Met Arg Phe Ala Asn Phe Gln Glu Asn Gly Leu Ile Leu Asn Asn Ser
210                 215                 220

Pro Ile Ile Pro Gly Ile Thr Pro His Thr Val Ser Glu Phe Thr Glu
225                 230                 235                 240

Ile Val Arg Ser Ser Ala Glu Lys His Pro Ser Ile Arg Ile Thr Gly
                245                 250                 255

Thr Pro Leu Glu Asp Pro Leu Ile Gly Ser Pro Phe Ala Ile Arg Asn
            260                 265                 270

Val Pro Glu Ala Leu Leu Lys Leu Pro Arg Val Ser Lys Lys Ala Thr
            275                 280                 285

Ile Ile Thr Gly Gln Val Ala Ala Ser Arg Leu Thr Glu Ile Phe Glu
290                 295                 300

Ala Leu Gly Gly Thr Val Asn Val Ile Pro Val Lys Lys Asp Ile Gly
305                 310                 315                 320

Cys Leu Ile Thr Ile Asp Asp Phe Lys Ala Leu Asp Leu Ser Glu Val
                325                 330                 335

Thr Glu Thr Val Phe Ile Pro Gly Arg Ala Phe Val His Asp Met Glu
            340                 345                 350

Ile Lys Glu Ala Leu Arg Arg Asp Gly Val Asp Arg Ile Val Arg Arg
        355                 360                 365

Gly Pro Glu Arg Leu Ser Val Asp Gly Glu Met Ser Ile Gly Met Thr
    370                 375                 380

Arg Glu Glu Val Leu Glu Leu Glu Val Glu Asn Phe Thr Glu Leu Ile
385                 390                 395                 400

Gly Gln Ile Asn Ser Leu Gly Leu Pro Leu Glu
            405                 410

<210> SEQ ID NO 164
<211> LENGTH: 223
<212> TYPE: PRT
<213> ORGANISM: Methanosarcina acetivorans C2A

<400> SEQUENCE: 164

Met Glu Lys Lys Met Lys Ala Arg Ala Val Ile Phe Thr Gly Asn Ser
1               5                   10                  15

Ile Ser His Glu Asp Ala Lys Lys Ile Leu Arg Ala Asn Tyr Gln Pro
                20                  25                  30

Pro Val Arg Arg Phe Gln Leu Glu Lys Phe Val Gln Gln Gly Tyr Lys
            35                  40                  45

Val Ile Gly Ile Ile Asp Gly Ile Phe Phe Asp Arg Ala Ala Val Gly
        50                  55                  60

His Arg Glu Ile Leu Ser Ala Leu Asn Ala Gly Val Lys Val Val Gly
65                  70                  75                  80

Gly Ala Ser Met Gly Ala Leu Arg Ala Ser Glu Leu Asp Thr His Gly
                85                  90                  95
```

```
Met Val Gly Val Gly Lys Val Tyr Glu Trp Tyr Arg Asp Gly Val Ile
            100                 105                 110

Glu Ser Asp Asp Glu Val Ala Val Ser Thr Asn Pro Asp Thr Phe Glu
            115                 120                 125

Pro Ile Ser Val Pro Leu Val Asn Ile Arg Glu Thr Leu Lys Ala Ala
            130                 135                 140

Leu Asp Thr Gly Leu Val Ser Glu Lys Glu His Asn Ala Leu Leu Asp
145                 150                 155                 160

Leu Ala Ile Asn Thr Tyr Tyr Pro Asp Arg Ser Tyr Leu Gly Leu Thr
                165                 170                 175

Lys Glu Gly Gly Lys Lys Gly Leu Ile Pro Lys Glu Lys Gly Lys Gln
            180                 185                 190

Leu Leu Asp Phe Cys Leu Asn Ser Glu Val Asp Ile Lys Arg Gln Asp
            195                 200                 205

Ala Val Leu Val Leu Glu Thr Val Lys Lys Leu Ile Glu Glu Ala
            210                 215                 220

<210> SEQ ID NO 165
<211> LENGTH: 229
<212> TYPE: PRT
<213> ORGANISM: Methanosarcina acetivorans C2A

<400> SEQUENCE: 165

Met Lys Phe Ile Asp Gly Ile Ile His Lys Leu Val Leu Ser Arg Gly
1               5                   10                  15

Phe Arg Tyr Tyr Pro Glu Asp Arg Tyr Phe Ile Lys Gln Ile Leu Lys
            20                  25                  30

Phe Ser Glu Asn Lys Asn Thr Lys Val Leu Asp Val Gly Cys Gly Asn
            35                  40                  45

Gly His Tyr Ser Phe Leu Phe Glu Ala Cys Gly Ala Glu Val Thr Ala
        50                  55                  60

Phe Asp Tyr Asp Lys Ala Leu Ile Lys Lys Ala Asn Glu Arg Lys Lys
65                  70                  75                  80

Glu Leu Asn Ser Lys Val Glu Phe Leu Val Ala Asp Gly Arg Tyr Pro
                85                  90                  95

Glu Lys Tyr Phe Thr Asp Lys Phe Gly Ile Ile Phe Leu Ser Gly Phe
            100                 105                 110

Ala Leu Phe Gly Ile Lys Gln Asp Ser Glu Leu Met Glu Lys Tyr Leu
            115                 120                 125

Leu Leu Leu Asp Asn Gly Gly Lys Leu Val Phe Val His Ser Ser Asn
            130                 135                 140

Leu Thr Gly Asp Ile Arg Lys Thr Arg Trp Arg Asn His Lys Ile Glu
145                 150                 155                 160

Glu Leu Lys Leu Phe Phe Glu Asp Leu Asp Cys Ile Glu Glu Val
                165                 170                 175

Tyr Phe Tyr Asp Arg Gln Phe Ile Ile Lys Met Phe His Ser Leu Val
            180                 185                 190

Phe Asn Lys Phe Ser Thr Lys Ile His Ile Leu Ile Ser Lys Leu Thr
            195                 200                 205

Lys Leu Pro Cys Ser Leu Val Phe Ile Val Lys Lys His Gly Gln Asn
            210                 215                 220

Ala Glu Ser Cys Ile
225
```

-continued

```
<210> SEQ ID NO 166
<211> LENGTH: 438
<212> TYPE: PRT
<213> ORGANISM: Methanosarcina acetivorans C2A

<400> SEQUENCE: 166

Met Thr Gly Asn Ser Glu Glu Ile Asn Ser Lys Asn Ala Tyr Asp Val
1               5                   10                  15

Glu Lys Lys Thr Lys Arg Asp Ser Gln Asn Met Pro Asp Ile Phe Thr
            20                  25                  30

Asp Asn Thr Asp Lys Gln Asp Ser Asp Pro Ser Arg Gln Gly Phe Glu
        35                  40                  45

Gly Gln Pro Asn Val Val Ile Val Arg Tyr Gly Glu Leu Ala Leu Lys
    50                  55                  60

Ser Thr Gly Val Arg Asn Trp Tyr Glu Lys Ile Leu Met Lys Asn Ile
65                  70                  75                  80

Ala Ala Met Leu Asp Ser Arg Asn Ile Pro Tyr Ser Leu Leu Arg Arg
                85                  90                  95

Glu Trp Gly Arg Ile Phe Ile Glu Thr Thr Asp Pro Arg Ala Ala Glu
            100                 105                 110

Ala Ala Ala Asp Val Phe Gly Val Val Ser Thr Ser Pro Ala Leu Val
        115                 120                 125

Thr Lys Pro Asp Leu Glu Ser Ala Ala Arg Thr Cys Ala Phe Leu Gly
    130                 135                 140

Thr Gly Leu Ile Arg Glu Gly Glu Ser Phe Ala Ile Arg Ala Arg Arg
145                 150                 155                 160

Ser Gly Asn His Pro Phe Ser Ser Ala Asp Val Gly Arg Asn Cys Gly
                165                 170                 175

Asp Ala Val Trp Asp Ser Leu Glu Lys Glu Gly Lys His Pro Arg Val
            180                 185                 190

Asn Leu Thr Ser Pro Asp Lys Glu Ile Phe Val Glu Met Arg Gln Asn
        195                 200                 205

Leu Ala Tyr Val Tyr Leu Glu Thr Val Lys Gly Val Gly Gly Leu Pro
    210                 215                 220

Leu Gly Thr Gln Gly Ser Met Val Val Leu Met Ser Gly Gly Leu Asp
225                 230                 235                 240

Ser Pro Val Ala Ala Trp Leu Met Met Lys Arg Gly Val Met Ile Thr
                245                 250                 255

Pro Val Tyr Cys Asn Asn Ser Pro Tyr Ala Glu Asp Ala Ala Arg Glu
            260                 265                 270

Arg Ala Phe Asp Cys Ile Arg Gln Leu Gln Thr Trp Ala Pro Gly His
        275                 280                 285

Gln Phe Ala Thr Tyr Glu Ile Pro His Gly Pro Asn Leu Arg Ala Phe
    290                 295                 300

Ile Gly Thr Cys Asp Arg Lys Asn Thr Cys Leu Leu Cys Lys Arg Met
305                 310                 315                 320

Met Tyr Arg Glu Ala Tyr Glu Val Met Lys Lys Val Gly Ala Ser Gly
                325                 330                 335

Ile Ile Thr Gly Ser Ser Leu Gly Gln Val Ala Ser Gln Thr Ala Ala
            340                 345                 350

Asn Met His Ala Glu Ile Tyr Gln Leu Ala Ile Pro Ile Tyr His Pro
        355                 360                 365

Leu Ile Ala Phe Asp Lys Ser Glu Ile Val Asp Ile Ala Arg Arg Ile
    370                 375                 380
```

```
Gly Thr Tyr Asp Ile Ser Thr Arg Pro Ala Gly Ile Cys Thr Ala Val
385                 390                 395                 400

Pro Glu Arg Pro Glu Val Lys Ala Asn Tyr Asp Leu Ile Val Leu Glu
                405                 410                 415

Glu Lys Lys Leu Gly Ile Glu Thr Met Val Gly Asp Ala Leu Lys Ala
            420                 425                 430

Val Lys Ile Leu Lys Leu
            435

<210> SEQ ID NO 167
<211> LENGTH: 255
<212> TYPE: PRT
<213> ORGANISM: Methanosarcina acetivorans C2A

<400> SEQUENCE: 167

Met Ser Glu Asn Tyr Gly Lys Val Tyr Leu Val Gly Ser Gly Pro Gly
1               5                   10                  15

Asp Pro Glu Leu Leu Thr Leu Lys Ala Arg Arg Leu Ile Asp Asn Ala
            20                  25                  30

Glu Val Ile Val Tyr Asp Gln Leu Pro Gly Lys Ser Ile Leu Gly Ser
        35                  40                  45

Met Pro Lys Ser Ala Glu Lys Ile Asp Val Gly Lys Tyr Ala Gly Asn
    50                  55                  60

His Thr Met Thr Gln Ser Glu Ile Asn Glu Val Leu Val Trp Lys Ala
65                  70                  75                  80

Lys Glu Gly Lys Met Val Val Arg Leu Lys Gly Gly Asp Pro Tyr Val
                85                  90                  95

Phe Gly Arg Gly Gly Glu Glu Ala Glu Val Leu Val Ala Glu Gly Ile
            100                 105                 110

Glu Phe Glu Ile Val Pro Gly Ile Thr Ser Ala Ile Ala Val Pro Ala
        115                 120                 125

Tyr Ala Gly Ile Pro Val Thr His Arg Glu Ser Thr Ser Met Val Thr
    130                 135                 140

Phe Ile Thr Gly His Glu Asp Pro Thr Lys Glu Glu Ser Gly Leu Asp
145                 150                 155                 160

Trp Glu Thr Leu Ala Lys Phe Asp Gly Thr Ile Val Ile Phe Met Gly
                165                 170                 175

Val Lys Met Leu Arg Arg Asn Thr Glu Glu Leu Met Lys Tyr Gly Lys
            180                 185                 190

Asp Pro Lys Thr Pro Val Ala Val Ile Glu Arg Gly Thr Arg Pro Asp
        195                 200                 205

Gln Arg Val Thr Val Gly Ser Leu Glu Asn Ile Ala Asp Leu Ala Glu
    210                 215                 220

Glu Arg Lys Val Lys Ala Pro Ala Ile Thr Val Ile Gly Asp Val Val
225                 230                 235                 240

Asn Leu His Ala Ile Leu Gly Glu Gln Ile Ala Gly Lys Asp Phe
                245                 250                 255

<210> SEQ ID NO 168
<211> LENGTH: 426
<212> TYPE: PRT
<213> ORGANISM: Escherichia coli

<400> SEQUENCE: 168

Met Ser Lys Ser Glu Asn Leu Tyr Ser Ala Ala Arg Glu Leu Ile Pro
1               5                   10                  15
```

-continued

```
Gly Gly Val Asn Ser Pro Val Arg Ala Phe Thr Gly Val Gly Gly Thr
             20                  25                  30
Pro Leu Phe Ile Glu Lys Ala Asp Gly Ala Tyr Leu Tyr Asp Val Asp
         35                  40                  45
Gly Lys Ala Tyr Ile Asp Tyr Val Gly Ser Trp Gly Pro Met Val Leu
     50                  55                  60
Gly His Asn His Pro Ala Ile Arg Asn Ala Val Ile Glu Ala Ala Glu
 65                  70                  75                  80
Arg Gly Leu Ser Phe Gly Ala Pro Thr Glu Met Glu Val Lys Met Ala
                 85                  90                  95
Gln Leu Val Thr Glu Leu Val Pro Thr Met Asp Met Val Arg Met Val
            100                 105                 110
Asn Ser Gly Thr Glu Ala Thr Met Ser Ala Ile Arg Leu Ala Arg Gly
        115                 120                 125
Phe Thr Gly Arg Asp Lys Ile Ile Lys Phe Glu Gly Cys Tyr His Gly
    130                 135                 140
His Ala Asp Cys Leu Leu Val Lys Ala Gly Ser Gly Ala Leu Thr Leu
145                 150                 155                 160
Gly Gln Pro Asn Ser Pro Gly Val Pro Ala Asp Phe Ala Lys His Thr
                165                 170                 175
Leu Thr Cys Thr Tyr Asn Asp Leu Ala Ser Val Arg Ala Ala Phe Glu
            180                 185                 190
Gln Tyr Pro Gln Glu Ile Ala Cys Ile Ile Val Glu Pro Val Ala Gly
        195                 200                 205
Asn Met Asn Cys Val Pro Pro Leu Pro Glu Phe Leu Pro Gly Leu Arg
    210                 215                 220
Ala Leu Cys Asp Glu Phe Gly Ala Leu Leu Ile Ile Asp Glu Val Met
225                 230                 235                 240
Thr Gly Phe Arg Val Ala Leu Ala Gly Ala Gln Asp Tyr Tyr Gly Val
                245                 250                 255
Glu Pro Asp Leu Thr Cys Leu Gly Lys Ile Ile Gly Gly Gly Met Pro
            260                 265                 270
Val Gly Ala Phe Gly Gly Arg Arg Asp Val Met Asp Ala Leu Ala Pro
        275                 280                 285
Thr Gly Pro Val Tyr Gln Ala Gly Thr Leu Ser Gly Asn Pro Ile Ala
    290                 295                 300
Met Ala Ala Gly Phe Ala Cys Leu Asn Glu Val Ala Gln Pro Gly Val
305                 310                 315                 320
His Glu Thr Leu Asp Glu Leu Thr Ser Arg Leu Ala Glu Gly Leu Leu
                325                 330                 335
Glu Ala Ala Glu Glu Ala Gly Ile Pro Leu Val Val Asn His Val Gly
            340                 345                 350
Gly Met Phe Gly Ile Phe Phe Thr Asp Ala Glu Ser Val Thr Cys Tyr
        355                 360                 365
Gln Asp Val Met Ala Cys Asp Val Glu Arg Phe Lys Arg Phe Phe His
    370                 375                 380
Met Met Leu Asp Glu Gly Val Tyr Leu Ala Pro Ser Ala Phe Glu Ala
385                 390                 395                 400
Gly Phe Met Ser Val Ala His Ser Met Glu Asp Ile Asn Asn Thr Ile
                405                 410                 415
Asp Ala Ala Arg Arg Val Phe Ala Lys Leu
            420                 425
```

<210> SEQ ID NO 169
<211> LENGTH: 324
<212> TYPE: PRT
<213> ORGANISM: Escherichia coli

<400> SEQUENCE: 169

Met Thr Asp Leu Ile Gln Arg Pro Arg Arg Leu Arg Lys Ser Pro Ala
1               5                   10                  15

Leu Arg Ala Met Phe Glu Glu Thr Thr Leu Ser Leu Asn Asp Leu Val
            20                  25                  30

Leu Pro Ile Phe Val Glu Glu Ile Asp Asp Tyr Lys Ala Val Glu
        35                  40                  45

Ala Met Pro Gly Val Met Arg Ile Pro Glu Lys His Leu Ala Arg Glu
    50                  55                  60

Ile Glu Arg Ile Ala Asn Ala Gly Ile Arg Ser Val Met Thr Phe Gly
65                  70                  75                  80

Ile Ser His His Thr Asp Glu Thr Gly Ser Asp Ala Trp Arg Glu Asp
                85                  90                  95

Gly Leu Val Ala Arg Met Ser Arg Ile Cys Lys Gln Thr Val Pro Glu
            100                 105                 110

Met Ile Val Met Ser Asp Thr Cys Phe Cys Glu Tyr Thr Ser His Gly
        115                 120                 125

His Cys Gly Val Leu Cys Glu His Gly Val Asp Asn Asp Ala Thr Leu
    130                 135                 140

Glu Asn Leu Gly Lys Gln Ala Val Val Ala Ala Ala Gly Ala Asp
145                 150                 155                 160

Phe Ile Ala Pro Ser Ala Ala Met Asp Gly Gln Val Gln Ala Ile Arg
                165                 170                 175

Gln Ala Leu Asp Ala Ala Gly Phe Lys Asp Thr Ala Ile Met Ser Tyr
            180                 185                 190

Ser Thr Lys Phe Ala Ser Ser Phe Tyr Gly Pro Phe Arg Glu Ala Ala
        195                 200                 205

Gly Ser Ala Leu Lys Gly Asp Arg Lys Ser Tyr Gln Met Asn Pro Met
    210                 215                 220

Asn Arg Arg Glu Ala Ile Arg Glu Ser Leu Leu Asp Glu Ala Gln Gly
225                 230                 235                 240

Ala Asp Cys Leu Met Val Lys Pro Ala Gly Ala Tyr Leu Asp Ile Val
                245                 250                 255

Arg Glu Leu Arg Glu Arg Thr Glu Leu Pro Ile Gly Ala Tyr Gln Val
            260                 265                 270

Ser Gly Glu Tyr Ala Met Ile Lys Phe Ala Ala Leu Ala Gly Ala Ile
        275                 280                 285

Asp Glu Glu Lys Val Val Leu Glu Ser Leu Gly Ser Ile Lys Arg Ala
    290                 295                 300

Gly Ala Asp Leu Ile Phe Ser Tyr Phe Ala Met Asp Leu Ala Glu Lys
305                 310                 315                 320

Lys Ile Leu Arg

<210> SEQ ID NO 170
<211> LENGTH: 418
<212> TYPE: PRT
<213> ORGANISM: Escherichia coli

<400> SEQUENCE: 170

Met Thr Leu Leu Ala Leu Gly Ile Asn His Lys Thr Ala Pro Val Ser
1               5                   10                  15

```
Leu Arg Glu Arg Val Ser Phe Ser Pro Asp Lys Leu Asp Gln Ala Leu
         20                  25                  30
Asp Ser Leu Leu Ala Gln Pro Met Val Gln Gly Gly Val Leu Ser
     35                  40                  45
Thr Cys Asn Arg Thr Glu Leu Tyr Leu Ser Val Glu Glu Gln Asp Asn
 50                  55                  60
Leu Gln Glu Ala Leu Ile Arg Trp Leu Cys Asp Tyr His Asn Leu Asn
 65                  70                  75                  80
Glu Glu Asp Leu Arg Lys Ser Leu Tyr Trp His Gln Asp Asn Asp Ala
                 85                  90                  95
Val Ser His Leu Met Arg Val Ala Ser Gly Leu Asp Ser Leu Val Leu
                100                 105                 110
Gly Glu Pro Gln Ile Leu Gly Gln Val Lys Lys Ala Phe Ala Asp Ser
                115                 120                 125
Gln Lys Gly His Met Lys Ala Ser Glu Leu Glu Arg Met Phe Gln Lys
    130                 135                 140
Ser Phe Ser Val Ala Lys Arg Val Arg Thr Glu Thr Asp Ile Gly Ala
145                 150                 155                 160
Ser Ala Val Ser Val Ala Phe Ala Ala Cys Thr Leu Ala Arg Gln Ile
                165                 170                 175
Phe Glu Ser Leu Ser Thr Val Thr Val Leu Leu Val Gly Ala Gly Glu
                180                 185                 190
Thr Ile Glu Leu Val Ala Arg His Leu Arg Glu His Lys Val Gln Lys
                195                 200                 205
Met Ile Ile Ala Asn Arg Thr Arg Glu Arg Ala Gln Ile Leu Ala Asp
    210                 215                 220
Glu Val Gly Ala Glu Val Ile Ala Leu Ser Glu Ile Asp Glu Arg Leu
225                 230                 235                 240
Arg Glu Ala Asp Ile Ile Ile Ser Ser Thr Ala Ser Pro Leu Pro Ile
                245                 250                 255
Ile Gly Lys Gly Met Val Glu Arg Ala Leu Lys Ser Arg Arg Asn Gln
                260                 265                 270
Pro Met Leu Leu Val Asp Ile Ala Val Pro Arg Asp Val Glu Pro Glu
    275                 280                 285
Val Gly Lys Leu Ala Asn Ala Tyr Leu Tyr Ser Val Asp Asp Leu Gln
    290                 295                 300
Ser Ile Ile Ser His Asn Leu Ala Gln Arg Lys Ala Ala Val Glu
305                 310                 315                 320
Ala Glu Thr Ile Val Ala Gln Glu Thr Ser Glu Phe Met Ala Trp Leu
                325                 330                 335
Arg Ala Gln Ser Ala Ser Glu Thr Ile Arg Glu Tyr Arg Ser Gln Ala
                340                 345                 350
Glu Gln Val Arg Asp Glu Leu Thr Ala Lys Ala Leu Ala Ala Leu Glu
                355                 360                 365
Gln Gly Gly Asp Ala Gln Ala Ile Met Gln Asp Leu Ala Trp Lys Leu
                370                 375                 380
Thr Asn Arg Leu Ile His Ala Pro Thr Lys Ser Leu Gln Gln Ala Ala
385                 390                 395                 400
Arg Asp Gly Asp Asn Glu Arg Leu Asn Ile Leu Arg Asp Ser Leu Gly
                405                 410                 415

Leu Glu
```

<210> SEQ ID NO 171
<211> LENGTH: 471
<212> TYPE: PRT
<213> ORGANISM: Escherichia coli

<400> SEQUENCE: 171

```
Met Lys Ile Lys Thr Arg Phe Ala Pro Ser Pro Thr Gly Tyr Leu His
1               5                   10                  15

Val Gly Gly Ala Arg Thr Ala Leu Tyr Ser Trp Leu Phe Ala Arg Asn
            20                  25                  30

His Gly Gly Glu Phe Val Leu Arg Ile Glu Asp Thr Asp Leu Glu Arg
        35                  40                  45

Ser Thr Pro Glu Ala Ile Glu Ala Ile Met Asp Gly Met Asn Trp Leu
    50                  55                  60

Ser Leu Glu Trp Asp Glu Gly Pro Tyr Tyr Gln Thr Lys Arg Phe Asp
65                  70                  75                  80

Arg Tyr Asn Ala Val Ile Asp Gln Met Leu Glu Gly Thr Ala Tyr
                85                  90                  95

Lys Cys Tyr Cys Ser Lys Glu Arg Leu Glu Ala Leu Arg Glu Glu Gln
            100                 105                 110

Met Ala Lys Gly Glu Lys Pro Arg Tyr Asp Gly Arg Cys Arg His Ser
        115                 120                 125

His Glu His His Ala Asp Asp Glu Pro Cys Val Val Arg Phe Ala Asn
    130                 135                 140

Pro Gln Glu Gly Ser Val Val Phe Asp Asp Gln Ile Arg Gly Pro Ile
145                 150                 155                 160

Glu Phe Ser Asn Gln Glu Leu Asp Asp Leu Ile Ile Arg Arg Thr Asp
                165                 170                 175

Gly Ser Pro Thr Tyr Asn Phe Cys Val Val Asp Asp Trp Asp Met
            180                 185                 190

Glu Ile Thr His Val Ile Arg Gly Glu Asp His Ile Asn Asn Thr Pro
        195                 200                 205

Arg Gln Ile Asn Ile Leu Lys Ala Leu Lys Ala Pro Val Pro Val Tyr
    210                 215                 220

Ala His Val Ser Met Ile Asn Gly Asp Gly Lys Lys Leu Ser Lys
225                 230                 235                 240

Arg His Gly Ala Val Ser Val Met Gln Tyr Arg Asp Asp Gly Tyr Leu
                245                 250                 255

Pro Glu Ala Leu Leu Asn Tyr Leu Val Arg Leu Gly Trp Ser His Gly
            260                 265                 270

Asp Gln Glu Ile Phe Thr Arg Glu Met Ile Lys Tyr Phe Thr Leu
        275                 280                 285

Asn Ala Val Ser Lys Ser Ala Ser Ala Phe Asn Thr Asp Lys Leu Leu
    290                 295                 300

Trp Leu Asn His His Tyr Ile Asn Ala Leu Pro Pro Glu Tyr Val Ala
305                 310                 315                 320

Thr His Leu Gln Trp His Ile Glu Gln Glu Asn Ile Asp Thr Arg Asn
                325                 330                 335

Gly Pro Gln Leu Ala Asp Leu Val Lys Leu Leu Gly Glu Arg Cys Lys
            340                 345                 350

Thr Leu Lys Glu Met Ala Gln Ser Cys Arg Tyr Phe Tyr Glu Asp Phe
        355                 360                 365

Ala Glu Phe Asp Ala Asp Ala Ala Lys Lys His Leu Arg Pro Val Ala
    370                 375                 380
```

```
Arg Gln Pro Leu Glu Val Val Arg Asp Lys Leu Ala Ala Ile Thr Asp
385                 390                 395                 400

Trp Thr Ala Glu Asn Val His His Ala Ile Gln Ala Thr Ala Asp Glu
                405                 410                 415

Leu Glu Val Gly Met Gly Lys Val Gly Met Pro Leu Arg Val Ala Val
                420                 425                 430

Thr Gly Ala Gly Gln Ser Pro Ala Leu Asp Val Thr Val His Ala Ile
                435                 440                 445

Gly Lys Thr Arg Ser Ile Glu Arg Ile Asn Lys Ala Leu Asp Phe Ile
450                 455                 460

Ala Glu Arg Glu Asn Gln Gln
465                 470

<210> SEQ ID NO 172
<211> LENGTH: 246
<212> TYPE: PRT
<213> ORGANISM: Escherichia coli

<400> SEQUENCE: 172

Met Ser Ile Leu Val Thr Arg Pro Ser Pro Ala Gly Glu Glu Leu Val
1               5                   10                  15

Ser Arg Leu Arg Thr Leu Gly Gln Val Ala Trp His Phe Pro Leu Ile
                20                  25                  30

Glu Phe Ser Pro Gly Arg Gln Leu Pro Gln Leu Ala Asp Gln Leu Ala
            35                  40                  45

Ala Leu Gly Glu Ser Asp Leu Leu Phe Ala Leu Ser Gln His Ala Val
    50                  55                  60

Ala Phe Ala Gln Ser Gln Leu His Gln Asp Arg Lys Trp Pro Arg
65                  70                  75                  80

Leu Pro Asp Tyr Phe Ala Ile Gly Arg Thr Thr Ala Leu Ala Leu His
                85                  90                  95

Thr Val Ser Gly Gln Lys Ile Leu Tyr Pro Gln Asp Arg Glu Ile Ser
                100                 105                 110

Glu Val Leu Leu Gln Leu Pro Glu Leu Gln Asn Ile Ala Gly Lys Arg
            115                 120                 125

Ala Leu Ile Leu Arg Gly Asn Gly Gly Arg Glu Leu Ile Gly Asp Thr
    130                 135                 140

Leu Thr Ala Arg Gly Ala Glu Val Thr Phe Cys Glu Cys Tyr Gln Arg
145                 150                 155                 160

Cys Ala Ile His Tyr Asp Gly Ala Glu Glu Ala Met Arg Trp Gln Ser
                165                 170                 175

Arg Glu Val Thr Thr Val Val Thr Ser Gly Glu Met Leu Gln Gln
            180                 185                 190

Leu Trp Ser Leu Ile Pro Gln Trp Tyr Arg Glu His Trp Leu Leu His
            195                 200                 205

Cys Arg Leu Leu Val Val Ser Glu Arg Leu Ala Lys Leu Ala Arg Glu
    210                 215                 220

Leu Gly Trp Gln Asp Ile Lys Val Ala Asp Asn Ala Asp Asn Asp Ala
225                 230                 235                 240

Leu Leu Arg Ala Leu Gln
                245

<210> SEQ ID NO 173
<211> LENGTH: 313
<212> TYPE: PRT
<213> ORGANISM: Escherichia coli
```

<400> SEQUENCE: 173

```
Met Leu Asp Asn Val Leu Arg Ile Ala Thr Arg Gln Ser Pro Leu Ala
1               5                   10                  15
Leu Trp Gln Ala His Tyr Val Lys Asp Lys Leu Met Ala Ser His Pro
            20                  25                  30
Gly Leu Val Glu Leu Val Pro Met Val Thr Arg Gly Asp Val Ile
        35                  40                  45
Leu Asp Thr Pro Leu Ala Lys Val Gly Lys Gly Leu Phe Val Lys
    50                  55                  60
Glu Leu Glu Val Ala Leu Leu Glu Asn Arg Ala Asp Ile Ala Val His
65                  70                  75                  80
Ser Met Lys Asp Val Pro Val Glu Phe Pro Gln Gly Leu Gly Leu Val
                85                  90                  95
Thr Ile Cys Glu Arg Glu Asp Pro Arg Asp Ala Phe Val Ser Asn Asn
            100                 105                 110
Tyr Asp Asn Leu Asp Ala Leu Pro Ala Gly Ser Ile Val Gly Thr Ser
            115                 120                 125
Ser Leu Arg Arg Gln Cys Gln Leu Ala Glu Arg Pro Asp Leu Ile
130                 135                 140
Ile Arg Ser Leu Arg Gly Asn Val Gly Thr Arg Leu Ser Lys Leu Asp
145                 150                 155                 160
Asn Gly Glu Tyr Asp Ala Ile Ile Leu Ala Val Ala Gly Leu Lys Arg
                165                 170                 175
Leu Gly Leu Glu Ser Arg Ile Arg Ala Ala Leu Pro Pro Glu Ile Ser
            180                 185                 190
Leu Pro Ala Val Gly Gln Gly Ala Val Gly Ile Glu Cys Arg Leu Asp
        195                 200                 205
Asp Ser Arg Thr Arg Glu Leu Leu Ala Ala Leu Asn His His Glu Thr
    210                 215                 220
Ala Leu Arg Val Thr Ala Glu Arg Ala Met Asn Thr Arg Leu Glu Gly
225                 230                 235                 240
Gly Cys Gln Val Pro Ile Gly Ser Tyr Ala Glu Leu Ile Asp Gly Glu
                245                 250                 255
Ile Trp Leu Arg Ala Leu Val Gly Ala Pro Asp Gly Ser Gln Ile Ile
            260                 265                 270
Arg Gly Glu Arg Arg Gly Ala Pro Gln Asp Ala Glu Gln Met Gly Ile
        275                 280                 285
Ser Leu Ala Glu Glu Leu Leu Asn Asn Gly Ala Arg Glu Ile Leu Ala
    290                 295                 300
Glu Val Tyr Asn Gly Asp Ala Pro Ala
305                 310
```

<210> SEQ ID NO 174
<211> LENGTH: 35
<212> TYPE: DNA
<213> ORGANISM: Artificial Sequence
<220> FEATURE:
<223> OTHER INFORMATION: PCR primer

<400> SEQUENCE: 174
gcggccatat gttagacaat gttttaagaa ttgcc    35

<210> SEQ ID NO 175
<211> LENGTH: 26
<212> TYPE: DNA

```
<213> ORGANISM: artificial sequence
<220> FEATURE:
<223> OTHER INFORMATION: pcr primer

<400> SEQUENCE: 175
tataactcga gtcatgccgg agcgtc                                           26

<210> SEQ ID NO 176
<211> LENGTH: 23
<212> TYPE: DNA
<213> ORGANISM: Artificial sequence
<220> FEATURE:
<223> OTHER INFORMATION: PCR primer

<400> SEQUENCE: 176
tgggccatat gagtatcctg gtc                                              23

<210> SEQ ID NO 177
<211> LENGTH: 26
<212> TYPE: DNA
<213> ORGANISM: Artificial sequence
<220> FEATURE:
<223> OTHER INFORMATION: PCR primer

<400> SEQUENCE: 177
taggactcga gttattgtaa tgcccg                                           26

<210> SEQ ID NO 178
<211> LENGTH: 25
<212> TYPE: DNA
<213> ORGANISM: Artificial sequence
<220> FEATURE:
<223> OTHER INFORMATION: PCR primer

<400> SEQUENCE: 178
cggcgcatat gtcagaaaat tacgg                                            25

<210> SEQ ID NO 179
<211> LENGTH: 29
<212> TYPE: DNA
<213> ORGANISM: Artificial sequence
<220> FEATURE:
<223> OTHER INFORMATION: PCR primer

<400> SEQUENCE: 179
atgagctcga gtcagaaatc ctttcctgc                                        29

<210> SEQ ID NO 180
<211> LENGTH: 33
<212> TYPE: DNA
<213> ORGANISM: Artificial sequence
<220> FEATURE:
<223> OTHER INFORMATION: PCR primer

<400> SEQUENCE: 180
gaggacatat gatggctgaa acaaataatt ttc                                   33

<210> SEQ ID NO 181
<211> LENGTH: 30
<212> TYPE: DNA
<213> ORGANISM: Artificial sequence
<220> FEATURE:
<223> OTHER INFORMATION: PCR primer

<400> SEQUENCE: 181
taggactcga gttattcgag cttatccgag                                       30
```

<210> SEQ ID NO 182
<211> LENGTH: 25
<212> TYPE: DNA
<213> ORGANISM: Artificial sequence
<220> FEATURE:
<223> OTHER INFORMATION: PCR primer

<400> SEQUENCE: 182
ggcaccatat gactgagaaa ctcgg                                        25

<210> SEQ ID NO 183
<211> LENGTH: 26
<212> TYPE: DNA
<213> ORGANISM: Artificial sequence
<220> FEATURE:
<223> OTHER INFORMATION: PCR primer

<400> SEQUENCE: 183
attacggatc cttacagggc ttcctg                                       26

<210> SEQ ID NO 184
<211> LENGTH: 28
<212> TYPE: DNA
<213> ORGANISM: Artificial sequence
<220> FEATURE:
<223> OTHER INFORMATION: PCR primer

<400> SEQUENCE: 184
ccacacatat gtcccacagc aaacaatc                                     28

<210> SEQ ID NO 185
<211> LENGTH: 25
<212> TYPE: DNA
<213> ORGANISM: Artificial sequence
<220> FEATURE:
<223> OTHER INFORMATION: PCR primer

<400> SEQUENCE: 185
attaaggtac cctaccgggg agccc                                        25

<210> SEQ ID NO 186
<211> LENGTH: 31
<212> TYPE: DNA
<213> ORGANISM: Artificial sequence
<220> FEATURE:
<223> OTHER INFORMATION: PCR primer

<400> SEQUENCE: 186
cgctgcatat gaaaaaacaa aagatcgttg c                                 31

<210> SEQ ID NO 187
<211> LENGTH: 28
<212> TYPE: DNA
<213> ORGANISM: Artificial sequence
<220> FEATURE:
<223> OTHER INFORMATION: PCR primer

<400> SEQUENCE: 187
ccgcgaagct tttattttgt catttccc                                     28

<210> SEQ ID NO 188
<211> LENGTH: 30
<212> TYPE: DNA
<213> ORGANISM: Artificial sequence
<220> FEATURE:

<223> OTHER INFORMATION: PCR primer

<400> SEQUENCE: 188
attatggccg gccttatttt gtcatttccc                                          30

<210> SEQ ID NO 189
<211> LENGTH: 27
<212> TYPE: DNA
<213> ORGANISM: Artificial sequence
<220> FEATURE:
<223> OTHER INFORMATION: PCR primer

<400> SEQUENCE: 189
cgccgtcatg actcaaaaag agatctc                                             27

<210> SEQ ID NO 190
<211> LENGTH: 29
<212> TYPE: DNA
<213> ORGANISM: Artificial sequence
<220> FEATURE:
<223> OTHER INFORMATION: PCR primer

<400> SEQUENCE: 190
atcacaagct tcaggcttc ttttgcaac                                            29

<210> SEQ ID NO 191
<211> LENGTH: 23
<212> TYPE: DNA
<213> ORGANISM: Artificial sequence
<220> FEATURE:
<223> OTHER INFORMATION: PCR primer

<400> SEQUENCE: 191
gacaccatat ggacctgttc cgg                                                 23

<210> SEQ ID NO 192
<211> LENGTH: 27
<212> TYPE: DNA
<213> ORGANISM: Artificial sequence
<220> FEATURE:
<223> OTHER INFORMATION: PCR primer

<400> SEQUENCE: 192
cgcacctcga gttaacggaa acatttc                                             27

<210> SEQ ID NO 193
<211> LENGTH: 32
<212> TYPE: DNA
<213> ORGANISM: Artificial sequence
<220> FEATURE:
<223> OTHER INFORMATION: PCR primer

<400> SEQUENCE: 193
aatctcatat gtcagactct gcttcaaaca cg                                       32

<210> SEQ ID NO 194
<211> LENGTH: 32
<212> TYPE: DNA
<213> ORGANISM: Artificial sequence
<220> FEATURE:
<223> OTHER INFORMATION: PCR primer

<400> SEQUENCE: 194
gctctctcga gtcactcatc tttatcagtg tc                                       32

```
<210> SEQ ID NO 195
<211> LENGTH: 220
<212> TYPE: PRT
<213> ORGANISM: Methanosarcina acetivorans C2A

<400> SEQUENCE: 195

Met Ala Glu Thr Asn Asn Phe Leu Pro Leu Met Leu Asp Leu Ser Gly
1               5                   10                  15

Arg Lys Ile Val Ile Phe Gly Gly Ser Val Gly Glu Arg Lys Ala
            20                  25                  30

Glu Leu Phe Cys Gly Cys Ala Asp Thr Val Val Ser Leu Asp Phe
        35                  40                  45

Ser Glu Lys Leu Gln Glu Leu Gly Ala Ser Gly Gln Val Arg Leu Leu
    50                  55                  60

Arg Leu Asp Leu Ala Ala Ala Thr Asp Ser Glu Leu Gly Glu Ile Ile
65                  70                  75                  80

Ser Gly Ala Phe Leu Val Ile Pro Ala Thr Ser Ser Ser Glu Leu Asn
                85                  90                  95

Arg Lys Ile Thr Asp Ile Ala Gly Glu Ser Asp Ile Leu Ile Asn Gln
            100                 105                 110

Val Asp Ala Leu Gly Ser Val Val Ile Pro Ser Val Ile Lys Arg Gly
            115                 120                 125

Asp Leu Val Ile Gly Ile Ser Thr Leu Gly His Ser Pro Ala Val Ser
    130                 135                 140

Lys Tyr Thr Arg Arg Gln Ile Glu Gly Val Ile Thr Pro Ala Tyr Ser
145                 150                 155                 160

Asp Met Ile Arg Leu Gln Asp Glu Leu Arg Thr Tyr Leu Lys Leu His
                165                 170                 175

Val Lys Glu Gln Arg Lys Arg Lys Ala Leu Leu Trp Lys Val Leu Glu
            180                 185                 190

Ser Glu Gly Val Trp Asn Gly Phe Ser Glu Ser Tyr Glu Lys Ala Ala
            195                 200                 205

Glu Asn Ala Tyr Ala Ile Ile Ser Asp Lys Leu Glu
            210                 215                 220
```

SYNTHESIS AND OXIDATION OF METHANE

CROSS-REFERENCE TO RELATED APPLICATIONS

This application is a continuation under 35 USC 120 of U.S. patent application Ser. No. 15/588,396, filed on 5 May 2017 (pending); which cites the benefit of U.S. Provisional Patent Application No. 62/332,658, filed on 6 May 2016. Both of the foregoing applications are incorporated herein by reference in their entireties.

STATEMENT REGARDING FEDERAL FUNDING

This invention was made with government support under the U.S. Department of Energy Advanced Research Projects Agency-Energy (ARPA-E) grant numbers DE-AR0000428 and DE-AR0000433. The government has certain rights in the invention.

In this context "government" refers to the government of the United States of America.

BACKGROUND

Field

The present disclosure relates generally to biotechnology, and specifically to the biosynthesis of tetrapyrrole compounds.

Background

Methane is a compound of critical importance as an energy source and as a cause of global climate change. Methane is commonly found in fossil fuel deposits, and is the main component of natural gas (which also contains ethane, propane and heavier hydrocarbons). Geologic methane is an abundant and inexpensive energy source, but it contributes to climate change in two ways. The combustion of geologic methane produces carbon dioxide, which is a "greenhouse gas," and causes a net increase in atmospheric carbon dioxide. Methane is a powerful greenhouse gas in its own right (more potent than carbon dioxide), and the second way it contributes to climate change is by the escape of unburned geologic methane. Methane escapes from oil wells in huge volumes if measures are not taken to recapture it.

However, methane burning need not contribute to climate change. Methane is also biologically produced from carbon dioxide (and other small carbon compounds) by microorganisms. When burned, biogenic methane does not increase the net amount of carbon dioxide in the atmosphere, because carbon dioxide is absorbed from the atmosphere as part of the process. This process, "methanogenesis," is performed by a family of unicellular organisms that are unrelated to bacteria or to organisms with nucleated cells (eukaryotic cells), this family being known as "archaea" (or "archaebacteria" in the older literature, due to an incorrect belief that the archaea were merely a branch of bacteria). The methane synthesizing archaea are the methanogens, and their habitat it strictly limited to environments without even the tiniest traces of oxygen or other oxidizing agents. Methanogens are difficult to grow in culture, as they require fastidious growth conditions, grow slowly, and are killed by trace amounts of oxygen.

Methanogenesis is important to global carbon cycle, producing nearly 1 billion metric tons of methane annually. The terminal step of methanogenesis is catalyzed by methylcoenzyme M reductase (MCR) and involves the conversion of coenzyme B (CoB-SH) and methylcoenzyme M (MeS-CoM) to the mixed heterodisulfide CoB-S-S-CoM and methane (FIG. 1). MCR uses the unique nickel-containing tetrapyrrole coenzyme F430 to carry out its catalytic function (FIG. 1).

Many attempts have been made to harness methanogenesis to produce methane for fuel (and other purposes) without impacting climate change. However, these attempts have been hampered by the difficulty in cultivating methanogens. Consequently, there is a need in the art to create genetically modified organisms capable of performing methanogenesis that are not so sensitive and fastidious. Although some individual components of the methanogenesis pathway have been identified and cloned into other organisms, coenzyme F430 is a critical component in the process, and previously all efforts to identify the genes and proteins involved have failed.

Another process that relies on coenzyme F430 is the biological oxidation of methane in the absence of oxygen. This process is performed by anaerobic methanotrophic archaea (ANME). ANME ultimately convert methane to carbon dioxide, but produce biomass and other compounds in the process. ANME could potentially be used to convert the energy from waste methane to biomass and convert methane to more easily transportable forms, such as liquid biodiesel. ANME have a homolog of MCR to catalyze the anaerobic oxidation of methane. This oxidation is thought to operate, at least in part, as the reverse of methanogenesis, with MCR catalyzing the critical first step in the pathway, the activation of methane with CoB-S-S-CoM. There is great interest in strategies to convert methane to liquid fuel or other more easily transported commodity chemicals. The development of a bioconversion process for methane that uses AOM is an attractive solution; however, efforts to engineer industrially viable anaerobic methanotrophic strains are hindered by the lack of genetic and biochemical information about the biosynthesis of coenzyme F430 and the formation of holo-MCR.

Consequently, there is a need for genes and proteins for the biosynthesis of coenzyme F430.

SUMMARY

The present disclosure describes genes and proteins of the coenzyme F430 synthetic pathway. It has been unexpectedly discovered that several otherwise unrelated genes and proteins are involved in the synthesis of coenzyme F430 and other tetrapyrrole compounds. Such genes and proteins find uses generating tetrapyrrole compounds (notably coenzyme F430), oxidizing methane, generating methane, modulating the generation of methane, modulating the oxidation of methane, and genetically modifying organisms. The pathway converts sirohydrochlorin to coenzyme F430 in four steps, catalyzed by five enzymes. The enzymes, styled CfbA, CfbB, CfbC, CfbD, and CfbE, are encoded by genes named cfbA, cfbB, cfbC, cfbD, and cfbE.

In a first aspect, an isolated nucleic acid is provided, comprising a cfb gene and a heterologous promoter.

In a second aspect, an isolated nucleic acid is provided, comprising a cfb gene with at least one substitution as compared to wild type.

In a third aspect, a transformation vector is provided comprising a polynucleotide encoding a Cfb protein.

In a fourth aspect, a transformation medium is provided, comprising a first transformation vector comprising a first polynucleotide encoding a first Cfb protein, and a second transformation vector comprising a second polynucleotide encoding a second Cfb protein.

In a fifth aspect, a cell is provided comprising a heterologous polynucleotide encoding a Cfb protein.

In a sixth aspect, a method of modulating methanogenesis in a methanogenic organism is provided, comprising modulating the expression of a cfb gene.

In a seventh aspect, a method of modulating methane oxidation in an anaerobic methanotrophic organism is provided, comprising modulating the expression of a cfb gene.

In an eighth aspect, a method of making a tetrapyrrole compound is provided, the method comprising: providing a bacterial or eukaryotic cell comprising two or more cfb genes; and culturing the cell under conditions to permit synthesis of the tetrapyrrole compound.

In a ninth aspect, a method of oxidizing methane is provided, the method comprising: providing a bacterial or eukaryotic cell comprising two or more cfb genes; and culturing the cell in the presence of methane.

In a tenth aspect, a method of biogenic methane synthesis is provided, comprising: providing a bacterial or eukaryotic cell comprising two or more cfb genes; and culturing the cell in the presence of at least one of $H_2$, $CO_2$, and an organic compound.

In an eleventh aspect, a method of assaying an organism for potential methanogenic or methanotrophic activity is provided, the method comprising detecting the presence of a plurality of cfb genes.

In a twelfth aspect, a protein mixture is provided, comprising a plurality of isolated Cfb polypeptides.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 3. Forward and reverse primers utilized in PCR reactions. The underlined sequences indicate the restriction sites (for BamHI, BspHI, FseI, HindIII, NdeI, PciI, or XhoI) incorporated into the PCR products.

FIG. 4. Coenzyme F430 biosynthesis (cfb) genes from representative methanogens and ANME identified by comparative genomics.

DETAILED DESCRIPTION

A. Definitions

Figure 1:
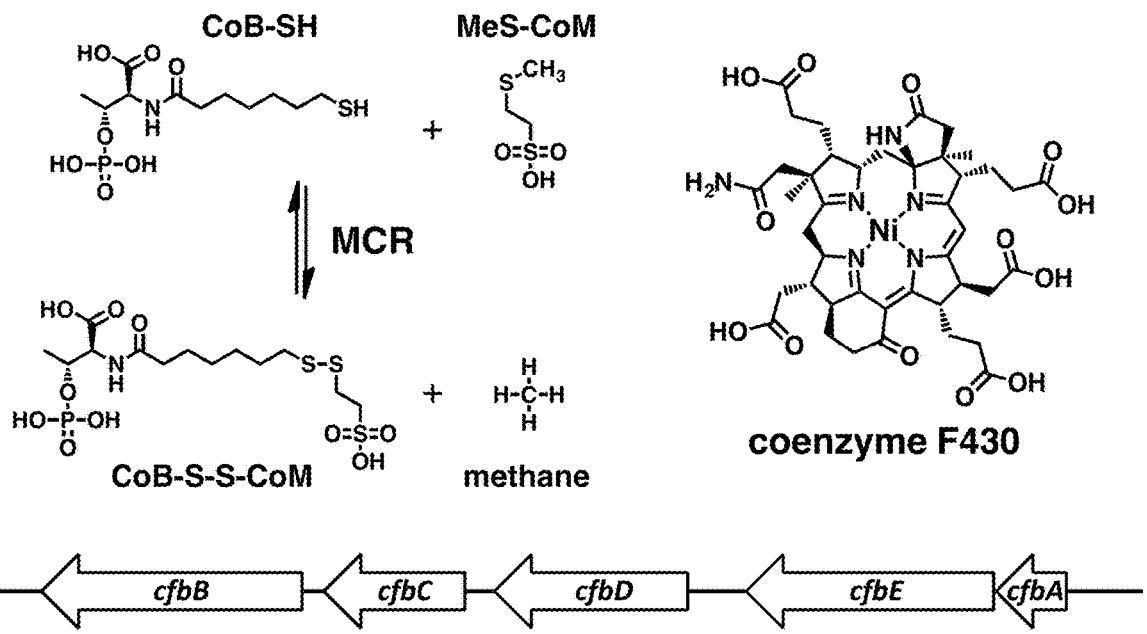
FIG. 1. The MCR-catalyzed reaction, the structure of coenzyme F430, and the identified coenzyme F430 biosynthesis (cfb) gene cluster from *M. acetivorans* C2A. Arrows indicate the relative size and orientation of each cfb gene.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

In some places reference is made to standard methods and accession numbers in public databases. It is to be understood that such standards and database entries are revised from time to time, and unless explicitly stated otherwise reference to such standard and database record in this disclosure must be interpreted to refer to the most recent published standard or record as of the time of filing.

The term "nucleotide" as used herein refer to any such known groups, natural or synthetic. It includes conventional DNA or RNA bases (A, G, C, T, U), base analogs (e.g., inosine, 5-nitroindazole and others), imidazole-4-carboxamide, pyrimidine or purine derivatives (e.g., modified pyrimidine base 6H,8H-3,4-dihydropyrimido[4,5-c][1,2]oxazin-7-one (sometimes designated "P" base that binds A or G)) and modified purine base N6-methoxy-2,6-diaminopurine (sometimes designated "K" base that binds C or T), hypoxanthine, N-4-methyl deoxyguanosine, 4-ethyl-2'-deoxycytidine, 4,6-difluorobenzimidazole and 2,4-difluorobenzene nucleoside analogues, pyrene-functionalized LNA nucleoside analogues, deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methyl-aminopurine, O-6-methylguanine, 4-thio-pyrimidines, 4-amino-pyrimidines, 4-dimethylhydrazine-pyrimidines, O-4-alkyl-pyrimidines and hydrophobic nucleobases that form duplex DNA without hydrogen bonding. Nucleobases can be joined together by a variety of linkages or conformations, including phosphodiester, phosphorothioate or methylphosphonate linkages, peptide-nucleic acid linkages.

The term "polynucleotide" as used herein refers to a multimeric compound comprising nucleotides linked together to form a polymer, including conventional RNA, DNA, LNA, BNA, copolymers of any of the foregoing, and analogs thereof.

The term "nucleic acid" as used herein refers to a single stranded polynucleotide or a duplex of two polynucleotides. Such duplexes need not be annealed at all locations, and may contain gaps or overhangs.

B. Polynucleotides

Polynucleotides are provided that encode one or more polypeptides involved in the synthesis of coenzyme F430. The polypeptides in question are enzymes that participate in the conversion of sirohydrochlorin to coenzyme F430. Without wishing to be bound by a single hypothetical model, it is believed that the pathway proceeds as shown in FIGS. 2A-E. This is a four step process involving five enzymes. The genes involved in the coenzyme F430 biosynthesis cluster are referred to herein as "cfb" genes. These five genes from *Methanosarcina acetivorans*, their peptide gene products, and loci are shown in the table in FIG. 1. As per convention, in this disclosure the polypeptide products of cfbA, cfbB, cfbC, cfbD, and cfbE are referred to as CfbA, CfbB, CfbC, CfbD, and CfbE. These genes are widely distributed among methanogens and methanotrophic archaea, and the GenBank accession numbers of the corresponding polypeptides in numerous other exemplary species are provided in Table 1. Each polypeptide sequence provided in the GenBank records referred to in Table 1 is incorporated herein in its entirety.

The polynucleotide encodes at least one Cfb polypeptide or a functional derivative thereof. The Cfb polypeptide may be a wild-type Cfb from any species of methanogenic or methanotrophic archaeon, such as *Methanosarcina acetivorans* or any of the exemplary organisms listed in Table 1 (consequently the polynucleotide may be any one of SEQ ID NOS: 1-155). The Cfb derivative may have an activity that is comparable to or increased (in one embodiment, 50% or more) as compared to the wild-type Cfb activity and as such may be used to increase a Cfb activity; alternatively, the Cfb derivative may have an activity that is decreased (in one embodiment, less than 50%) as compared to a wild-type Cfb activity and as such may be used to decrease a Cfb activity. In some cases the derivative will retain antigenic specificity of Cfb.

Although Cfb polypeptides are critical in the synthesis of coenzyme F430, it has been discovered that several other genes are either required or increase the rate of synthesis. Genes of the methyl-coenzyme M reductase (mcr) cluster may also be used in conjunction with polynucleotides encoding one or more Cfb polypeptides. These include the following polypeptides with GenBank accession numbers for exemplary canonical peptide sequences: cobyrinic acid a,c-diamide synthase (GenBank: AAM06981.1—SEQ ID NO: 156), nitrogenase (iron protein) (GenBank: AAM06982.1—SEQ ID NO: 157), nitrogenase-related protein (GenBank: AAM06983.1—SEQ ID NO: 158), UDP-N-acetylmuramoylalanine-D-glutamate ligase (GenBank: AAM06985.1—SEQ ID NO: 160), and cobalamin biosynthesis protein (GenBank: AAM06986.1—SEQ ID NO: 161).

Additional genes have been identified that are believed to increase coenzyme F430 biosynthesis. Without wishing to be bound by a single hypothetical model, it is believed that the following genes cause post-translational modifications in Mcr that increase rates of coenzyme F430-catalyzed methane conversion. These are believed to encode polypeptides that include conserved hypothetical proteins recorded at the following accession numbers: GenBank: AAM07884.1 (SEQ ID NO: 162), GenBank: AAM07890.1 (SEQ ID NO: 163), GenBank: AAM03617.1 (SEQ ID NO: 164), and GenBank: AAM04490.1 (SEQ ID NO: 165); and a thiazole biosynthesis protein (GenBank: AAM04880.1—SEQ ID NO: 166). Any of the above may also be used in conjunction with polynucleotides encoding one or more Cfb polypeptides.

It is also believed that polypeptides encoding uroporphyrinogen-III C-methyltransferase and precorrin-2 dehydrogenase will increase coenzyme F430 biosynthesis, including the polypeptides designated GenBank AAM06406.1 (SEQ ID NO: 167) and AAM04020.1 (SEQ ID NO: 195). Additionally, it is believed that genes of a uroporphyrinogen-III synthetic pathway from glutamate may increase coenzyme F430 synthesis. These include polynucleotides that encode the following polypeptides, each said polypeptide followed by an exemplary sequence: glutamate-1-semialdehyde aminotransferase (GenBank CAQ30669.1—SEQ ID NO: 168), porphobilinogen synthase (GenBank CAQ30840.1—SEQ ID NO: 169), glutamyl-tRNA reductase (GenBank CAQ31712.1—SEQ ID NO: 170), glutamyl-tRNA synthetase (GenBank CAQ32784—SEQ ID NO: 171), uroporphyrinogen III synthase (GenBank CAQ34145—SEQ ID NO: 172), and hydroxymethylbilane synthase (GenBank CAQ34146—SEQ ID NO: 173). Alternatively, another pathway of tetrapyrrole biosynthesis (which is present in eukaryotes and some bacteria) that starts from glycine rather than glutamate could be used. This alternative pathway utilizes HemT and succinyl-CoA to produce 5-aminolevulinic acid (as opposed to GltX, HemA, and HemL). The remaining steps in the pathway (catalyzed by HemB, HemC, and HemD) are the same).

The nucleic acids discussed above may encode functional variants of their respective polypeptide products. A "functional variant" is a polypeptide with less than 100% sequence identity to the native polypeptide, but which retains at least some of the native polypeptide's relevant activity.

The polypeptide activity in question will depend on the specific polypeptide. Specifically, CfbA activity refers to the ability to catalyze the conversion of sirohydrochlorin to Ni-sirohydrochlorin; CfbB activity refers to the ability to catalyze the conversion of Ni-sirohydrochlorin to Ni-sirohydrochlorin a,c-diamide; CfbC and cfbD activity refers to the ability to jointly catalyze the conversion of Ni-sirohydrochlorin a,c-diamide to $15,17^3$-seco-F430-$17^3$-acid; CfbE activity refers to the ability to catalyze the conversion of $15,17^3$-seco-F430-$17^3$-acid to coenzyme F430. Thus a functional derivative of any of the foregoing is capable of catalyzing the specific reaction in question.

A fragment of a polypeptide is any polypeptide consisting of any number of adjacent amino acid residues having the same identity and order as any segment of the polypeptide. Conservative modifications to the amino acid sequence of any fragment are also included (conservative substitutions are discussed below). Such fragments can be produced for example by digestion of the polypeptide with an endoprotease (which will produce two or more fragments) or an exoprotease. A fragment may be of any length up to the length of the polypeptide. A fragment may be, for example, at least 3 residues in length. A fragment that is at least 6 residues in length will generally function as an antigenic group. Such groups would be expected by those of ordinary skill in the art to be cross-recognized by some antibodies specific for the polypeptide. Fragments that are homologous to parts of the polypeptide are functional derivatives if they have the corresponding activity as defined above.

Derivatives of the polypeptide will have some degree of identity with the wild type polypeptide. For example, those skilled in the art would expect that most derivatives having from 95-100% identity with the native polypeptide would retain the function of [Protein/Polypeptide]. It is also within the abilities of those skilled in the art to predict the likelihood that functionality would be retained by a homolog to the polypeptide with at least any of the following levels of sequence identity: 70, 80, 90, 95, 99, and 99.5%. Persons having ordinary skill in the art will understand that the minimum desirable identity can be determined in some cases by identifying a known non-functional homolog to the polypeptide, and establishing that the minimum desirable identity must be above the identity between the polypeptide and the known non-functional identity. Persons having ordinary skill in the art will also understand that the minimum desirable identity can be determined in some cases by identifying a known functional homolog to the Cfb polypeptide, and establishing that the range of desirable identity must encompass the percent identity between the Cfb polypeptide and the known non-functional identity.

The deletions, additions and substitutions can be selected, as would be known to one of ordinary skill in the art, to generate a desired polypeptide derivative. For example, it is not expected that deletions, additions and substitutions in a non-functional region of a polypeptide would alter the polypeptide activity. Likewise conservative substitutions or substitutions of amino acids with similar properties is expected to be tolerated in a conserved region. Of course non-conservative substitutions in these regions would be expected to decrease or eliminate the polypeptide activity.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine. Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

For example, non-conservative substitutions may involve the exchange of a member of one of these classes for a member from another class.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (Kyte et al., *J. Mol. Biol.*, 157:105-131, 1982). It is known that certain amino acids may be substituted for other amino acids having a similar hydropathic index or score and still retain a similar biological activity. In making changes based upon the hydropathic index, the substitution of amino acids whose hydropathic indices are within +/−2 may be used; in an alternate embodiment, the hydropathic indices are with +/−1; in yet another alternate embodiment, the hydropathic indices are within +/−0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein. The following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within +/−2 may be used; in an alternate embodiment, the hydrophilicity values are with +/−1; in yet another alternate embodiment, the hydrophilicity values are within +/−0.5.

Desired amino acid substitutions (whether conservative or non-conservative) can be determined by those skilled in the art at the time such substitutions are desired. For example, amino acid substitutions can be used to identify important residues of the polypeptide, or to increase or decrease the affinity of the polypeptide with a particular binding target in order to increase or decrease the polypeptide activity.

Exemplary amino acid substitutions are set forth in Table 2.

A skilled artisan will be able to determine suitable variants of any polypeptide as set forth in Table 1, including combinations thereof, using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a given polypeptide to such similar polypeptides. With such a comparison, one can identify residues and portions of the molecules that are conserved among similar polypeptides. It will be appreciated that changes in areas of the polypeptide that are not conserved relative to such similar polypeptides would be less likely to adversely affect the biological activity and/or structure of the polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in the Cfb polypeptide that correspond to amino acid residues that are important for activity or structure in similar polypeptides. One skilled in the art may opt for chemically similar amino acid substitutions for such predicted important amino acid residues of the polypeptide.

One skilled in the art can also analyze the three-dimensional structure and amino acid sequence in relation to that structure in similar polypeptides. In view of that information, one skilled in the art may predict the alignment of amino acid residues of a polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test polypeptide derivatives containing a single amino acid substitution at each desired amino acid residue. The derivatives can then be screened using activity assays known to those skilled in the art and as disclosed herein. Such derivatives could be used to gather information about suitable substitution. For example, if one discovered that a change to a particular amino acid residue resulted in destroyed, undesirably reduced, or unsuitable activity, derivatives with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure from analyses of amino acid sequences (see Chou et al., *Biochemistry,* 13(2):222-245, 1974; Chou et al., *Biochemistry,* 113(2):211-222, 1974; Chou et al., *Adv. Enzymol. Relat. Areas Mol. Biol.,* 47:45-148, 1978; Chou et al., *Ann. Rev. Biochem.,* 47:251-276, 1979; and Chou et al., *Biophys. J.,* 26:367-384, 1979). Moreover, computer programs are currently available to assist with predicting secondary structure of polypeptides. Examples include those programs based upon the Jameson-Wolf analysis (Jameson et al., *Comput. Appl. Biosci.,* 4(1): 181-186, 1998; and Wolf et al., *Comput. Appl. Biosci.,* 4(1):187-191; 1988), the program PepPlot® (Brutlag et al., *CABS,* 6:237-245, 1990; and Weinberger et al., *Science,* 228:740-742, 1985), and other new programs for protein tertiary structure prediction (Fetrow. et al., *Biotechnology,* 11:479-483, 1993).

Moreover, computer programs are currently available to assist with predicting secondary structure. One method of predicting secondary structure is based upon identity modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure (see Holm et al., *Nucl. Acid. Res.,* 27(1):244-247, 1999).

Additional methods of predicting secondary structure include "threading" (Jones, D., *Curr. Opin. Struct. Biol.,* 7(3):377-87, 1997; Suppl et al., *Structure,* 4(1):15-9, 1996), "profile analysis" (Bowie et al., *Science,* 253:164-170, 1991; Gribskov et al., *Meth. Enzym.,* 183:146-159, 1990; and Gribskov et al., *Proc. Nat. Acad. Sci.,* 84(13): 4355-4358, 1987), and. "evolutionary linkage" (See Home, supra, and Brenner, supra).

The Cfb polypeptide encoded by the polynucleotide may have any of the sequences identified in the GenBank accession numbers provided in Table 1. It may also have a sequence that differs from those provided in Table 1, with any level of sequence identity described above as suitable for a functional variant of a Cfb polypeptide.

A general embodiment of the polynucleotide comprises a coding region that encodes any polypeptide described above. Some embodiments of the polynucleotide comprise a second coding region that encodes a second polypeptide described above, which may be the same as the first polypeptide or another Cfb polypeptide. An alternative general embodiment of the polynucleotide comprises a coding region that is complementary to a sequence that encodes the polypeptide. The complementary region may be perfectly complementary to the sequence that encodes the peptide, or it may hybridize with the sequence that encodes the peptide under conditions of maximum, high, intermediate, or poor stringency. The polynucleotide may further comprise one or more regulatory regions operatively coupled with the coding region, such as a promoter, an enhancer, a repressor binding region, or a silencer. In some embodiments of the polynucleotide, the promoter is immediately upstream (in the 5' direction) of the coding region. In a specific embodiment of the polynucleotide the promoter is a constitutive promoter.

In some embodiments of the polynucleotide the promoter is a heterologous promoter. The term "heterologous promoter" refers to a promoter that is not naturally operatively linked to the coding region. Examples of heterologous promoters operatively linked to a region coding a Cfb polypeptide or functional derivative thereof include: a bacterial promoter and a eukaryotic promoter. Further examples of heterologous promoters operatively linked to a region coding a Cfb polypeptide include: archaeal promoters from non-methanogenic and non-methanotrophic archaea. Further such examples include: archaeal promoters from methanogenic or methanotrophic archaea that are not naturally operatively linked to a region coding a Cfb polypeptide, or that are not naturally operatively linked to a region coding the specific Cfb polypeptide in question. For example, if two species of methanogenic archaea have different and distinct promoters operatively linked to the cfbA gene, then substituting the promoter in one species for the promoter in the other would result in the cfbA gene being operatively linked to a heterologous promoter. If a promoter is naturally operatively linked to the coding region in question, then this is not a "heterologous promoter."

A cell comprising any of the nucleic acids disclosed above is also provided. The cell may find utility for example in the production of the polypeptide for subsequent isolation or analysis, in the production of a tetrapyrrole compound (such as F430 or any member of the F430 pathway), in the production of methane by biogenic methanogenesis, and in the oxidation of methane by an anaerobic methanotrophic pathway. Some embodiments of the cell contain multiple copies of a given cfb gene as described above. Such embodiments of the cell may have the advantage of increased activity in the F430 pathway. Some embodiments of the cell contain a heterologous cfb gene or genes. In this context a "heterologous gene" refers to a gene that is not identical to a gene naturally found in the cell. The heterologous gene may be from a different species, or it may be artificial and not found naturally in any species. Generally the presence of a heterologous sequence is the result of genetic modification, and some embodiments of the cell are a genetically modified cell. The cell is considered to be genetically modified if its genetic material has been altered by human intervention; such alteration may have been performed on the cell in question, or on an ancestor of the cell from whom the cell has acquired the heterologous polynucleotide.

The cell may be a unicellular organism or a cell of a multicellular organism. Many unicellular organisms have the advantage of being easier to culture in vitro than cells from multicellular organisms. Unicellular organisms are particularly useful in cloning, replicating, and maintaining nucleic acids of interest. In some embodiments, the cell is a unicellular eukaryotic organism. Unicellular eukaryotic organisms suitable for the method include fungi and protists. Model unicellular organisms that are commonly used for this purpose include yeasts, other fungi, bacteria, protists, and archaea. Specific model organisms are well known in the art, and include bacteria such as *Escherichia coli, Salmonella typhimurium, Pseudomonas fluorescens, Bacillus subtilis, Mycoplasma genitalium*, and various *Synechocystis* sp.; protists such as *Dictyostelium discoideum, Tetrahymena thermophila, Emiliania huxleyi*, and *Thalassiosira pseudonana*; and fungi such as *Aspergillus* sp., *Neurospora crassa, Saccharomyces cerevisiae*, and *Schizosaccharomyces pombe*.

A methanogenic or methanotrophic cell is provided comprising one or more additional copies of a cfb gene. The additional copy may be identical to a naturally occurring cfb gene in the species, or it may be a heterologous cfb gene. The additional copy may be operatively linked to a promoter, either heterologous or non-heterologous. A specific embodiment of the cell is *Methanosarcina acetivorans*.

A vector is also provided, comprising any of the polynucleotides disclosed above, alone or in any combination with one another. Many suitable vectors are known in the art, such as viruses, plasmids, cosmids, fosmids, phagmids, artificial chromosomes, yeast artificial chromosomes, human artificial chromosomes, plant transformation vectors, and liposomes. A specific embodiment of the vector is an expression vector comprising coding regions encoding a CfbA, CfbB, CfbC, CfbD, and CfbE polypeptide, each said coding region operatively linked to a promoter (with the understanding that two or more regions may be linked to the same promoter, so long as each region is linked to a promoter).

C. Method of Modulating Methane Metabolism

Methods of modulating the generation and oxidation of methane are provided. Such methods involve modulating (increasing or decreasing) the concentration or activity of one or more Cfb polypeptides in a cell. Such modulation may be achieved, for example, by altering the expression of one or more cfb genes or by altering the activity of one or more Cfb polypeptides post-expression. Because coenzyme F430 is critical to both methanogenesis and anaerobic methane oxidation, any increase in expression or activity of the coenzyme F430 pathway would be expected to increase rates of methanogenesis and anaerobic methane oxidation. This could be useful in the production of methane from hydrogen and organic compounds (from sources such as organic waste or biomass) and in the conversion of methane to less volatile compounds for reuse (from sources such as landfills and natural gas deposits).

If the modulation is a decrease in expression or activity, it may be achieved by exposing a methanogenic or methanotrophic cell to an inhibitor of a Cfb polypeptide. The inhibitor may be any known in the art or any that is discovered to effectively reduce the activity of a Cfb polypeptide expressed in the cell. The inhibitor may act directly on the Cfb polypeptide, by binding to the polypeptide, or indirectly. Indirect forms of inhibition include but are not limited to sequestration of cofactors and the inhibition of upstream enzymes or cofactors required to synthesize the Cfb polypeptide. Inhibition of expression may similarly be direct or indirect. Examples of direct inhibition of expression includes the use of a repressor protein to block the operator, promoter or silencers associated with the cfb gene in question. Such methods find use for example in anaerobic environments in which it is desirable to prevent the conversion of hydrogen or small carbon molecules to methane. In waste treatment, this could result in the accumulation of useful carbon compounds such as methanol, acetic acid, and methylamines. In ruminant digestion, this could result in increased carbon assimilation by the animal. In numerous applications it could reduce unwanted methane production, for example to control greenhouse gas emissions or to prevent the accumulation of explosive gasses.

In some embodiments of the method, the activity of any Cfb polypeptide may be modulated by means of an antibody. Suitable antibodies that increase Cfb activity include antibodies with antagonistic or inhibitory properties of antagonists of the Cfb polypeptide, and antibodies against proteases for degradation of the Cfb polypeptide. Suitable antibodies that decrease Cfb activity include antibodies with antagonistic or inhibitory properties of agonists of the Cfb polypeptide, and antibodies that target the Cfb polypeptide. In addition to intact immunoglobulin molecules, fragments, chimeras, or polymers of immunoglobulin molecules are also useful in the methods taught herein, as long as they retain the desired activity. The antibodies can be tested for their desired activity using in vitro assays, or by analogous methods, after which their in vivo therapeutic or prophylactic activities are tested according to known clinical testing methods.

The term antibody is used herein in a broad sense and includes both polyclonal and monoclonal antibodies. Monoclonal antibodies can be made using any known procedure. For example, disclosed monoclonal antibodies can be prepared using hybridoma methods, such as those described by Kohler and Milstein, *Nature*, 256:495 (1975) (which is incorporated by reference herein for this teaching). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The monoclonal antibodies may also be made by recombinant DNA methods, such as those described in U.S. Pat. No. 4,816,567 (which is hereby incorporated by reference for this teaching). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, as described in U.S. Pat. Nos. 5,804,440 and 6,096,441 (which are hereby incorporated by reference for this teaching).

Antibody fragments include Fv, Fab, Fab' or other antigen binding portion of an antibody. Digestion of antibodies to produce fragments thereof can be accomplished using routine techniques known in the art. For instance, digestion can be performed using a protease, such as papain. Examples of papain digestion are described in WO 94/29348 published and U.S. Pat. No. 4,342,566 (which are hereby incorporated by reference for this teaching). Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The antibodies or antibody fragments may also include insertions, deletions, substitutions, or other selected modifications of particular regions or specific amino acids residues. These modifications can provide additional or improved function. For example, the removal or addition of acids capable of disulfide bonding may increase the biolongevity of the antibody. In any case, the modified antibody or antibody fragment retains a desired bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment (Zoller, M. J. *Curr. Opin. Biotechnol.* 3:348-354, 1992).

The antibody or antibody fragment can be a mammalian antibody or an avian antibody. The antibody may be a human antibody or a humanized antibody. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991). The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551 255 (1993); Jakobovits et al., *Nature*, 362:255-258 (1993); Bruggermann et al., *Year in Immunol.*, 7:33 (1993)).

Modulation may also be achieved using a functional nucleic acid. In one embodiment, the inhibitors of the present disclosure are functional nucleic acids. Functional nucleic acids are nucleic acid molecules that carry out a specific function in a cell, such as binding a target molecule or catalyzing a specific reaction. Such functional nucleic acids may inhibit the activity of an inhibition target (nucleic acid inhibitors). Functional nucleic acids include but are not limited to antisense molecules, aptamers, ribozymes, triplex forming molecules, small interfering RNA (siRNA), RNA interference (RNAi), single guide RNA (sgRNA), CRISPR RNA (crRNA), and external guide sequences (EGS). In one embodiment, a siRNA could be used to reduce or eliminate expression of at least one inhibition target. In another embodiment, sgRNA could be used in combination with Cas9 endonuclease to create a deletion at a target genetic locus.

Antisense molecules are designed to interact with the mRNA of a cfb gene through either canonical or non-canonical base pairing. The interaction of the antisense molecule and the target molecule is designed to promote the destruction of the inhibition target through, for example, RNAseH mediated RNA-DNA hybrid degradation.

Alternatively, the antisense molecule is designed to interrupt a processing function that normally would take place on the target nucleic acid molecule, such as transcription or replication. Antisense molecules can be designed based on the sequence of the target nucleic acid molecule (such as a nucleic acid encoding an inhibition target). Numerous methods for optimization of antisense efficiency by finding the most accessible regions of the target nucleic acid molecule exist. Exemplary methods include, but are not limited to, in vitro selection experiments and DNA modification studies using DMS and DEPC.

Aptamers are molecules that interact with a target nucleic acid molecule, often in a specific way. Typically aptamers are small nucleic acids ranging from 15-50 bases in length that fold into defined secondary and tertiary structures, such as stem-loops or G-quartets. Representative examples of how to make and use aptamers to bind a variety of different target nucleic acid molecules can be found in, for example, U.S. Pat. Nos. 5,476,766 and 6,051,698 (which are hereby incorporated by reference for this teaching). The secondary structure inhibits expression of the polypeptide encoded by the gene or inhibits a processing function as discussed above.

Ribozymes are nucleic acid molecules that are capable of catalyzing a chemical reaction, either intramolecularly or intermolecularly. There are a number of different types of ribozymes that catalyze nuclease or nucleic acid polymerase type reactions which are based on ribozymes found in natural systems, such as, but not limited to, hammerhead ribozymes, hairpin ribozymes and tetrahymena ribozymes. There are also a number of ribozymes that are not found in natural systems, but which have been engineered to catalyze specific reactions de novo (including, but not limited to, those described in U.S. Pat. Nos. 5,807,718, and 5,910,408, which are hereby incorporated by reference for this teaching). Ribozymes may cleave RNA or DNA substrates. Representative examples of how to make and use ribozymes to catalyze a variety of different reactions can be found in U.S. Pat. Nos. 5,837,855; 5,877,022; 5,989,906; and 6,017,756 (which are hereby incorporated by reference for this teaching).

Triplex forming functional nucleic acid molecules are nucleic acid molecules that can interact with either double-stranded or single-stranded nucleic acid. When triplex forming nucleic acids interact with a target region, a structure called a triplex is formed, in which three strands of DNA form a complex dependent on both Watson-Crick and Hoogsteen base-pairing. Triplex molecules can bind target regions with high affinity and specificity. Representative examples of how to make and use triplex forming molecules to bind a variety of different target nucleic acid molecules can be found in U.S. Pat. Nos. 5,650,316; 5,683,874; 5,693,773; 5,834,185; 5,869,246; 5,874,566; and 5,962,426 (which are hereby incorporated by reference for this teaching).

EGSs are molecules that bind a target nucleic acid molecule forming a complex, which is recognized by RNase P. RNase P then cleaves the target nucleic acid molecule. EGSs can be designed to specifically target a RNA molecule of choice. Representative examples of how to make and use EGS molecules to facilitate cleavage of a variety of different target nucleic acid molecules may be found in U.S. Pat. Nos. 5,168,053; 5,624,824; 5,683,873; 5,728,521; 5869,248; and 5,877,162 (which are hereby incorporated by reference for this teaching).

Gene expression can also be effectively silenced in a highly specific manner through RNA interference ("RNAi"). Small interfering RNA ("siRNA") is a double-stranded RNA that can induce sequence-specific post-transcriptional gene silencing, thereby decreasing or even inhibiting gene expression from a target nucleic acid. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. siRNA can also be synthesized in vitro using kits such as Ambion's SILENCER® siRNA Construction Kit (Ambion, Austin, TX).

D. Method of Making a Tetrapyrrole Compound

A method of making a tetrapyrrole compound is disclosed, the method comprising: providing a cell comprising one or more cfb genes (i.e., a polynucleotide encoding a Cfb polypeptide) and culturing the cell under conditions to permit synthesis of the tetrapyrrole compound or a precursor thereof. By way of example, the tetrapyrrole compound may be any one of sirohydrochlorin, Ni-sirohydrochlorin, Ni-sirohydrochlorin a,c-diamide, $15,17^3$-seco-F430-$17^3$-acid, and coenzyme F430. The cell may contain more than one cfb gene. Some embodiments of the cell contain a cfbA gene, a cfbB gene, a cfbC gene, a cfbD gene, and a cfbE gene; in such embodiments the cell should be capable of synthesizing all of sirohydrochlorin, Ni-sirohydrochlorin, Ni-sirohydrochlorin a,c-diamide, $15,17^3$-seco-F430-$17^3$-acid, and coenzyme F430. Further embodiments of the cell may contain a subset of the cfb genes, to enable the cell to synthesize a tetrapyrrole in the coenzyme F430 pathway other than coenzyme F430 and sirohydrochlorin. For example, a cell containing a cfbA gene, but lacking a cfbB gene, would be useful to produce Ni-sirohydrochlorin.

The cell may be any described above, including a cell containing a heterologous cfb gene, a cell containing a cfb gene operatively linked to a heterologous promoter, a bacterial cell containing a cfb gene, a eukaryotic cell containing a cfb gene, and a cell containing multiple copies of a cfb gene.

The culture conditions will depend on the cell in question, and also depend on any special requirements to express the cfb gene. General culture conditions include temperature, salinity, nutrient concentration, pH, and oxidation potential. If the cfb gene is operably linked to an inducible promoter, then the culture conditions may include the presence of the inducer; as known in the art, the inducer may be a compound, radiation, temperature, heat shock, etc.

E. Method of Methane Production

A method of biogenic methane synthesis is provided, comprising providing cell comprising two or more genes selected from the group consisting of: cfbA, cfbB, cfbC, cfbD, and cfbE; and culturing the cell in the presence of at least one of $H_2$, $CO_2$, and an organic compound. The cell may be any that are disclosed above, including any combination of heterologous genes, promoters, or multiple gene copies as described above; the cfb genes may be any described above as well. Specific examples include a cell comprising a cfb gene with one or nucleotide substitutions compared to wild type, a cell comprising a heterologous cfb gene, a cell comprising a cfb gene operatively linked to a heterologous promoter, a bacterial cell comprising a cfb gene, a eukaryotic cell comprising a cfb gene, and a cell comprising multiple copies of a cfb gene.

The cell may be cultured under methanogenic conditions. Such conditions will vary based on the needs of the organism. In some embodiments of the method the cells are cultured under strictly anaerobic conditions. Such conditions may have redox conditions of 0 mV or less, −100 mV or less, −300 mV or less, or −800 mV or less. Various phyla of methanogens require various culture conditions, many of which can be found in the art (see, for example K. R. Sower and H. J. Schreier (1995) *Archaea, A Laboratory Manual: Methanogens*, Cold Spring Harbor Press, Plainview, New York, which is incorporated by reference as necessary to enable those of ordinary skill in the art to cultivate methanogens under methanogenic conditions). If the cell is a facultative or obligate anaerobe that is not a member of the methanogenic archaea (for example, if it contains only heterologous cfb genes), similar sources may be consulted to teach proper anaerobic culture conditions.

The substrate for methanogenesis may be one that is known to be utilized by methanogenic archaea. These include $H_2$ and various carbon compounds up to about 3 carbons in length, including but not limited to formate, carbon monoxide, acetate, methanol, methylamines, methanethiols, ethanol, and propionate. Alternatively, if organisms other than methanogenic archaea are present, either as part of a consortium or as the host for the cfb gene, heavier organic compounds may be used.

F. Methods of Methane Oxidation

A method of biological methane oxidation is provided. Such methane oxidation may be a form of anaerobic methane oxidation. The oxidation of methane is useful for the conversion of unwanted methane to $CO_2$, as well as the conversion of unwanted methane to useful oxidized products, such as methanol. The method generally comprises providing cell comprising two or more genes selected from the group consisting of: cfbA, cfbB, cfbC, cfbD, and cfbE; and culturing the cell in the presence of methane. The cell may be any that are disclosed above, including any combination of heterologous genes, promoters, or multiple gene copies as described above; the cfb genes may be any described above as well. Specific examples include a cell comprising a cfb gene with one or nucleotide substitutions compared to wild type, a cell comprising a heterologous cfb gene, a cell comprising a cfb gene operatively linked to a heterologous promoter, a bacterial cell comprising a cfb gene, a eukaryotic cell comprising a cfb gene, and a cell comprising multiple copies of a cfb gene.

The cell may be cultured under methanotrophic conditions. Such conditions will vary based on the needs of the organism. In some embodiments of the method the cells are cultured under strictly anaerobic conditions. Such conditions may have redox conditions of 0 mV or less, –100 mV or less, –200 mV or less, –300 mV or less, or –800 mV or less. Various phyla of anaerobic methanotrophs require various culture conditions, many of which can be found in the art. If the cell is a facultative or obligate anaerobe that is not a member of the anaerobic methanotrophic archaea (for example, if it contains only heterologous cfb genes), similar sources may be consulted to teach proper anaerobic culture conditions.

The oxidization products may be separated from the culture medium during the process. Such separation may be achieved by various techniques known in the art, such as distillation, reduction, chromatography, filtration, centrifugation, and extraction. Useful oxidation products of methane oxidation include methanol, formic acid, formaldehyde, and biomass.

G. Assay for Methane Metabolism

Assays are provided for identifying compounds that affect methane metabolism; and for identifying organisms capable of methanogenesis or anaerobic methanotrophy.

The present disclosure also relates to a method for identifying a compound effective for modulating methanogenesis or methanotrophy. Such compounds may be useful to promote methane generation, inhibit methane generation, promote methane oxidation, or inhibit methane oxidation. In one embodiment, the methods include determining the level of a polypeptide involved in methane metabolism, such as, but not limited to, a Cfb polypeptide.

In general, such screening methods comprise the steps of: providing an assay system (as described in more detail below) that expresses a polypeptide involved in methane metabolism, such as, but not limited to, a Cfb polypeptide; introducing into the assay system a test compound to be tested; and determining the effect of the test compound on the level the polypeptide. Such compounds may then be further tested in appropriate systems (such as, but not limited to, methanogenic digesters or methanotrophic culture) to determine the activity of the identified compounds.

Candidate compounds are identified using a variety of assays, such as, but not limited to, assays that employ cells which express a Cfb polypeptide or assays with isolated polypeptides. The various assays can employ a variety of variants of such polypeptides (e. g., full-length, a biologically active fragment, or a fusion protein which includes all or a portion of the desired polypeptide). Moreover, such polypeptides can be derived from any suitable species (e. g., methanogenic archaea or anaerobic methanotrophy); in a specific embodiment, the polypeptide is derived from *M. acetivorans*.

Where the assay involves the use of a whole cell, the cell may either naturally express the Cfb polypeptide, or may be modified to express the same. In the latter case, cells can be modified to express a desired polypeptide through conventional molecular biology techniques, such as by infecting the cell with a virus comprising such polypeptide. The cell can also be a prokaryotic or a eukaryotic cell that has been transfected with a nucleotide sequence encoding such polypeptide. In the foregoing, full length polypeptides, fragments or fusion proteins containing at least a part of such polypeptide may be used. Exemplary assay systems are described in the current specification.

In one embodiment, such a screening assay can be performed, for example, by determining the intracellular level of a Cfb polypeptide and detecting a difference in the level of such polypeptide in the presence of as compared to the absence of a test compound. Such screening assay may be in vitro, in vivo or ex vivo and may measure levels in whole cells or lysates. Any assay of the present disclosure may be used in the foregoing method.

An assay for identifying organisms capable of methanogenesis or anaerobic methanotrophy is provided, comprising detecting the presence of one or more cfb genes in the subject organism. A kit may be used for the assay, comprising: a means for measuring the expression of a first cfb gene; and means for detecting a second cfb gene. In specific embodiments of the method and the kit, the means for measuring the expression of the first and second genes may be independently selected from: a means for detecting a first target sequence of at least 15 bp that is present in a first or second cDNA or mRNA of the first or second gene; and a means for detecting a first protein product of the first or second gene.

In some embodiments of the method and the kit, the means for detecting the first target sequence is a first probe that may be any probe disclosed as suitable for measuring mRNA or cDNA below in this disclosure. In some embodiments of the method and the kit, the means for detecting the second target sequence is a second probe that may be any probe disclosed as suitable for measuring mRNA or cDNA below in this disclosure. In some embodiments of the method and the kit that comprise at least one nucleic acid probe, the method and the kit may include the use of a container of a reverse transcriptase for generating a cDNA reverse transcript from an mRNA. Such probes may be components in an expression screening apparatus, such as a DNA array or a DNA microarray.

In some embodiments of the method and the kit, the means for detecting the first protein product is a first probe that may be any probe disclosed as suitable for measuring such protein products below in this disclosure. In some embodiments of the method and the kit, the means for detecting the second protein product is a second probe that may be any probe disclosed as suitable for measuring such protein products above in this disclosure. Some versions of the probes may be immobilized to a substrate, such as a bead or multiwell titer plate, or in any other configuration known in the art for the use of protein probes.

Such probes fall into two general categories: those for measuring nucleic acids and those for measuring proteins. The nucleic acids measured by the probes include mRNA and cDNA of the gene to be detected. The proteins measured by the probes include protein products of the genes.

The nucleic acid probe binds specifically with a target sequence under highly stringent conditions. The target sequence is a sequence of at least 15 base pairs (bp) found in the mRNA or cDNA of the gene the expression of which is to be measured. Such mRNA or cDNA for the gene may be any that is known in the art. In some cases the mRNA will be non-coding, while in some cases the mRNA will comprise a sequence that encodes a protein product of the gene. Some embodiments of the mRNA encode a peptide having at least 90% identity with a cfb gene (including any cfb gene described above). In other cases the level of identity may be higher, for example 95%, 97.5%, 99%, 99.9%, or 100%. The cDNA may have a sequence that is complementary to any of the foregoing mRNAs, or a sequence that mimics any of the foregoing mRNAs but for the substitution of thymidine for uracil.

In some embodiments of the probe, the polynucleotide part of the probe and its target sequence are of at least 20 bp. In further embodiments of the probe, the polynucleotide part of the probe and its target sequence are of at least 25 bp. In many embodiments, the polynucleotide part of the probe will be single-stranded DNA. In other embodiments the polynucleotide part may be double-stranded DNA, RNA, LNA, or other nucleic acids. The design of nucleotide probes is a well understood technique, and given the knowledge of the target sequence it is within the capabilities of one of ordinary skill to design specific probes for the target. Multiple probes may of course be used to detect the mRNAs and cDNAs of multiple genes as necessary.

If the probe is intended to measure a protein product of the gene, the probe will comprise a ligand group that specifically binds to the protein product of the gene. It may target any known protein product of the gene. Some embodiments of the probe specifically bind a protein product of the gene that has at least 90% sequence identity to any one of the sequences listed above as associated with a Cfb polypeptide. Further embodiments of the probe specifically bind to a peptide that has at least 90% sequence identity to a Cfb polypeptide. In further embodiments of the probe, the level of identity is selected from 95%, 97.5%, 99%, 99.9%, and 100%. Multiple probes may be used for detecting the expression of more than one gene, each comprising a ligand to a product of one of the genes. The ligand is a compound with a specific affinity for the protein product. Many such ligands are known in the art. For example, the publicly available BioLip database, maintained by the University of Michigan, contains over 300,000 protein ligands, and is searchable based on the protein of interest. The ligand may be for example an antigen binding site of an antibody. Antibodies are macromolecular constructs that binds to proteinaceous and other types of targets with high affinity and specificity. Antibodies can be generated by various methods, the simplest of which is challenging a bird or mammal with the target (antigen) and harvesting the antibodies. Antibodies can also be produced monoclonally or polyclonally in cell culture by methods known in the art. Some embodiments of the ligand are a fragment of an antibody. Further embodiments of the ligand may be a Fab region of an antibody. Still further embodiments of the ligand are a light-chain variable region or a heavy-chain variable region of an antibody.

The ligand may be any that is known to specifically bind to the protein product of the gene. In some embodiments of the probe, the probe binds specifically to an epitope of the protein product of the gene. The epitope may be of any size. In some embodiments of the probe, the epitope is at least 5 residues long. In further embodiments of the probe, the epitope is at least 8 residues long. In still further embodiments of the probe, the epitope is at least 11 residues long. In still further embodiments of the probe, the epitope is at least 13 residues long.

The nucleic acid probe or protein probe may comprise a reporter group, which is a chemical group or structure than allows specific detection of the molecule to which the reporter is bound or conjugated. Myriad types of reporters are commercially available; examples include radionuclides, rare stable isotopes, fluorophores, chromophores (i.e., dyes or other groups that confer color in the visible spectrum), enzymes, magnetic particles, and quantum dots. Enzymes that are useful as reporters often generate a reaction product that is visually distinctive, such as precipitates, effervescence, chromophores, or luminescence. Frequently the use of the enzymatic reporter will require that the enzyme's substrate be added to a reaction mixture. Examples of such enzymes that are useful as reporters include horseradish peroxidase and luciferase. Many others are well known in the art.

Suitable test compounds for use in the screening methods can be obtained from any suitable source, such as conventional compound libraries. The test compounds can also be obtained using any of the numerous approaches in combinatorial library methods known in the art, including: biological libraries, spatially addressable parallel solid phase or solution phase libraries, synthetic library methods requiring deconvolution, the "one-bead one-compound" library method and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

The present disclosure also provides kits for carrying out any method of the present disclosure, which can contain any of the compounds and/or compositions disclosed herein or otherwise useful for practicing a method of the disclosure.

H. Examples

The genomes of methanogenic archaea were searched for homologs of known chelatase genes, whose products are responsible for metal ion insertion into tetrapyrrolic cofactors. Analysis of the genomic contexts of the chelatase homologs, along with knowledge of the chemistry required for the conversion of known precursors of C2 and C7 methylated tetrapyrroles to coenzyme F430, led to the identification of five genes, conserved in all methanogens, that are potentially involved in coenzyme F430 biosynthesis (FIGS. 1 and 4). These genes are also present in the genome of an ANME-2d strain (Candidatus Methanoperedens *nitroreducens*) (FIG. 4).

Included among these genes are homologs of the genes for sirohydrochlorin cobaltochelatase (cbiX$^S$) and cobyrinic acid a,c-diamide synthetase (cbiA2), which are involved in the biosynthesis of cobalamin. Also present are homologs of the nitrogenase genes nifD and nifH, which (together with nifK) encode subunits of the two-component metallo-enzyme responsible for the adenosine triphosphate (ATP)-dependent reduction of di-nitrogen to ammonia (nitrogen fixation). Nitrogenase is structurally and functionally related to the dark-operative protochlorophyllide oxido-reductase (DPOR), which is involved in chlorophyll and bacteriochlorophyll biosynthesis. However, methanogens are not photosynthetic microorganisms, and not all methanogens are diazotrophic (i.e., fix nitrogen). The presence of the nifD (methanogenesis marker 13) and nifH homologs in all methanogens was noted previously, and these genes were found to be constitutively expressed and the encoded proteins shown to associate with one another. Methanogenesis markers are found in prokaryotic genomes if, and only if, the species is an archaeal methanogen. The fifth gene is homologous to murD, a gene that encodes an ATP-dependent Mur ligase (uridine diphosphate N-acetylmuramoyl-Lalanine: D-glutamate ligase) involved in bacterial cell wall biosynthesis. Each of these genes (except for cbiA2) was targeted in a genome-wide transposon mutagenesis experiment in the methanogen *Methanococcus maripaludis* and were all found to be essential.

Figure 5:
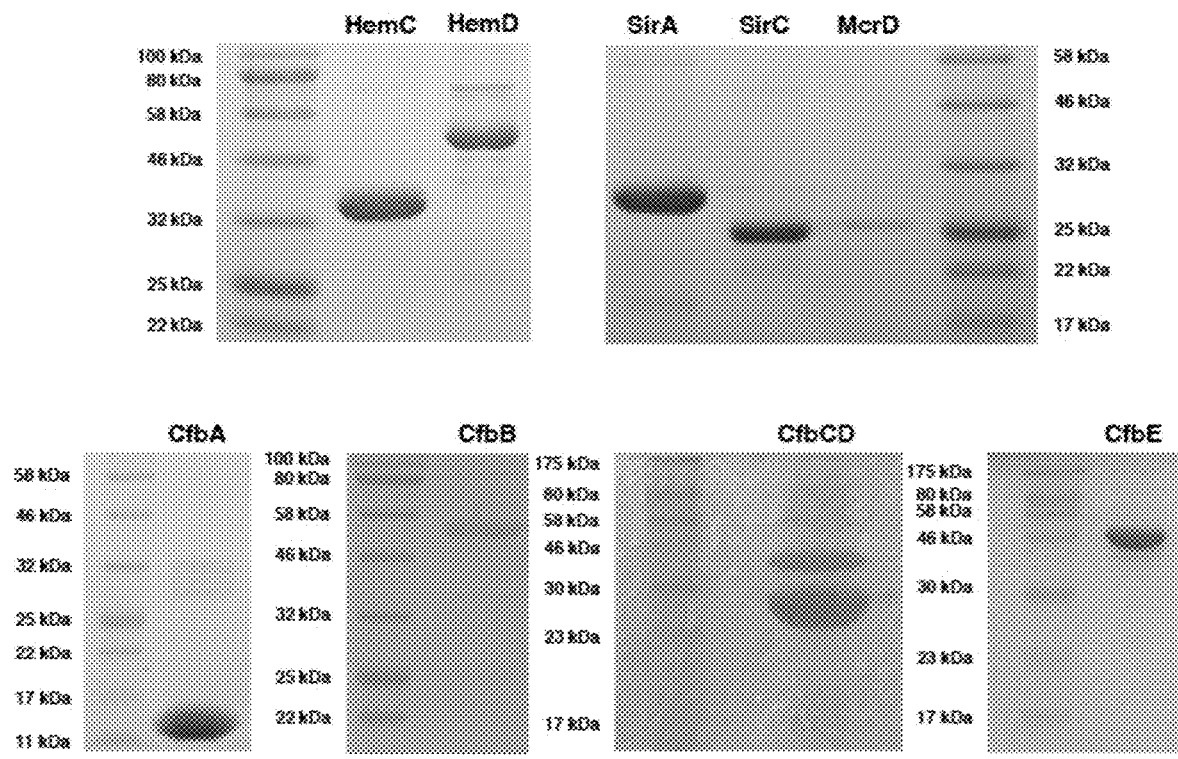
FIG. 5. Sodium dodecyl sulfate-polyacrylamide gel electrophoresis (SDS-PAGE) analysis of the purified enzymes used in the coenzyme F430 biosynthetic reactions.

The identified genes were cloned from *Methanosarcina acetivorans* C2A and ligated into expression vectors for heterologous production of the encoded enzymes in *Escherichia coli*. The enzymes were then purified as N-terminal His6-tagged fusion proteins and systematically tested for activity (FIG. 5).

Figure 2:
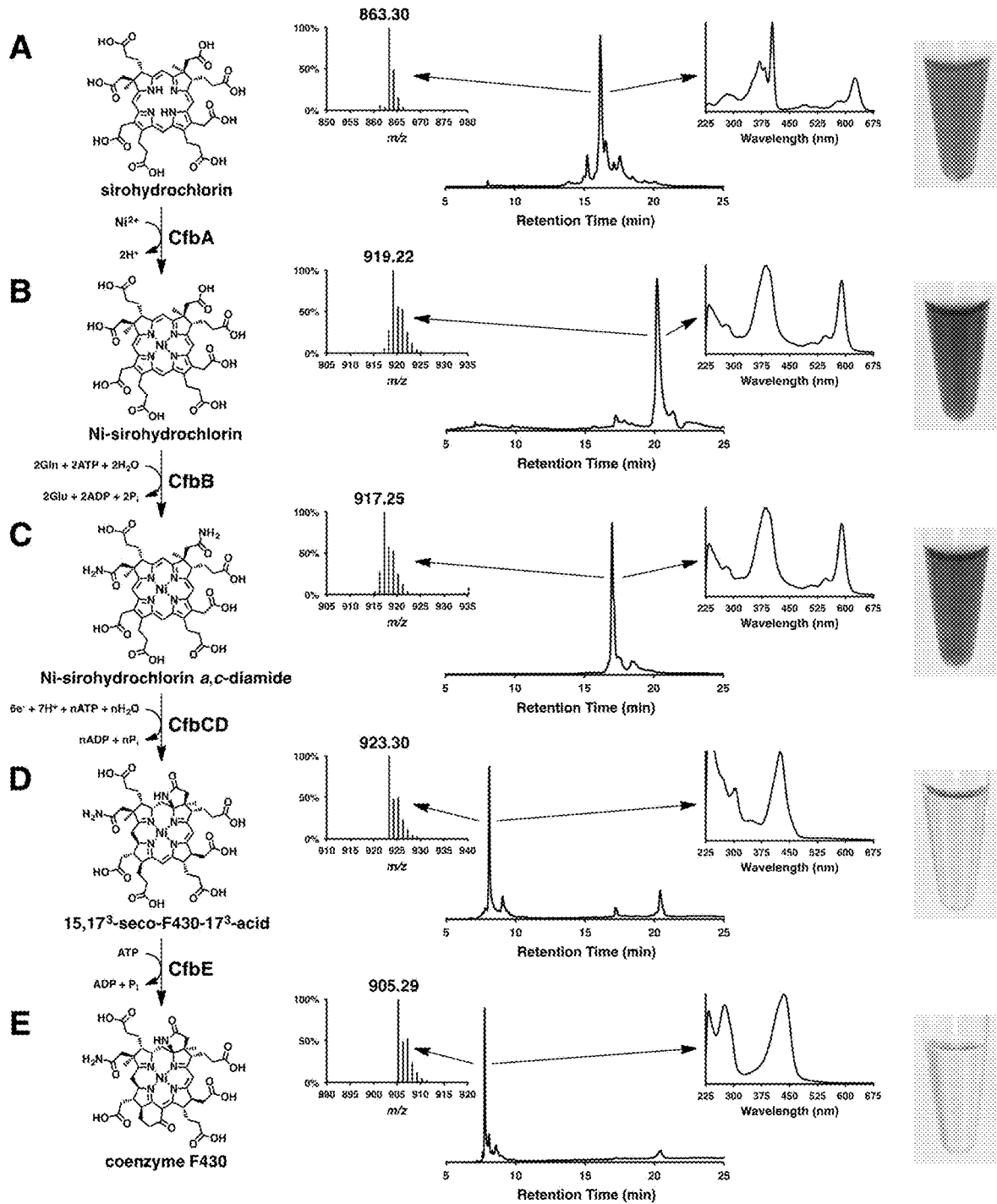
FIG. 2. In vitro activity assays of the coenzyme F430 biosynthesis enzymes. Reversed-phase HPLC traces, liquid chromatography-mass spectrometry (LC-MS) data, and UV-visible spectra for each of the biosynthetic reactions are shown. (A) Sirohydrochlorin prepared from porphobilinogen by using HemC, HemD, SirA, SirC, S-adenosyl-L-methionine (SAM), and nicotinamide adenine dinucleotide (phosphate). (B) Ni-sirohydrochlorin prepared by adding CfbA and $NiCl_2$ to the sirohydrochlorin reaction (along with CfbB to alleviate product inhibition). (C) Ni-sirohydrochlorin a,c-diamide prepared by adding CfbB, glutamine, adenosine triphosphate (ATP), and an ATP regeneration system (phosphoenolpyruvate (PEP) and pyruvate kinase (PK)) to the Ni-sirohydrochlorin reaction (along with CfbCD to alleviate product inhibition). (D) $15,17^3$-seco-F430-$17^3$-acid prepared by adding CfbCD, sodium dithionite, ATP, and an ATP regeneration system (PEP and PK) to the Ni-sirohydrochlorin a,c-diamide reaction. (E) Coenzyme F430 prepared by adding CfbE, ATP, and an ATP regeneration system (PEP and PK) to the $15,17^3$-seco-F430-$17^3$-acid reaction (along with McrD to alleviate product inhibition).
Figure 6:
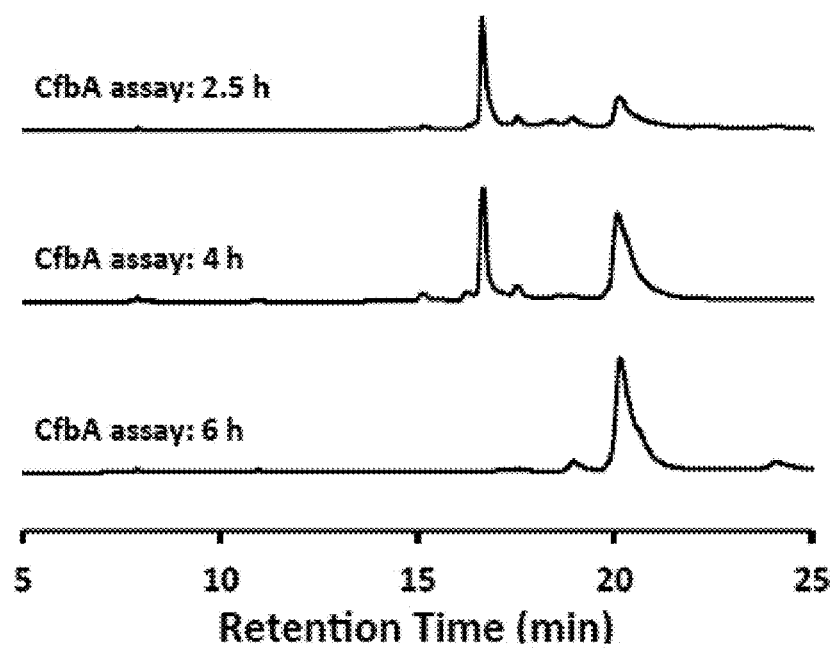
FIG. 6. HPLC assays showing the time course of the CfbA-catalyzed reaction. The reaction mixtures contain CfbA, $NiCl_2$, and enzymatically prepared sirohydrochlorin (along with CfbB to alleviate product inhibition).

The "small" sirohydrochlorin cobaltochelatase (CbiXS) homolog was tested, designated as CfbA, for nickelochelatase activity with enzymatically prepared sirohydrochlorin and dihydrosirohydrochlorin (precorrin 2) (18). Precorrin 2 is the immediate biosynthetic precursor of sirohydrochlorin and is two-electrons more reduced than the latter (19). Because coenzyme F430 is a highly reduced tetrapyrrole, it was thought that precorrin 2 might be the substrate of CfbA. However, no nickel chelation activity was observed with precorrin 2 under any of the assay conditions tested. For sirohydrochlorin, it was observed that, unlike other divalent transition metal ions (e.g., $Fe^{2+}$, $Co^{2+}$, and $Zn^{2+}$), there was no evidence of rapid, nonenzymatic insertion of $Ni^{2+}$ into sirohydrochlorin under the assay conditions used. However, in the presence of both $Ni^{2+}$ and CfbA (and only if the His6-tag of CfbA was first removed by thrombin cleavage), the reaction mixture changed from the bright magenta color characteristic of sirohydrochlorin to a deep purple (FIGS. 2 and 6). Analysis of the reaction mixtures by reversed-phase high-performance liquid chromatography (HPLC) showed the near-complete conversion of sirohydrochlorin (which has a retention time of 16.1 min) to a new compound that eluted at min (FIG. 2). The ultraviolet (UV)-visible absorption properties [wavelengths of maximum light absorption ($\lambda_{max}$)=386 and 590 nm] and the mass spectrum of this compound were consistent with those of Ni-sirohydrochlorin [calculated mass to charge ratio (m/z) of the protonated molecule ([M+H]$^+_{calc}$)=919.22 m/z] (20). Thus, CfbA was a sirohydrochlorin nickelochelatase.

Figure 7:
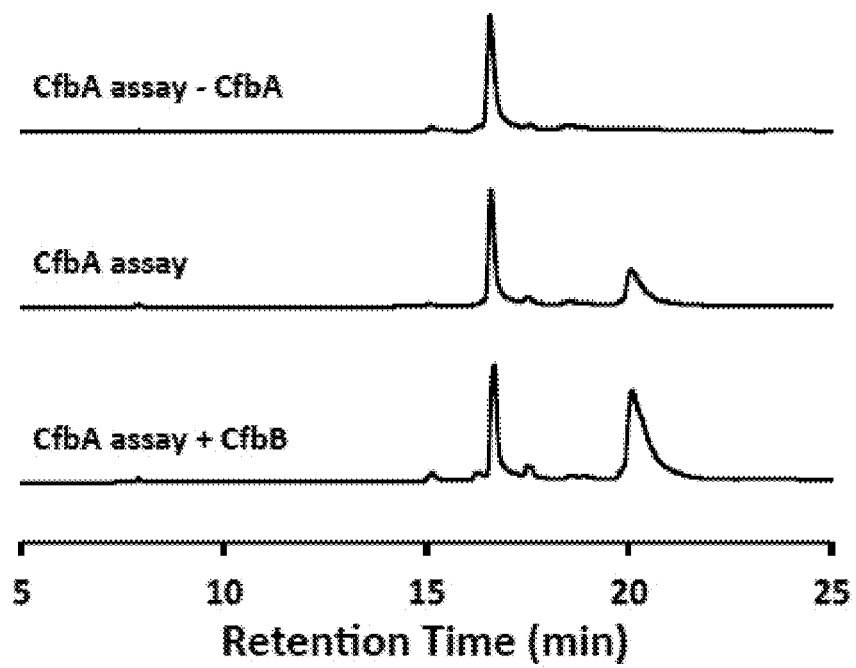
FIG. 7. HPLC assays of the CfbA-catalyzed reaction showing the enzyme/substrate requirements and the effect of the subsequent enzyme in the pathway (CfbB) on product yield. Each reaction was quenched after a 4 h incubation.

The addition of the cobyrinic acid a,c-diamide synthetase homolog (CfbB) to the reaction mixture enhanced the yield of Ni-sirohydrochlorin (FIG. 7). Intermediates in tetrapyrrole biosynthesis often remain tightly bound to their cognate enzyme and are thought to be transferred to the next enzyme in the pathway by substrate channeling (21). Therefore, tetrapyrrole biosynthetic enzymes often exhibit substantial product inhibition, which can be relieved by the addition of the subsequent pathway enzyme in vitro. This suggests that CfbB acts next in the pathway and will accept Ni-sirohydrochlorin as a substrate.

Figure 8:
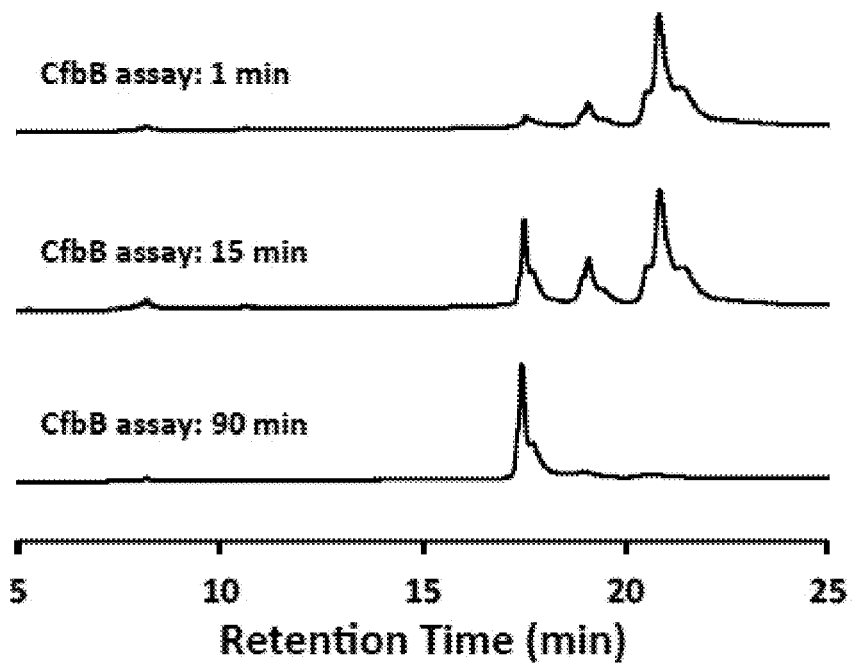
FIG. 8. HPLC assays showing the time course of the CfbB-catalyzed reaction. The reaction mixtures contain CfbB, glutamine, ATP, an ATP regeneration system (PEP/PK), and enzymatically prepared Ni-sirohydrochlorin (along with CfbCD to alleviate product inhibition).
Figure 9:
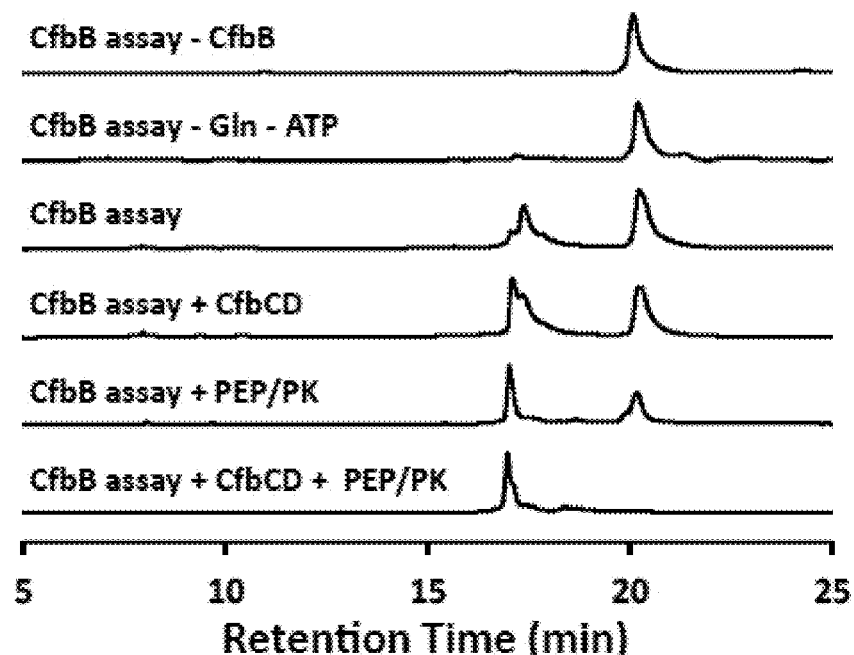
FIG. 9. HPLC assays of the CfbB-catalyzed reaction showing the cosubstrate (glutamine and ATP) requirements and the effect of an ATP regeneration system (PEP/PK) and the subsequent enzyme in the pathway (CfbCD) on product yield. Each reaction was quenched after a 12 h incubation.

CbiA is a glutamine amidotransferase that catalyzes the ATP-dependent amidation of the a- and c-carboxylic acid moieties of cobyrinic acid in the cobalamin biosynthetic pathway (22). Coenzyme F430 also has amide functional groups at these positions, and it was reasoned that CfbB was a Ni-sirohydrochlorin a,c-diamide synthetase. Indeed, addition of both ATP and glutamine to the reaction mixture led to the formation of a new intermediate with a nearly identical UV-visible spectrum to that of Ni-sirohydrochlorin ($\lambda_{max}$=386 and 590 nm), although its HPLC retention time was shorter by 3 min ($R_t$=17.0 min) and its observed mass was lighter by 1.97 atomic mass units, with a m/z identical to the [M+H]$^+_{calc}$ for Ni-sirohydrochlorin a,c-diamide (FIGS. 2 and 8). The yield of Ni-sirohydrochlorin a,c-diamide could again be enhanced by the addition of the subsequent enzyme in the pathway (CfbCD, a complex of CfbC and CfbD), without the reductant required for its activity (vide infra), to alleviate product inhibition (FIG. 9). The inclusion of an ATP regeneration system [phosphoenolpyruvate (PEP) and pyruvate kinase (PK)] also helped to drive the CfbB reaction forward (FIG. 9).

Figure 10:
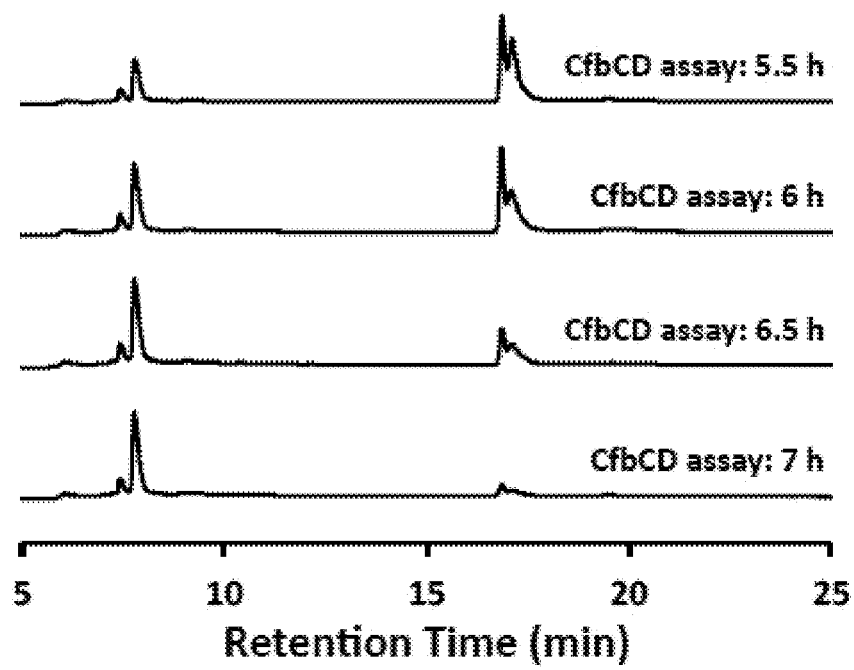
FIG. 10. HPLC assays showing the time course of the CfbCD-catalyzed reaction. The reaction mixtures contain CfbCD, sodium dithionite, ATP, an ATP regeneration system (PEP/PK), and enzymatically prepared Ni-sirohydrochlorin a,c-diamide.

Two distinctive structural features of coenzyme F430 are the presence of the y-lactam E ring and the carbocyclic F ring, which form from the c-acetamide and g-propionate side chains of Ni-sirohydrochlorin a,c-diamide, respectively. The high degree of similarity between the UV-visible spectra of Ni-sirohydrochlorin and Ni-sirohydrochlorin a,c-diamide indicated that the product of the CfbB reaction lacked the y-lactam ring and contained the free amide (FIG. 2). When the purified CfbCD complex was included in the CfbB reaction, along with the reductant sodium dithionite, ATP, and an ATP regeneration system (all of which were required for activity), the solution changed from the deep purple color characteristic of Ni-sirohydrochlorin a,c-diamide to a pale yellow. Analysis of the reaction mixture by HPLC showed the disappearance of the 17.0-min peak and the formation of a new peak with a retention time of 8.1 min (FIGS. 2 and 10). The UV-visible and mass spectra of this new intermediate were indistinguishable from those of the only previously identified intermediate unique to the coenzyme F430 biosynthetic pathway, 15,17$^3$-seco-F430-17$^3$-acid ([M]$^+_{calc}$=923.30 m/z) (23) (FIG. 2). This intermediate was identical in structure to coenzyme F430, except for the presence of the g-propionate side chain instead of the F ring. Thus, CfbCD effected both the six-electron reduction of the tetrahydroporphyrin ring system of Ni-sirohydrochlorin a,c-diamide and the y-lactamization of its c-acetamide side chain to form the E ring.

As noted above, CfbC is homologous to the Fe protein (NifH) and CfbD to the NifD subunit of the MoFe protein (NifDK) of nitrogenase, which catalyzes an eight-electron reduction of $N_2$ to $NH_3$ and two protons to $H_2$ (12). The nifD and nifK genes were proposed to have arisen from the paralogous gene duplication and divergence of an ancient shared precursor (24). The nitrogenase homolog DPOR was an analogous two-component system (BchH and BchNB) with similar structural topology and catalyzed a two-electron reduction of the C17=C18 double bond of protochlorophyllide to form chlorophyllidea in the chlorophyll biosynthetic pathway (13). Unlike nitrogenase and DPOR, the Ni-sirohydrochlorin a,c-diamide reductive cyclase contained a homomeric MoFe protein homolog (CfbD) and was thus representative of an early branching lineage of this enzyme family. A study of the molecular phylogeny of nitrogenase homologs placed the ancestral cfbC and cfbD genes in the last common ancestor of modern organisms and positioned them basal to the emergence of the groups involved in nitrogen fixation and the biosynthesis of photosynthetic pigments (14).

Figure 11:
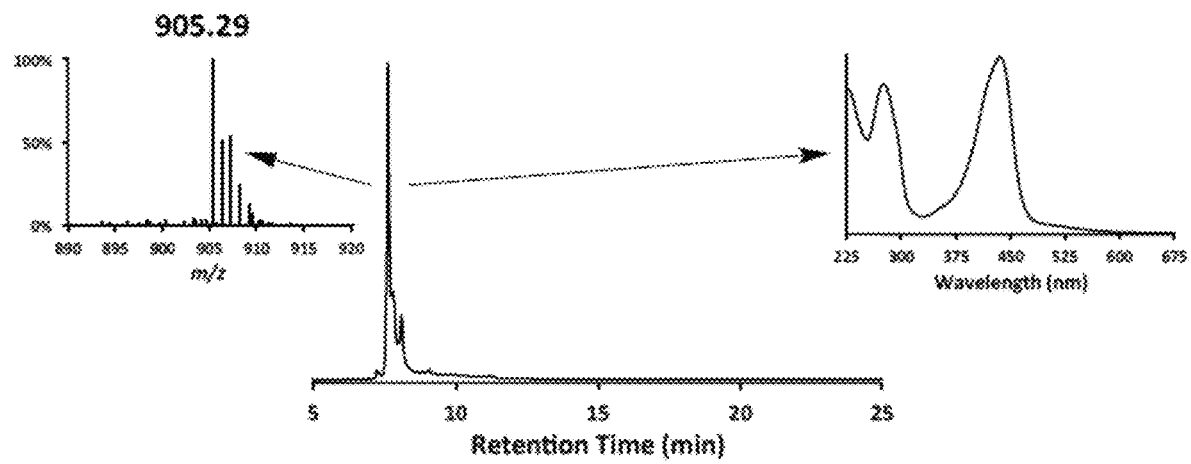
FIG. 11. HPLC, LC-MS, and UV-visible spectrophotometric analysis of authentic coenzyme F430 extracted from *M. marburgensis* MCR.

The last enzyme encoded by the cfb cluster, CfbE, is homologous to an ATP-dependent Mur ligase. Mur ligases use ATP to activate a carboxylic acid group as an acylphosphate for non-ribosomal peptide bond formation during the biosynthesis of peptidoglycan (25). It was reasoned that CfbE could use similar chemistry to activate the g-propionate side chain for intramolecular C—C bond formation to produce the carbocyclic F ring and thus function as a coenzyme F430 synthetase. As expected, addition of CfbE to reaction mixtures containing 15,17$^3$-seco-F430-17$^3$-acid resulted in the production of a new compound in low yield, which had an identical HPLC retention time (7.6 min), UV-visible spectrum, and isotopic mass distribution to authentic coenzyme F430 (FIG. 11).

Figure 12:
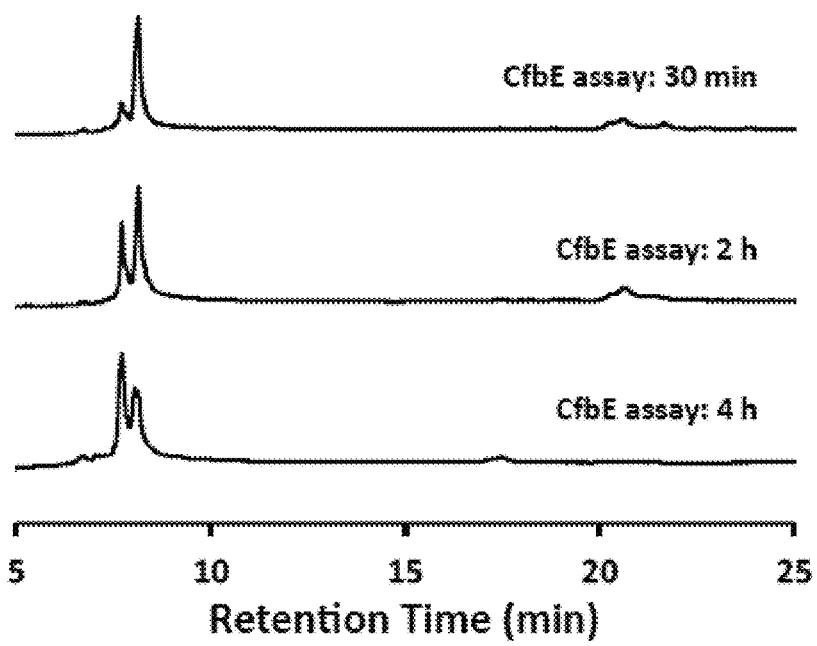
FIG. 12. HPLC assays showing the time course of the CfbE-catalyzed reaction. The reaction mixtures contain CfbE, ATP, an ATP regeneration system (PEP/PK), and enzymatically prepared $15,17^3$-seco-F430-$17^3$-acid (along with McrD to alleviate product inhibition).
Figure 13:
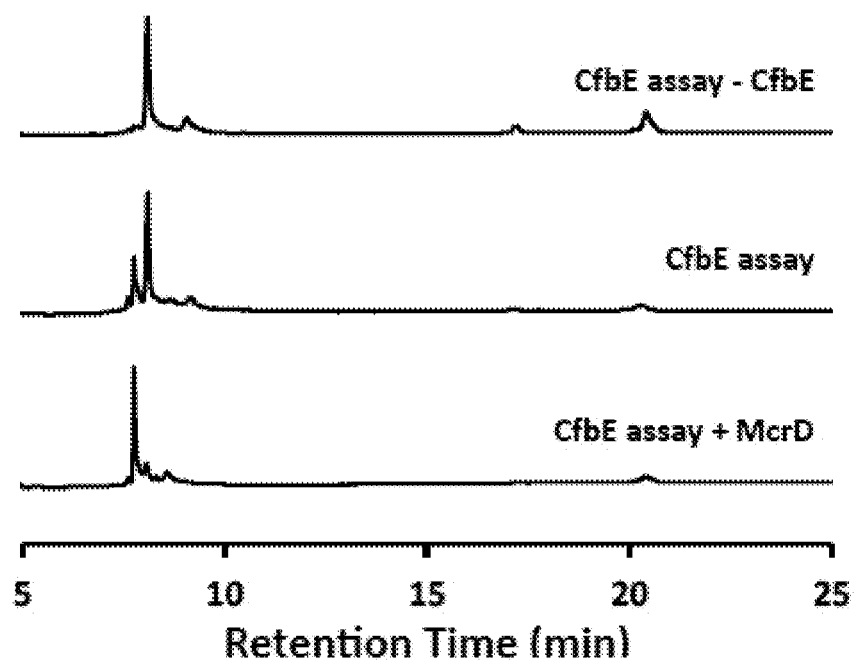
FIG. 13. HPLC assays of the CfbE-catalyzed reaction showing the enzyme requirement and the effect of McrD on the yield of coenzyme F430. Each reaction was quenched after a 12 h incubation.

It was hypothesized that the low yield of coenzyme F430 was due to product inhibition of the CfbE reaction. The mcr gene cluster encoding the -α, β, and γ subunits of MCR, which has been identified previously and is distinct from the cfb cluster, contains two genes, mcrC and mcrD, of unknown function (26). Recently, McrC was identified as a component of a large reductase complex capable of reducing coenzyme F430 to the $Ni^{1+}$ form, and thus it may play a role in MCR activation (27). McrD has been shown to physically interact with MCR through co-precipitation experiments, though it is not required for in vitro MCR activity (28). It was postulated that McrD may function as a chaperone protein that could bind coenzyme F430 and deliver it to apo-MCR. McrD was cloned from *M. acetivorans* C2A and expressed and purified the encoded protein to determine whether it was capable of accepting coenzyme F430 from CfbE and alleviating the observed inhibition. Consistent with this expectation, nearly full conversion of 15,17$^3$-seco-F430-17$^3$-acid to coenzyme F430 was observed when McrD was included in the reaction mixtures (FIGS. 2, 12 and 13).

Each of the identified coenzyme F430 biosynthetic enzymes represents a new target for inhibitors of methanogenesis. The data show that these enzymes are sufficient for the synthesis of coenzyme F430 from the common tetrapyrrolic intermediate sirohydrochlorin and can be produced in an active form in *E. coli*. Furthermore, if McrD is confirmed as a coenzyme F430— binding protein that chaperones the coenzyme to MCR, this protein will also be required for the heterologous production of holo-MCR. Taken together, these findings set the stage for metabolic engineering efforts using MCR for anaerobic methane conversion.

Materials and Methods

Plasmid Construction. The hemCD genes were amplified by polymerase chain reaction (PCR) from the genomic DNA of *Escherichia coli* BL21 (DE3) (New England Biolabs). The sirAC, cfbABCDE, and mcrD genes were amplified from the genomic DNA of *Methanosarcina acetivorans* C2A (DSM-2834). Primers were synthesized by Sigma-Aldrich and their sequences are provided in FIG. 3. Phusion High-Fidelity DNA Polymerase (New England Biolabs) was utilized for all PCR reactions in accordance with the manufacturer's protocol. The aforementioned PCR products (with the exception of cfbD and the cfbC PCR product obtained with reverse primer 2) were digested using the appropriate restriction enzymes from New England Biolabs and cloned into the pET-28b (+) vector (Novagen) for heterologous expression in *E. coli*. Each of the recombinant proteins thus produced contained a thrombincleavableHis6-tag incorporated at the N-terminus for purification using immobilized metal ion affinity chromatography (IMAC). The cfbD and cfbC genes were ligated into the 1st and 2'd multiple cloning sites (MCSs) of pRSFDuet-1 (Novagen), respectively, without the incorporation of affinity tags. The cfbC gene (obtained with reverse primer 1) was then sub-cloned from pET-28b(+) into the 1st MCS of pCDFDuet-1 (Novagen) using the NcoI and HindIII restriction enzymes, allowing the co-expression of CfbC containing a cleavable N-terminal His6-tag with untagged CfbD (and CfbC) for IMAC purification of the entire CfbCD complex. The sequences of the cloned genes within each of the constructed plasmids were verified by the Genomics and Sequencing Laboratory (GSL) at Auburn University or Eurofins Scientific.

Protein Expression and Purification. The HemC, HemD, SirA, SirC, CfbA, CfbB, CfbE, and McrD proteins were prepared by transforming *E. coli* BL21 (DE3) with the appropriate pET-28b(+) vector and culturing the resulting cells in Luria-Bertani (LB) medium supplemented with 50 µg/mL kanamycin at 37° C. in an incubator shaker. The CfbCD complex was obtained by sequentially transforming *E. coli* BL21 (DE3) with the pRSFDuet-1 and pCDFDuet-1 vectors described above, along with the pDB1282 vector containing the iron-sulfur cluster (isc) biosynthetic gene cluster from *Azotobacter vinelandii* (a generous gift from Prof. Dennis R. Dean, Virginia Polytechnic Institute and State University). The resulting cells were then propagated in LB medium containing kanamycin (50 µg/mL), spectinomycin (25 µg/mL), and ampicillin (100 µg/mL) at 37° C. in an incubator shaker. For the purification of HemC, the temperature of the culture was lowered to 15° C. after the culture reached an OD600~0.5. After incubating for an additional 1 h at 15° C., the cells were induced with 40 µM isopropyl β-D-thiogalactoside (IPTG), supplemented with 10 µM 5-aminolevulinic acid (ALA) (Ark Pharm, Inc.), and incubated for an additional 8 h. The production of HemD was also induced with 40 µM IPTG once the culture reached an $OD_{600}$~0.6, after which the culture was incubated for an additional 8 h at 18° C. The production of SirA, SirC, CfbB, and CfbE was induced with 100 µM IPTG when each of the cultures reached an $OD_{600}$~0.5. Similarly, CfbA was induced with 400 µM IPTG when the cultures reached an $OD_{600}$~0.5. For the production of the CfbCD complex, the isc operon was first induced with 3.0 g/L L-(+)-arabinose and the culture was supplemented with 3.0 mM each of $FeSO_4$ and L-cysteine. After incubation for 3 h, expression of the CfbCD complex was induced with 300 Mm IPTG. The cultures were then allowed to incubate with shaking for 12 h (at 18° C. for SirA, SirC, CfbA, and the CFbCD complex, and 25° C. for CfbB and CfbE). For the production of McrD, cells were induced with 400 µM IPTG and the culture reached an $OD_{600}$~0.6. The culture was then grown for an additional 16 h at 25° C.

Cells from each of the cultures were harvested by centrifugation at 15,970×g and 4° C. The remaining steps of the purification for HemC and the CfbCD complex were carried in a Coy anaerobic chamber with degassed buffers, while those for the rest of the enzymes were carried out aerobically. Cells were resuspended in lysis buffer consisting of 50 mM sodium phosphate (pH 8.0), 300 mM NaCl, 5 mM imidazole, lysozyme (1 mg/ml), and Ameresco's Protease Inhibitor Cocktail. The cell suspension was then sonicated and centrifuged at 104,600×g for 20 min at 4° C. The supernatant was applied to a Bio-Rad Econo-Pac column packed with Profinity IMAC Ni-Charged Resin. The column was then washed with 50 mM sodium phosphate (pH 8.0) buffer containing 300 mM NaCl and 5 mM imidazole. All of the proteins (except for CfbA and CfbB) were then eluted with a 50 mM sodium phosphate (pH 8.0) buffer containing 300 mM NaCl and 500 mM imidazole. The columns containing CfbA and CfbB were washed with 100 mM Tris-HCl (pH 8.0) buffer and then thrombin (80 units/mL of IMAC resin) was applied to the columns to cleave off the N-terminal His6-tags. The columns were capped at both ends and incubated at 25° C. with shaking for 16 h. CfbA and CfbB were then eluted from their respective columns with 100 mM Tris-HCl (pH 8.0) buffer and the eluates were applied to columns containing Benzamidine Sepharose 4 Fast Flow (GE Healthcare) to remove the thrombin. The buffers of all of the proteins were then exchanged with 100 mM Tris-HCl (pH 8.0) containing 16% glycerol.

Activity assays of coenzyme F430 biosynthesis enzymes. All coenzyme F430 biosynthetic reactions were carried out in an M Braun LABmaster Glove Box Workstation under a $N_2$ atmosphere containing <0.1 ppm $O_2$. All chemicals, unless otherwise noted, were obtained from Sigma-Aldrich. In a typical reaction, sirohydrochlorin was synthesized by incubating porphobilinogen (PBG) (0.88 mM) (Frontier Scientific) with HemC (0.06 mg/mL), HemD (0.06 mg/mL), SirA (0.12 mg/mL), SirC (0.36 mg/mL), S-adenosyl-L-methionine (SAM) (1.0 mM) (Carbosynth), NAD(P)+(1.0 mM), and $MgCl_2$ (4 mM) in 100 mM Tris-HCl buffer (pH 8.0) at 37° C. for 12 hours unless otherwise noted.

The sirohydrochlorin nickelochelatase was assayed by including CfbA (0.09 mg/mL) and $NiCl_2$ (200 μM) in a reaction otherwise identical to the above for sirohydrochlorin. An identical reaction was also prepared with the inclusion of 13 μL of a 3.6 mg/mL solution of CfbB (the subsequent enzyme in the pathway), but without the co-substrates (i.e., glutamine, ATP) required for its activity, in order to help drive the CfbA reaction forward by alleviating any potential product inhibition. In this reaction, the molar ratio of potential product (Ni-sirohydrochlorin) to CfbA and CfbB was ~200:4:1.

Ni-sirohydrochlorin a,c-diamide synthetase was assayed by adding 50 μL of a 3.6 mg/mL solution of CfbB, 23 μL of a 50 mM solution of L-glutamine, 2.5 μL of a 200 mM solution of ATP, 4.0 μL of a 500 mM solution of phosphoenolpyruvate (PEP), and 4 units of (1 unit/μL) *Bacillus stearothermophilus* pyruvate kinase (PK) to 250 μL of the completed Ni-sirohydrochlorin reaction and incubating for 12 hours at 37° C. The last two components were used to regenerate ATP to help drive the CfbB reaction forward. An identical reaction was also prepared with 10 μL of a 4.8 mg/mL solution of the CfbCD complex (which catalyzes the next step in the pathway, and was once again added without a necessary component for activity, the reductant sodium dithionite) to help alleviate any product inhibition. In this reaction, the molar ratio of potential product (Ni-sirohydrochlorin a,c-diamide) to CfbB and the CfbCD complex was $^{18}$ 400:30:1.

The Ni-sirohydrochlorin a,c-diamide reductive cyclase was assayed by incubating 2004 of the completed Ni-sirohydrochlorin a,c-diamide reaction with 30 μL of a 4.8 mg/mL solution of the CfbCD complex, 6.0 μL of a 1.0 M solution of sodium dithionite, 2.0 μL of a 200 mM solution of ATP, 8 μL of a 500 mM solution of PEP, and 4 units of pyruvate kinase for 12 hours at 37° C. This reaction, which produces the known coenzyme F430 biosynthetic intermediate 15,173-seco-F430-173-acid, could not be driven in the same way by the addition of CfbE, since the co-substrate required for its activity (ATP) could not be omitted from the reaction. The molar ratio of potential product ($15,17^3$-seco-$F430$-$17^3$-acid) to the CfbCD complex was ~30:1.

Finally, coenzyme F430 synthetase was assayed by adding 20 μL of a 1.4 mg/mL solution of CfbE, 1.0 μL of a 200 mM solution of ATP, 2.5 μL of a 500 mM solution of PEP, and 2 units of pyruvate kinase to 80 μl of the completed $15,17^3$-seco-$F430$-$17^3$-acid reaction and incubating for 12 hours at 37° C. The CfbE reaction was also driven forward by the inclusion of 20 μL of a 2.6 mg/mL solution of McrD (a putative coenzyme F430-binding protein/MCR chaperone) in the assay mixture. In this reaction, the molar ratio of potential product (coenzyme F430) to CfbE and McrD was approximately 20:1:5.

After completion of each of the assays described above, the reaction mixtures were quenched with an equal volume of methanol and centrifuged at 6,153×g for 20 min. The pellet containing precipitated proteins and insoluble material was discarded and the supernatant was subjected to chromatographic analysis. An authentic coenzyme F430 standard was extracted in an identical manner from MCR purified from *Methanothermobacter marburgensis* (a generous gift from Prof. Eduardus C. Duin, Auburn University).

High-performance liquid chromatography (HPLC). Reversed-phase HPLC analysis was performed on an Agilent 1260 Infinity Quaternary LC System equipped with a Diode Array Detector (DAD) VL+ and an Agilent Poroshell 120 EC-C18 (4.6×150 mm, 2.7 μm) column. The Agilent OpenLAB ChemStation Edition software was used for data analysis. The chromatographic method utilized for characterization of the coenzyme F430 biosynthetic reactions consisted of the following gradient of water (solvent A) and acetonitrile (solvent B), each containing 0.5% formic acid: 0% B for 2 min, 0-20% B over 3 min, 20% B for 5 min, 20-25% B over 5 min, 25% B for 5 min, 25-30% B over 5 min, 30-100% B over 5 min. The flow rate was 1.0 mL/min and the chromatogram was acquired with detection at 400 nm.

Mass spectrometry (MS). LC-MS analysis was performed on a Waters Acquity UPLC/Q-TOF Premier Mass Spectrometer equipped with an identical Agilent Poroshell 120 EC-C18 column. The Waters MassLynx MS software was used for data analysis. The LC method consisted of the same solvent system and gradient as described above. The electrospray ionization (ESI) mass detector was configured to positive ion mode with scanning between 0-1100 m/z. The inline Tunable UV (TUV) detector was set to 400 nm to match the peaks observed in the mass chromatograms to those observed by HPLC analysis.

I. REFERENCES

1. R. K. Thauer, A. K. Kaster, H. Seedorf, W. Buckel, R. Hedderich, Nat. Rev. Microbiol. 6, 579-591 (2008).

2. J. G. Ferry, Science 278, 1413-1414 (1997).
3. T. Wongnate et al., Science 352, 953-958(2016).
4. G. Diekert, R. Jaenchen, R. K. Thauer, FEBS Lett. 119, 118-120(1980).
5. K. Knittel, A. Boetius, Annu. Rev. Microbiol. 63, 311-334 (2009).
6. S. Scheller, M. Goenrich, R. Boecher, R. K. Thauer, B. Jaun, Nature 465, 606-608 (2010).
7. T. J. Mueller et al., J. Ind. Microbiol. Biotechnol. 42, 391-401(2015).
8. H. L. Schubert, E. Raux, K. S. Wilson, M. J. Warren, Biochemistry 38, 10660-10669 (1999).
9. H. Mucha, E. Keller, H. Weber, F. Lingens, W. Trösch, FEBS Lett. 190, 169-171 (1985).
10. M. F. Haroon et al., Nature 500, 567-570 (2013).
11. J. R. Roth, J. G. Lawrence, M. Rubenfield, S. Kieffer-Higgins, G. M. Church, J. Bacteriol. 175, 3303-3316 (1993).
12. H. Schindelin, C. Kisker, J. L. Schlessman, J. B. Howard, D. C. Rees, Nature 387, 370-376 (1997).
13. N. Muraki et al., Nature 465, 110-114 (2010).
14. J. Raymond, J. L. Siefert, C. R. Staples, R. E. Blankenship, Mol. Biol. Evol. 21, 541-554 (2004).
15. C. R. Staples et al., J. Bacteriol. 189, 7392-7398(2007).
16. F. Pratviel-Sosa, D. Mengin-Lecreulx, J. van Heijenoort, Eur. J. Biochem. 202, 1169-1176 (1991).
17. F. Sarmiento, J. Mrazek, W. B. Whitman, Proc. Natl. Acad. Sci. U.S.A. 110, 4726-4731 (2013).
18. A. G. Smith, M. Witty, Heme, Chlorophyll, and Bilins: Methodsand Protocols (Humana Press, 2002).
19. M. J. Warren et al., FEBS Lett. 261, 76-80(1990).
20. H. K. Leech, E. Raux-Deery, P. Heathcote, M. J. Warren, Biochem. Soc. Trans. 30, 610-613 (2002).
21. E. Deery et al., Nat. Chem. Biol. 8, 933-940(2012).
22. V. Fresquet, L. Williams, F. M. Raushel, Biochemistry 43, 10619-10627 (2004).
23. A. Pfaltz, A. Kobelt, R. Fluster, R. K. Thauer, Eur. J. Biochem. 170, 459-467 (1987).
24. R. Fani, R. Gallo, P. Lie), J. Mol. Evol. 51, 1-11(2000).
25. I. Kouidmi, R. C. Levesque, C. Paradis-Bleau, Mol. Microbiol. 94, 242-253 (2014).
26. M. Bokranz, A. Klein, Nucleic Acids Res. 15, 4350-4351(1987).
27. D. Prakash, Y. Wu, S.-J. Suh, E. C. Duin, J. Bacteriol. 196, 2491-2498 (2014).
28. B. A. Sherf, J. N. Reeve, J. Bacteriol. 172, 1828-1833 (1990).

CONCLUSION

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

TABLE 1A

Exemplar CfbA, CfbB, and CfbC Polypeptides

| Species | cfbA | SIDN | cfbB | SIDN | cfbC | SIDN |
|---|---|---|---|---|---|---|
| *Methanobacterium formicicum* DSM 3637 | EKF86817.1 | 1 | EKF86965.1 | 32 | EKF86281.1 | 63 |
| *Methanobrevibacter ruminantium* M1 | ADC48050.1 | 2 | ADC48001.1 | 33 | ADC47316.1 | 64 |
| *Methanocaldococcus jannaschii* DSM 2661 | AAB98975.1 | 3 | AAB99432.1 | 34 | AAB98883.1 | 65 |
| *Methanocella arvoryzae* MRE50 | CAJ37161.1 | 4 | CAJ37157.1 | 35 | CAJ37158.1 | 66 |
| *Methanococcoides methylutens* MM1 | AKB85570.1 | 5 | AKB85574.1 | 36 | AKB85573.1 | 67 |
| *Methanococcus maripaludis* C7 | ABR66230.1 | 6 | ABR65789.1 | 37 | ABR66213.1 | 68 |
| *Methanocorpusculum labreanum* Z | ABN06692.1 | 7 | ABN06695.1 | 38 | ABN06341.1 | 69 |
| *Methanoculleus bourgensis* MS2 | CCJ35643.1 | 8 | CCJ35640.1 | 39 | CCJ35251.1 | 70 |
| *Methanofollis liminatans* DSM 4140 | EJG07637.1 | 9 | EJG07640.1 | 40 | EJG07797.1 | 71 |
| *Methanohalobium evestigatum* Z-7303 | ADI73469.1 | 10 | ADI73465.1 | 41 | ADI73466.1 | 72 |
| *Methanohalophilus mahii* DSM 5219 | ADE36908.1 | 11 | ADE36912.1 | 42 | ADE36911.1 | 73 |
| *Methanolacinia petrolearia* DSM 11571 | ADN35767.1 | 12 | ADN35770.1 | 43 | ADN37126.1 | 74 |
| *Methanolobus psychrophilus* R15 | AFV24956.1 | 13 | AFV23166.1 | 44 | AFV23167.1 | 75 |
| *Methanomassiliicoccus luminyensis* B10 | WP_019176686.1 | 14 | WP_019176682.1 | 45 | WP_019176683.1 | 76 |
| *Methanomethylovorans hollandica* DSM 15978 | A G848984.1 | 15 | AGB48806.1 | 46 | AGB48807.1 | 77 |
| *Methanomicrobium mobile* BP | WP_042706480.1 | 16 | WP_042706482.1 | 47 | WP_042705951.1 | 78 |
| *Methanoplanus limicola* DSM 2279 | EHQ34594.1 | 17 | EHQ34597.1 | 48 | EHQ36875.1 | 79 |
| *Methanopyrus kandleri* AV19 | AAM01643.1 | 18 | AAM02856.1 | 49 | AAM02629.1 | 80 |
| *Methanoregula formicica* SMSP | AGB02774.1 | 19 | AGB02771.1 | 50 | AGB01831.1 | 81 |
| *Methanosaeta concilii* GP6 | AEB68503.1 | 20 | AEB67347.1 | 51 | AEB67348.1 | 82 |
| *Methanosalsum zhilinae* DSM 4017 | AEH60345.1 | 21 | AEH60341.1 | 52 | AEH60342.1 | 83 |

TABLE 1A-continued

Exemplar CfbA, CfbB, and CfbC Polypeptides

| Species | cfbA | SIDN | cfbB | SIDN | cfbC | SIDN |
|---|---|---|---|---|---|---|
| *Methanosarcina acetivorans* C2A | AAM06986.1 | 22 | AAM06981.1 | 53 | AAM06982.1 | 84 |
| *Methanosphaera stadtmanae* DSM 3091 | ABC57930.1 | 23 | ABC56580.1 | 54 | ABC57502.1 | 85 |
| *Methanosphaerula palustris* E1-9c | ACL16048.1 | 24 | ACL16045.1 | 55 | ACL15621.1 | 86 |
| *Methanospirillum hungatei* JF-1 | ABD40424.1 | 25 | ABD40427.1 | 56 | ABD40545.1 | 87 |
| *Methanothermobacter marburgensis* str. Marburg | ADL59351.1 | 26 | ADL57656.1 | 57 | ADL58617.1 | 88 |
| *Methanothermococcus okinawensis* IH1 | AEH06629.1 | 27 | AEH06058.1 | 58 | AEH06784.1 | 89 |
| *Methanothermus fervidus* DSM 2088 | ADP77758.1 | 28 | ADP77644.1 | 59 | ADP77182.1 | 90 |
| *Methanotorris igneus* Kol 5 | AEF95825.1 | 29 | AEF96349.1 | 60 | AEF96745.1 | 91 |
| *Methermicoccus shengliensis* DSM 18856 | WP_052353065.1 | 30 | WP_042685296.1 | 61 | WP_042684816.1 | 92 |
| ANME-2 cluster | KCZ71124.1 | 31 | KCZ71643.1 | 62 | KCZ71645.1 | 93 |

TABLE 1B

Exemplar CfbD and CfbE Polypeptides

| Species | cfbD | SIDN | cfbE | SIDN |
|---|---|---|---|---|
| *Methanobacterium formicicum* DSM 3637 | EKF87013.1 | 94 | EKF86338.1 | 125 |
| *Methanobrevibacter ruminantium* M1 | ADC46033.1 | 95 | ADC47595.1 | 126 |
| *Methanocaldococcus jannaschii* DSM 2661 | AAB99434.1 | 96 | AAB98245.1 | 127 |
| *Methanocella arvoryzae* MRE50 | CAJ37159.1 | 97 | CAJ37160.1 | 128 |
| *Methanococcoides methylutens* MM1 | AKB85572.1 | 98 | AKB85571.1 | 129 |
| *Methanococcus maripaludis* C7 | ABR66488.1 | 99 | ABR66239.1 | 130 |
| *Methanocorpusculum labreanum* Z | ABN06694.1 | 100 | ABN06693.1 | 131 |
| *Methanoculleus bourgensis* MS2 | CCJ35641.1 | 101 | CCJ35642.1 | 132 |
| *Methanofollis liminatans* DSM 4140 | EJG07639.1 | 102 | EJG07638.1 | 133 |
| *Methanohalobium evestigatum* Z-7303 | ADI73467.1 | 103 | ADI73468.1 | 134 |
| *Methanohalophilus mahii* DSM 5219 | ADE36910.1 | 104 | ADE36909.1 | 135 |
| *Methanolacinia petrolearia* DSM 11571 | ADN35769.1 | 105 | ADN35768.1 | 136 |
| *Methanolobus psychrophilus* R15 | AFV23168.1 | 106 | AFV23170.1 | 137 |
| *Methanomassiliicoccus luminyensis* B10 | WP_081579794.1 | 107 | WP_019176685.1 | 138 |
| *Methanomethylovorans hollandica* DSM 15978 | AGB48808.1 | 108 | AGB48809.1 | 139 |
| *Methanomicrobium mobile* BP | WP_042706481.1 | 109 | WP_052359236.1 | 140 |
| *Methanoplanus limicola* DSM 2279 | EHQ34596.1 | 110 | EHQ34595.1 | 141 |
| *Methanopyrus kandleri* AV19 | AAM02598.1 | 111 | AAM02803.1 | 142 |
| *Methanoregula formicica* SMSP | AGB02772.1 | 112 | AGB02773.1 | 143 |
| *Methanosaeta concilii* GP6 | AEB68505.1 | 113 | AEB68504.1 | 144 |
| *Methanosalsum zhilinae* DSM 4017 | AEH60343.1 | 114 | AEH60344.1 | 145 |
| *Methanosarcina acetivorans* C2A | AAM06983.1 | 115 | AAM06985.1 | 146 |
| *Methanosphaera stadtmanae* DSM 3091 | ABC57831.1 | 116 | ABC57708.1 | 147 |
| *Methanosphaerula palustris* E1-9c | ACL16046.1 | 117 | ACL16047.1 | 148 |
| *Methanospirillum hungatei* JF-1 | ABD40426.1 | 118 | ABD40425.1 | 149 |
| *Methanothermobacter marburgensis* str. Marburg | ADL57715.1 | 119 | ADL58856.1 | 150 |
| *Methanothermococcus okinawensis* IH1 | AEH06560.1 | 120 | AEH06773.1 | 151 |
| *Methanothermus fervidus* DSM 2088 | ADP77164.1 | 121 | ADP77991.1 | 152 |
| *Methanotorris igneus* Kol 5 | AEF97255.1 | 122 | AEF95924.1 | 153 |
| *Methermicoccus shengliensis* DSM 18856 | WP_042685764.1 | 123 | WP_042684478.1 | 154 |
| ANME-2 cluster | KCZ71646.1 | 124 | KCZ71123.1 | 155 |

TABLE 2

Conservative Amino Acid Substitutions

| Original Amino Acid | Exemplary substitution | Preferred substitution |
|---|---|---|
| Ala | Val, Leu, Ile | Val |
| Arg | Lys, Gln, Asn | Lys |
| Asn | Glu | Glu |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4-diaminobutyric acid, Gln, Asn | Arg |
| Met | Leu, Phe, Ile | Leu |
| Phe | Leu, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

I claim:

1. A genetically modified cell comprising: a first nucleotide sequence encoding a first Cfb polypeptide, and a second nucleotide sequence encoding a second Cfb polypeptide having at least 70% sequence identity to the first Cfb polypeptide, wherein the first and second Cfb polypeptides are both one of a CfbA (sirohydrochlorin cobaltochelatase), CfbB (cobyrinic acid a,c-diamide synthetase), CfbC (nitrogenase iron protein), CfbD (nitrogenase molybdenum-iron protein), and CfbE (UDP-N-acetylmuramoylalanine:D-glutamate ligase) polypeptide.

2. The cell of claim 1, wherein the first Cfb polypeptide has at least 70% sequence identity with a first CfbA polypeptide shown in Table 1A (SEQ ID NO: 1-31), and wherein the second Cfb polypeptide has at least 70% sequence identity with a second CfbA polypeptide shown in Table 1A (SEQ ID NO: 1-31).

3. The cell of claim 1, wherein the first Cfb polypeptide has at least 70% sequence identity with a first CfbB polypeptide shown in Table 1A (SEQ ID NO: 32-62), and wherein the second Cfb polypeptide has at least 70% sequence identity with a second CfbB polypeptide shown in Table 1A (SEQ ID NO: 32-62).

4. The cell of claim 1, wherein the first Cfb polypeptide has at least 70% sequence identity with a first CfbC polypeptide shown in Table 1A (SEQ ID NO: 63-93), and wherein the second Cfb polypeptide has at least 70% sequence identity with a second CfbC polypeptide shown in Table 1A (SEQ ID NO: 63-93).

5. The cell of claim 1, wherein the first Cfb polypeptide has at least 70% sequence identity with a first CfbD polypeptide shown in Table 1B (SEQ ID NO: 94-124), and wherein the second Cfb polypeptide has at least 70% sequence identity with a second CfbD polypeptide shown in Table 1A (SEQ ID NO: 94-124).

6. The cell of claim 1, wherein the first Cfb polypeptide has at least 70% sequence identity with a first CfbE polypeptide shown in Table 1A (SEQ ID NO: 125-155), and wherein the second Cfb polypeptide has at least 70% sequence identity with a second CfbE polypeptide shown in Table 1A (SEQ ID NO: 125-155).

7. The cell of claim 1, wherein the first Cfb polypeptide has at least 80% sequence identity with the second Cfb polypeptide.

8. The cell of claim 1, wherein the first Cfb polypeptide has at least 90% sequence identity with the second Cfb polypeptide.

9. The cell of claim 1, wherein the first Cfb polypeptide has at least 95% sequence identity with the second Cfb polypeptide.

10. The cell of claim 1, wherein the first Cfb polypeptide has 100% sequence identity with the second Cfb polypeptide.

11. The cell of claim 1, wherein the first Cfb polypeptide and the second Cfb polypeptide are both operatively linked to a common promoter.

12. The cell of claim 1, wherein at least one of the first polynucleotide and the second polynucleotide is a heterologous polynucleotide.

13. The cell of claim 1, wherein at least one of the first polynucleotide and the second polynucleotide is operatively linked to a heterologous promoter.

14. The cell of claim 1, comprising: a third nucleotide sequence encoding a third Cfb polypeptide having at least 70% sequence identity to the first Cfb polypeptide.

15. The cell of claim 1, comprising: a third nucleotide sequence encoding a third Cfb polypeptide having at least 70% sequence identity to the first Cfb polypeptide; and a fourth nucleotide sequence encoding a fourth Cfb polypeptide having at least 70% sequence identity to the first Cfb polypeptide.

16. The cell of claim 1, wherein the cell is a methanogenic archaeal cell.

17. A method of methane generation, comprising maintaining a culture of the cell of claim 16 under methanogenic conditions.

18. The cell of claim 1, wherein the cell is a methanotrophic cell.

19. A method of methane removal, comprising providing methane to a culture of the cell of claim 18 under methanotrophic conditions.

20. The cell of claim 1, wherein the cell has increased coenzyme F430 biosynthetic activity compared to wild-type.

* * * * *